(12) United States Patent
Pfeifer et al.

(10) Patent No.: US 10,100,104 B2
(45) Date of Patent: Oct. 16, 2018

(54) METHODS OF DIAGNOSING TAU-PROTEIN-ASSOCIATED DISEASE

(71) Applicants: KATHOLIEKE UNIVERSITEIT LEUVEN, Leuven (BE); AC IMMUNE S.A., Lausanne (CH)

(72) Inventors: Andrea Pfeifer, St. Legier (CH); Andreas Muhs, Pully (CH); Fred Van Leuven, Leuven (BE); Maria Pihlgren, Montsur-Lausanne (CH); Oskar Adolfsson, Bercher (CH)

(73) Assignees: KATHOLIEKE UNIVERSITEIT LEUVEN, Leuven (BE); AC IMMUNE S.A., Lausanne (CH)

( * ) Notice: Subject to any disclaimer, the term of this patent is extended or adjusted under 35 U.S.C. 154(b) by 0 days.

(21) Appl. No.: 15/045,804

(22) Filed: Feb. 17, 2016

(65) Prior Publication Data

US 2016/0304590 A1    Oct. 20, 2016

Related U.S. Application Data

(62) Division of application No. 13/500,608, filed as application No. PCT/EP2011/067604 on Oct. 7, 2011, now Pat. No. 9,304,138.

(30) Foreign Application Priority Data

Oct. 7, 2010 (EP) ..................................... 10186810
Jul. 15, 2011 (EP) ..................................... 11174248

(51) Int. Cl.
*C07K 16/18* (2006.01)
*G01N 33/68* (2006.01)
*A61K 39/00* (2006.01)

(52) U.S. Cl.
CPC .......... *C07K 16/18* (2013.01); *A61K 39/0005* (2013.01); *G01N 33/6896* (2013.01); *A61K 2039/505* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | |
|---|---|---|
| 2002/0086009 A1 | 7/2002 | Ishiguro et al. |
| 2005/0196844 A1 | 9/2005 | Lee |
| 2005/0221391 A1 | 10/2005 | Davies |
| 2008/0050383 A1 | 2/2008 | Sigurdsson et al. |
| 2008/0220449 A1 | 9/2008 | Vasan et al. |

FOREIGN PATENT DOCUMENTS

| | | |
|---|---|---|
| EP | 2 210 901 A1 | 7/2010 |
| RU | 2007 119 382 A | 11/2008 |
| WO | WO 93/011231 | 6/1993 |
| WO | WO 98/22120 A1 | 5/1998 |
| WO | WO 2006/055178 A2 | 5/2006 |
| WO | WO 2008/157302 | 12/2008 |
| WO | WO 2010/106127 A2 | 9/2010 |
| WO | WO 2010/115843 A2 | 10/2010 |
| WO | WO 2010/144711 A2 | 12/2010 |
| WO | WO 2011/013034 A1 | 2/2011 |

OTHER PUBLICATIONS

Jicha et al., J Neuroscience, 19(17):7486-7494, Sep. 1, 1999.*
Vanhelmont et al., FEMS Yeast Res, 10 992-1005, published online Jul. 21, 2010.*
Bhaskar, K. et al., "Tyrosine Phosphorylation of Tau Accompanies Disease Progression in Transgenic Mouse Models of Taupathy," Neuropathology and Applied Neurobiology, 2010, vol. 36, pp. 462-477.
Bellucci et al., "Abnormal processing of tau in the brain of aged TgCRND8 mice," Neurobiol. Dis., 27(3): 328-338 (2007).
Boutajangout et al., "Passive immunization targeting pathological phospho-tau protein in a mouse model reduces functional decline and clears tau aggregates from the brain," J. Neurochem., 118: 658-667 (2011).
Chai et al., "Passive Immunization with Anti-Tau Antibodies in Two Transgenic Models," J. Biol. Chem., 286(39): 34457-34467 (2011).
Communication of Partial European Search Report for EP Patent Application No. 15177523.6, dated Jan. 14, 2016 (14 pages).
D'Abramo et al., "Tau Passive Immunotherapy in Mutant P301L Mice: Antibody Affinity versus Specificity," PLOSone, 8(4): e62402, published Apr. 29, 2013.
D'Abramo et al., "Passive Immunization in JNPL3 Transgenic Mice Using an Array of Phospho-Tau Specific Antibodies," PLOS ONE, 10(8): e0135774 doi: 10.1371.pone.0135774, pp. 1-8 (2015).
Dunn et al., "Fine mapping of the binding sites of monoclonal antibodies raised against the Pk tag," J. Immunol. Methods, 224(1-2): 141-150 (1999).
Hirata-Fukae, C. et al., "Levels of Soluble and Insoluble Tau Reflect Overall Status of Tau Phosphorylation in Vivo," Neuroscience Letters, Jan. 23, 2009, vol. 450, No. 1, pp. 51-55.

(Continued)

*Primary Examiner* — Kimberly Ballard
*Assistant Examiner* — Stacey N MacFarlane
(74) *Attorney, Agent, or Firm* — McNeill Baur PLLC

(57) ABSTRACT

The present invention relates to methods and compositions for the therapeutic and diagnostic use in the treatment of diseases and disorders which are caused by or associated with neurofibrillary tangles. In particular, the invention relates to antibodies, which specifically recognize and bind to phosphorylated pathological protein tau-conformers and to methods and compositions involving said antibodies for the therapeutic and diagnostic use in the treatment of tauopathies including Alzheimer's Disease (AD).

26 Claims, 22 Drawing Sheets

Specification includes a Sequence Listing.

(56) References Cited

OTHER PUBLICATIONS

Hoffman, R. et al., "Unique Alzheimer's Disease Paired Helical Filament Specific Epitopes Involve Double Phosphorylation at Specific Sites," Biochemistry, Jul. 1, 1997, vol. 36, No. 26, pp. 8114-8124.
"Instructions for Authors", The Journal of Neuroscience, published [online] Jun. 29, 1998. Retrieved [online] from <https://web.archive.org/web/19980629153321/http://www.jneurosci.org/misc/itoa.shtml> on Jan. 7, 2015.
International Search Report and Written Opinion dated Apr. 3, 2012 in co-pending International Application No. PCT/EP2011/067604.
Jicha et al., "cAMP-Dependent Protein Kinase Phosphorylations on Tau in Alzheimer's Disease," The Journal of Neuroscience, 19(17):7486-7494, Sep. 1, 1999.
Lee, G. et al., "Phosphorylation of Tau by Fyn: Implications for Alzheimer's Disease," The Journal of Neuroscience, Mar. 3, 2004, vol. 24, No. 9, pp. 2304-2312.
Lichtenberg-Kraag, B. et al., "Phosphorylation-Dependent Epitopes of Neurofilament Antibodies on Tau Protein and Relationship with Alzheimer Tau," Proceedings of the National Academy of Sciences of USA, Jun. 1, 1992, vol. 89, No. 12, pp. 5384-5388.
Oddo, S. et al., "Reduction of Soluble Abeta and Tau, but Not Soluble Abeta Alone, Ameliorates Cognitive Decline in Transgenic Mice with Plaques and Tangles," Journal of Biological Chemistry, Jan. 1, 2006, vol. 281, No. 51, pp. 39413-39423.
Otvos, L. et al., "Monoclonal Antibody PHF4 Recognizes Tau Protein Phosphorylated at Serine Residues 396 and 404," Journal of Neuroscience Research, Jan. 1, 1994, vol. 39, pp. 669-673.
Rankin et al., "Tau Phosphorylation by GSK-3beta Promotes Tangle-Like Filament Morphology," Mol. Neurodegener, 2007. 2:12.
Roder, H. et al., "Phosphorylation-Dependent Monoclonal Tau Antibodies Do Not Reliably Report Phosphorylation by Extracellular Signal-Regulated Kinase 2 at Specific Sites," Journal of Biological Chemistry, Feb. 14, 1997, vol. 272, No. 7, pp. 4509-4515.
Sahara et al., "Phosphorylated p38MAPK specific antibodies cross-react with sarkosyl-insoluble hyperphosphorylated tau proteins," J. Neurochem., 90: 829-838 (2004).
Singer, D. et al., "Immuno-PCR-Based Quantification of Multiple Phosphorylated Tau-Epitopes Linked to Alzheimer's Disease," Analytical and Bioanalytical Chemistry, vol. 395, No. 7, Oct. 11, 2009, pp. 2263-2267.
Singer, D. et al., "Characterization of Phosphorylation Dependent Antibodies to Study the Phosphorylation Dependent Antibodies to Study the Phosphorylation Status of the Tau Protein," International Journal of Peptide Research and Therapeutics (formerly known as Letters in Peptide Science), Dec. 1, 2005, vol. 11, No. 4, pp. 279-289.
Torreilles, F. et al., "Binding Specificity of Monoclonal Antibody AD2: Influence of the Phosphorylation State of Tau," Molecular Brain Research, Jan. 1, 2000, vol. 78, pp. 181-185.
Vandebroek, T. et al., "Identification and Isolation of a Hyperphosphorylated, Conformationally Changed Intermediate of Human Protein Tau Expressed in Yeast," Biochemistry, 44: 11466-11475 (2005).
Vanhelmont, T. et al., "Serine-409 Phosphorylation and Oxidative Damage Define Aggregation of Human Protein Tau in Yeast," Fems Yeast Research, Dec. 1, 2010, vol. 10, No. 8, pp. 992-1005.
Zemlan, F. et al., "Monoclonal Antibody PHF-9 Recognizes Phosphorylated Serine 404 of Tau Protein and Labels Paired Helical Filaments," Journal of Neuroscience Research, Oct. 1, 1996, vol. 46, No. 1, pp. 90-97.
Zheng-Fischhoefer, Q. et al., "Sequential Phosphorylation of Tau by Glycogen Synthase Kinase-3beta and Protein Kinase A at Thr212 and Ser214 Generates the Alzheimer-Specific Epitope of Antibody A T100 and Requires a Paired-Helical-Filament-Like Conformation," European Journal of Biochemistry, Mar. 1, 1998, vol. 252, No. 3, pp. 542-552.
Andreasen et al., "Evaluation of CSF-tau and CSF-Aβ42 as Diagnostic Markers for Alzheimer Disease in Clinical Practice," Arch Neurol., 58: 373-379 (2001).
Andreasson et al., "Update on ultrasensitive technologies to facilitate research on blood biomarkers for central nervous system disorders," Alzheimer's & Dementia: Diagnosis, Assessment & Disease Monitoring, 3: 98-102 (2016).
Blennow, "A Review of Fluid Biomarkers for Alzheimer's Disease: Moving from CSF to Blood," Neurol. Ther., 6(Supp 1): S15-S24 (2017).
Forlenza et al., "Cerebrospinal fluid biomarkers in Alzheimer's disease: Diagnostic accuracy and prediction of dementia," Alzheimer's & Dementia: Diagnosis, Assessment & Disease Monitoring, 1: 455-463 (2015).
Kimura et al., "Sequential changes of tau-site-specific phosphorylation during development of paired helical filaments," Dementia, 7(4): 177-181 (1996).
Otto et al., "Elevated levels of tau-protein in cerebrospinal fluid of patients with Creutzfeldt-Jakob disease," Neurosci. Lett., 225(3): 210-212 (1997) Abstract Only.

* cited by examiner

| Clone | Cortex | Hippocampus (CA1) | Clone | Cortex | Hippocampus (CA1) |
|---|---|---|---|---|---|
| 6C10F9 C12A11 | | | 6C10E5 E9C12 | | |
| 6H1A11 C11 | | | 6H1G6E 6 | | |
| 2B6A10 C11 | | | 2B6G7A 12 | | |
| 3A8A12 G7 | | | 3A8E12 H8 | | |
| 7C2(1) F10C10 D3 | | | 7C2(2) B9F11D 5 | | |
| *Control* AT100 antibody | | | *Control* PG5 antibody | | |
| *Control* No primary antibody | | | | | |

*FIG. 1A*

| Clone | Cortex | Hippocampus (CA1) | Clone | Cortex | Hippocampus (CA1) |
|---|---|---|---|---|---|
| A4-2A1-18 |  |  | A6-2G5-08 |  |  |
| A4-4A6-48 |  |  | A6-2G5-30 |  |  |
| A4-2A1-40 |  |  | A6-2G5-41 |  |  |
| A6-1D2-12 |  |  | A4-4A6-18 |  |  |
| *Control* AT100 antibody |  |  | *Control* PG5 antibody |  |  |
| *Control* No primary antibody |  |  | | | |

| Diagnosis | Region | ACI-3A8-Ab1 TAUPIR staining |
|---|---|---|
| AD | Hippocampus |  |
| FAD | Anterior hippocampus |  |
| AGD | Anterior hippocampus |  |
| PSP | Pallidum |  |
| FTDP-17 | Frontal cortex |  |
| CBD | Frontal cortex |  |
| Healthy control | Hippocampus |  |

Cortex, soluble fraction (S1) transgenic/human pTau (pT231/AT180)

SEQUENCE LISTING

<160> NUMBER OF SEQ ID NOS: 221

<210> SEQ ID NO 1
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"

/organism="Mus musculus"

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Arg Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Tyr Tyr Ala Val Gly Tyr Trp Gly Gln Gly Thr Thr Leu Thr
            100                 105                 110

Val Ser Ser
        115

<210> SEQ ID NO 2
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 2

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Arg Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ser Tyr Tyr Ala Val Gly Tyr Trp Gly Gln Gly Thr Thr Leu Thr
            100                 105                 110

Val Ser Ser
        115

<210> SEQ ID NO 3
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 3

Glu Val Gln Leu Gln Gln Ser Gly Pro Glu Leu Val Lys Pro Gly Ala

```
            1               5                  10                  15
        Ser Val Lys Ile Ser Cys Lys Ala Ser Gly Tyr Thr Phe Thr Asp Tyr
                        20                  25                  30

Tyr Met Asn Trp Val Lys Gln Ser His Gly Lys Ser Leu Glu Trp Ile
                    35                  40                  45

Gly Asp Ile Asn Pro Asn Arg Gly Gly Thr Thr Tyr Asn Gln Lys Phe
                50                  55                  60

Lys Gly Lys Ala Thr Leu Thr Val Asp Thr Ser Ser Thr Ala Tyr
        65                  70                  75                  80

Met Glu Leu Arg Ser Leu Thr Ser Glu Asp Ser Ala Val Tyr Tyr Cys
                        85                  90                  95

Ala Ser Tyr Tyr Ala Val Gly Tyr Trp Gly Gln Gly Thr Thr Leu Thr
                        100                 105                 110

Val Ser Ser
                115

<210> SEQ ID NO 4
<211> LENGTH: 120
<212> TYPE: PRT
<213> ORGANISM: Mus musculus
<220> FEATURE:
<221> NAME/KEY: SOURCE
<222> LOCATION: 1..120
<223> OTHER INFORMATION: /mol_type="protein"
      /organism="Mus musculus"

<400> SEQUENCE: 4

Glu Val Gln Leu Val Glu Ser Gly Gly Gly Leu Val Lys Pro Gly Gly
        1               5                   10                  15

Ser Leu Lys Leu Ser Cys Ala Pro Ser Gly Phe Thr Phe Ser Asp Tyr
                        20                  25                  30

Gly Met His Trp Val Arg Gln Ala Pro Glu Lys Gly Leu Glu Trp Val
                    35                  40                  45

Ala Tyr Ile Ser Ser Gly Ser Ser Thr Ile Tyr Tyr Gly Asp Thr Val
                50                  55                  60

Lys Gly Arg Phe Thr Ile Ser Arg Asp Asn Ala Lys Asn Thr Leu Phe
        65                  70                  75                  80

Leu Gln Met Thr Ser Leu Arg Ser Glu Asp Thr Ala Met Tyr Tyr Cys
                        85                  90                  95

Ala Arg Arg Gly Gln Leu Arg Leu Arg Leu Phe Ala Tyr Trp Gly Gln
                        100                 105                 110

Gly Thr Leu Val Thr Val Ser Ala
                115                 120

<210> SEQ ID NO 5
<211> LENGTH: 119
<212> TYPE: PRT
<213> ORGANISM: Mus musculus
<220> FEATURE:
<221> NAME/KEY: SOURCE
<222> LOCATION: 1..119
<223> OTHER INFORMATION: /mol_type="protein"
      /organism="Mus musculus"

<400> SEQUENCE: 5

Glu Val Lys Leu Met Glu Ser Gly Gly Gly Leu Val His Pro Gly Ala
        1               5                   10                  15

Ser Leu Arg Leu Tyr Cys Ala Ala Ser Gly Phe Thr Phe Thr Asp Tyr
                        20                  25                  30
```

```
Tyr Met Ser Trp Val Arg Gln Pro Gly Lys Ala Pro Glu Trp Leu
        35                  40                  45

Ala Leu Ile Arg Asn Lys Ala Asn Gly Tyr Thr Thr Glu Tyr Thr Ala
 50                  55                  60

Ser Val Lys Gly Arg Phe Thr Ile Ser Arg Asp Asn Ser Gln Asn Ile
 65                  70                  75                  80

Leu Tyr Leu Gln Met Asn Thr Leu Arg Ala Glu Asp Ser Ala Thr Tyr
                 85                  90                  95

Tyr Cys Val Lys Ala Leu Gly Arg Tyr Phe Asp Val Trp Gly Thr Gly
                100                 105                 110

Thr Thr Val Thr Val Ser Ser
            115
```

```
<210> SEQ ID NO 6
<211> LENGTH: 113
<212> TYPE: PRT
<213> ORGANISM: Mus musculus
<220> FEATURE:
<221> NAME/KEY: SOURCE
<222> LOCATION: 1..113
<223> OTHER INFORMATION: /mol_type="protein"
      /organism="Mus musculus"

<400> SEQUENCE: 6

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Val Phe Asn Ser
                 20                  25                  30

Gly Asn Gln Lys Asn Ser Leu Ala Trp Tyr Gln Gln Lys Pro Gly Gln
             35                  40                  45

Ser Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Ser Leu Thr
 65                  70                  75                  80

Ile Ser Ser Val Gln Ala Glu Asp Leu Ala Asp Tyr Phe Cys Gln Glu
                 85                  90                  95

His Tyr Thr Thr Pro Pro Thr Phe Gly Thr Gly Thr Lys Leu Glu Leu
                100                 105                 110

Lys
```

```
<210> SEQ ID NO 7
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 7

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Arg Leu Val His Ser
                 20                  25                  30

His Gly Lys Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
            100                 105                 110
```

<210> SEQ ID NO 8
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 8

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

His Gly Lys Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
            100                 105                 110
```

<210> SEQ ID NO 9
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 9

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
                20                  25                  30

His Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Ala His Phe Pro Tyr Thr Phe Gly Gly Gly Thr Lys Leu Glu Ile Lys
            100                 105                 110
```

<210> SEQ ID NO 10

<211> LENGTH: 107
<212> TYPE: PRT
<213> ORGANISM: Mus musculus
<220> FEATURE:
<221> NAME/KEY: SOURCE
<222> LOCATION: 1..107
<223> OTHER INFORMATION: /mol_type="protein"
      /organism="Mus musculus"

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 11
<211> LENGTH: 113
<212> TYPE: PRT
<213> ORGANISM: Mus musculus
<220> FEATURE:
<221> NAME/KEY: SOURCE
<222> LOCATION: 1..113
<223> OTHER INFORMATION: /mol_type="protein"
      /organism="Mus musculus"

<400> SEQUENCE: 11

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ser Gly Thr Lys Leu Glu Ile
            100                 105                 110

Lys

<210> SEQ ID NO 12
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

```
<400> SEQUENCE: 12

Gly Tyr Thr Phe Thr Asp Tyr Tyr Met Asn
1               5                   10

<210> SEQ ID NO 13
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 13

Asp Ile Asn Pro Asn Arg Gly Gly Thr Thr Tyr Asn Gln Lys Phe Lys
1               5                   10                  15
Gly

<210> SEQ ID NO 14
<211> LENGTH: 6
<212> TYPE: PRT
<213> ORGANISM: Mus musculus
<220> FEATURE:
<221> NAME/KEY: SOURCE
<222> LOCATION: 1..6
<223> OTHER INFORMATION: /mol_type="protein"
      /organism="Mus musculus"

<400> SEQUENCE: 14

Tyr Tyr Ala Val Gly Tyr
1               5

<210> SEQ ID NO 15
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 15

Gly Phe Thr Phe Ser Asp Tyr Gly Met His
1               5                   10

<210> SEQ ID NO 16
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 16

Tyr Ile Ser Ser Gly Ser Ser Thr Ile Tyr Tyr Gly Asp Thr Val Lys
1               5                   10                  15
Gly

<210> SEQ ID NO 17
<211> LENGTH: 11
<212> TYPE: PRT
<213> ORGANISM: Mus musculus
<220> FEATURE:
```

```
<221> NAME/KEY: SOURCE
<222> LOCATION: 1..11
<223> OTHER INFORMATION: /mol_type="protein"
      /organism="Mus musculus"

<400> SEQUENCE: 17

Arg Gly Gln Leu Arg Leu Arg Leu Phe Ala Tyr
1               5                   10

<210> SEQ ID NO 18
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 18

Gly Phe Thr Phe Thr Asp Tyr Tyr Met Ser
1               5                   10

<210> SEQ ID NO 19
<211> LENGTH: 19
<212> TYPE: PRT
<213> ORGANISM: Mus musculus
<220> FEATURE:
<221> NAME/KEY: SOURCE
<222> LOCATION: 1..19
<223> OTHER INFORMATION: /mol_type="protein"
      /organism="Mus musculus"

<400> SEQUENCE: 19

Leu Ile Arg Asn Lys Ala Asn Gly Tyr Thr Thr Glu Tyr Thr Ala Ser
1               5                   10                  15

Val Lys Gly

<210> SEQ ID NO 20
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 20

Ala Leu Gly Arg Tyr Phe Asp Val
1               5

<210> SEQ ID NO 21
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 21

Lys Ser Ser Gln Ser Val Phe Asn Ser Gly Asn Gln Lys Asn Ser Leu
1               5                   10                  15

Ala
```

```
<210> SEQ ID NO 22
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 22

Phe Ala Ser Thr Arg Glu Ser
1               5

<210> SEQ ID NO 23
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 23

Gln Glu His Tyr Thr Thr Pro Pro Thr
1               5

<210> SEQ ID NO 24
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 24

Arg Ser Ser Gln Arg Leu Val His Ser His Gly Lys Thr Tyr Leu His
1               5                   10                  15

<210> SEQ ID NO 25
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 25

Lys Val Ser Asn Arg Phe Ser
1               5

<210> SEQ ID NO 26
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 26

Ser Gln Thr Ala His Phe Pro Tyr Thr
1               5
```

```
<210> SEQ ID NO 27
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 27

Arg Ser Ser Gln Ser Leu Val His Ser His Gly Lys Thr Tyr Leu His
1               5                   10                  15

<210> SEQ ID NO 28
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 28

Arg Ser Ser Gln Ser Leu Leu His Ser His Gly Asn Thr Tyr Leu His
1               5                   10                  15

<210> SEQ ID NO 29
<211> LENGTH: 11
<212> TYPE: PRT
<213> ORGANISM: Mus musculus
<220> FEATURE:
<221> NAME/KEY: SOURCE
<222> LOCATION: 1..11
<223> OTHER INFORMATION: /mol_type="protein"
      /organism="Mus musculus"

<400> SEQUENCE: 29

Lys Ala Ser Gln Asp Val Ser Thr Ala Val Ala
1               5                   10

<210> SEQ ID NO 30
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 30

Ser Ala Ser Tyr Arg Tyr Thr
1               5

<210> SEQ ID NO 31
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 31

Gln Gln His Tyr Thr Thr Pro Leu Thr
1               5
```

<210> SEQ ID NO 32
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 32

Lys Ser Ser Gln Ser Leu Leu Tyr Ser Ser Asn Gln Lys Asn Tyr Leu
1               5                   10                  15

Ala

<210> SEQ ID NO 33
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 33

Trp Ala Ser Thr Arg Glu Ser
1               5

<210> SEQ ID NO 34
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 34

Gln Gln Tyr Tyr Ser Tyr Pro Phe Thr
1               5

<210> SEQ ID NO 35
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 35
gaggtccagc tgcaacaatc tggacctgaa ctggtgaagc ctggggcttc agtgaagata      60
tcctgtaagg cttctggata tacgttcact gactactaca tgaactgggt gaagcagagc    120
catggaaaga gccttgagtg gattggagat attaatccta accgtggtgg aactacttac    180
aaccagaagt tcaagggcaa ggccacgttg actgtagaca gtcctccag cacagcctac     240 atggaactcc gcagcctgac atctgaggac tctgcagtct attactgtgc aagttactac    300
gccgtgggct actggggcca aggcaccact ctcacagtct cctca                    345

<210> SEQ ID NO 36
<211> LENGTH: 345

```
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 36
gaggtccagc tgcaacaatc tggacctgaa ctggtgaagc ctgggacttc agtgaagata    60
tcctgtaagg cttctggata tacgttcact gactactaca tgaactgggt gaagcagagc   120
catggaaaga gccttgagtg gattggagat attaatccta accgtggtgg aactacttac   180
aaccagaagt ttaagggcaa ggccacgttg actgtagaca agtcctccag cacagcctac   240 atgaactcc gcagcctgac atctgaggac tctgcagtct attactgtgc aagttactac    300
gccgtgggct actggggcca aggcaccact ctcacagtct cctca                   345

<210> SEQ ID NO 37
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 37
gaggtccagc tgcaacaatc tggacctgaa ctggtgaagc ctggggcttc agtgaagata    60
tcctgtaagg cttctggata cacgttcact gactactaca tgaactgggt gaagcagagc   120
catggaaaga gccttgagtg gattggagat attaatccta accgtggtgg aactacttac   180
aaccagaagt tcaagggcaa ggccacgttg actgtagaca cgtcctccag cacagcctac   240
atggagctcc gcagcctgac atctgaggac tctgcagtct attactgtgc aagttactac    300
gccgtgggct actggggcca aggcaccact ctcacagtct cctca                   345

<210> SEQ ID NO 38
<211> LENGTH: 360
<212> TYPE: DNA
<213> ORGANISM: Mus musculus
<220> FEATURE:
<221> NAME/KEY: source
<222> LOCATION: 1..360
<223> OTHER INFORMATION: /mol_type="DNA"
      /organism="Mus musculus"

<400> SEQUENCE: 38
gaggtgcagc tggtggagtc tgggggaggc ttagtgaagc ctggagggtc cctgaaactc    60
tcctgtgcac cctctggatt cactttcagt gactatggaa tgcactgggt tcgtcaggct   120
ccagagaagg gactggagtg ggttgcatac attagtagtg gcagtagtac catctactat   180
ggagacacag tgaagggccg attcaccatc tccagagaca atgccaagaa cacctgttc    240 ctgcaaatga ccagtctgag gtctgaggac acggccatgt attactgtgc aagaagggga   300
cagctcaggc tacgcctgtt tgcttactgg ggccaaggga ctctggtcac tgtctctgca   360

<210> SEQ ID NO 39
<211> LENGTH: 357
<212> TYPE: DNA
<213> ORGANISM: Mus musculus
<220> FEATURE:
<221> NAME/KEY: source
```

```
<222> LOCATION: 1..357
<223> OTHER INFORMATION: /mol_type="DNA"
      /organism="Mus musculus"

<400> SEQUENCE: 39
gaggtgaagc tgatggaatc tggaggaggc ttggtacacc ctggggcttc tctgagactc      60
tactgtgcag cttctggatt cacctttact gattactaca tgagctgggt ccgccagcct     120
ccagggaagg cacctgagtg gttggctttg attagaaaca aagctaatgg ttacacaaca     180
gagtatactg catctgttaa gggtcggttc accatctcca gagataattc ccaaaacatc     240
ctctatcttc aaatgaacac cctgagggct gaggacagtg ccacttatta ctgtgtaaaa     300
gctctgggac gttacttcga tgtctggggc acagggacca cggtcaccgt ctcctca        357

<210> SEQ ID NO 40
<211> LENGTH: 339
<212> TYPE: DNA
<213> ORGANISM: Mus musculus
<220> FEATURE:
<221> NAME/KEY: source
<222> LOCATION: 1..339
<223> OTHER INFORMATION: /mol_type="DNA"
      /organism="Mus musculus"

<400> SEQUENCE: 40
gacattgtga tgacacagtc tccatcctcc ctggctatgt cagtaggaca gaaggtcact      60
atgagctgca agtccagtca gagtgttttt aatagtggca atcaaaagaa ctctttggcc     120
tggtaccagc agaaaccagg acagtctcct aaacttctgg tatactttgc atccactagg     180
gaatctgggg tccctgatcg cttcataggc agtggatctg ggacagattt cagtcttacc     240
atcagcagtg tgcaggctga ggacctggca gattacttct gtcaggaaca ttataccact     300
cctcccacgt tcggtactgg gaccaagctg gagctgaaa                           339

<210> SEQ ID NO 41
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 41
gatgttgtga tgacccaaac tccactctcc ctgcctgtca gtcttggaga tcaagcctcc      60
atctcttgca gatctagtca gaggcttgta cacagtcatg gaaaaaccta tttacattgg     120
tacctgcaga agccaggcca gtctccaaag ctcctgatct acaaagtttc caaccggttt     180
tctggggtcc cagacaggtt cagtggcagt ggatcaggga cagatttcac actcaagatc     240
agcagagtgg aggctgagga tctgggagtt tatttctgtt ctcaaactgc acattttccg     300
tacacgttcg gagggggga caagctggaa ataaaa                               336

<210> SEQ ID NO 42
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"
```

-continued

<400> SEQUENCE: 42

| gatgttgtga tgacccaaac tccactctcc ctgcctgtca gtcttggaga tcaagcctcc | 60 |
| atctcttgca gatctagtca gagccttgta cacagtcatg gaaaaaccta tttacattgg | 120 |
| tacctgcaga agccaggcca gtctccaaag ctcctgatct acaaagtttc caaccggttt | 180 |
| tctggggtcc cagacaggtt cagtggcagt ggatcaggga cagatttcac actcaagatc | 240 |
| agcagagtgg aggctgagga tctgggagtt tatttctgtt ctcaaactgc acattttccg | 300 |
| tacacgttcg gaggggggac caagctggaa ataaaa | 336 |

<210> SEQ ID NO 43
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 43

| gatgttgtga tgacccaaac tccactctcc ctgcctgtca gtcttggaga tcaagcctcc | 60 |
| atctcttgca gatctagtca gagccttcta cacagtcatg gaaacaccta tttacattgg | 120 |
| tacctgcaga agccaggcca gtctccaaag ctcctgatct acaaagtttc caaccggttt | 180 |
| tctggggtcc cagacaggtt cagtggcagt ggatcaggga cagatttcac actcaagatc | 240 |
| agcagagtgg aggctgagga tctgggagtt tatttctgct ctcaaactgc acattttccg | 300 |
| tacacgttcg gaggggggac caagctggaa ataaaa | 336 |

<210> SEQ ID NO 44
<211> LENGTH: 321
<212> TYPE: DNA
<213> ORGANISM: Mus musculus
<220> FEATURE:
<221> NAME/KEY: source
<222> LOCATION: 1..321
<223> OTHER INFORMATION: /mol_type="DNA"
      /organism="Mus musculus"

<400> SEQUENCE: 44

| gacattgtga tgacccagtc tcacaaattc atgtccacat cagtaggaga cagggtcagc | 60 |
| atcacctgca aggccagtca ggatgtgagt actgctgtag cctggtatca acagaaacca | 120 |
| ggacaatctc ctaaactact gatttactcg gcatcctacc ggtacactgg agtccctgat | 180 |
| cgcttcactg gcagtggatc tgggacggat ttcactttca ccatcagcag tgtgcaggct | 240 |
| gaagacctgg cagtttatta ctgtcagcaa cattatacta ctccgctcac gttcggtgct | 300 |
| gggaccaagc tggagctgaa a | 321 |

<210> SEQ ID NO 45
<211> LENGTH: 339
<212> TYPE: DNA
<213> ORGANISM: Mus musculus
<220> FEATURE:
<221> NAME/KEY: source
<222> LOCATION: 1..339
<223> OTHER INFORMATION: /mol_type="DNA"
      /organism="Mus musculus"

<400> SEQUENCE: 45

| gacattgtga tgtcacagtc tccatcctcc ctagctgtgt cagttggaga aaggttact | 60 |

```
atgagctgca agtccagtca gagccttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatagctat    300
ccattcacgt tcggctcggg gacaaagttg gaaataaaa                           339
```

<210> SEQ ID NO 46
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 46

```
gggaattcat graatgsasc tgggtywtyc tctt                                34
```

<210> SEQ ID NO 47
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 30..30
<223> OTHER INFORMATION: /replace="n=i"

<400> SEQUENCE: 47

```
cccaagcttc cagggrccar kggataracn grtgg                               35
```

<210> SEQ ID NO 48
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 48

```
gggaattcat gragwcacak wcycaggtct tt                                  32
```

<210> SEQ ID NO 49
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 49

```
actagtcgac atgggcwtca agatgragtc acakwyycwg g                        41
```

```
<210> SEQ ID NO 50
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 50
actagtcgac atgaagttgc ctgttaggct gttggtgct                              39

<210> SEQ ID NO 51
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="DNA"
      /note="Description of artificial sequence: primer"
      /organism="Artificial Sequence"

<400> SEQUENCE: 51
cccaagctta ctggatggtg ggaagatgga                                       30

<210> SEQ ID NO 52
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 52
actagtcgac atgggatgga gctrtatcat sytctt                                36

<210> SEQ ID NO 53
<211> LENGTH: 33
<212> TYPE: DNA
<213> ORGANISM: artificial seuqence
<220> FEATURE:
<221> NAME/KEY: source
<222> LOCATION: 1..33
<223> OTHER INFORMATION: /mol_type="DNA"
      /note="Description of artificial sequence: primer"
      /organism="artificial seuqence"

<400> SEQUENCE: 53
gggaattcat grasttskgg ytmarctkgr ttt                                   33

<210> SEQ ID NO 54
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 54
actagtcgac atggactcca ggctcaattt agttttcct                             39
```

```
<210> SEQ ID NO 55
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 55
actagtcgac atgaagwtgt ggbtraactg grt                              33

<210> SEQ ID NO 56
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"
<220> FEATURE:
<221> NAME/KEY: misc_feature
<222> LOCATION: 27..27
<223> OTHER INFORMATION: /note="n=i"

<400> SEQUENCE: 56
actagtcgac atggagwcag acacacnsct gytatgggt                        39

<210> SEQ ID NO 57
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="DNA"
      /note="Description of artificial sequence: primer"
      /organism="Artificial Sequence"

<400> SEQUENCE: 57
actagtcgac atggtyctya tvttrctgct gctatgg                          37

<210> SEQ ID NO 58
<211> LENGTH: 30
<212> TYPE: PRT
<213> ORGANISM: artificial sequences
<220> FEATURE:
<221> NAME/KEY: SOURCE
<222> LOCATION: 1..30
<223> OTHER INFORMATION: /mol_type="protein"
      /note="Description of artifiial sequence: ACI-37"
      /organism="artificial sequences"
<220> FEATURE:
<221> NAME/KEY: VARIANT
<222> LOCATION: 18..18
<223> OTHER INFORMATION: phosphorylated serine
<220> FEATURE:
<221> NAME/KEY: VARIANT
<222> LOCATION: 26..26
<223> OTHER INFORMATION: phosphorylated serine

<400> SEQUENCE: 58

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30
```

```
<210> SEQ ID NO 59
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Description of artificial sequence: ACI-33"
      /organism="artificial sequences"
<220> FEATURE:
<221> NAME/KEY: VARIANT
<222> LOCATION: 14..14
<223> OTHER INFORMATION: phosphorylated serine

<400> SEQUENCE: 59

Arg Gln Glu Phe Glu Val Met Glu Asp His Ala Gly Thr Tyr Gly Leu
1               5                   10                  15

<210> SEQ ID NO 60
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Description of artificial sequence: ACI-39"
      /organism="artificial sequences"
<220> FEATURE:
<221> NAME/KEY: VARIANT
<222> LOCATION: 7..7
<223> OTHER INFORMATION: phosphorylated threonine
<220> FEATURE:
<221> NAME/KEY: VARIANT
<222> LOCATION: 9..9
<223> OTHER INFORMATION: phosphorylated serine

<400> SEQUENCE: 60

Pro Gly Ser Arg Ser Arg Thr Pro Ser Leu Pro Thr Pro Pro Thr Arg
1               5                   10                  15

<210> SEQ ID NO 61
<211> LENGTH: 16
<212> TYPE: PRT
<213> ORGANISM: artificial sequences
<220> FEATURE:
<221> NAME/KEY: SOURCE
<222> LOCATION: 1..16
<223> OTHER INFORMATION: /mol_type="protein"
      /note="Description of artificial sequence: ACI-39"
      /organism="Artificial Sequence"
<220> FEATURE:
<221> NAME/KEY: VARIANT
<222> LOCATION: 7..7
<223> OTHER INFORMATION: phosphorylated serine
<220> FEATURE:
<221> NAME/KEY: VARIANT
<222> LOCATION: 10..10
<223> OTHER INFORMATION: phosphorylated threonine

<400> SEQUENCE: 61

Gly Tyr Ser Ser Pro Gly Ser Pro Gly Thr Pro Gly Ser Arg Ser Arg
1               5                   10                  15

<210> SEQ ID NO 62
<211> LENGTH: 16
<212> TYPE: PRT
<213> ORGANISM: artificial sequences
<220> FEATURE:
<221> NAME/KEY: SOURCE
```

```
<222> LOCATION: 1..16
<223> OTHER INFORMATION: /mol_type="protein"
      /note="Description of artificial sequence: ACI-35"
      /organism="artificial sequences"
<220> FEATURE:
<221> NAME/KEY: VARIANT
<222> LOCATION: 4..4
<223> OTHER INFORMATION: phosphorylated serine
<220> FEATURE:
<221> NAME/KEY: VARIANT
<222> LOCATION: 12..12
<223> OTHER INFORMATION: phosphorylated serine

<400> SEQUENCE: 62

Val Tyr Lys Ser Pro Val Val Ser Gly Asp Thr Ser Pro Arg His Leu
1               5                   10                  15

<210> SEQ ID NO 63
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="Description of artificial sequence: ACI-36"
      /organism="artificial sequences"
<220> FEATURE:
<221> NAME/KEY: VARIANT
<222> LOCATION: 4..4
<223> OTHER INFORMATION: phosphorylated serine
<220> FEATURE:
<221> NAME/KEY: VARIANT
<222> LOCATION: 9..9
<223> OTHER INFORMATION: phosphorylated serine

<400> SEQUENCE: 63

Gly Asp Thr Ser Pro Arg His Leu Ser Asn Val Ser Ser Thr Gly Ser
1               5                   10                  15

Ile Asp

<210> SEQ ID NO 64
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
      /note="Description of artificial sequence: ACI-34"
      /organism="artificial sequences"
<220> FEATURE:
<221> NAME/KEY: VARIANT
<222> LOCATION: 3..3
<223> OTHER INFORMATION: phosphorylated serine
<220> FEATURE:
<221> NAME/KEY: VARIANT
<222> LOCATION: 6..6
<223> OTHER INFORMATION: phosphorylated threonine
<220> FEATURE:
<221> NAME/KEY: VARIANT
<222> LOCATION: 13..13
<223> OTHER INFORMATION: phosphorylated threonine
<220> FEATURE:
<221> NAME/KEY: VARIANT
<222> LOCATION: 15..15
<223> OTHER INFORMATION: phosphorylated serine

<400> SEQUENCE: 64

Pro Gly Ser Pro Gly Thr Pro Gly Ser Arg Ser Arg Thr Pro Ser Leu
1               5                   10                  15

Pro
```

```
<210> SEQ ID NO 65
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="Description of artificial sequence: ACI-42"
      /organism="artificial sequences"
<220> FEATURE:
<221> NAME/KEY: VARIANT
<222> LOCATION: 3..3
<223> OTHER INFORMATION: phosphorylated serine

<400> SEQUENCE: 65

His Leu Ser Asn Val Ser Ser Thr Gly Ser Ile Asp
1               5                   10

<210> SEQ ID NO 66
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /mol_type="protein"
      /note="Description of artificial sequence: ACI-43"
      /organism="artificial sequences"
<220> FEATURE:
<221> NAME/KEY: VARIANT
<222> LOCATION: 6..6
<223> OTHER INFORMATION: phosphorylated serine

<400> SEQUENCE: 66

Val Ser Gly Asp Thr Ser Pro Arg His Leu
1               5                   10

<210> SEQ ID NO 67
<211> LENGTH: 441
<212> TYPE: PRT
<213> ORGANISM: Homo sapiens
<220> FEATURE:
<221> NAME/KEY: SOURCE
<222> LOCATION: 1..441
<223> OTHER INFORMATION: /mol_type="protein"
      /organism="Homo sapiens"

<400> SEQUENCE: 67

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125
```

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
435                 440

<210> SEQ ID NO 68
<211> LENGTH: 117
<212> TYPE: PRT
<213> ORGANISM: Mus musculus
<220> FEATURE:
<221> NAME/KEY: SOURCE
<222> LOCATION: 1..117
<223> OTHER INFORMATION: /mol_type="protein"
      /organism="Mus musculus"

<400> SEQUENCE: 68

Gln Val Gln Leu Gln Gln Pro Gly Ala Glu Leu Leu Lys Pro Gly Ala
1               5                   10                  15

Ser Val Lys Leu Ser Cys Lys Ala Ser Gly Tyr Thr Phe Thr Ser Tyr
                20                  25                  30

```
Trp Met His Trp Val Lys Gln Arg Pro Gly Arg Gly Leu Glu Trp Ile
        35                  40                  45

Gly Arg Ile Asp Pro Asn Ser Asp Arg Thr Lys Tyr Asn Glu Lys Phe
 50                  55                  60

Lys Arg Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Asp Tyr Ala Trp Phe Ala Tyr Trp Gly Gln Gly Thr Leu
            100                 105                 110

Val Thr Val Ser Ala
            115
```

<210> SEQ ID NO 69
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 69

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Leu Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Lys Leu Glu Ile Lys
            100                 105                 110
```

<210> SEQ ID NO 70
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 70

```
Gly Tyr Thr Phe Thr Ser Tyr Trp Met His
 1               5                  10
```

<210> SEQ ID NO 71
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 71

Arg Ile Asp Pro Asn Ser Asp Arg Thr Lys Tyr Asn Glu Lys Phe Lys
1               5                   10                  15

Arg

<210> SEQ ID NO 72
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 72

Asp Asp Tyr Ala Trp Phe Ala Tyr
1               5

<210> SEQ ID NO 73
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 73

Arg Ser Ser Gln Ser Ile Val His Ser Asn Gly Asn Thr Tyr Leu Glu
1               5                   10                  15

<210> SEQ ID NO 74
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 74

Lys Leu Ser Asn Arg Phe Ser
1               5

<210> SEQ ID NO 75
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 75

Phe Gln Gly Ser His Val Pro Pro Thr
1               5

<210> SEQ ID NO 76
<211> LENGTH: 119
<212> TYPE: PRT
<213> ORGANISM: Mus musculus
<220> FEATURE:
<221> NAME/KEY: SOURCE

```
<222> LOCATION: 1..119
<223> OTHER INFORMATION: /mol_type="protein"
      /organism="Mus musculus"

<400> SEQUENCE: 76

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Ala Ser
50                  55                  60

Leu Lys Ser Arg Leu Thr Ile Ser Lys Asp Thr Ser Arg Asn Gln Val
65                  70                  75                  80

Phe Leu Lys Ile Thr Cys Val Asp Thr Ala Asp Thr Ala Thr Tyr Tyr
                85                  90                  95

Cys Ala Arg Leu Leu Arg Pro Tyr Ala Leu Asp Tyr Trp Gly Gln Gly
            100                 105                 110

Thr Ser Val Thr Val Ser Ser
        115

<210> SEQ ID NO 77
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 77

Asn Ile Leu Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Leu Gln
                85                  90                  95

Tyr Leu Ser Leu Thr Phe Gly Ala Gly Thr Lys Leu Glu Leu Lys
            100                 105                 110

<210> SEQ ID NO 78
<211> LENGTH: 12
<212> TYPE: PRT
<213> ORGANISM: Mus musculus
<220> FEATURE:
<221> NAME/KEY: SOURCE
<222> LOCATION: 1..12
<223> OTHER INFORMATION: /mol_type="protein"
      /organism="Mus musculus"

<400> SEQUENCE: 78

Gly Phe Ser Leu Ser Thr Ser Gly Met Gly Val Ser
1               5                   10
```

```
<210> SEQ ID NO 79
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 79

His Ile Tyr Trp Asp Asp Asp Lys Arg Tyr Asn Ala Ser Leu Lys Ser
1               5                   10                  15

<210> SEQ ID NO 80
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 80

Leu Leu Arg Pro Tyr Ala Leu Asp Tyr
1               5

<210> SEQ ID NO 81
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 81

Lys Ser Ser Gln Ser Val Leu Tyr Ser Ser Asn Gln Lys Asn Tyr Leu
1               5                   10                  15

Ala

<210> SEQ ID NO 82
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 82

Trp Ala Ser Thr Arg Glu Ser
1               5

<210> SEQ ID NO 83
<211> LENGTH: 8
<212> TYPE: PRT
<213> ORGANISM: Mus musculus
<220> FEATURE:
<221> NAME/KEY: SOURCE
<222> LOCATION: 1..8
<223> OTHER INFORMATION: /mol_type="protein"
      /organism="Mus musculus"

<400> SEQUENCE: 83
```

Leu Gln Tyr Leu Ser Ser Leu Thr
1               5

<210> SEQ ID NO 84
<211> LENGTH: 351
<212> TYPE: DNA
<213> ORGANISM: Mus musculus
<220> FEATURE:
<221> NAME/KEY: source
<222> LOCATION: 1..351
<223> OTHER INFORMATION: /mol_type="DNA"
      /organism="Mus musculus"

<400> SEQUENCE: 84
caggtccaac tgcagcagcc tggggctgag cttctgaagc ctggggcttc agtgaaactg      60
tcctgcaagg cttctggcta caccttcacc agctactgga tgcactgggt gaagcagagg     120
cctggacgag gccttgagtg gattggaagg attgatccta atagtgatcg tactaagtac     180
aatgagaagt tcaagcgcaa ggccacactg actgtagaca atcctccag cacagcctac      240 atgcagctca gcagcctgac atctgaggac tctgcggtct attattgtgc aagggatgat     300
tacgcctggt ttgcttactg gggccaaggg actctggtca ctgtctctgc a             351

<210> SEQ ID NO 85
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 85
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaactttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caagctggaa atcaaa                              336

<210> SEQ ID NO 86
<211> LENGTH: 357
<212> TYPE: DNA
<213> ORGANISM: Mus musculus
<220> FEATURE:
<221> NAME/KEY: source
<222> LOCATION: 1..357
<223> OTHER INFORMATION: /mol_type="DNA"
      /organism="Mus musculus"

<400> SEQUENCE: 86
caggttactc tgaaagagtc tggccctggg atattgcagt cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacgcat ccctgaagag ccggctcaca atctccaagg atacctccag aaaccaggta     240
ttcctcaaga tcacctgtgt ggacactgca gatactgcca catactactg tgctcggtta     300
ctgcgtcctt atgctttgga ctactggggt caaggaacct cagtcaccgt ctcctca       357

<210> SEQ ID NO 87
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 87
aacattttga tgacacagtc gccatcatct ctggctgtgt ctgcaggaga aaaggtcact    60
atgagctgta agtccagtca aagtgtttta tacagttcaa atcagaagaa ctacttggcc   120
tggtaccagc agaaaccagg gcagtctcct aaactgctga tctactgggc atccactagg   180
gaatctggtg tccctgatcg cttcacaggc agtggatctg ggacagattt tactcttacc   240
atcagcagtg tacaagctga agacctggca gtttattact gtcttcaata cctctcctcg   300
ctcacgttcg gtgctgggac caagctggag ctgaaa                              336

<210> SEQ ID NO 88
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 88

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Glu Gly Arg Phe Ala Tyr Trp Gly His Gly Thr Leu Val Thr
            100                 105                 110

Val Ser Ala
        115

<210> SEQ ID NO 89
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 89

Gly Phe Thr Phe Thr Asp Tyr Tyr Met Asn
1               5                   10

-continued

```
<210> SEQ ID NO 90
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 90

Asp Ile Asn Pro Asn Asn Gly Gly Thr Ser Tyr Asn Gln Lys Phe Lys
1               5                   10                  15

Gly

<210> SEQ ID NO 91
<211> LENGTH: 6
<212> TYPE: PRT
<213> ORGANISM: Mus musculus
<220> FEATURE:
<221> NAME/KEY: SOURCE
<222> LOCATION: 1..6
<223> OTHER INFORMATION: /mol_type="protein"
      /organism="Mus musculus"

<400> SEQUENCE: 91

Glu Gly Arg Phe Ala Tyr
1               5

<210> SEQ ID NO 92
<211> LENGTH: 112
<212> TYPE: PRT
<213> ORGANISM: Mus musculus
<220> FEATURE:
<221> NAME/KEY: SITE
<222> LOCATION: 3..3
<223> OTHER INFORMATION: Xaa is Met or Val
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 92

Asp Ile Xaa Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Lys Ser Pro Tyr Thr Phe Gly Gly Gly Thr Lys Leu Glu Ile Lys
            100                 105                 110

<210> SEQ ID NO 93
<211> LENGTH: 16
<212> TYPE: PRT
<213> ORGANISM: Mus musculus
<220> FEATURE:
<221> NAME/KEY: SOURCE
<222> LOCATION: 1..16
```

<223> OTHER INFORMATION: /mol_type="protein"
/organism="Mus musculus"

<400> SEQUENCE: 93

Arg Ser Ser Lys Ser Leu Leu His Ser Asn Gly Asn Thr Tyr Leu Tyr
1               5                   10                  15

<210> SEQ ID NO 94
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
/organism="Mus musculus"

<400> SEQUENCE: 94

Arg Met Ser Asn Leu Ala Ser
1               5

<210> SEQ ID NO 95
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
/organism="Mus musculus"

<400> SEQUENCE: 95

Met Gln His Leu Lys Ser Pro Tyr Thr
1               5

<210> SEQ ID NO 96
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
/organism="Mus musculus"

<400> SEQUENCE: 96

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Arg Gly Asn Ile Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Phe Trp Asp Val Thr Trp Gly Gln Gly Thr Leu Val Thr
            100                 105                 110

Val Ser Ala
        115

<210> SEQ ID NO 97

```
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 97
```

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

```
<210> SEQ ID NO 98
<211> LENGTH: 10
<212> TYPE: PRT
<213> ORGANISM: Mus musculus
<220> FEATURE:
<221> NAME/KEY: SOURCE
<222> LOCATION: 1..10
<223> OTHER INFORMATION: /mol_type="protein"
      /organism="Mus musculus"

<400> SEQUENCE: 98
```

Gly Tyr Thr Phe Thr Asp Tyr Tyr Ile Asn
1               5                   10

```
<210> SEQ ID NO 99
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 99
```

Arg Ile Tyr Pro Gly Arg Gly Asn Ile Tyr Tyr Asn Glu Lys Phe Lys
1               5                   10                  15

Gly

```
<210> SEQ ID NO 100
<211> LENGTH: 6
<212> TYPE: PRT
<213> ORGANISM: Mus musculus
<220> FEATURE:
<221> NAME/KEY: SOURCE
<222> LOCATION: 1..6
<223> OTHER INFORMATION: /mol_type="protein"
      /organism="Mus musculus"

<400> SEQUENCE: 100
```

```
Phe Trp Asp Val Thr Tyr
1               5
```

<210> SEQ ID NO 101
<211> LENGTH: 16
<212> TYPE: PRT
<213> ORGANISM: Mus musculus
<220> FEATURE:
<221> NAME/KEY: SOURCE
<222> LOCATION: 1..16
<223> OTHER INFORMATION: /mol_type="protein"
      /organism="Mus musculus"

<400> SEQUENCE: 101

```
Arg Ser Ser Gln Ser Ile Val His Ser Asn Gly Asn Thr Tyr Leu Glu
1               5                   10                  15
```

<210> SEQ ID NO 102
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 102

```
Lys Val Ser Asn Arg Phe Ser
1               5
```

<210> SEQ ID NO 103
<211> LENGTH: 9
<212> TYPE: PRT
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 103

```
Phe Gln Gly Ser His Val Pro Tyr Thr
1               5
```

<210> SEQ ID NO 104
<211> LENGTH: 115
<212> TYPE: PRT
<213> ORGANISM: Mus musculus
<220> FEATURE:
<221> NAME/KEY: SOURCE
<222> LOCATION: 1..115
<223> OTHER INFORMATION: /mol_type="protein"
      /organism="Mus musculus"

<400> SEQUENCE: 104

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Phe Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Tyr His Gln Lys Phe
        50                  55                  60

Lys Gly Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Val Arg Glu Gly Arg Phe Ala Tyr Trp Gly Gln Gly Thr Leu Val Thr
            100                 105                 110

Val Ser Ala
        115

<210> SEQ ID NO 105
<211> LENGTH: 107
<212> TYPE: PRT
<213> ORGANISM: Mus musculus
<220> FEATURE:
<221> NAME/KEY: SOURCE
<222> LOCATION: 1..107
<223> OTHER INFORMATION: /mol_type="protein"
      /organism="Mus musculus"

<400> SEQUENCE: 105

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 106
<211> LENGTH: 11
<212> TYPE: PRT
<213> ORGANISM: Mus musculus
<220> FEATURE:
<221> NAME/KEY: SOURCE
<222> LOCATION: 1..11
<223> OTHER INFORMATION: /mol_type="protein"
      /organism="Mus musculus"

<400> SEQUENCE: 106

Lys Ala Ser Gln Asn Val Gly Thr Asn Val Ala
1               5                   10

<210> SEQ ID NO 107
<211> LENGTH: 7
<212> TYPE: PRT
<213> ORGANISM: Mus musculus
<220> FEATURE:
<221> NAME/KEY: SOURCE
<222> LOCATION: 1..7
<223> OTHER INFORMATION: /mol_type="protein"
      /organism="Mus musculus"

<400> SEQUENCE: 107

Ser Ala Ser Tyr Arg Tyr Ser
1               5

<210> SEQ ID NO 108
<211> LENGTH: 9
<212> TYPE: PRT
```

```
<213> ORGANISM: Mus musculus
<220> FEATURE:
<221> NAME/KEY: SOURCE
<222> LOCATION: 1..9
<223> OTHER INFORMATION: /mol_type="protein"
      /organism="Mus musculus"

<400> SEQUENCE: 108

Gln Gln Tyr Asn Ser Tyr Pro Tyr Thr
1               5

<210> SEQ ID NO 109
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 109
gaggtccagc tgcaacaatc tggacctgag ctggtgaagc ctggggcttc agtgaagata      60
tcctgtaagg cttctggata cacgttcact gactactaca tgaactgggt gaagcagagc     120
catggaaaga gccttgagtg gattggagat attaatccta acaatggtgg tactagctac     180
aaccagaagt tcaagggcaa ggccacattg actgtagaca gtcctccag cacagcctac      240 atggagctcc gcagtctgac atctgaggac tctgcagtct attattgtgt aagagagggg     300
cggtttgctt actggggtca tgggactctg gtcactgtct ctgca                     345

<210> SEQ ID NO 110
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 110
gatattrtga tgactcaggc tgcaccctct gtacctgtca ctcctggaga gtcagtatcc      60
atctcctgca ggtctagtaa gagtctcctg catagtaatg caacactta cttgtattgg     120 ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct aaaatctccg     300
tacacgttcg gaggggggac caagctggaa ataaaa                              336

<210> SEQ ID NO 111
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 111
caggtccagc tgaagcagtc tggggctgag ctggtgaggc ctggggcttc agtgaaactg      60
tcctgcaagg cttctggcta cactttcact gactactata taaactgggt gaagcagagg     120
```

```
cctggacagg gacttgagtg gattgcaagg atttatcctg gaagaggtaa tatttactac      180
aatgagaagt tcaagggcaa ggccacactg actgcagaaa aatcctccag cactgcctac      240
atgcagctca gcagcctgac atctgaggac tctgctgtct atttctgtgc aagattctgg      300
gacgtgactt actggggcca agggactctg gtcactgtct ctgca                     345
```

<210> SEQ ID NO 112
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 112

```
gatgttttga tgacccaaac tccactctcc ctgcctgtca gtcttggaga tcaagcctcc      60
atctcttgca gatctagtca gagcattgta catagtaatg gaaacaccta tttagaatgg     120
ttcctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gaggggggac caagctggaa ataaaa                               336
```

<210> SEQ ID NO 113
<211> LENGTH: 345
<212> TYPE: DNA
<213> ORGANISM: Mus musculus
<220> FEATURE:
<221> NAME/KEY: source
<222> LOCATION: 1..345
<223> OTHER INFORMATION: /mol_type="DNA"
      /organism="Mus musculus"

<400> SEQUENCE: 113

```
gaggtccagc tgcaacaatc tggacctgag ctggtgaagc ctggggcttc agtgaagata      60
tcctgtaagg cttctggatt cacgttcact gactactaca tgaactgggt gaagcagagc     120
catggaaaga gccttgagtg gattggagat attaatccta caatggtgg tactagctac      180 caccagaagt tcaagggcaa ggccacattg actgtagaca gtcctccag cacagcctac     240 atggagctcc gcagcctgac atctgaggac tctgcagtct attactgtgt aagagaggga     300
agatttgctt actggggcca agggactctg gtcactgtct ctgca                    345
```

<210> SEQ ID NO 114
<211> LENGTH: 321
<212> TYPE: DNA
<213> ORGANISM: Mus musculus
<220> FEATURE:
<221> NAME/KEY: source
<222> LOCATION: 1..321
<223> OTHER INFORMATION: /mol_type="DNA"
      /organism="Mus musculus"

<400> SEQUENCE: 114

```
gacattgtga tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
```

```
gaagacttgg cagagtattt ctgtcagcaa tataacagct atccgtacac gttcggaggg    300
gggaccaagc tggaaataaa a                                              321
```

<210> SEQ ID NO 115
<211> LENGTH: 17
<212> TYPE: PRT
<213> ORGANISM: Mus musculus
<220> FEATURE:
<221> NAME/KEY: SOURCE
<222> LOCATION: 1..17
<223> OTHER INFORMATION: /mol_type="protein"
      /organism="Mus musculus"

<400> SEQUENCE: 115

Asp Ile Asn Pro Asn Asn Gly Gly Thr Ser Tyr His Gln Lys Phe Lys
1               5                   10                  15

Gly

<210> SEQ ID NO 116
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 116

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile His Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Lys Ser Pro Tyr Thr Phe Gly Gly Gly Thr Lys Leu Glu Ile Lys
            100                 105                 110

<210> SEQ ID NO 117
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 117

```
gatattgtga tgactcaggc tgcaccctct gtacctgtca ctcctggaga gtcagtatcc    60
atctcctgca ggtctagtaa gagtctcctg catagtaatg gcaacactta cttgtattgg   120
ttcctgcaga ggccaggcca gtctcctcag ctcctgatac atcggatgtc caaccttgcc   180
tcaggagtcc cagacaggtt cagtggcagt gggtcaggaa ctgctttcac actgagaatc   240
agtagagtgg aggctgagga tgtgggtgtt tattactgta tgcaacatct aaaatctccg   300
```

```
tacacgttcg agggggggac caagctggaa ataaaa                               336
```

<210> SEQ ID NO 118
<211> LENGTH: 112
<212> TYPE: PRT
<213> ORGANISM: Mus musculus
<220> FEATURE:
<221> NAME/KEY: SOURCE
<222> LOCATION: 1..112
<223> OTHER INFORMATION: /mol_type="protein"
      /organism="Mus musculus"

<400> SEQUENCE: 118

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Lys Ser Pro Tyr Thr Phe Gly Gly Gly Thr Lys Leu Glu Ile Lys
            100                 105                 110
```

<210> SEQ ID NO 119
<211> LENGTH: 336
<212> TYPE: DNA
<213> ORGANISM: Mus musculus
<220> FEATURE:
<221> NAME/KEY: source
<222> LOCATION: 1..336
<223> OTHER INFORMATION: /mol_type="DNA"
      /organism="Mus musculus"

<400> SEQUENCE: 119

```
gatattgtga tgactcaggc tgcaccctct gtacctgtca ctcctggaga gtcagtatcc    60
atctcctgca ggtctagtaa gagtctcctg catagtaatg gcaacactta cttgtattgg   120
ttcctgcaga ggccaggcca gtctcctcag ctcctgtatat atcggatgtc caaccttgcc  180
tcaggagtcc cagacaggtt cagtggcagt gggtcaggaa ctgctttcac actgagaatc   240
agtagagtgg aggctgagga tgtgggtgtt tattactgta tgcaacatct aaaatctccg   300
tacacgttcg agggggggac caagctggaa ataaaa                             336
```

<210> SEQ ID NO 120
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 120

```
gggaattcat ggaatgcagc tgggtttttc tctt                                34
```

<210> SEQ ID NO 121

```
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 121
gggaattcat ggaatggagc tgggtctttc tctt                                      34

<210> SEQ ID NO 122
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="Description of artificial sequence: primer"
      /organism="artificial sequences"

<400> SEQUENCE: 122
gggaattcat ggaatgcagc tgggtcattc tctt                                      34

<210> SEQ ID NO 123
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 123
gggaattcat ggaatggagc tgggttttc tctt                                       34

<210> SEQ ID NO 124
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 124
gggaattcat ggaatggagc tgggttattc tctt                                      34

<210> SEQ ID NO 125
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 125
gggaattcat ggaatggagc tgggttattc tctt                                      34
```

```
<210> SEQ ID NO 126
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 126
gggaattcat ggaatgcagc tgggtcttcc tctt                              34

<210> SEQ ID NO 127
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 127
gggaattcat ggaatggagc tgggttttcc tcttc                             35

<210> SEQ ID NO 128
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 128
cccaagcttc cagggaccaa tggataacgg gtgg                              34

<210> SEQ ID NO 129
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 129
cccaagcttc cagggaccaa tggataaacg atgg                              34

<210> SEQ ID NO 130
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 130
cccaagcttc cagggaccaa tggataaacg gtgg                              34
```

```
<210> SEQ ID NO 131
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 131
cccaagcttc cagggaccaa tggataaacg gatgg                              35

<210> SEQ ID NO 132
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 132
cccaagcttc cagggaccag tggatagacg ggtgg                              35

<210> SEQ ID NO 133
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 133
cccaagcttc cagggaccaa gggatagatg atgg                               34

<210> SEQ ID NO 134
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 134
cccaagcttc caggggccaa tggataaacg ggtgg                              35

<210> SEQ ID NO 135
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 135
cccaagcttc caggggccaa tggataaacg atgg                               34
```

<210> SEQ ID NO 136
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 136
gggaattcat ggaatggagc tgggtcattc tctt                               34

<210> SEQ ID NO 137
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 137
gggaattcat ggaatgcacc tgggttttcc tctt                               34

<210> SEQ ID NO 138
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 138
gggaattcat ggaatggagc tgggtcttcc tctt                               34

<210> SEQ ID NO 139
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 139
gggaattcat ggaatggagc tgggtcatcc tctt                               34

<210> SEQ ID NO 140
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 140
actagtcgac atggatgag cttatcatcc tctt                34

<210> SEQ ID NO 141
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 141
cccaagcttc caggggccaa tggataacgg tgg                33

<210> SEQ ID NO 142
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 142
cccaagcttc cagggaccag tgggataaac gggtgg             36

<210> SEQ ID NO 143
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 143
cccaagcttc cagggaccaa gggatagacg ggtgg              35

<210> SEQ ID NO 144
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 144
cccaagcttc cagggaccaa gggataaacg gatgg              35

<210> SEQ ID NO 145
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 145
cccaagcttc cagggaccag gggataaacg gatgg         35

<210> SEQ ID NO 146
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 146
cccaagcttc caggggccag ggataaacgg gtgg          34

<210> SEQ ID NO 147
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 147
cccaagcttc caggggccaa tggataaacc ggtgg         35

<210> SEQ ID NO 148
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 148
cccaagcttc cagggaccag tggataaacg gtgg          34

<210> SEQ ID NO 149
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 149
actagtcgac atggtgtcca cagctcagtt ccttg         35

<210> SEQ ID NO 150
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 150
gggaattcat gaaatggagc tgggtcttcc tctt                                      34

<210> SEQ ID NO 151
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 151
gggaattcat ggaatgcagc tgggttattc tctt                                      34

<210> SEQ ID NO 152
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 152
gggaatttat ggaatggagc tgggtcttcc tctt                                      34

<210> SEQ ID NO 153
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 153
gggaattcat ggaatgcagc tgggtcatcc tctt                                      34

<210> SEQ ID NO 154
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 154
gggaattcat ggaatgcagc tgggttttcc tctt                                      34

<210> SEQ ID NO 155
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 155
gggaattcat ggaatgcagc tgggtctttc tctt                    34

<210> SEQ ID NO 156
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 156
actagtcgac atgggatgga gctatatcat cctctt                  36

<210> SEQ ID NO 157
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 157
actagtcgac atgggatgga gcttatcatc ttctt                   35

<210> SEQ ID NO 158
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 158
actagtcgac atgtagatgt ggttaaactg ggt                     33

<210> SEQ ID NO 159
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 159
cccaagcttc caggggccag gggataaacg gatgg                   35

<210> SEQ ID NO 160
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"

/organism="Artificial Sequence"

<400> SEQUENCE: 160
cccaagcttc caggggccaa gggatagacg gatgg    35

<210> SEQ ID NO 161
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
     /note="Description of artificial sequence: primer"
     /organism="Artificial Sequence"

<400> SEQUENCE: 161
cccaagcttc cagggaccag gggatagacg ggtgg    35

<210> SEQ ID NO 162
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
     /note="Description of artificial sequence: primer"
     /organism="Artificial Sequence"

<400> SEQUENCE: 162
cccaagcttc cagggaccag gggatagacg gatgg    35

<210> SEQ ID NO 163
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
     /note="Description of artificial sequence: primer"
     /organism="Artificial Sequence"

<400> SEQUENCE: 163
cccaagcttc caggggccag tggataaacg gatgg    35

<210> SEQ ID NO 164
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
     /note="Description of artificial sequence: primer"
     /organism="Artificial Sequence"

<400> SEQUENCE: 164
cccaagcttc caggggccaa tggataacga tgg    33

<210> SEQ ID NO 165
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"

/note="Description of artificial sequence: primer"
/organism="Artificial Sequence"

<400> SEQUENCE: 165
cccaagcttc cagggggccag tggataaacg atgg        34

<210> SEQ ID NO 166
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
/note="Description of artificial sequence: primer"
/organism="Artificial Sequence"

<400> SEQUENCE: 166
cccaagcttc cagggaccag tggataaacg atgg        34

<210> SEQ ID NO 167
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
/note="Description of artificial sequence: primer"
/organism="Artificial Sequence"

<400> SEQUENCE: 167
cccaagcttc cagggaccaa tggataacga tgg        33

<210> SEQ ID NO 168
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
/note="Description of artificial sequence: primer"
/organism="Artificial Sequence"

<400> SEQUENCE: 168
cccaagcttc cagggaccat ggataaacgg gtgg        34

<210> SEQ ID NO 169
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
/note="Description of artificial sequence: primer"
/organism="Artificial Sequence"

<400> SEQUENCE: 169
actagtcgac atgggcatca agatgaagtc acatactctg g        41

<210> SEQ ID NO 170
<211> LENGTH: 40
<212> TYPE: DNA
<213> ORGANISM: Artificial Sequence
<220> FEATURE:
<221> NAME/KEY: source
<222> LOCATION: 1..40

```
<223> OTHER INFORMATION: /mol_type="DNA"
        /note="Description of artificial sequence: primer"
        /organism="Artificial Sequence"

<400> SEQUENCE: 170
actagtcgac atgggcatca agatgagtca catactctgg                              40

<210> SEQ ID NO 171
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="DNA"
        /note="Description of artificial sequence: primer"
        /organism="Artificial Sequence"

<400> SEQUENCE: 171
actagtcgac tgggcatcag atgagtcaca tactctgg                                38

<210> SEQ ID NO 172
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
        /note="Description of artificial sequence: primer"
        /organism="Artificial Sequence"

<400> SEQUENCE: 172
actagtcgac atgggcatca agatgaagtc acagacccag g                            41

<210> SEQ ID NO 173
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
        /note="Description of artificial sequence: primer"
        /organism="Artificial Sequence"

<400> SEQUENCE: 173
actagtcgac atgggcttca agatgaagtc acattctctg g                            41

<210> SEQ ID NO 174
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
        /note="Description of artificial sequence: primer"
        /organism="Artificial Sequence"

<400> SEQUENCE: 174
actagtcgac atgggcttca agatgaagtc acatattcag g                            41

<210> SEQ ID NO 175
<211> LENGTH: 34
<212> TYPE: DNA
<213> ORGANISM: Artificial Sequence
<220> FEATURE:
<221> NAME/KEY: source
```

```
<222> LOCATION: 1..34
<223> OTHER INFORMATION: /mol_type="DNA"
      /note="Description of artificial sequence: primer"
      /organism="Artificial Sequence"

<400> SEQUENCE: 175
actagtcgac atggatggag cttatcatcc tctt                              34

<210> SEQ ID NO 176
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 176
cccaagcttc cagggaccaa gggataaacg gtgg                              34

<210> SEQ ID NO 177
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 177
cccaagcttc caggggccag tggataaacg ggtgg                             35

<210> SEQ ID NO 178
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 178
actagtcgac atgaggtact cggctcagtt cctggg                            36

<210> SEQ ID NO 179
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 179
actagtcgac atgaggtccc cggctcagtt cctggg                            36

<210> SEQ ID NO 180
<211> LENGTH: 36
<212> TYPE: DNA
<213> ORGANISM: Artificial Sequence
<220> FEATURE:
```

```
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 180
actagtcgac atgaggacgt cgattcagtt cttggg                               36

<210> SEQ ID NO 181
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 181
gggaattcat ggaatggacc tgggtcatcc tctt                                 34

<210> SEQ ID NO 182
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 182
gggaattcat ggaatgcagc tgggttatcc tctt                                 34

<210> SEQ ID NO 183
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="Description of artificial sequence: primer"
      /organism="Artificial Sequence"

<400> SEQUENCE: 183
gggaattcat gaatggatct gggttattct ctt                                  33

<210> SEQ ID NO 184
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 184
cccaagcttc cagggaccag gggataaacg ggtgg                                35

<210> SEQ ID NO 185
<211> LENGTH: 31
<212> TYPE: DNA
<213> ORGANISM: Artificial Sequence
```

-continued

```
<220> FEATURE:
<221> NAME/KEY: source
<222> LOCATION: 1..31
<223> OTHER INFORMATION: /mol_type="DNA"
      /note="Description of artificial sequence: primer"
      /organism="Artificial Sequence"

<400> SEQUENCE: 185
cccaagcttc cagggaccaa gggacgggtg g                                       31

<210> SEQ ID NO 186
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 186
cccaagcttc cagggaccaa tggataaaca gatgg                                   35

<210> SEQ ID NO 187
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 187
cccaagcttc cagggaccaa gggataaacg ggtgg                                   35

<210> SEQ ID NO 188
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 188
gggaattcat ggagacacat tcccaggtct tt                                      32

<210> SEQ ID NO 189
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"

<400> SEQUENCE: 189
gggaattcat ggagtcacag tctcaggtct tt                                      32

<210> SEQ ID NO 190
<211> LENGTH: 41
<212> TYPE: DNA
```

<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 190
actagtcgac atgggcttca agatggagtc acattttcag g    41

<210> SEQ ID NO 191
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 191
actagtcgac atgggcatca agatgaagtc acatattcag g    41

<210> SEQ ID NO 192
<211> LENGTH: 41
<212> TYPE: DNA
<213> ORGANISM: Artificial Sequence
<220> FEATURE:
<221> NAME/KEY: source
<222> LOCATION: 1..41
<223> OTHER INFORMATION: /mol_type="DNA"
      /note="Description of artificial sequence: primer"
      /organism="Artificial Sequence"

<400> SEQUENCE: 192
actagtcgac atgggcttca agatgaagtc acattctcag g    41

<210> SEQ ID NO 193
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 193
actagtcgac atgggatgga gcttatcatg ttctt    35

<210> SEQ ID NO 194
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 194
actagtcgac atgggatgga gcttatcatg ctctt    35

<210> SEQ ID NO 195
<211> LENGTH: 34

```
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 195
gggaattcat ggaatggacc tgggttttcc tctt                              34

<210> SEQ ID NO 196
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 196
gggaattcat ggaatggacc tgggtctttc tctt                              34

<210> SEQ ID NO 197
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 197
gggaattcat gaaatggagc tgggttattc tctt                              34

<210> SEQ ID NO 198
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 198
cccaagcttc cagggggccaa tggatagacg atgg                             34

<210> SEQ ID NO 199
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="DNA"
      /note="Description of artificial sequence: primer"
      /organism="Artificial Sequence"

<400> SEQUENCE: 199
cccaagcttc cagggaccaa gggatagacg gatgg                             35

<210> SEQ ID NO 200
```

```
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"
      /note="Description of artificial sequence: primer"
      /organism="Artificial Sequence"

<400> SEQUENCE: 200
cccaagcttc cagggaccaa gggatagacg atgg                               34

<210> SEQ ID NO 201
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 201
actagtcgac atgatgtacc cggctcagtt tctggg                             36

<210> SEQ ID NO 202
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="DNA"
      /note="Description of artificial sequence: primer"
      /organism="Artificial Sequence"

<400> SEQUENCE: 202
actagtcgac atgaggactt cgattcagtt cttggg                             36

<210> SEQ ID NO 203
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 203
actagtctac atgaagttgc ctgttaggct gttggtgct                          39

<210> SEQ ID NO 204
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="DNA"
      /note="Description of artificial sequence: primer"
      /organism="Artificial Sequence"

<400> SEQUENCE: 204
actagtcgac atgaagttgt ctgttaggct gttggtgct                          39
```

```
<210> SEQ ID NO 205
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 205
atgggatgga gctrtatcat sytctt                                      26

<210> SEQ ID NO 206
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="DNA"
      /note="Description of artificial sequence: primer"
      /organism="Artificial Sequence"

<400> SEQUENCE: 206
atgaagwtgt ggbtraactg grt                                         23

<210> SEQ ID NO 207
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 15
<223> OTHER INFORMATION: /replace="n=i"

<400> SEQUENCE: 207
atggratgga sckknrtctt tmtct                                       25

<210> SEQ ID NO 208
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 21
<223> OTHER INFORMATION: /replace="n=i"

<400> SEQUENCE: 208
ccagggrcca rkggatarac ngrtgg                                      26

<210> SEQ ID NO 209
<211> LENGTH: 25
<212> TYPE: DNA
<213> ORGANISM: Artificial Sequence
<220> FEATURE:
<221> NAME/KEY: source
<222> LOCATION: 1..25
```

<223> OTHER INFORMATION: /mol_type="DNA"
        /note="Description of artificial sequence: primer"
        /organism="Artificial Sequence"

<400> SEQUENCE: 209
atggagacag acacactcct gctat                                    25

<210> SEQ ID NO 210
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
        /note="Description of artificial sequence: primer"
        /organism="Artificial Sequence"

<400> SEQUENCE: 210
atggagwcag acacactsct gytatgggt                                29

<210> SEQ ID NO 211
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
        /note="Description of artificial sequence: primer"
        /organism="Artificial Sequence"

<400> SEQUENCE: 211
atgaagttgc ctgttaggct gttggtgct                                29

<210> SEQ ID NO 212
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
        /note="Description of artificial sequence: primer"
        /organism="Artificial Sequence"

<400> SEQUENCE: 212
atggatttwc argtgcagat twtcagctt                                29

<210> SEQ ID NO 213
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
        /note="Description of artificial sequence: primer"
        /organism="Artificial Sequence"

<400> SEQUENCE: 213
atggtyctya tvtccttgct gttctgg                                  27

<210> SEQ ID NO 214
<211> LENGTH: 27
<212> TYPE: DNA
<213> ORGANISM: Artificial Sequence
<220> FEATURE:
<221> NAME/KEY: source

```
<222> LOCATION: 1..27
<223> OTHER INFORMATION: /mol_type="DNA"
      /note="Description of artificial sequence: primer"
      /organism="Artificial Sequence"

<400> SEQUENCE: 214
atggtyctya tvttrctgct gctatgg                                            27

<210> SEQ ID NO 215
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="DNA"
      /note="Description of artificial sequence: primer"
      /organism="Artificial Sequence"

<400> SEQUENCE: 215
actggatggt gggaagatgg a                                                  21

<210> SEQ ID NO 216
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 216
atgaaatgca gctggrtyat sttctt                                             26

<210> SEQ ID NO 217
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 217
atggrcagrc ttacwtyytc attcct                                             26

<210> SEQ ID NO 218
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /mol_type="DNA"
      /note="Description of artificial sequence: primer"
      /organism="Artificial Sequence"

<400> SEQUENCE: 218
atgatggtgt taagtcttct gtacct                                             26

<210> SEQ ID NO 219
<211> LENGTH: 24
<212> TYPE: DNA
<213> ORGANISM: Artificial Sequence
<220> FEATURE:
```

-continued

```
<221> NAME/KEY: source
<222> LOCATION: 1..24
<223> OTHER INFORMATION: /mol_type="DNA"
      /note="Description of artificial sequence: primer"
      /organism="Artificial Sequence"

<400> SEQUENCE: 219
atgragwcac akwcycaggt cttt                                              24

<210> SEQ ID NO 220
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="DNA"
      /note="Description of artificial sequence: primer"
      /organism="Artificial Sequence"
<220> FEATURE:
<221> NAME/KEY: variation
<222> LOCATION: 27
<223> OTHER INFORMATION: /replace="n=i"

<400> SEQUENCE: 220
atgaggrccc ctgctcagwt tyttggnwtc tt                                     32

<210> SEQ ID NO 221
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="Description of artificial sequence: primer"
      /organism="Artificial Sequence"

<400> SEQUENCE: 221
atgggcwtca agatgragtc acakwyycwg g                                      31
```

METHODS OF DIAGNOSING TAU-PROTEIN-ASSOCIATED DISEASE

This application is a divisional of U.S. application Ser. No. 13/500,608, which has a 371(c) completion date of Apr. 5, 2012, which is the US national stage of International Application No. PCT/EP2011/067604, filed Oct. 7, 2011, which claims priority to European Application No. 11174248.2, filed Jul. 15, 2011, and European Application No. 10186810.7, filed Oct. 7, 2010, each of which is incorporated herein by reference in its entirety for any purpose.

REFERENCE TO SEQUENCE LISTING

A sequence listing is submitted concurrently with this application as an ASCII formatted text file via EFS-Web, with a file name of "2016-02-17_01147-0001-01US_Seq-Listing.txt", a creation date of Feb. 2, 2016, and a size of 96,356 bytes. The sequence listing filed via EFS-Web is part of the specification and is hereby incorporated by reference in its entirety.

The present invention is related to methods and compositions for the therapeutic and diagnostic use in the treatment of diseases and disorders which are caused by or associated with neurofibrillary tangles. In particular, the invention relates to antibodies, which specifically recognize and bind to phosphorylated pathological protein tau-conformers and to methods and compositions involving said antibodies for the therapeutic and diagnostic use in the treatment of tauopathies including Alzheimer's Disease (AD).

Neurofibrillary tangles and neuropil threads (NTs) are the major neuropathological hallmarks of Alzheimer's Disease (AD). They are composed of the microtubule-associated protein tau that has undergone posttranslational modifications; including phosphorylation, deamidation and isomerization on asparaginyl or aspartyl residues. They originate by the aggregation of hyper-phosphorylated protein tau and its conformers. AD shares this pathology with many neurodegenerative tauopathies, in particularly with specified types of frontotemporal dementia (FTD).

Protein Tau is a freely soluble, "naturally unfolded" protein that binds avidly to microtubuli (MT) to promote their assembly and stability. MTs are of major importance for the cytoskeletal integrity of neurons—and thereby for the proper formation and functioning of neuronal circuits, hence for learning and memory. The binding of tau to MT is controlled by dynamic phosphorylation and de-phosphorylation, as demonstrated mainly in vitro and in non-neuronal cells. Due to the large number of possible phosphorylation sites (>80), the exact contribution of each and the identity of the responsible kinases remain largely undefined in vivo.

In AD brain, tau pathology develops later than, and therefore probably in response to amyloid pathology, which constitutes the essence of the amyloid cascade hypothesis. This is based on and indicated by studies in AD and Down syndrome patients, and is corroborated by studies in transgenic mice with combined amyloid and tau pathology (Lewis et al., 2001; Oddo et al., 2004; Ribe et al., 2005; Muyllaert et al, 2006; 2008; Terwel et al, 2008).

The exact timing of both pathologies in human AD patients as well as mechanisms that link amyloid to tau pathology remain largely unknown, but are proposed to involve activation of neuronal signaling pathways that act on or by GSK3 and cdk5 as the major "tau-kinases" (reviewed by Muyllaert et al, 2006, 2008).

The hypothesis that tauopathy is not an innocent side-effect but a major pathological executor in AD is based on sound genetic, pathological and experimental observations that corroborate each other fully:

in early-onset familial AD cases that are due to mutations in amyloid protein precursor (APP) or presenilin, the obligate pathogenic cause is amyloid accumulation, but invariably the pathology comprises collateral tauopathy, identical to that in the late-onset sporadic AD cases;

severity of cognitive dysfunction and dementia correlates with tauopathy, not with amyloid pathology, exemplified most recently by several clinical phase-1&2 studies that include PIB-PET imaging for amyloid and identify many "false positives": cognitively normal individuals with high brain amyloid load;

in familial FTD, the tauopathy is provoked by mutant tau and causes neurodegeneration directly, without amyloid pathology;

in experimental mouse models the cognitive defects caused by amyloid pathology are nearly completely alleviated by the absence of protein tau (Roberson et al, 2007).

The combined arguments support the hypothesis that protein tau is a major player in the cognitive demise in AD and related neurodegenerative tauopathies.

A prominent emerging treatment of AD is by passive immunotherapy with specific mAbs, to clear amyloid peptides and their aggregates that are presumed to be neurotoxic or synapto-toxic.

Immunotherapy targeting tau pathology, as proposed here, is anticipated to counteract the pathological protein tau-conformers that are known or postulated to cause synaptic dysfunction and neurodegeneration. Amyloid pathology caused and intra-neuronal aggregates of hyper-phosphorylated protein tau are proposed to act synergistically in the cognitive and degenerative cascade of pathological events that lead from mild cognitive impairment (MCI) to the severe dementia of AD. The combination of tau-directed medication with amyloid-directed (or any other) medication will therefore constitute the preferred and, substantially more efficacious treatment of AD, as opposed to current mono-therapy.

Other therapeutic approaches that target protein tau are scarce and comprise mainly:

inhibitors of the kinases that are thought to increase the phosphorylation of tau to pathological levels compounds that block the cytoplasmic aggregation of hyper-phosphorylated protein tau.

These approaches suffer various draw-backs of specificity and efficacy, a problem they share with attempts to modify the metabolism of APP and amyloid, all emphasizing the importance of a continuous search for additional treatment options, including immunotherapy against tau.

Practically no efforts have been devoted to define—let alone target—the pathological tau conformers in vivo. In the Aβ42 phase II clinical trial, the tangle pathology did not appear to be well considered nor analyzed in much depth (Nicoll et al., 2003; Masliah et al., 2005). On the other hand, experimental immunotherapy targeting amyloid in a preclinical mouse model with combined AD-like pathology demonstrated also an effect on tau pathology although tau aggregates persisted (Oddo et al., 2004).

Some doubts have been cast on the feasibility of approaching intra-cellular protein tau by immunotherapy. These have been countered by the most recent experimental study in a tauopathy mouse model (Asuni et al., 2007). They showed reduction in tangle pathology and functional improvements by vaccination with a protein tau derived phospho-peptide. These data corroborate previous reports of immunotherapy targeting α-synuclein in Parkinson's Disease (PD) and Lewy body disease models (Masliah et al., 2005, 2011) and of superoxide dismutase in an amyotrophic lateral sclerosis (ALS) model (Urushitani et al., 2007). These diseases are examples wherein intra-cellular proteins lead to synaptic defects and neurodegeneration by as yet not fully understood mechanisms. On the other hand, full-length recombinant protein tau produced in and isolated from bacteria appears not suitable as vaccine, although the adjuvants used, i.e. complete Freunds and pertussis toxin, could have contributed to the negative outcome of that study (Rosenmann et al., 2006).

There is an unmet need for passive and/or active immunotherapies that work to counteract the pathological protein conformers that are known—or presumed—to cause neurodegenerative disorders, such as amyloid pathology in AD caused, for example, by intra-neuronal aggregates of hyperphosphorylated protein tau that are as typical for AD as amyloid.

This unmet need could be met within the scope of the present invention by providing binding proteins recognizing and binding to major pathological phospho-epitopes of the tau protein. In particular, the present invention provides specific antibodies against linear and conformational, simple and complex phospho-epitopes on protein tau, particularly on aggregated tau protein that are believed to be responsible for synapto- and neuro-toxicity in tauopathies, including AD.

Accordingly, the present invention relates in one embodiment to a binding peptide or protein or a functional part thereof, particularly to an antibody, particularly a monoclonal antibody or a functional part thereof, which binding peptide or protein or antibody recognizes and specifically binds to a phospho-epitope on a mammalian, particularly on the human Tau protein or on a fragment thereof, particularly to a phospho-epitope on aggregated Tau protein, particularly to a pathological protein tau conformer, but, in one embodiment, does not bind to the corresponding unphosphorylated epitope and/or to non-related epitopes, wherein said binding peptide or antibody has a high binding affinity to soluble and insoluble Tau protein, and modulates soluble and insoluble Tau levels, particularly in the brain, particularly with a dissociation constant of at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM.

In a second embodiment, the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has an association rate constant of $10^4$ $M^{-1}s^{-1}$ or greater, particularly of between $3-5\times10^4$ $M^{-1}s^{-1}$ or greater, particularly of $10^5$ $M^{-1}s^{-1}$ or greater; particularly of $2-9\times10^5$ $M^{-1}s^{-1}$ or greater; particularly of $10^6$ $M^{-1}s^{-1}$ or greater, particularly of $1-4\times10^6$ $M^{-1}s^{-1}$ or greater, particularly of $10^7$ $M^{-1}s^{-1}$ or greater.

In a third embodiment, the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity with a dissociation constant of at least 4 nM and an association rate constant of $10^5$ $M^{-1}s^{-1}$ or greater, particularly a dissociation constant of at least 3 nM and an association rate constant of $10^6$ $M^{-1}s^{-1}$ or greater, particularly a dissociation constant of at least 2 nM and an association rate constant of $10^4$ $M^{-1}s^{-1}$ or greater, particularly a dissociation constant of at least 1 nM and an association rate constant of $10^5$ $M^{-1}s^{-1}$ or greater, particularly a dissociation constant of at least 200 pM and an association rate constant of $10^5$ $M^{-1}s^{-1}$ or greater, particularly a dissociation constant of at least 100 pM and an association rate constant of $10^6$ $M^{-1}s^{-1}$ or greater.

One embodiment (4) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody binds to an epitope on a mammalian, particularly on the human Tau protein as shown in SEQ ID NO: 67, selected from the group consisting of Tau aa 15-20 comprising a phosphorylated Tyr at position 18 (Y18), Tau aa 405-412 comprising a phosphorylated Ser at position 409 (pS409), Tau aa 405-411 comprising a phosphorylated Ser at position 409 (pS409); and Tau aa 208-218 comprising a phosphorylated Thr at position 212 (pT212) and a phosphorylated Ser at position 214 (pS214).

One embodiment (5) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 15-20 with a phosphorylated Tyr at position 18 (Y18).

One embodiment (6) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 405-412 with a phosphorylated Ser at position 409 (pS409).

One embodiment (7) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 405-411 with a phosphorylated Ser at position 409 (pS409).

One embodiment (8) relates to the binding peptide or antibody of any of the preceding embodiments, wherein said peptide binds to an epitope on a mammalian, particularly on the human Tau protein, but especially the human Tau protein as shown in SEQ ID NO: 67, comprising Tau aa 208-218 with a phosphorylated Thr at position 212 (pT212) and a phosphorylated Ser at position 214 (pS214).

In another embodiment (9), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains, particularly in sequence, a CDR1 with the amino acid sequence shown in SEQ ID NO: 21, 24, 27, 28, 29, 32, 73, 81, 93, 101, 106, or an amino acid sequence at least 70%, particularly at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto; a CDR2 with the amino acid sequence shown in SEQ ID NO: 22, 25, 30, 33, 74, 82, 94, 102, 107, or an amino acid sequence at least 90%, at least 91%, at least 92%, at least 93%, at least 94%, particularly at least 95%, particularly at least 96%, particularly at least 97%, particularly at least 98%, particularly at least 99% or 100% identical thereto and a CDR3 with the amino acid sequence shown in SEQ ID NO: 23, 26, 31, 34, 75, 83, 95, 103, 108, or an amino acid sequence at least 60%, particularly at least 70%, particularly at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto; and/or a second binding domain which contains in sequence a CDR1 with the amino acid sequence shown in SEQ ID NO: 12, 15, 18, 70, 78, 89, 98, or an amino acid sequence at least 90%, at least 91%, at least 92%, at least 93%, at least 94%, particularly at least 95%, particularly at least 96%, particularly at least 97%, particularly at least 98%, particularly at least 99% or 100% identical thereto; a CDR2 with the amino acid sequence shown in SEQ ID NO: 13, 16, 19, 71, 79, 90, 99, 115, or an amino acid sequence at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and a CDR3 with the amino acid sequence shown in SEQ ID NO: 14, 17, 20, 72, 80, 91, 100, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment (10) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: SEQ ID NO: 21, 24, 27, 28, 29, 32, 73, 81, or an amino acid sequence at least 85% identical thereto; a CDR2 with the amino acid sequence shown in SEQ ID NO: 22, 25, 30, 33, 74, 82, or an amino acid sequence at least 95% identical thereto and a CDR3 with the amino acid sequence shown in SEQ ID NO: 23, 26, 31, 34, 75, 83, or an amino acid sequence at least 80% identical thereto; and/or an antibody domain which contains a CDR1 with the amino acid sequence shown in SEQ ID NO: 12, 15, 18, 70, 78, or an amino acid sequence at least 95% identical thereto; a CDR2 with the amino acid sequence shown in SEQ ID NO: 13, 16, 19, 71, 79, or an amino acid sequence at least 85% identical thereto and a CDR3 with the amino acid sequence shown in SEQ ID NO: 14, 17, 20, 72, 80, or an amino acid sequence at least 85% identical thereto.

One embodiment (11) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 21, 24, 27, 28, 29, 32, 73, 81, or an amino acid sequence at least 90% identical thereto; a CDR2 with the amino acid sequence shown in SEQ ID NO: 22, 25, 30, 33, 74, 82, or an amino acid sequence at least 95% identical thereto and a CDR3 with the amino acid sequence shown in SEQ ID NO: 23, 26, 31, 34, 75, 83, or an amino acid sequence at least 90% identical thereto; and/or a second binding domain which contains in sequence a CDR1 with the amino acid sequence shown in SEQ ID NO: 12, 15, 18, 70, 78, or an amino acid sequence at least 95% identical thereto; a CDR2 with the amino acid sequence shown in SEQ ID NO: 13, 16, 19, 71, 79, or an amino acid sequence at least 95% identical thereto and a CDR3 with the amino acid sequence shown in SEQ ID NO: 14, 17, 20, 72, 80, or an amino acid sequence at least 90% identical thereto One embodiment (12) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain (antibody domain) which contains in sequence a CDR1 with the amino acid sequence shown in SEQ ID NO: 21, 24, 27, 28, 29, 32, 73, 81, or an amino acid sequence at least 90% identical thereto; a CDR2 with the amino acid sequence shown in SEQ ID NO: 22, 25, 30, 33, 74, 82, and a CDR3 with the amino acid sequence shown in SEQ ID NO: 23, 26, 31, 34, 75, 83, or an amino acid sequence at least 90% identical thereto; and/or a second binding domain which contains in sequence a CDR1 with the amino acid sequence shown in SEQ ID NO: 12, 15, 18, 70, 78, a CDR2 with the amino acid sequence shown in SEQ ID NO: 13, 16, 19, 71, 79, or an amino acid sequence at least 95% identical thereto and a CDR3 with the amino acid sequence shown in SEQ ID NO: 14, 17, 20, 72, 80, or an amino acid sequence at least 90% identical thereto.

One embodiment (13) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 21, 24, 27, 28, 29, 32, or an amino acid sequence at least 98% identical thereto; a CDR2 with the amino acid sequence shown in SEQ ID NO: 22, 25, 30, 33, and a CDR3 with the amino acid sequence shown in SEQ ID NO: 23, 26, 31, 34, or an amino acid sequence at least 95% identical thereto; and/or a second binding domain which contains in sequence a CDR1 with the amino acid sequence shown in SEQ ID NO: 12, 15, 18, a CDR2 with the amino acid sequence shown in SEQ ID NO: 13, 16, 19, or an amino acid sequence at least 95% identical thereto and a CDR3 with the amino acid sequence shown in SEQ ID NO: 14, 17, 20, or an amino acid sequence at least 90% identical thereto.

One embodiment (14) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 21, 24, 27, 28, 29, 32, or an amino acid sequence at least 98% identical thereto; a CDR2 with the amino acid sequence shown in SEQ ID NO: 22, 25, 30, 33, and a CDR3 with the amino acid sequence shown in SEQ ID NO: 23, 26, 31, 34, or an amino acid sequence at least 98% identical thereto; and/or a second binding domain which contains in sequence a CDR1 with the amino acid sequence shown in SEQ ID NO: 12, 15, 18, a CDR2 with the amino acid sequence shown in SEQ ID NO: 13, 16, 19, or an amino acid sequence at least 98% identical thereto, and a CDR3 with the amino acid sequence shown in SEQ ID NO: 14, 17, 20, or an amino acid sequence at least 90% identical thereto.

One embodiment (15) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 21, 24, 27, 28, 29, 32, 73, 81, 93, 101, or 106, a CDR2 with the amino acid sequence shown in SEQ ID NO: 22, 25, 30, 33, 74, 82, 94, 102, or 107, and a CDR3 with the amino acid sequence shown in SEQ ID NO: 23, 26, 31, 34, 75, 83, 95, 103, or 108, and/or a second binding domain which contains in sequence a CDR1 with the amino acid sequence shown in SEQ ID NO: 12, 15, 18, 70, 78, 89, or 98, a CDR2 with the amino acid sequence shown in SEQ ID NO: 13, 16, 19, 71, 79, 90, 99, or 115, and a CDR3 with the amino acid sequence shown in SEQ ID NO: 14, 17, 20, 72, 80, 91, or 100.

One embodiment (16) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 21, or an amino acid sequence at least 76%, particularly at least 80%, particularly at least 85%, particularly at least 90%, particularly at least 95%, particularly at least 98%, particularly at least 99% identical thereto, a CDR2 with the amino acid sequence shown in SEQ ID NO: 22, or an amino acid sequence at least 95%, particularly 98%, particularly 99% identical thereto, and a CDR3 with the amino acid sequence shown in SEQ ID NO: 23, or an amino acid sequence at least 66%, particularly at least 70%, particularly at least 75%, particularly at least 80%, particularly at least 85%, particularly at least 90%, particularly at least 95%, particularly at least 98%, particularly at least 99% identical thereto, and/or a second binding domain which contains in sequence a CDR1 with the amino acid sequence shown in SEQ ID NO: 12, or an amino acid sequence at least 95%, particularly 98%, particularly 99% identical thereto, a CDR2 with the amino acid sequence shown in SEQ ID NO: 13, or an amino acid sequence at least 88%, particularly at least 90%, particularly at least 95%, particularly at least 98%, particularly at least 99% identical thereto, and a CDR3 with the amino acid sequence shown in SEQ ID NO: 14, or an amino acid sequence at least 66%, particularly at least 70%, particularly at least 75%, particularly at least 80%, particularly at least 85%, particularly at least 90%, particularly at least 95%, particularly at least 98%, particularly at least 99% identical thereto.

One embodiment (17) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 24, or SEQ ID NO: 27, or SEQ ID NO: 28, or an amino acid sequence at least 88%, particularly at least 85%, particularly at least 90%, particularly at least 95%, particularly at least 98%, particularly at least 99% identical thereto, a CDR2 with the amino acid sequence shown in SEQ ID NO: 25, or an amino acid sequence at least 95%, particularly 98%, particularly 99% and a CDR3 with the amino acid sequence shown in SEQ ID NO: 26, or an amino acid sequence at least 66%, particularly at least 70%, particularly at least 75%, particularly at least 80%, particularly at least 85%, particularly at least 90%, particularly at least 95%, particularly at least 98%, particularly at least 99% identical thereto and/or a second binding domain which contains in sequence a CDR1 with the amino acid sequence shown in SEQ ID NO: 12, or an amino acid sequence at least 95%, particularly 98%, particularly 99% identical thereto, a CDR2 with the amino acid sequence shown in SEQ ID NO: 13, or an amino acid sequence at least 88%, particularly at least 90%, particularly at least 95%, particularly at least 98%, particularly at least 99% identical thereto, and a CDR3 with the amino acid sequence shown in SEQ ID NO: 14, or an amino acid sequence at least 66%, particularly at least 70%, particularly at least 75%, particularly at least 80%, particularly at least 85%, particularly at least 90%, particularly at least 95%, particularly at least 98%, particularly at least 99% identical thereto.

One embodiment (18) of the present invention relates to a binding peptide or protein or a functional part thereof, particularly to an antibody, particularly a monoclonal antibody or a functional part thereof, according to embodiment (15) comprising a first binding domain, wherein the CDR1 has the amino acid sequence shown in SEQ ID NO: 27, or an amino acid sequence at least 88% identical thereto.

One embodiment (19) of the present invention relates to a binding peptide or protein or a functional part thereof, particularly to an antibody, particularly a monoclonal antibody or a functional part thereof, according to embodiment (15) comprising a first binding domain wherein the CDR1 has the amino acid sequence shown in SEQ ID NO: 28, or an amino acid sequence at least 88% identical thereto.

One embodiment (20) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 29, a CDR2 with the amino acid sequence shown in SEQ ID NO: 30, and a CDR3 with the amino acid sequence shown in SEQ ID NO: 31, or an amino acid sequence at least 95%, particularly 98%, particularly 99% identical thereto and/or a second binding domain which contains in sequence a CDR1 with the amino acid sequence shown in SEQ ID NO: 15, or an amino acid sequence at least 95%, particularly 98%, particularly 99% identical thereto, a CDR2 with the amino acid sequence shown in SEQ ID NO: 16, or an amino acid sequence at least 94%, 95%, 96%, 97%, 98%, or 99% identical thereto, and a CDR3 with the amino acid sequence shown in SEQ ID NO: 17, or an amino acid sequence at least 36%, particularly at least 40%, particularly at least 50%, particularly at least 60%, particularly at least 70%, particularly at least 75%, particularly at least 80%, particularly at least 85%, particularly at least 90%, particularly at least 95%, particularly at least 98%, particularly at least 99% identical thereto.

One embodiment (21) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody comprises a first binding domain which contains in sequence a CDR1 with the amino acid sequence shown in SEQ ID NO: 32, a CDR2 with the amino acid sequence shown in SEQ ID NO: 33, and a CDR3 with the amino acid sequence shown in SEQ ID NO: 34, or an amino acid sequence at least 95%, particularly 98%, particularly 99% identical thereto and/or a second binding domain which contains in sequence a CDR1 with the amino acid sequence shown in SEQ ID NO: 18, or an amino acid sequence at least 95%, particularly 98%, particularly 99% identical thereto, a CDR2 with the amino acid sequence shown in SEQ ID NO: 19, or an amino acid sequence at least 95%, 96%, 97%, 98% or 99% identical thereto, and a CDR3 with the amino acid sequence shown in SEQ ID NO: 20, or an amino acid sequence at least 63%, particularly at least 70%, particularly at least 75%, particularly at least 80%, particularly at least 85%, particularly at least 90%, particularly at least 95%, particularly at least 98%, particularly at least 99% identical thereto.

One embodiment (22) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 73, a CDR2 with the amino acid sequence shown in SEQ ID NO: 74, and a CDR3 with the amino acid sequence shown in SEQ ID NO: 75, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain which contains in sequence a CDR1 with the amino acid sequence shown in SEQ ID NO: 70, or an amino acid sequence at least 95%, particularly 98%, particularly 99% identical thereto, a CDR2 with the amino acid sequence shown in SEQ ID NO: 71, or an amino acid sequence at least 94%, 95%, 96%, 97%, 98%, or 99% identical thereto, and a CDR3 with the amino acid sequence shown in SEQ ID NO: 72, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment (23) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 81, a CDR2 with the amino acid sequence shown in SEQ ID NO: 82, and a CDR3 with the amino acid sequence shown in SEQ ID NO: 83, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain which contains in sequence a CDR1 with the amino acid sequence shown in SEQ ID NO: 78, a CDR2 with the amino acid sequence shown in SEQ ID NO: 79, and a CDR3 with the amino acid sequence shown in SEQ ID NO: 80, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment (24) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 93, a CDR2 with the amino acid sequence shown in SEQ ID NO: 94, and a CDR3 with the amino acid sequence shown in SEQ ID NO: 95, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain which contains in sequence a CDR1 with the amino acid sequence shown in SEQ ID NO: 89, a CDR2 with the amino acid sequence shown in SEQ ID NO: 90, and a CDR3 with the amino acid sequence shown in SEQ ID NO: 91, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

One embodiment (25) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 101, a CDR2 with the amino acid sequence shown in SEQ ID NO: 102, and a CDR3 with the amino acid sequence shown in SEQ ID NO: 103, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain which contains in sequence a CDR1 with the amino acid sequence shown in SEQ ID NO: 98, a CDR2 with the amino acid sequence shown in SEQ ID NO: 99, and a CDR3 with the amino acid sequence shown in SEQ ID NO: 100, or an amino acid sequence at least at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

One embodiment (26) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains in sequence a CDR1 with the amino acid sequence shown in SEQ ID NO: 106, a CDR2 with the amino acid sequence shown in SEQ ID NO: 107, and a CDR3 with the amino acid sequence shown in SEQ ID NO: 108, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs and/or a second binding domain which contains in sequence a CDR1 with the amino acid sequence shown in SEQ ID NO: 89, a CDR2 with the amino acid sequence shown in SEQ ID NO: 115, and a CDR3 with the amino acid sequence shown in SEQ ID NO: 91, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical to any one of the above CDRs.

In another embodiment (27), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody comprises a first binding domain which contains the amino acid sequence shown in SEQ ID NO: 6, 7, 8, 9, 10, 11, or an amino acid sequence at least 90% identical thereto, and/or a second binding domain which contains the amino acid sequence shown in SEQ ID NO: 1, 2, 3, 4, 5, or an amino acid sequence at least 85% identical thereto.

In one embodiment (28), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 6, 7, 8, 9, 10, 11, or an amino acid sequence at least 90% identical thereto, and/or a second binding domain which contains the amino acid sequence shown in SEQ ID NO: 1, 2, 3, 4, 5, or an amino acid sequence at least 91% identical thereto.

One embodiment (29) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain (antibody domain) which contains the amino acid sequence shown in SEQ ID NO: 6, 7, 8, 9, 10, 11, or an amino acid sequence at least 95% identical thereto; and/or a second binding domain which contains the amino acid sequence shown in SEQ ID NO: 1, 2, 3, 4, 5, or an amino acid sequence at least 91% identical thereto.

In another embodiment (30), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody comprises a first binding domain which contains the amino acid sequence shown in SEQ ID NO: 69, 77, 116/92, 97, 105, or an amino acid sequence particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, and/or a second binding domain which contains the amino acid sequence shown in SEQ ID NO: 68, 76, 88, 96, 104, or an amino acid sequence at least 80%, particularly at least 85%, particularly at least 86%, particularly at least 87%, particularly at least 88%, particularly at least 89%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment (31) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 6 or SEQ ID NO: 7, or an amino acid sequence at least 90% and 94%, respectively, identical thereto; and/or a second binding domain which contains the amino acid sequence shown in SEQ ID NO: 1, or an amino acid sequence at least 91% identical thereto.

One embodiment (32) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 8, or an amino acid sequence at least 95% identical thereto; and/or a second binding domain which contains the amino acid sequence shown in SEQ ID NO: 2, or an amino acid sequence at least 90% identical thereto.

One embodiment (33) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 9, or an amino acid sequence at least 95% identical thereto; and/or a second binding domain which contains the amino acid sequence shown in SEQ ID NO: 3, or an amino acid sequence at least 90% identical thereto.

One embodiment (34) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 10, or an amino acid sequence at least 99% identical thereto; and/or a second binding domain which contains the amino acid sequence shown in SEQ ID NO: 4, or an amino acid sequence at least 89% identical thereto.

One embodiment (35) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 11, or an amino acid sequence at least 98% identical thereto; and/or a second binding domain which contains the amino acid sequence shown in SEQ ID NO: 5, or an amino acid sequence at least 87% identical thereto.

One embodiment (36) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 69, or an amino acid sequence at least 98% or 99% identical thereto; and/or a second binding domain which contains the amino acid sequence shown in SEQ ID NO: 68, or an amino acid sequence at least 90%, 91%, 92% or 93% identical thereto.

One embodiment (37) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 77, or an amino acid sequence at least 93%, 94% or 95% identical thereto; and/or a second binding domain which contains the amino acid sequence shown in SEQ ID NO: 76, or an amino acid sequence at least 88%, 89%, or 90% identical thereto.

One embodiment (38) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 116, 92, or 118, or an amino acid sequence at least 93%, 94% or 95% identical thereto; and/or a second binding domain which contains the amino acid sequence shown in SEQ ID NO: 88, or an amino acid sequence at least 90%, 91%, 92% or 93% identical thereto.

One embodiment (39) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 97, or an amino acid sequence at least 99% identical thereto; and/or a second binding domain which contains the amino acid sequence shown in SEQ ID NO: 96, or an amino acid sequence at least 86%, 87%, 88% or 90% identical thereto.

One embodiment (40) of the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a first binding domain which contains the amino acid sequence shown in SEQ ID NO: 105, or an amino acid sequence at least 98%, or 99% identical thereto; and/or a second binding domain which contains the amino acid sequence shown in SEQ ID NO: 104, or an amino acid sequence at least 88%, 89%, or 90% identical thereto.

In another embodiment (41), the present invention relates to a binding peptide or protein or a functional part thereof, particularly to an antibody, particularly a monoclonal antibody or a functional part thereof, according to embodiments (22)-(24), wherein said first binding domain contains the CDRs as shown in SEQ ID NOs: 21-34 and said second binding domain contains the CDRs as shown in SEQ ID NOs: 12-20.

One embodiment (42) of the present invention relates to a binding peptide or protein or a functional part thereof, particularly to an antibody, particularly a monoclonal antibody or a functional part thereof, according to embodiment (31), wherein said first binding domain contains the CDRs as shown in SEQ ID NOs: 21-23 and SEQ ID NOs: 24-26, respectively, and said second binding domain contains the CDRs as shown in SEQ ID NOs: 12-14.

One embodiment (43) of the present invention relates to a binding peptide or protein or a functional part thereof, particularly to an antibody, particularly a monoclonal antibody or a functional part thereof, according to embodiment (32), wherein said first binding domain contains the CDRs as shown in SEQ ID NOs: 27, 25, 26 and said second binding domain contains the CDRs as shown in SEQ ID NOs: 12-14.

One embodiment (44) of the present invention relates to a binding peptide or protein or a functional part thereof, particularly to an antibody, particularly a monoclonal antibody or a functional part thereof, according to embodiment (33), wherein said first binding domain contains the CDRs as shown in SEQ ID NOs: 28, 25 and 26, and said second binding domain contains the CDRs as shown in SEQ ID NOs: 12-14.

One embodiment (45) of the present invention relates to a binding peptide or protein or a functional part thereof, particularly to an antibody, particularly a monoclonal antibody or a functional part thereof, according to embodiment (34), wherein said first binding domain contains the CDRs as shown in SEQ ID NOs: 29-31, and said second binding domain contains the CDRs as shown in SEQ ID NOs: 15-17.

One embodiment (46) of the present invention relates to a binding peptide or protein or a functional part thereof, particularly to an antibody, particularly a monoclonal antibody or a functional part thereof, according to embodiment (35), wherein said first binding domain contains the CDRs as shown in SEQ ID NOs: 32-34, and said second binding domain contains the CDRs as shown in SEQ ID NOs: 18-20.

One embodiment (47) of the present invention relates to a binding peptide or protein or a functional part thereof, particularly to an antibody, particularly a monoclonal antibody or a functional part thereof, according to embodiment (27), wherein said first binding domain contains the CDRs as shown in SEQ ID NOs: 73-75, and said second binding domain contains the CDRs as shown in SEQ ID NOs: 70-72.

One embodiment (48) of the present invention relates to a binding peptide or protein or a functional part thereof, particularly to an antibody, particularly a monoclonal antibody or a functional part thereof, according to embodiment (27), wherein said first binding domain contains the CDRs as shown in SEQ ID NOs: 81-83, and said second binding domain contains the CDRs as shown in SEQ ID NOs: 78-80.

One embodiment (49) of the present invention relates to a binding peptide or protein or a functional part thereof, particularly to an antibody, particularly a monoclonal antibody or a functional part thereof, according to embodiment (27), wherein said first binding domain contains the CDRs as shown in SEQ ID NOs: 101-103, and said second binding domain contains the CDRs as shown in SEQ ID NOs: 98-100.

One embodiment (50) of the present invention relates to a binding peptide or protein or a functional part thereof, particularly to an antibody, particularly a monoclonal antibody or a functional part thereof, according to embodiment (27), wherein said first binding domain contains the CDRs as shown in SEQ ID NOs: 89, 115, and 91, and said second binding domain contains the CDRs as shown in SEQ ID NOs: 106-108.

In still another embodiment (51), the present invention relates to a binding peptide or protein or a functional part thereof, particularly to an antibody, particularly a monoclonal antibody or a functional part thereof, particularly a binding peptide or antibody of any of the preceding embodiments, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding peptide or antibody comprises a a. first binding domain which contains the amino acid sequence shown in SEQ ID NO: 6 and/or a second binding domain which contains the amino acid sequence shown in SEQ ID NO: 1; or a b. first binding domain which contains the amino acid sequence shown in SEQ ID NO: 7 and/or a second binding domain which contains the amino acid sequence shown in SEQ ID NO: 1; or a c. first binding domain which contains the amino acid sequence shown in SEQ ID NO: 8 and/or a second binding domain which contains the amino acid sequence shown in SEQ ID NO: 2; or a d. first binding domain which contains the amino acid sequence shown in SEQ ID NO: 9 and/or a second binding domain which contains the amino acid sequence shown in SEQ ID NO: 3; or a e. first binding domain which contains the amino acid sequence shown in SEQ ID NO: 10 and/or a second binding domain which contains the amino acid sequence shown in SEQ ID NO: 4; or a f. first binding domain which contains the amino acid sequence shown in SEQ ID NO: 11 and/or a second binding domain which contains the amino acid sequence shown in SEQ ID NO: 5; or a g. first binding domain which contains the amino acid sequence shown in SEQ ID NO: 69 and/or a second binding domain which contains the amino acid sequence shown in SEQ ID NO: 68; or a h. first binding domain which contains the amino acid sequence shown in SEQ ID NO: 77 and/or a second binding domain which contains the amino acid sequence shown in SEQ ID NO: 76; or a i. first binding domain which contains the amino acid sequence shown in SEQ ID NO: 116 and/or a second binding domain which contains the amino acid sequence shown in SEQ ID NO: 88; or a;

j. first binding domain which contains the amino acid sequence shown in SEQ ID NO: 92 and/or a second binding domain which contains the amino acid sequence shown in SEQ ID NO: 88; or a k. first binding domain which contains the amino acid sequence shown in SEQ ID NO: 97 and/or a second binding domain which contains the amino acid sequence shown in SEQ ID NO: 6; or a l. first binding domain which contains the amino acid sequence shown in SEQ ID NO: 105 and/or a second binding domain which contains the amino acid sequence shown in SEQ ID NO: 104.

In one embodiment (52) of the invention, the binding peptide of any of the preceding embodiments is an antibody, particularly an antibody of the IgG2a, IgG2b or the IgG3 isotype, particularly a polyclonal antibody, a monoclonal antibody, a chimeric antibody, a humanized antibody or a fully human antibody.

One embodiment (48) of the invention relates to a polynucleotide encoding the binding peptide of any one of the preceding embodiments.

In on embodiment (53), said polynucleotide comprises a nucleic acid molecule selected from the group consisting of
a. a nucleic acid molecule comprising a nucleotide sequence encoding a polypeptide comprising the amino acid sequence as depicted in SEQ ID NOs: 35-45, SEQ ID NOs: 84-87, SEQ ID NO: 109-112 and 117;
b. a nucleic acid molecule comprising a nucleotide sequence that has at least 85% sequence identity to the sequence shown in SEQ ID NOs: 35-45, SEQ ID NOs: 84-87, SEQ ID NO: 109-112 and 117;
c. a nucleic acid molecule comprising a nucleotide sequence that has at least 90% sequence identity to the sequence shown in SEQ ID NOs: 35-45, SEQ ID NOs: 84-87, SEQ ID NO: 109-112 and 117;
d. a nucleic acid molecule comprising a nucleotide sequence that has at least 95% sequence identity to the sequence shown in SEQ ID NOs: 35-45, SEQ ID NOs: 84-87, SEQ ID NO: 109-112 and 117;
e. a nucleic acid molecule comprising a nucleotide sequence that has at least 98% sequence identity to the sequence shown in SEQ ID NOs: 35-45, SEQ ID NOs: 84-87, SEQ ID NO: 109-112 and 117;
f. a nucleic acid molecule comprising a nucleotide sequence that has at least 99% sequence identity to the sequence shown in SEQ ID NOs: 35-45, SEQ ID NOs: 84-87, SEQ ID NO: 109-112 and 117;
g. a nucleic acid molecule comprising a nucleotide sequence the complementary strand of which hybridizes to the nucleic acid molecule of any of a)-f);
h. a nucleic acid molecule comprising a nucleotide sequence that deviates from the nucleotide sequence defined in any of a)-g) by the degeneracy of the genetic code, wherein said nucleic acid molecule as defined in any of a)-h) recognizes and specifically binds to a phospho-epitope on a mammalian, particularly on the human Tau protein or on a fragment thereof, particularly on the human Tau protein as shown in SEQ ID NO: 67, selected from the group consisting of Tau aa 15-20 comprising a phosphorylated Tyr at position 18 (Y18), Tau aa 405-412 comprising a phosphorylated Ser at position 409 (pS409), Tau aa 405-411 comprising a phosphorylated Ser at position 409 (pS409); and Tau aa 208-218 comprising a phosphorylated Thr at position 212 (pT212) and a phosphorylated Ser at position 214 (pS214), Tau aa 393-401, comprising a phosphorylated Ser at position 396 (pS396), Tau aa 396-401 comprising a phosphorylated Ser at position 396 (pS396), Tau aa 394-400 comprising a phosphorylated Ser at position 396 (pS396), Tau aa 402-406 comprising a phosphorylated Ser at position 404 (pS404), and Tau aa 393-400 comprising a phosphorylated Ser at position 396 (pS396), wherein, in one embodiment, said binding peptide has a high binding affinity with a dissociation constant of at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM and/or has an association rate constant of $10^4$ $M^{-1}s^{-1}$ or greater, particularly of between 3-5×$10^4$ 5 or greater, particularly of $10^5$ $M^{-1}s^{-1}$ or greater; particularly of 6-9×$10^5$ $M^{-1}s^{-1}$ or greater; particularly of $10^6$ $M^{-1}s^{-1}$ or greater, particularly of 1-4×$10^6$ $M^{-1}s^{-1}$ or greater, particularly of $10^7$ $M^{-1}s^{-1}$ or greater, but, in one embodiment, does not bind to the corresponding unphosphorylated epitope and/or to non-related epitopes.

In various embodiments (54) of the invention, a binding peptide is provided or a functional part thereof, particularly an antibody, particularly a monoclonal antibody or a functional part thereof, or a polynucleotide, according to any one of the preceding embodiments, or a combination thereof, which is capable of specifically recognizing and binding to a phospho-epitope on a mammalian, particularly on the human Tau protein, particularly a microtubule-associated protein tau, particularly an aggregated microtubule-associated and hyperphosphorylated protein tau such as that present in paired helical filaments (PHF), which are the predominant structures in neurofibrillary tangles, neuropil threads and dystrophic neurites, but, in one embodiment, does not bind to the corresponding unphosphorylated epitope and/or to non-related epitopes.

In a specific embodiment (55) of the invention, the human tau protein is the human Tau protein as shown in SEQ ID NO: 67.

The binding peptides and antibodies according to any one of the preceding embodiments can thus be used (56) for reducing the levels of total soluble tau protein, particularly of soluble phosphorylated tau protein, in the brain, particularly in the brain cortex and/or hippocampus, of a mammal or a human containing increased levels of soluble tau protein and/or soluble phosphorylated tau protein.

The binding peptides and antibodies according to any one of the preceding embodiments can also be used (57) for reducing the levels of paired helical filaments containing hyperphosphorylated tau protein (pTau PHF) in the brain, particularly in the brain cortex and/or hippocampus, of a mammal or a human containing increased levels of said pTau paired helical filaments (pTau PHF).

Reduction of the level of total soluble tau protein and/or soluble phosphorylated tau protein and/or pTau paired helical filaments (pTau PHF) in the brain, particularly in the brain cortex and/or hippocampus, of a mammal or a human containing increased levels of said tau protein variants, which contribute to tau-protein-associated diseases, disorders or conditions in said mammal or human, may lead to an improvement and/or alleviation of the symptoms associated with such tau-protein-associated diseases, disorders or conditions (58).

The binding peptides and antibodies according to any one of the preceding embodiments can therefore be used (59) in therapy, particularly in human therapy, for slowing or halting the progression of a tau-protein-associated disease, disorder or condition.

The binding peptides and antibodies according to any one of the preceding embodiments can further be used (60) in therapy, particularly in human therapy, for improving or alleviating the symptoms associated with tau-protein-associated diseases, disorders or conditions such as, for example, impairment or loss of cognitive functions including reasoning, situational judgement, memory capacity, learning, special navigation, etc.

In one embodiment (61), the invention relates to the binding peptides and antibodies according to any one of the preceding embodiments for use in therapy, particularly for use in the treatment of tauopathies, a group of tau-protein-associated diseases and disorders, or for alleviating the symptoms associated with tauopathies.

In one embodiment (62), the invention relates to the binding peptides and antibodies according to any one of the preceding embodiments for retaining or increasing cognitive memory capacity in a mammal suffering from a tauopathy.

In a specific embodiment (63) of the invention, binding peptides and antibodies comprising at least one or all of the light chain CDRs of antibodies ACI-36-2B6-Ab1, ACI-36-2B6-Ab2, ACI-36-3A8-Ab1, and ACI-36-3A8-Ab2 as given in SEQ ID NOs: 25, 26, 27, and SEQ ID NOs: 21, 22, 23, respectively, and/or at least one or all of the heavy chain CDRs of antibodies ACI-36-2B6-Ab1, ACI-36-2B6-Ab2, ACI-36-3A8-Ab1, and ACI-36-3A8-Ab2 as given in SEQ ID NOs: 12, 13, 14, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (64) of the invention, the antibodies comprising the light chain of antibodies ACI-36-2B6-Ab1, ACI-36-2B6-Ab2, ACI-36-3A8-Ab1, and ACI-36-3A8-Ab2 as given in SEQ ID NO: 8 and SEQ ID NOs: 6, 7, respectively, and/or the heavy chain of antibodies ACI-36-2B6-Ab1, ACI-36-2B6-Ab12, ACI-36-3A8-Ab1, and ACI-36-3A8-Ab2 as given in SEQ ID NO: 1 and SEQ ID NO: 2, respectively, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (65) of the invention, binding peptides and antibodies comprising at least one or all of the light chain CDRs of antibodies ACI-33-6C10-Ab1 and ACI-33-6C10-Ab2 as given in SEQ ID NOs: 29, 30, 31, and/or at least one or all of the heavy chain CDRs of antibodies ACI-33-6C10-Ab1 and ACI-33-6C10-Ab2 as given in SEQ ID NOs: 15, 16, 17, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (66) of the invention, binding peptides and antibodies comprising at least one or all of the light chain CDRs of antibodies ACI-41-7C2-Ab1 and ACI-41-7C2-Ab2 as given in SEQ ID NOs: 32, 33, 34, and/or at least one or all of the heavy chain CDRs of antibodies ACI-41-7C2-Ab1 and ACI-41-7C2-Ab2 as given in SEQ ID NOs: 18, 19, 20, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (67) of the invention, binding peptides and antibodies comprising at least one or all of the light chain CDRs of antibodies ACI-35-2A1-Ab1; ACI-35-2A1-Ab2; ACI-35-4A6-Ab1; ACI-35-4A6-Ab2; ACI-35-1D2-Ab1; ACI-35-2G5-Ab1; as given in SEQ ID NOs: 73-75, 81-83, 93-95, 101-103, 106-108 and/or at least one or all of the heavy chain CDRs of antibodies ACI-35-2A1-Ab1; ACI-35-2A1-Ab2; ACI-35-4A6-Ab1; ACI-35-4A6-Ab2; ACI-35-1D2-Ab1; ACI-35-2G5-Ab1; as given in SEQ ID NOs: 70-72, 78-80, 89-91, 98-100, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

In another specific embodiment (68) of the invention, binding peptides and antibodies comprising at least one or all of the light chain CDRs of antibodies ACI-35-2G5-Ab2; ACI-35-2G5-Ab3 as given in SEQ ID NOs: 106-108 and/or at least one or all of the heavy chain CDRs of antibodies ACI-35-2G5-Ab2; ACI-35-2G5-Ab3; as given in SEQ ID NOs: 89, 115 and 91, are used in therapy, particularly in human therapy, for improving or alleviating the symptoms associated with tau-protein-associated diseases, disorders or conditions such as, for example, impairment or loss of cognitive functions including reasoning, situational judgement, memory, learning, special navigation, etc.

Binding of the peptides or antibodies according to the preceding embodiments to tau tangles and pTau on brains may be determined by applying protein immuno-reactivity testing of selected brain sections and by Western blotting of brain homogenates, respectively, as described in the Examples.

In another embodiment (69), the present invention provides a pharmaceutical composition comprising a binding peptide or a functional part thereof, particularly an antibody, particularly a monoclonal antibody or a functional part thereof, or a polynucleotide, according to any one of the preceding embodiments, or a combination thereof, in a therapeutically effective amount together with a pharmaceutically acceptable carrier.

In one embodiment (70), the binding peptide or a functional part thereof, particularly an antibody, particularly a monoclonal antibody or a functional part thereof, or a polynucleotide, or a pharmaceutical composition, according to any one of the preceding embodiments, or a combination thereof, is used in therapy, particularly in human therapy for the treatment or alleviation of the symptoms of tau-protein-associated diseases or disorders including neurodegenerative disorders such as tauopathies.

The binding peptides, antibodies and/or pharmaceutical compositions according to any one of the preceding embodiments may thus be used (71) for slowing or halting the progression of a tau-protein-associated disease, disorder or condition, upon administration of said binding peptides, antibodies and/or pharmaceutical compositions to an animal, particularly a mammal, particularly a human, suffering from such a disease or condition.

The binding peptides, antibodies and/or pharmaceutical compositions according to any one of the preceding embodiments may further be used (72) for improving or alleviating the symptoms associated with tau-protein-associated diseases, disorders or conditions such as, for example, impairment or loss of cognitive functions including reasoning, situational judgement, memory capacity, learning, special navigation, etc, upon administration of said binding peptides, antibodies and/or pharmaceutical compositions to an animal, particularly a mammal, particularly a human, suffering from such a disease or condition.

In one embodiment (73), the binding peptide or a functional part thereof, particularly an antibody, particularly a monoclonal antibody or a functional part thereof, or a polynucleotide or a pharmaceutical composition, according to any one of the preceding embodiments, or a combination thereof, is used in the treatment of diseases and disorders which are caused by or associated with the formation of neurofibrillary lesions, the predominant brain pathology in tauopathy comprising a heterogenous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis, Tangle only dementia, Postencephalitic Parkinsonism, Myotonic dystrophy.

In one embodiment (74), the binding peptide or a functional part thereof, particularly an antibody, particularly a monoclonal antibody or a functional part thereof, or a polynucleotide or a pharmaceutical composition, according to any one of the preceding embodiments, or a combination thereof, is used in the treatment of Alzheimer's Disease.

In one embodiment (75) of the invention, a method is provided for modulating soluble and/or insoluble Tau levels, particularly in the brain, particularly in the brain cortex and/or hippocampus, of an animal, particularly a mammal or a human, comprising administering to said animal, particularly to said mammal or human, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one aspect, modulation relates to reducing the levels of soluble tau protein, particularly of soluble phosphorylated tau protein, in the brain, particularly in the brain cortex and/or hippocampus, of an animal, particularly a mammal or a human containing increased levels of soluble tau protein and/or soluble phosphorylated tau protein.

In one embodiment (76) of the invention, a method is provided for reducing the levels of insoluble tau protein, particularly of paired helical filaments containing hyperphosphorylated tau protein (pTau PHF) in the brain, particularly in the brain cortex and/or hippocampus, of an animal, particularly a mammal or a human, containing increased levels of insoluble tau protein, particularly of pTau paired helical filaments (pTau PHF) comprising administering to said animal, particularly to said mammal or human, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (77), the present invention relates to a method for slowing or halting the progression of a tau-protein-associated disease, disorder or condition in an animal, particularly a mammal or human comprising administering to said animal, particularly said mammal or human, suffering from such a disease or condition, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (78), the present invention relates to a method for improving or alleviating the symptoms associated with tau-protein-associated diseases, disorders or conditions such as, for example, impairment or loss of cognitive functions including reasoning, situational judgement, memory capacity, learning, special navigation, etc., in an animal, particularly a mammal or a human, comprising administering to said animal, particularly to said mammal or human, suffering from such a disease or condition, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (79), the present invention relates to a method for retaining or increasing cognitive memory capacity in a mammal suffering from a tauopathy.

In still another embodiment (80) of the invention, a method is provided for the treatment of a tau-protein-associated disease or disorder including a neurodegenerative disease or disorder such as a tauopathy comprising administering to an animal, particularly to a mammal, but especially to human, suffering from such a disease or disorder, the binding peptide or a functional part thereof, particularly an antibody, particularly a monoclonal antibody or a functional part thereof, or a polynucleotide or a pharmaceutical composition, according to any one of the preceding embodiments, or a combination thereof.

In one embodiment (81) of the invention, a method is provided for the treatment of diseases and disorders which are caused by or associated with the formation of neurofibrillary lesions, the predominant brain pathology in tauopathy comprising a heterogenous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, Myotonic dystrophy, which method comprises administering to an animal, particularly to a mammal, but especially to human, suffering from such a disease or disorder, the binding peptide or a functional part thereof, particularly an antibody, particularly a monoclonal antibody or a functional part thereof, or a polynucleotide or a pharmaceutical composition according to any one of the preceding embodiments, or a combination thereof.

In another embodiment (82) of the invention, a method is provided for inducing a passive immune response in an animal, particularly a mammal or a human, suffering from a neurodegenerative disorder such as tauopathy by administering to said animal or human the binding peptide or a functional part thereof, particularly an antibody, particularly a monoclonal antibody or a functional part thereof, or a polynucleotide, or a pharmaceutical composition, according to any one of the preceding embodiments, or a combination thereof.

In still another embodiment (83) of the invention, a method of diagnosing a tau-protein-associated disease, disorder or condition in a patient is provided comprising detecting the immunospecific binding of a binding peptide or an active fragment thereof, particularly an antibody, particularly a monoclonal antibody or a functional part thereof, according to any one of the preceding embodiments, to an epitope of the tau protein in a sample or in situ which includes the steps of
  a. bringing the sample or a specific body part or body area suspected to contain the tau protein into contact with a binding peptide or a fragment thereof, particularly an antibody, particularly a monoclonal antibody or a functional part thereof, according to any one of the preceding claims, wherein said binding peptide or antibody or fragment thereof binds an epitope of the tau protein;
  b. allowing said binding peptide, particularly said antibody, particularly said monoclonal antibody or a functional part thereof, to bind to the tau protein to form an immunological complex;
  c. detecting the formation of the immunological complex; and
  d. correlating the presence or absence of the immunological complex with the presence or absence of tau protein in the sample or specific body part or area.

In still another embodiment (84) of the invention, a method for diagnosing a predisposition to tau-protein-associated disease, disorder or condition in a patient is provided comprising detecting the immunospecific binding of a binding peptide or an active fragment thereof, particularly an antibody, particularly a monoclonal antibody or a functional part thereof, according to any one of the preceding embodiments, to an epitope of the tau protein in a sample or in situ, which includes the steps of
  a. bringing the sample or a specific body part or body area suspected to contain the tau antigen into contact with a binding peptide or an active fragment thereof, particularly an antibody, particularly a monoclonal antibody or a functional part thereof, according to any one of the preceding embodiments, which peptide or fragment thereof binds an epitope of the tau protein;
  b. allowing said binding peptide, particularly said antibody, particularly said monoclonal antibody or a functional part thereof, to bind to the tau antigen to form an immunological complex;
  c. detecting the formation of the immunological complex; and
  d. correlating the presence or absence of the immunological complex with the presence or absence of tau antigen in the sample or specific body part or area;
  e. comparing the amount of said immunological complex to a normal control value;
  wherein an increase in the amount of said aggregate compared to a normal control value indicates that said patient is suffering from or is at risk of developing an tau-protein-associated disease or condition.

In one embodiment (85) of the invention, a method is provided for monitoring minimal residual disease in a patient following treatment with the binding peptide or a functional part thereof, particularly an antibody, particularly a monoclonal antibody or a functional part thereof, or a polynucleotide, or a pharmaceutical composition, according to any one of the preceding embodiments, wherein said method comprises:
  a. bringing the sample or a specific body part or body area suspected to contain the tau antigen into contact with the binding peptide or a functional part thereof, particularly an antibody, particularly a monoclonal antibody or a functional part thereof, according to any one of the preceding embodiments, which peptide or fragment thereof binds to an epitope of the tau protein;
  b. allowing said binding peptide, particularly said antibody, particularly said monoclonal antibody or a functional part thereof, to bind to the tau antigen to form an immunological complex;
  c. detecting the formation of the immunological complex; and
  d. correlating the presence or absence of the immunological complex with the presence or absence of tau antigen in the sample or specific body part or area,
  e. comparing the amount of said immunological complex to a normal control value,
  wherein an increase in the amount of said aggregate compared to a normal control value indicates that said patient still suffers from a minimal residual disease.

In one embodiment (86), a method is provided for predicting responsiveness of a patient being treated with the binding peptide or a functional part thereof, particularly an antibody, particularly a monoclonal antibody or a functional part thereof, or a polynucleotide, or a pharmaceutical composition, according to any one of the preceding embodiments, comprising
  a. bringing the sample or a specific body part or body area suspected to contain the tau antigen into contact with a binding peptide or an active fragment thereof, particularly an antibody, particularly a monoclonal antibody or a functional part thereof according to any one of the preceding embodiments, which peptide or fragment thereof binds to an epitope of the tau protein;
  b. allowing said binding peptide, particularly said antibody, particularly said monoclonal antibody or a functional part thereof, to bind to the tau antigen to form an immunological complex;
  c. detecting the formation of the immunological complex; and
  d. correlating the presence or absence of the immunological complex with the presence or absence of tau antigen in the sample or specific body part or area,
  e. comparing the amount of said immunological complex before and after onset of the treatment,
  wherein a decrease in the amount of said aggregate indicates that said patient has a high potential of being responsive to the treatment.

In another embodiment (87), the invention relates to a test kit for detection and diagnosis of tau-protein-associated diseases, disorders or conditions comprising a binding peptide or an active fragment thereof, particularly an antibody, particularly a monoclonal antibody or a functional part thereof, according to any one of the preceding embodiments.

In one embodiment (88) said test kit comprises a container holding one or more binding peptides or active fragments thereof, particularly an antibody, particularly a monoclonal antibody or a functional part thereof, according to any one of the preceding embodiments and instructions for using the binding peptides or antibodies for the purpose of binding to tau antigen to form an immunological complex and detecting the formation of the immunological complex such that presence or absence of the immunological complex correlates with presence or absence of tau antigen.

In still another embodiment (89), the present invention relates to an epitope selected from the group consisting of Tau aa 15-20 of human tau protein shown in SEQ ID NO: 67 comprising a phosphorylated Tyr at position 18 (Y18), Tau aa 405-412 comprising a phosphorylated Ser at position 409 (pS409), Tau aa 405-411 comprising a phosphorylated Ser at position 409 (pS409); and Tau aa 208-218 comprising a phosphorylated Thr at position 212 (pT212) and a phosphorylated Ser at position 214 (pS214).

In one embodiment (90), said epitope consists of Tau aa 15-20 with a phosphorylated Tyr at position 18 (Y18).

In one embodiment (91), said epitope consists of Tau aa 405-412 with a phosphorylated Ser at position 409 (pS409).

In one embodiment (92), said epitope consists of Tau aa 405-411 with a phosphorylated Ser at position 409 (pS409).

In another embodiment (93), the invention relates to a cell line producing a binding peptide or an active fragment thereof, particularly an antibody, particularly a monoclonal antibody or a functional part thereof according to any one of the preceding embodiments.

In one embodiment (94), the invention relates to a cell line, which is hybridoma cell line 6C10F9C12A11 deposited on Aug. 25, 2010 as DSM ACC3079.

In one embodiment (95), the invention relates to a cell line, which is hybridoma cell line 6C10E5E9C12 deposited on Aug. 25, 2010 as DSM ACC3081.

In one embodiment (96), the invention relates to a cell line, which is hybridoma cell line 6H1A11C11 deposited on Aug. 25, 2010 as DSM ACC3080.

In one embodiment (97), the invention relates to a cell line, which is hybridoma cell line 6H1G6E6 deposited on Aug. 25, 2010 as DSM ACC3088.

In one embodiment (98), the invention relates to a cell line, which is hybridoma cell line 2B6A10C11 deposited on Aug. 25, 2010 as DSM ACC3084.

In one embodiment (99), the invention relates to a cell line, which is hybridoma cell line 2B6G7A12 deposited on Mar. 10, 2010 as DSM ACC3087.

In one embodiment (100), the invention relates to a cell line, which is hybridoma cell line 3A8A12G7 deposited on Aug. 25, 2010 as DSM ACC3086.

In one embodiment (101), the invention relates to a cell line, which is hybridoma cell line 3A8E12H8 deposited on Aug. 25, 2010 as DSM ACC3085.

In one embodiment (102), the invention relates to a cell line, which is hybridoma cell line 7C2(1)F10C10D3 deposited on Aug. 25, 2010 as DSM ACC3082.

In one embodiment (103), the invention relates to a cell line, which is hybridoma cell line 7C2(2)B9F11D5 deposited on Aug. 25, 2010 as DSM ACC3083.

In one embodiment (103a), the invention relates to a cell line, which is hybridoma cell line A4-4A6-48 deposited on Aug. 30, 2011 as DSM ACC3136.

In one embodiment (103b), the invention relates to a cell line, which is hybridoma cell line A6-2G5-30 deposited on Aug. 30, 2011 as DSM ACC3137.

In one embodiment (103c), the invention relates to a cell line, which is hybridoma cell line A6-2G5-41 deposited on Aug. 30, 2011 as DSM ACC3138.

In one embodiment (103d), the invention relates to a cell line, which is hybridoma cell line A4-2A1-18 deposited on Aug. 30, 2011 as DSM ACC3139.

In one embodiment (103e), the invention relates to a cell line, which is hybridoma cell line A4-2A1-40 deposited on Aug. 30, 2011 as DSM ACC3140.

In one embodiment (103e), the invention relates to a cell line, which is hybridoma cell line A6-1D2-12 deposited on Sep. 6, 2011 as DSM ACC3141.

In one embodiment (104), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 6C10F9C12A11 deposited on Aug. 25, 2010 as DSM ACC3079 using
  a. a primer pair comprising a 5'-primer of SEQ ID NO: 54 and a 3'-primer of SEQ ID NO: 51 for amplification of a first binding domain; and/or
  b. a mix of primers comprising a 5'-primer of SEQ ID NO: 53 and SEQ ID NO: 54 and a 3'-primer of SEQ ID NO: 47 for amplification of a second binding domain.

In one embodiment (105), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 6C10E5E9C12 deposited on Aug. 25, 2010 as DSM ACC3081 using
  a. a mix of primers comprising a 5'-primer of SEQ ID NO: 48 and SEQ ID NO: 49 and a 3'-primer of SEQ ID NO: 51 for amplification of a first binding domain; and/or
  b. a mix of primers comprising a 5'-primer of SEQ ID NO: 53 and SEQ ID NO: 54 and a 3'-primer of SEQ ID NO: 47 for amplification of a second binding domain.

In one embodiment (106), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 6H1A11C11 deposited on Aug. 25, 2010 as DSM ACC3080 using
  a. a primer pair comprising a 5'-primer of SEQ ID NO: 50 and a 3'-primer of SEQ ID NO: 51 for amplification of a first binding domain; and/or
  b. a primer pair comprising a 5'-primer of SEQ ID NO: 46 and a 3'-primer of SEQ ID NO: 47 for amplification of a second binding domain.

In one embodiment (107), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 6H1G6E6 deposited on Aug. 25, 2010 as DSM ACC3088 using
  a. a primer pair comprising a 5'-primer of SEQ ID NO: 50 and a 3'-primer of SEQ ID NO: 51 for amplification of a first binding domain; and/or
  b. a primer pair comprising a 5'-primer of SEQ ID NO: 46 and a 3'-primer of SEQ ID NO: 47 for amplification of a second binding domain.

In one embodiment (108), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 2B6A10C11 deposited on Aug. 25, 2010 as DSM ACC3084 using
   a. a primer pair comprising a 5'-primer of SEQ ID NO: 50 and a 3'-primer of SEQ ID NO: 51 for amplification of a first binding domain; and/or
   b. a mix of primers comprising a 5'-primer of SEQ ID NO: 46 and SEQ ID NO: 52 and a 3'-primer of SEQ ID NO: 47 for amplification of a second binding domain.

In one embodiment (109), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 2B6G7A12 deposited on Aug. 25, 2010 as DSM ACC3087 using
   a. a primer pair comprising a 5'-primer of SEQ ID NO: 50 and a 3'-primer of SEQ ID NO: 51 for amplification of a first binding domain; and/or
   b. a mix of primers comprising a 5'-primer of SEQ ID NO: 46 and SEQ ID NO: 52 and a 3'-primer of SEQ ID NO: 47 for amplification of a second binding domain.

In one embodiment (110), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 3A8A12G7 deposited on Aug. 25, 2010 as DSM ACC3086 using
   $a_1$. a mix of primers comprising a 5'-primer of SEQ ID NO: 48 and SEQ ID NO: 49 and a 3'-primer of SEQ ID NO: 51 for amplification of a first binding domain; or
   $a_2$. a primer pair comprising a 5'-primer of SEQ ID NO: 50 and a 3'-primer of SEQ ID NO: 51 for amplification of a first binding domain; and/or
   b. a primer pair comprising a 5'-primer of SEQ ID NO: 46 and a 3'-primer of SEQ ID NO: 47 for amplification of a second binding domain.

In one embodiment (111), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 3A8E12H8 deposited on Aug. 25, 2010 as DSM ACC3085 using
   $a_1$. a mix of primers comprising a 5'-primer of SEQ ID NO: 48 and SEQ ID NO: 49 and a 3'-primer of SEQ ID NO: 51 for amplification of a first binding domain; or
   $a_2$. a primer pair comprising a 5'-primer of SEQ ID NO: 50 and a 3'-primer of SEQ ID NO: 51 for amplification of a first binding domain; and/or
   b. a primer pair comprising a 5'-primer of SEQ ID NO: 46 and a 3'-primer of SEQ ID NO: 47 for amplification of a second binding domain.

In one embodiment (112), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 7C2(1)F10C10D3 deposited on Aug. 25, 2010 as DSM ACC3082 using
   a. a mix of primers comprising a 5'-primer of SEQ ID NO: 49; SEQ ID NO: 56 and SEQ ID NO: 57 and a 3'-primer of SEQ ID NO: 51 for amplification of a first binding domain;
   b. a mix of primers comprising a 5'-primer of SEQ ID NO: 53 and SEQ ID NO: 55 and a 3'-primer of SEQ ID NO: 47 for amplification of a second binding domain.

In one embodiment (113), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line 7C2(2)B9F11D5 deposited on Aug. 25, 2010 as DSM ACC3083 using
   a. a pair of primers comprising a 5'-primer of SEQ ID NO: 57 and a 3'-primer of SEQ ID NO: 51 for amplification of a first binding domain;
   b. a mix of primers comprising a 5'-primer of SEQ ID NO: 53 and SEQ ID NO: 55 and a 3'-primer of SEQ ID NO: 47 for amplification of a second binding domain.

In one embodiment (114), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-2A1-18 deposited on Aug. 30, 2011 as DSM ACC3139 using
   a. a primer pair comprising a 5'-primer of SEQ ID NO: 149 and a 3'-primer of SEQ ID NO: 51 for amplification of a first binding domain; and/or
   b. a mix of primers comprising a 5'-primer selected from the group consisting of SEQ ID NOs: 120, 123, 124, 136, 137, 138, 139, and 140 and a 3'-primer selected from the group consisting of SEQ ID NOs: 131, 134, and 141-148, for amplification of a second binding domain.

In one embodiment (115), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-2G5-30 deposited on Aug. 30, 2011 as DSM ACC3137 using
   a. a mix of primers comprising a 5'-primer selected from the group consisting of SEQ ID NOs: 51 and 169-174 and a 3'-primer of SEQ ID NO: 51, for amplification of a first binding domain; and/or
   b. a mix of primers comprising a 5'-primer selected from the group consisting of SEQ ID NOs: 124, 127, and 150-158 and a 3'-primer selected from the group consisting of SEQ ID NOs: 130, and 159-168, for amplification of a second binding domain.

In one embodiment (116), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-2A1-40 deposited on Aug. 30, 2011 as DSM ACC3140 using
   a. a mix of primers comprising a 5'-primer selected from the group consisting of SEQ ID NOs: 178, 179 and 180 and a 3'-primer of SEQ ID NO: 51, for amplification of a first binding domain; and/or
   b. a mix of primers comprising a 5'-primer selected from the group consisting of SEQ ID NOs: 121, 127, 139, 154, 155, and 175 and a 3'-primer selected from the group consisting of SEQ ID NOs: 128, 129, 147, 176, and 177, for amplification of a second binding domain.

In one embodiment (117), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-2G5-41 deposited on Aug. 30, 2011 as DSM ACC3138 using a. a mix of primers comprising a 5'-primer selected from the group consisting of SEQ ID NOs: 51 and 188-192 and a 3'-primer of SEQ ID NO: 51, for amplification of a first binding domain; and/or b. a mix of primers comprising a 5'-primer selected from the group consisting of SEQ ID NOs: 120, 124, 126, 181, 182 and 183 and a 3'-primer selected from the group consisting of SEQ ID NOs: 144, 145 and 184-187, for amplification of a second binding domain.

In one embodiment (118), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A4-4A6-48 deposited on Aug. 30, 2011 as DSM ACC3136 using a. a mix of primers comprising a 5'-primer selected from the group consisting of SEQ ID NOs: 50 and 201-204 and a 3'-primer of SEQ ID NO: 51, for amplification of a first binding domain; and/or b. a mix of primers comprising a 5'-primer selected from the group consisting of SEQ ID NOs: 121, 137, 151 and 193-197 and a 3'-primer selected from the group consisting of SEQ ID NOs: 131, 141, 144, 166, 198, 199 and 200, for amplification of a second binding domain.

In one embodiment (119), the invention relates to a monoclonal antibody or a functional part thereof comprising a light chain (VL) and/or a heavy chain (VH) domain, which is encoded by a polynucleotide located on a nucleotide fragment that can be obtained by PCR amplification of DNA of hybridoma cell line A6-1D2-12 deposited on Sep. 6, 2011 as DSM ACC3141 using a. a mix of primers comprising a 5'-primer selected from the group consisting of SEQ ID NOs: 209-214, and 219-221 a 3'-primer of SEQ ID NO: 215, for amplification of a first binding domain; and/or b. a mix of primers comprising a 5'-primer selected from the group consisting of SEQ ID NOs: 216, 217 and 218 and a 3'-primer of SEQ ID NOs: 208, for amplification of a second binding domain.

In one embodiment (120), the antibody according to any one of the preceding embodiments may be a polyclonal antibody, a monoclonal antibody, a chimeric antibody, a humanized antibody, a human antibody, a camelid antibody, a diabody, or a modified or engineered antibody.

In one embodiment (121), the binding peptide or functional part thereof may be a fragment comprising a heavy chain and/or a light chain, particularly a heavy chain as show in SEQ ID NOs: 1-5 and/or a light chain as shown in SEQ ID NOs: 6-11, particularly a Fab or a F(ab')$_2$ fragment.

In a specific embodiment (122), the invention relates to a heavy chain as show in SEQ ID NOs: 1-5.

In another specific embodiment (123), the invention relates to a light chain as shown in SEQ ID NOs: 6-11.

In one embodiment (124), the invention provides a method for producing the binding peptides or antibodies of any one of the preceding embodiments, comprising the step of culturing the cell line of any of the preceding embodiments in a suitable cultivation medium and, optionally, purifying the binding peptides or antibody from the cell line or cultivation medium.

BRIEF DESCRIPTION OF FIGURES AND SEQUENCES

Figures

FIGS. 1A and 1B show antibody binding to phospho-Tau in brain sections from biGT (Tau bigenic) mice using TAUPIR.

SEQUENCES

Figure 1B:
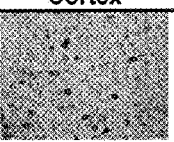
Figure 1B:
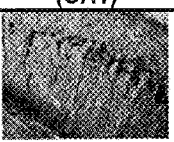
Figure 1B:
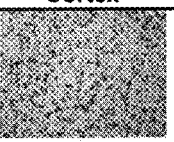
Figure 1B:
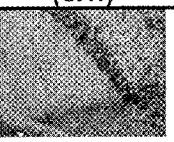
Figure 1B:
Figure 1B:
Figure 1B:
Figure 1B:
Figure 1B:
Figure 1B:
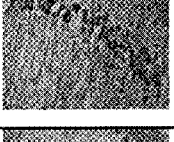
Figure 1B:
Figure 1B:
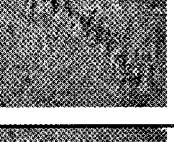
Figure 1B:
Figure 1B:
Figure 1B:
Figure 1B:
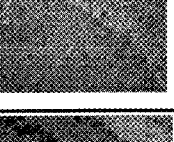
Figure 1B:
Figure 1B:
Figure 1B:
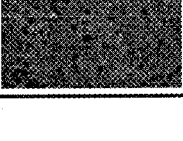
Figure 1B:
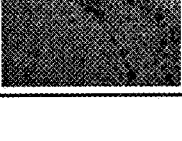
Figure 1B:
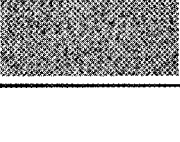
Figure 1B:
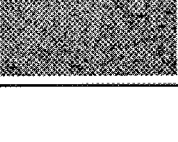

SEQ ID NO: 1 depicts the amino acid sequence of the heavy chain variable region (VH) of monoclonal antibody ACI-36-3A8-Ab1 produced by hybridoma cell line 3A8A12G7.

SEQ ID NO: 2 depicts the amino acid sequence of the heavy chain variable region (VH) of monoclonal antibody ACI-36-2B6-Ab1 produced by hybridoma cell line 2B6A10C11.

SEQ ID NO: 3 depicts the amino acid sequence of the heavy chain variable region (VH) of monoclonal antibody ACI-36-6H1-Ab1 and ACI-36-6H1-Ab2 produced by hybridoma cell line 6H1A11C11 and 6H1G6E6, respectively.

SEQ ID NO: 4 depicts the amino acid sequence of the heavy chain variable region (VH) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 5 depicts the amino acid sequence of the heavy chain variable region (VH) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 6 depicts the amino acid sequence of the light chain variable region (VK) of monoclonal antibody ACI-36-3A8-Ab1$_{VK-AD}$ and ACI-36-3A8-Ab2$_{VK-AD}$ produced by hybridoma cell line 3A8A12G7 and 3A8E12H8, respectively.

SEQ ID NO: 7 depicts the amino acid sequence of the light chain variable region (VK) of monoclonal antibody ACI-36-3A8-Ab1$_{VK-G}$ and ACI-36-3A8-Ab2$_{VK-G}$ produced by hybridoma cell line 3A8A12G7 and 3A8E12H8, respectively.

SEQ ID NO: 8 depicts the amino acid sequence of the light chain variable region (VK) of monoclonal antibody ACI-36-2B6-Ab1 and ACI-36-2B6-Ab2 produced by hybridoma cell line 2B6A10C11 and 2B6G7A12, respectively.

SEQ ID NO: 9 depicts the amino acid sequence of the light chain variable region (VK) of monoclonal antibody ACI-36-6H1-Ab1 and ACI-36-6H1-Ab2 produced by hybridoma cell line 6H1A11C11 and 6H1G6E6, respectively.

SEQ ID NO: 10 depicts the amino acid sequence of the light chain variable region (VK) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 11 depicts the amino acid sequence of the light chain variable region (VK) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 12 depicts the amino acid sequence of the CDR1 of the heavy chain variable region (VH) of monoclonal antibody ACI-36-3A8-Ab1, ACI-36-3A8-Ab2, ACI-36-2B6-Ab1, ACI-36-2B6-Ab2, ACI-36-6H1-Ab1 and ACI-36-6H1-Ab2 produced by hybridoma cell line 3A8A12G7, 3A8E12H8, 2B6A10C11, 2B6G7A12, 6H1A11C11 and 6H1G6E6, respectively.

SEQ ID NO: 13 depicts the amino acid sequence of the CDR2 of the heavy chain variable region (VH) of monoclonal antibody ACI-36-3A8-Ab1, ACI-36-3A8-Ab2, ACI-36-2B6-Ab1, ACI-36-2B6-Ab2, ACI-36-6H1-Ab1 and ACI-36-6H1-Ab2 produced by hybridoma cell line 3A8A12G7, 3A8E12H8, 2B6A10C11, 2B6G7A12, 6H1A11C11 and 6H1G6E6, respectively.

SEQ ID NO: 14 depicts the amino acid sequence of the CDR3 of the heavy chain variable region (VH) of monoclonal antibody ACI-36-3A8-Ab1, ACI-36-3A8-Ab2, ACI-36-2B6-Ab1, ACI-36-2B6-Ab2, ACI-36-6H1-Ab1 and ACI-36-6H1-Ab2 produced by hybridoma cell line 3A8A12G7, 3A8E12H8, 2B6A10C11, 2B6G7A12, 6H1A11C11 and 6H1G6E6, respectively.

SEQ ID NO: 15 depicts the amino acid sequence of the CDR1 of the heavy chain variable region (VH) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 16 depicts the amino acid sequence of the CDR2 of the heavy chain variable region (VH) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 17 depicts the amino acid sequence of the CDR3 of the heavy chain variable region (VH) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 18 depicts the amino acid sequence of the CDR1 of the heavy chain variable region (VH) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 19 depicts the amino acid sequence of the CDR2 of the heavy chain variable region (VH) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 20 depicts the amino acid sequence of the CDR3 of the heavy chain variable region (VH) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 21 depicts the amino acid sequence of the CDR1 of the light chain variable region (VK) of monoclonal antibody ACI-36-3A8-Ab1$_{VK-AD}$ and ACI-36-3A8-Ab2$_{VK-AD}$ produced by hybridoma cell line 3A8A12G7 and 3A8E12H8, respectively.

SEQ ID NO: 22 depicts the amino acid sequence of the CDR2 of the light chain variable region (VK) of monoclonal antibody ACI-36-3A8-Ab1$_{VK-AD}$ and ACI-36-3A8-Ab2$_{VK-AD}$ produced by hybridoma cell line 3A8A12G7 and 3A8E12H8, respectively.

SEQ ID NO: 23 depicts the amino acid sequence of the CDR3 of the light chain variable region (VK) of monoclonal antibody ACI-36-3A8-Ab1$_{VK-AD}$ and ACI-36-3A8-Ab2$_{VK-AD}$ produced by hybridoma cell line 3A8A12G7 and 3A8E12H8, respectively.

SEQ ID NO: 24 depicts the amino acid sequence of the CDR1 of the light chain variable region (VK) of monoclonal antibody ACI-36-3A8-Ab1$_{VK-G}$ and ACI-36-3A8-Ab2$_{VK-G}$ produced by hybridoma cell line 3A8A12G7 and 3A8E12H8, respectively.

SEQ ID NO: 25 depicts the amino acid sequence of the CDR2 of the light chain variable region (VK) of monoclonal antibody ACI-36-3A8-Ab1 VK-G, ACI-36-3A8-Ab2$_{VK-G}$, ACI-36-2B6-Ab1, ACI-36-2B6-Ab2, ACI-36-6H1-Ab1 and ACI-36-6H1-Ab2 produced by hybridoma cell line 3A8A12G7, 3A8E12H8, 2B6A10C11, 2B6G7A12, 6H1A11C11 and 6H1G6E6, respectively.

SEQ ID NO: 26 depicts the amino acid sequence of the CDR3 of the light chain variable region (VK) of monoclonal antibody ACI-36-3A8-Ab1 VK-G, ACI-36-3A8-Ab2$_{VK-G}$, ACI-36-2B6-Ab1, ACI-36-2B6-Ab2, ACI-36-6H1-Ab1 and ACI-36-6H1-Ab2 produced by hybridoma cell line 3A8A12G7, 3A8E12H8, 2B6A10C11, 2B6G7A12, 6H1A11C11 and 6H1G6E6, respectively.

SEQ ID NO: 27 depicts the amino acid sequence of the CDR1 of the light chain variable region (VK) of monoclonal antibody ACI-36-2B6-Ab1 and ACI-36-2B6-Ab2 produced by hybridoma cell line 2B6A10C11 and 2B6G7A12, respectively.

SEQ ID NO: 28 depicts the amino acid sequence of the CDR1 of the light chain variable region (VK) of monoclonal antibody ACI-36-6H1-Ab1 and ACI-36-6H1-Ab2 produced by hybridoma cell line 6H1A11C11 and 6H1G6E6, respectively.

SEQ ID NO: 29 depicts the amino acid sequence of the CDR1 of the light chain variable region (VK) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 30 depicts the amino acid sequence of the CDR2 of the light chain variable region (VK) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 31 depicts the amino acid sequence of the CDR3 of the light chain variable region (VK) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 32 depicts the amino acid sequence of the CDR1 of the light chain variable region (VK) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 33 depicts the amino acid sequence of the CDR2 of the light chain variable region (VK) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 34 depicts the amino acid sequence of the CDR3 of the light chain variable region (VK) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 35 depicts the nucleotide sequence of the heavy chain variable region (VH) of monoclonal antibody ACI-36-3A8-Ab1 and ACI-36-3A8-Ab2 produced by hybridoma cell line 3A8A12G7 and 3A8E12H8, respectively.

SEQ ID NO: 36 depicts the nucleotide sequence of the heavy chain variable region (VH) of monoclonal antibody ACI-36-2B6-Ab1 and ACI-36-2B6-Ab2 produced by hybridoma cell line 2B6A10C11 and 2B6G7A12, respectively.

SEQ ID NO: 37 depicts the nucleotide sequence of the heavy chain variable region (VH) of monoclonal antibody ACI-36-6H1-Ab1 and ACI-36-6H1-Ab2 produced by hybridoma cell line 6H1A11C11 and 6H1G6E6, respectively.

SEQ ID NO: 38 depicts the nucleotide sequence of the heavy chain variable region (VH) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 39 depicts the nucleotide sequence of the heavy chain variable region (VH) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 40 depicts the nucleotide sequence of the light chain variable region (VK) of monoclonal antibody ACI-36-3A8-Ab1 and ACI-36-3A8-Ab2 produced by hybridoma cell line 3A8A12G7 and 3A8E12H8, respectively.

SEQ ID NO: 41 depicts the nucleotide sequence of the light chain variable region (VK) of monoclonal antibody ACI-36-3A8-Ab1 and ACI-36-3A8-Ab2 produced by hybridoma cell line 3A8A12G7 and 3A8E12H8, respectively.

SEQ ID NO: 42 depicts the nucleotide sequence of the light chain variable region (VK) of monoclonal antibody ACI-36-2B6-Ab1 and ACI-36-2B6-Ab2 produced by hybridoma cell line 2B6A10C11 and 2B6G7A12, respectively.

SEQ ID NO: 43 depicts the nucleotide sequence of the light chain variable region (VK) of monoclonal antibody ACI-36-6H1-Ab1 and ACI-36-6H1-Ab2 produced by hybridoma cell line 6H1A11C11 and 6H1G6E6, respectively.

SEQ ID NO: 44 depicts the nucleotide sequence of the light chain variable region (VK) of monoclonal antibody ACI-33-6C10-Ab2 and ACI-33-6C10-Ab1 produced by hybridoma cell line 6C10E5E9C12 and 6C10F9C12A11, respectively.

SEQ ID NO: 45 depicts the nucleotide sequence of the light chain variable region (VK) of monoclonal antibody ACI-41-7C2-Ab1 and ACI-41-7C2-Ab2 produced by hybridoma cell line 7C2(1)F10C10D3 and 7C2(2)B9F11D5, respectively.

SEQ ID NO: 46-57 depicts the nucleotide sequences of VH/VK forward and reverse primers.

SEQ ID NO: 58 depicts the amino acid sequence of Tau 379-408 [pS396, pS404]

SEQ ID NO: 59 depicts the amino acid sequence of Tau 5-20 [pY18]

SEQ ID NO: 60 depicts the amino acid sequence of Tau 206-221 [pT212, pS214]

SEQ ID NO: 61 depicts the amino acid sequence of Tau 196-211 [pS202, pT205]

SEQ ID NO: 62 depicts the amino acid sequence of Tau 393-408 [pS396, pS404]

SEQ ID NO: 63 depicts the amino acid sequence of Tau 401-418 [pS404, pS409]

SEQ ID NO: 64 depicts the amino acid sequence of Tau 200-216 [pS202+pT205 & pT212+pS214]

SEQ ID NO: 65 depicts the amino acid sequence of Tau 407-418 [pS409]

SEQ ID NO: 66 depicts the amino acid sequence of Tau 399-408 [pS404]

SEQ ID NO: 67 depicts the amino acid sequence of longest isoform of human Tau (441aa), also called Tau40

SEQ ID NO: 68 depicts the amino acid sequence of the heavy chain variable region (VH) of monoclonal antibody ACI-35-4A6-Ab1 produced by hybridoma cell line A4-4A6-18.

SEQ ID NO: 69 depicts the amino acid sequence of the light chain variable region (VK) of monoclonal antibody ACI-35-4A6-Ab1 produced by hybridoma cell line A4-4A6-18.

SEQ ID NO: 70 depicts the amino acid sequence of the CDR1 of the heavy chain variable region (VH) of monoclonal antibody ACI-35-4A6-Ab1

SEQ ID NO: 71 depicts the amino acid sequence of the CDR2 of the heavy chain variable region (VH) of monoclonal antibody ACI-35-4A6-Ab1

SEQ ID NO: 72 depicts the amino acid sequence of the CDR3 of the heavy chain variable region (VH) of monoclonal antibody ACI-35-4A6-Ab1

SEQ ID NO: 73 depicts the amino acid sequence of the CDR1 of the light chain variable region (VK) of monoclonal antibody ACI-35-4A6-Ab1

SEQ ID NO: 74 depicts the amino acid sequence of the CDR2 of the light chain variable region (VK) of monoclonal antibody ACI-35-4A6-Ab1

SEQ ID NO: 75 depicts the amino acid sequence of the CDR3 of the light chain variable region (VK) of monoclonal antibody ACI-35-4A6-Ab1

SEQ ID NO: 76 depicts the amino acid sequence of the heavy chain variable region (VH) of monoclonal antibody ACI-35-1D2-Ab1 produced by hybridoma cell line A6-1D2-12.

SEQ ID NO: 77 depicts the amino acid sequence of the light chain variable region (VK) of monoclonal antibody ACI-35-1D2-Ab1 produced by hybridoma cell line A6-1D2-12.

SEQ ID NO: 78 depicts the amino acid sequence of the CDR1 of the heavy chain variable region (VH) of monoclonal antibody ACI-35-1 D2-Ab1.

SEQ ID NO: 79 depicts the amino acid sequence of the CDR2 of the heavy chain variable region (VH) of monoclonal antibody ACI-35-1 D2-Ab1.

SEQ ID NO: 80 depicts the amino acid sequence of the CDR3 of the heavy chain variable region (VH) of monoclonal antibody ACI-35-1 D2-Ab1

SEQ ID NO: 81 depicts the amino acid sequence of the CDR1 of the light chain variable region (VK) of monoclonal antibody ACI-35-1D2-Ab1

SEQ ID NO: 82 depicts the amino acid sequence of the CDR2 of the light chain variable region (VK) of monoclonal antibody ACI-35-1D2-Ab1

SEQ ID NO: 83 depicts the amino acid sequence of the CDR3 of the light chain variable region (VK) of monoclonal antibody ACI-35-1D2-Ab1

SEQ ID NO: 84 depicts the nucleotide sequence of the heavy chain variable region (VH) of monoclonal antibody ACI-35-4A6-Ab1 produced by hybridoma cell line A4-4A6-18.

SEQ ID NO: 85 depicts the nucleotide sequence of the light chain variable region (VK) of monoclonal antibody ACI-35-4A6-Ab1 produced by hybridoma cell line A4-4A6-18.

SEQ ID NO: 86 depicts the nucleotide sequence of the heavy chain variable region (VH) of monoclonal antibody ACI-35-1D2-Ab1 produced by hybridoma cell line A6-1D2-12.

SEQ ID NO: 87 depicts the nucleotide sequence of the light chain variable region (VK) of monoclonal antibody ACI-35-1D2-Ab1 produced by hybridoma cell line A6-1D2-12.

SEQ ID NO: 88 depicts the amino acid sequence of the heavy chain variable region (VH) of monoclonal antibody ACI-35-2A1-Ab1, ACI-35-2A1-Ab2, and ACI-35-4A6-Ab2, respectively, produced by hybridoma cell line A4-2A1-18, A4-2A1-40 and A4-4A6-48, respectively.

SEQ ID NO: 89 depicts the amino acid sequence of the CDR1 of the heavy chain variable region (VH) of monoclonal antibody ACI-35-2A1-Ab1, ACI-35-2A1-Ab2, ACI-35-4A6-Ab2, ACI-35-2G5-AB2 and ACI-35-2G5-AB3, respectively.

SEQ ID NO: 90 depicts the amino acid sequence of the CDR2 of the heavy chain variable region (VH) of monoclonal antibody ACI-35-2A1-Ab1, ACI-35-2A1-Ab2, and ACI-35-4A6-Ab2, respectively.

SEQ ID NO: 91 depicts the amino acid sequence of the CDR3 of the heavy chain variable region (VH) of monoclonal antibody ACI-35-2A1-Ab1, ACI-35-2A1-Ab2, ACI-35-4A6-Ab2, ACI-35-2G5-AB2 and ACI-35-2G5-AB3, respectively.

SEQ ID NO: 92 depicts the amino acid sequence of the light chain variable region (VK) of monoclonal antibody ACI-35-2A1-Ab2 produced by hybridoma cell line A4-2A1-40

SEQ ID NO: 93 depicts the amino acid sequence of the CDR1 of the light chain variable region (VK) of monoclonal antibody ACI-35-2A1-Ab2.

SEQ ID NO: 94 depicts the amino acid sequence of the CDR2 of the light chain variable region (VK) of monoclonal antibody ACI-35-2A1-Ab2.

SEQ ID NO: 95 depicts the amino acid sequence of the CDR3 of the light chain variable region (VK) of monoclonal antibody ACI-35-2A1-Ab2.

SEQ ID NO: 96 depicts the amino acid sequence of the heavy chain variable region (VH) of monoclonal antibody ACI-35-2G5-Ab1 produced by hybridoma cell line A6-2G5-08.

SEQ ID NO: 97 depicts the amino acid sequence of the light chain variable region (VK) of monoclonal antibody ACI-35-2G5-Ab1 produced by hybridoma cell line A6-2G5-08.

SEQ ID NO: 98 depicts the amino acid sequence of the CDR1 of the heavy chain variable region (VH) of monoclonal antibody ACI-35-2G5-Ab1.

SEQ ID NO: 99 depicts the amino acid sequence of the CDR2 of the heavy chain variable region (VH) of monoclonal antibody ACI-35-2G5-Ab1.

SEQ ID NO: 100 depicts the amino acid sequence of the CDR3 of the heavy chain variable region (VH) of monoclonal antibody ACI-35-2G5-Ab1.

SEQ ID NO: 101 depicts the amino acid sequence of the CDR1 of the light chain variable region (VK) of monoclonal antibody ACI-35-2G5-Ab1.

SEQ ID NO: 102 depicts the amino acid sequence of the CDR2 of the light chain variable region (VK) of monoclonal antibody ACI-35-2G5-Ab1.

SEQ ID NO: 103 depicts the amino acid sequence of the CDR3 of the light chain variable region (VK) of monoclonal antibody ACI-35-2G5-Ab1.

SEQ ID NO: 104 depicts the amino acid sequence of the heavy chain variable region (VH) of monoclonal antibody ACI-35-2G5-AB2 and ACI-35-2G5-AB3, respectively, produced by hybridoma cell line A6-2G5-30 and A6-2G5-41, respectively.

SEQ ID NO: 105 depicts the amino acid sequence of the light chain variable region (VK) of monoclonal antibody ACI-35-2G5-AB2 and ACI-35-2G5-AB3, respectively, produced by hybridoma cell line A6-2G5-30 and A6-2G5-41, respectively.

SEQ ID NO: 106 depicts the amino acid sequence of the CDR1 of the light chain variable region (VK) of monoclonal antibody ACI-35-2G5-AB2 and ACI-35-2G5-AB3, respectively.

SEQ ID NO: 107 depicts the amino acid sequence of the CDR2 of the light chain variable region (VK) of monoclonal antibody ACI-35-2G5-AB2 and ACI-35-2G5-AB3, respectively.

SEQ ID NO: 108 depicts the amino acid sequence of the CDR3 of the light chain variable region (VK) of monoclonal antibody ACI-35-2G5-AB2 and ACI-35-2G5-AB3, respectively.

SEQ ID NO: 109 depicts the nucleotide sequence of the heavy chain variable region (VH) of monoclonal antibody ACI-35-2A1-Ab1, ACI-35-2A1-Ab2, and ACI-35-4A6-Ab2, respectively, produced by hybridoma cell line A4-2A1-18, A4-2A1-40 and A4-4A6-48, respectively.

SEQ ID NO: 110 depicts the nucleotide sequence of the light chain variable region (VK) of monoclonal antibody ACI-35-2A1-Ab2 produced by hybridoma cell line A4-2A1-40.

SEQ ID NO: 111 depicts the nucleotide sequence of the heavy chain variable region (VH) of monoclonal antibody ACI-35-2G5-AB1 produced by hybridoma cell line A6-2G5-08.

SEQ ID NO: 112 depicts the nucleotide sequence of the light chain variable region (VK) of monoclonal antibody ACI-35-2G5-AB1 produced by hybridoma cell line A6-2G5-08.

SEQ ID NO: 113 depicts the nucleotide sequence of the heavy chain variable region (VH) of monoclonal antibody ACI-35-2G5-AB2 and ACI-35-2G5-AB3, respectively, produced by hybridoma cell line A6-2G5-30 and A6-2G5-41, respectively.

SEQ ID NO: 114 depicts the nucleotide sequence of the light chain variable region (VK) of monoclonal antibody ACI-35-2G5-AB2 and ACI-35-2G5-AB3, respectively, produced by hybridoma cell line A6-2G5-30 and A6-2G5-41, respectively.

SEQ ID NO: 115 depicts the amino acid sequence of the CDR2 of the heavy chain variable region (VH) of monoclonal antibody ACI-35-2G5-AB2 and ACI-35-2G5-AB3.

SEQ ID NO: 116 depicts the amino acid sequence of the light chain variable region (VK) of monoclonal antibody ACI-35-2A1-Ab1 produced by hybridoma cell line A4-2A1-18.

SEQ ID NO: 117 depicts the nucleotide sequence of the light chain variable region (VK) of monoclonal antibody ACI-35-2A1-Ab1 produced by hybridoma cell line A4-2A1-18.

SEQ ID NO: 118 depicts the amino acid sequence of the light chain variable region (VK) of monoclonal antibody ACI-35-4A6-Ab2 produced by hybridoma cell line A4-4A6-48.

SEQ ID NO: 119 depicts the nucleotide sequence of the light chain variable region (VK) of monoclonal antibody ACI-35-4A6-Ab2 produced by hybridoma cell line A4-4A6-48.

SEQ ID NO: 120-221 depicts the nucleotide sequences of VH/VK forward and reverse primers Definition of Terms The terms "polypeptide", "peptide", and "protein", as used herein, are interchangeably and are defined to mean a biomolecule composed of amino acids linked by a peptide bond.

The term "peptides," or "binding peptide" are used herein interchangeably and refer to chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide. A binding peptide may constitutes antibodies such as polyclonal or monoclonal antibodies, human or humanized antibodies, diabodies, camelid antibodies, etc, or functional parts thereof as defined herein.

The terms "fragment thereof" or "fragment" as used herein refer to a functional peptide fragment which has essentially the same (biological) activity as the peptides defined herein (e.g. as shown in SEQ ID NOs 59-66 in Table 1 respectively), i.e. said fragments are still capable of eliciting a highly specific, particularly a conformation specific, immune response in an organism, but particularly within an animal, particularly a mammal or a human, which is highly effective and capable of preventing or alleviating tauopathies, or the symptoms associated with tauopathies. In particular, said fragments still contain the specific pathological phospho-epitope or -epitopes of the tau peptide, as used and defined herein.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95 homogeneity are preferred, and 80% to 95% or greater homogeneity is most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", an and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody", "antibodies" or "functional parts thereof" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies, camelid antibodies, diabodies, as well as functional parts or active fragments thereof. Examples of active fragments of molecules that bind to known antigens include Fab and F(ab')$_2$ fragments, including the products of a Fab immunoglobulin expression library and epitope-binding fragments of any of the antibodies and fragments mentioned above. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, (1986).

A "humanized antibody" refers to a type of engineered antibody having its CDRs derived from a non-human donor immunoglobulin, the remaining immunoglobulin-derived parts of the molecule being derived from one (or more) human immunoglobulin(s).

A humanized antibody may further refer to an antibody having a variable region where one or more of its framework regions have human or primate amino acids. In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech-.com/bioventures/therapeutic.php).

The term "fully human antibody" or "human" antibody is meant to refer to an antibody derived from transgenic mice carrying human antibody genes or from human cells. To the human immune system, however, the difference between "fully human", "human", and "humanized" antibodies may be negligible or nonexistent and as such all three may be of equal efficacy and safety.

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

Carrier proteins that can be used in the supramolecular antigenic construct compositions of the present invention include, but are not limited to, maltose binding peptide "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "therapeutically effective amount" or "pharmaceutically effective amount" refers to the amount of binding peptide which, when administered to a human or animal, is sufficient to result in a therapeutic effect in said human or animal. The effective amount is readily determined by one of ordinary skill in the art following routine procedures.

"pTau PHF", "PHF", and "paired helical filaments" are used herein synonymously and refer to pairs of approximately 10 nm filaments wound into helices with a periodicity of 160 nm visible on electron microscopy. Width varies between 10 and 22 nm. PHF are the predominant structures in neurofibrillary tangles of Alzheimer's Disease (AD) and neuropil threads. PHF may also be seen in some but not all dystrophic neurites associated with neuritic plaques. The major component of PHF is a hyperphosphorylated form of microtubule-associated protein tau. PHF are composed of disulfide-linked antiparallel hyper-phosphorylated tau proteins. PHF tau may be truncated of its C-terminal 20 amino acid residues. The mechanisms underlying PHF formation are uncertain but hyper-phosphorylation of tau may disengage it from microtubules, increasing the soluble pool of tau.

Within the scope of the present invention, it was demonstrated that the antibody induced response to the antigenic composition according to the invention is largely T-cell independent. A nude mouse model was used in this respect and nude mice were vaccinated and antibody responses measured to evaluate the Aβ-specific antibody response induced by the antigenic composition according to the invention in the immunized nude mice. The nude mice carry the Foxn1nu mutation and as a consequence, have reduced T-cell function due to the lack of a proper thymus.

A "pharmaceutically effective amount" as used herein refers to a dose of the active ingredient in a pharmaceutical composition adequate to cure, or at least partially arrest, the symptoms of the disease, disorder or condition to be treated or any complications associated therewith.

The present invention provides binding peptides recognizing and binding to major pathological phospho-epitopes of the tau protein. In particular, the present invention provides specific antibodies against linear and conformational, simple and complex phospho-epitopes on protein tau that are believed to be responsible for synapto- and neuro-toxicity in tauopathies, including AD.

Accordingly, the present invention relates in one embodiment to a binding peptide or a functional part thereof, particularly to an antibody, particularly a monoclonal antibody or a functional part thereof, which binding peptide or antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity with a dissociation constant of at least 10 nM, particularly of at least 8 nM, particularly of at least 5 nM, particularly of at least 2 nM, particularly of at least 1 nM, particularly of at least 500 pM, particularly of at least 400 pM particularly of at least 300 pM, particularly of at least 200 pM, particularly of at least 100 pM, particularly of at least 50 pM.

"Soluble Tau" protein as used herein refers to proteins consisting of both completely solubilized Tau protein/peptide monomers or of Tau-like peptides/proteins, or of modified or truncated Tau peptides/proteins or of other derivates of Tau peptides/proteins monomers, and of Tau protein oligomers. "Soluble Tau" excludes particularly neurofibrillary tangles (NFT).

"Insoluble Tau" as used herein refers to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble in the mammalian or human body more particularly in the brain, respectively. "Insoluble Tau" particularly includes neurofibrillary tangles (NFT).

"Monomeric Tau" or "Tau monomer" as used herein refers to completely solubilized Tau proteins without aggregated complexes in aqueous medium.

"Aggregated Tau", "oligomeric Tau" and "Tau oligomer" refer to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble or soluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble or soluble in the mammalian or human body more particularly in the brain, respectively."

In one embodiment, the present invention provides a pharmaceutical composition comprising a binding peptide or a functional part thereof, particularly an antibody, particularly a monoclonal antibody or a functional part thereof, or a polynucleotide comprising a nucleic acid sequence encoding said binding peptide or antibody, according to any one of the embodiments described and claimed herein, or a combination thereof, in a therapeutically effective amount together with a pharmaceutically acceptable carrier.

Suitable pharmaceutical carriers, diluents and/or excipients are well known in the art and include, for example, phosphate buffered saline solutions, water, emulsions such as oil/water emulsions, various types of wetting agents, sterile solutions, etc.

The binding peptides according to the invention including antibodies, particularly monoclonal antibodies and active fragments thereof, can be prepared in a physiologically acceptable formulation and may comprise a pharmaceutically acceptable carrier, diluent and/or excipient using known techniques. For example, the binding peptides according to the invention and as described herein including any functionally equivalent binding peptides or functional parts thereof, in particular, the monoclonal antibodies of the invention including any functionally equivalent antibodies or functional parts thereof, are combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes.

In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition according to the invention may be administered in combination with other compositions comprising an biologically active substance or compound such as, for example, a known compound used in the medication of tauopathies and/or of amyloidoses, a group of diseases and disorders associated with amyloid or amyloid-like protein such as the amyloid β protein involved in Alzheimer's Disease.

The other biologically active substance or compound may exert its biological effect by the same or a similar mechanism as the therapeutic vaccine according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the biologically active agent or compound may comprise at least one compound selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), secretase activators, [beta]- and 7-secretase inhibitors, tau proteins, neurotransmitter, /3-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, *Ginkgo biloba*, acetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a binding peptide according to the invention including antibodies, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the binding peptide according to the invention including antibodies, particularly monoclonal antibodies and active fragments thereof, and, optionally, a pharmaceutically acceptable carrier and/or a diluent and/or an excipient.

Other compounds that can be suitably used in compositions in addition to the binding peptide according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), antipsychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, e.g. intravenously. Preparations for parenteral administration include sterile aqueous or non-aqueous solutions, suspensions and emulsions. Non-aqueous solvents include, without being limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringers dextrose, dextrose and sodium chloride, lactated Ringers, or fixed oils. Intravenous vehicles include fluid and nutrient replenishers, electrolyte replenishers (such as those based on Ringers dextrose) and others. Preservatives may also be present such as, for example, antimicrobials, antioxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the binding peptide according to the invention including antibodies, particularly monoclonal antibodies and active fragments thereof, to traverse the blood-brain barrier. Certain neurodegenerative diseases are associated with an increase in permeability of the blood-brain barrier, such that the binding peptide according to the invention including antibodies, particularly monoclonal antibodies or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the binding peptide according to the invention including antibodies, particularly monoclonal antibodies, or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N. Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the binding peptide or antigen-binding fragment (see, e.g., U.S. Patent Publication No. 2003/0083299).

Lipid-based methods of transporting the binding peptide according to the invention including antibodies, particularly monoclonal antibodies, or an active fragment thereof across the blood-brain barrier include, but are not limited to, encapsulating the binding peptide according to the invention including antibodies, particularly monoclonal antibodies, or active fragment thereof in liposomes that are coupled to active fragments thereof that bind to receptors on the vascular endothelium of the blood-brain barrier (see, e.g., U.S. Patent Application Publication No. 20020025313), and coating the binding peptide according to the invention including antibodies, particularly monoclonal antibodies, or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the binding peptide according to the invention including antibodies, particularly monoclonal antibodies, or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Single or repeated administrations of the binding peptide according to the invention including antibodies, particularly monoclonal antibodies, or an active fragment thereof, or of a pharmaceutical composition according to the invention may be provided to a subject over an extended period of time. The duration of administration may be between 1 week and up to 12 month or more. During this time the binding peptide, antibody or pharmaceutical composition may be administered once a week, once every two weeks, three weeks, four weeks, etc, or at a higher or lower frequency depending on the needs of the subject to be treated.

In a further embodiment the present invention provides methods and kits for the detection and diagnosis of tau-protein-associated diseases, disorders or conditions, including neurodegenerative diseases or disorders such as tauopathies comprising a heterogenous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further of diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, Myotonic dystrophy. The pathological abnormalities may be caused by or associated with the formation of neurofibrillary lesions, the predominant brain pathology in tauopathy.

Further, the present invention provides methods and kits for diagnosing a predisposition to tau-protein-associated diseases, disorders or conditions, including neurodegenerative diseases or disorders such as tauopathies comprising a heterogenous group of neurodegenerative diseases or disorders including diseases or disorders which show co-existence of tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein. These methods include known immunological methods commonly used for detecting or quantifying substances in biological samples or in an in situ condition.

Diagnosis of a tau-protein-associated disease or condition or of a predisposition to an tau-protein-associated disease or condition in a subject in need thereof, particularly a mammal, more particularly a human, including neurodegenerative diseases or disorders such as tauopathies comprising a heterogenous group of neurodegenerative diseases or disorders including diseases or disorders which show co-existence of tau and amyloid pathologies, may be achieved by detecting the immunospecific binding of a binding peptide of the invention, particularly of an antibody, particularly of a monoclonal antibody or an active fragment thereof, to an epitope of the tau protein in a sample or in situ, which includes bringing the sample or a specific body part or body area suspected to contain the tau protein into contact with an antibody which binds an epitope of the tau protein, allowing the antibody to bind to the tau protein to form an immunologic complex, detecting the formation of the immunologic complex and correlating the presence or absence of the immunologic complex with the presence or absence of tau protein in the sample or specific body part or area, optionally comparing the amount of the immunologic complex to a normal control value, wherein an increase in the amount of the immunologic complex compared to a normal control value indicates that the subject is suffering from or is at risk of developing an tau protein-associated disease or condition.

Monitoring minimal residual disease in a subject, particularly a mammal, more particularly a human, following treatment with a binding peptide according to the invention including antibodies, particularly monoclonal antibodies and active fragments thereof, or a composition according to the invention may be achieved by detecting the immunospecific binding of a binding peptide of the invention, particularly of an antibody, particularly a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the binding peptide according to the invention including antibodies, particularly monoclonal antibodies and active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex to a normal control value, wherein an increase in the amount of said immunologic complex compared to a normal control value indicates that the subject may still suffer from a minimal residual disease.

Predicting responsiveness of a subject, particularly a mammal, more particularly a human, to a treatment with a binding peptide according to the invention including antibodies, particularly monoclonal antibodies and active fragments thereof, or a composition according to the invention may be achieved by detecting the immunospecific binding of a binding peptide, particularly of a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the binding peptide according to the invention including antibodies, particularly monoclonal antibodies and active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex before and after onset of the treatment, wherein an decrease in the amount of said immunologic complex indicates that said patient has a high potential of being responsive to the treatment.

Biological samples that may be used in the diagnosis of a tau protein-associated disease or condition, for diagnosing a predisposition to a tau protein-associated disease or condition, including neurodegenerative diseases or disorders such as tauopathies comprising a heterogenous group of neurodegenerative diseases or disorders including diseases or disorders which show co-existence of tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the tau protein in a sample, any immunoassay known to those of ordinary skill in the art may be used such as, for example, assays which utilize indirect detection methods using secondary reagents for detection, ELISAs and immunoprecipitation and agglutination assays.

A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the binding peptide according to the invention including antibodies, particularly monoclonal antibodies and active fragments thereof, of the invention or any active and functional part thereof may be administered to the organism to be diagnosed by methods known in the art such as, for example, intravenous, intranasal, intraperitoneal, intracerebral, intraarterial injection such that a specific binding between an antibody according to the invention with an epitopic region on the amyloid protein may occur. The binding peptide/antigen complex may conveniently be detected through a label attached to the binding peptide according to the invention including antibodies, particularly monoclonal antibodies, or a functional fragment thereof or any other art-known method of detection.

The immunoassays used in diagnostic applications or in applications for diagnosing a predisposition to a tau protein-associated disease or condition, including neurodegenerative diseases or disorders such as tauopathies comprising a heterogenous group of neurodegenerative diseases or disorders including diseases or disorders which show co-existence of tau and amyloid pathologies, or for monitoring minimal residual disease in a patient or for predicting responsiveness of a patient to a treatment with a binding peptide according to the invention including antibodies, particularly monoclonal antibodies and active fragments thereof, or a composition according to the invention and as described herein typically rely on labelled antigens, binding peptides, or secondary reagents for detection. These proteins or reagents can be labelled with compounds generally known to those of ordinary skill in the art including enzymes, radioisotopes, and fluorescent, luminescent and chromogenic substances including, but not limited to colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Binding peptides useful in these assays are those disclosed claimed herein including antibodies, particularly monoclonal antibodies, polyclonal antibodies, and affinity purified polyclonal antibodies.

Alternatively, the binding peptide according to the invention including antibodies, particularly monoclonal antibodies and active fragments thereof, may be labelled indirectly by reaction with labelled substances that have an affinity for immunoglobulin, such as protein A or G or second antibodies. The binding peptide according to the invention including antibodies, particularly monoclonal antibodies and active fragments thereof, may be conjugated with a second substance and detected with a labelled third substance having an affinity for the second substance conjugated to the antibody. For example, the binding peptide according to the invention including antibodies, particularly monoclonal antibodies and active fragments thereof, may be conjugated to biotin and the binding peptide/biotin conjugate detected using labelled avidin or streptavidin. Similarly, the binding peptide may be conjugated to a hapten and the binding peptide/hapten conjugate detected using labelled anti-hapten binding peptide.

Those of ordinary skill in the art will know of these and other suitable labels which may be employed in accordance with the present invention. The binding of these labels to binding peptides or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 57:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the antibody to be used in the assay described herein, this label is preferably an antibody-coated bead, particularly a magnetic bead. For the antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid protein in a sample of biological fluid. In this method, the analyte (amyloid protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those of ordinary skill in the art. More recently, a number of porous material such as nylon, nitrocellulose, cellulose acetate, glass fibers and other porous polymers have been employed as solid supports.

The present invention also relates to a diagnostic kit for detecting tau protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of tau protein-associated diseases and conditions, comprising binding peptides according to the present invention. For immunoprobes, the binding peptides are directly or indirectly attached to a suitable reporter molecule, e.g., an enzyme or a radionuclide. The test kit includes a container holding one or more binding peptides according to the present invention and instructions for using the binding peptides for the purpose of binding to tau antigen to form an immunologic complex and detecting the formation of the immunologic complex such that presence or absence of the immunologic complex correlates with presence or absence of tau protein.

EXAMPLES

Example 1: Generation and Screening of Hybridomas and Antibodies

The objective of this study was to generate and screen anti-Tau mAbs (monoclonal antibodies). Hybridomas were generated by fusion of tau vaccine immunized mouse spleen with a myeloma cell line. The hybridomas were assessed for reactivity against both phosphorylated and non-phosphorylated full-length Tau protein, as well as the phosphorylated and non-phosphorylated Tau antigenic peptides used in the vaccine preparation. Hybridoma screening was also performed for reactivity of hybridomas supernatant for tau tangles using immunochemistry on Tau transgenic mouse brain slices.

1.1 Methods
1.1.1 Fusion

A wild type C57BL/6 mouse vaccinated with ACI-33 (Tau5-20 [pY18]) was used for hybridoma production. The mouse was boosted with ACI-33 vaccine on day 0 then again on day 4 and the fusion was performed on day 7. 173×10$^6$ (ACI-33), splenocytes from the immunized mouse were fused with SP2-O-Ag14 myeloma cells at a ratio of 5 splenocytes/1 myeloma cell.

A wild type C57BL/6 mouse vaccinated with ACI-35 (Tau393-408 [pS396, pS404]) was used for hybridoma production. The mouse was boosted with ACI-35 vaccine on day 0 then again on day 4 and the fusion was performed on day 6×10$^7$ (ACI-35), splenocytes from the immunized mouse were fused with 2×10$^7$ SP2-O-Ag14 myeloma cells at a ratio of 3 splenocytes/1 myeloma cell.

A wild type C57BL/6 mouse vaccinated with ACI-36 (Tau401-418 [pS404/S409]) was used for hybridoma production. The mouse was boosted with ACI-36 vaccine on day 0 then again on day 4 and the fusion was performed on day 7. 84×10$^6$ splenocytes from the immunized mouse were fused with SP2-O-Ag14 myeloma cells at a ratio of 5 splenocytes/1 myeloma cell.

A wild type C57BL/6 mouse vaccinated with ACI-41 (mix of Tau206-221 [pT212/pS214] and Tau196-211 [pS202/pT205]) was used for hybridoma production. The mouse was boosted with ACI-41 vaccine on day 0 then again on day 4 and the fusion was performed on day 8. 162×106 splenocytes from the immunized mouse were fused with SP2-O-Ag14 myeloma cells at a ratio of 5 splenocytes/1 myeloma cell.

The four fusions resulted in 8×96 well plates and the clones were name according to the plate (1-8) then the row (A-G) and finally the column (1-12).
1.1.2 Screening Method to Select Clones The 8×96 well plates were first screened twice for IgG expression. Positive expressing clones were then transferred in 24 well plates and cell supernatants (=clones) of growing cells were tested in a Tau ELISA screen and a immunohistochemistry TAUPIR screen. Positive supernatants in ELISA and/or TAUPIR were transferred to T25 flasks and clones were screened again for IgG expression in aTau ELISA screen and TAUPIR screen.
1.1.3 IgG Screen Elisa plates were coated with 50 ul/well of anti-mouse IgG antibody (CER Groupe, Marloie, Belgium) in coating buffer for 16 hrs at 4° C. After washing plates with PBS/Tween 100 ul/well of a blocking solution was applied for 1 hr at RT. 50 ul of undiluted hybridoma supernatant were incubated for 1 hr at RT. After a washing step, a mix of the HorseRadish Peroxydase (HRP)-conjugated anti-mouse IgG1, IgG2a, IgG2b and IgG3 (Ab Serotec, Raleigh, N.C., USA) was applied on the plates for 1 hr at RT. After a final washing, detection was performed with TMB (3-3',5,5'-tetramethylbenzidine), the phosphatase substrate for HRP, and plates were read at 405 nm using an ELISA plate reader. Results are expressed as O.D. (Optical Density).
1.1.4 Hybridomas Tau ELISA Screen Hybridomas ELISA screen was performed on pTau peptide (ACI-33, T1.5: Tau5-20 [pY18]; ACI-35, T3.5: Tau393-408[pS396/pS404]; ACI-36, T4.5: Tau401-418 [pS404/S409]; ACI-41, T8.5: Tau206-221 [pT212/pS214] and T9.5: Tau196-211 [pS202/pT205] PolyPeptide Laboratories, HiHerød, Denmark), corresponding Tau peptide (ACI-33, T1.6: Tau5-20; ACI-36, T4.6: Tau401-4; ACI-41, T8.6: Tau206-221 and T9.6: Tau196-211, PolyPeptide Laboratories, HiHerød, Denmark), phosphorylated full-length (441aa) Tau protein (pTau protein, Vandebroek et al., 2005) and full-length (441aa) Tau protein (Tau protein, SignalChem, Richmond, Canada). Finally Bovine Serum Albumin (BSA) was used as negative control.

Plates were coated with 10 μg/ml of corresponding Tau peptide and 1 μg/ml of corresponding Tau protein overnight at 4° C. After washing each well with PBS-0.05% Tween 20 and blocking with 1% BSA in PBS-0.05% Tween 20, undiluted hybridoma supernatant or medium negative control were added to the plates and incubated at 37° C. for 2 hours. After washing plates were incubated with an alkaline phosphatase (AP)-conjugated anti-mouse IgG total antibody (Jackson Laboratories, Baltimore, Pa., USA) for 2 hours at 37° C. After washing plates were incubated with pNPP (para-nitro-phenyl-phosphate), the phosphatase substrate for AP, and read at 405 nm using an ELISA plate reader. Results are expressed as O.D. (Optical Density).
1.1.5 Hybridomas IHC Screen: Binding of Anti-Tau Antibodies to Tangles in Brain Sections from Transgenic Mice (TAUPIR)

TAUPIR experiments were done according to protocol from EXAMPLE 3.1.2.
1.1.6 T25 Flasks IgG Screen Elisa plates were coated with 5 ug/ml of anti-mouse IgG F(ab')2 fragment specific antibody (Jackson Laboratories, Baltimore, Pa., USA) in carbonate-bicarbonate coating buffer pH 9.6 (Sigma, Buchs, Switzerland) overnight at 4° C. After washing plates, undiluted hybridoma supernatant, positive control IgG1 antibody (6E10 at 1 ug/ml: Covance, Emeryville, Calif., USA) or negative control (culture medium alone) were incubated for 1 hr at RT. After a washing step, the secondary AP-conjugated goat anti-mouse IgG (subclasses 1+2a+2b+3) Fcγ fragment specific antibody (Jackson Laboratories, Baltimore, Pa., USA) was incubated on the plates for 2 hrs at 37° C. After a final washing, detection was performed with pNPP (para-nitro-phenyl-phosphate), the phosphatase substrate for AP, and plates were read at 405 nm using an ELISA plate reader. Results are expressed as O.D. (Optical Density).

1.2 Results 1.2.1 ACI-33 Hybridomas

The cell supernatants from the 8×96 well plates resulting from the fusion were screened for production of IgG. In the 768 wells (8×96 wells) tested 277 wells were positive for IgG expression and were transferred to 24 wells plates. In the 24 well plates 79 clones were growing and supernatant from those cells were analysed. Positive clones were further transferred in T25 flasks and supernatants screened for IgG production, ELISA and TAUPIR (Table 2).

The clone 6C10 was the only one positive in the 3 screens and was selected for subcloning.

1.2.2 ACI-36 Hybridomas

The cell supernatants from the 8×96 well plates resulting from the fusion were screened for production of IgG. In the 768 wells (8×96 wells) tested 333 wells were positive for IgG expression and were transferred to 24 wells plates. In the 24 well plates 75 clones were growing and supernatant from those cells were analysed. Positive clones were further transferred in T25 flasks and supernatants screened for IgG production, ELISA and TAUPIR (Table 3).

In order to select clones for the next steps a ranking of all supernatants positives for IgG/ELISA/TAUPIR screens was performed based on the ELISA and TAUPIR results. Ranking the ELISA and TAUPIR results was performed as explained in the methods section. TAUPIR staining was almost identical for the five first clones and this corresponded to the ELISA results. 4C12 was discarded as it was found in the same plate as 4C1 which increased the likelihood of the 2 clones being the same (recognizing the same epitope). The best 4 clones selected were 3A8, 2B6, 4C1 and 6H1. The other 6 clones (4C12, 2G1, 2F9, 7D6, 3B9, 4E12) were kept as back-up.

A ranking of the 10 clones that showed positivity in ELISA screen and TAUPIR screen was performed to select the best ones (Table 4). The best 5 clones are indicated with underlining and italics.

1.2.3 ACI-41 Hybridomas

The cell supernatants from the 8×96 well plates resulting from the fusion were screened for production of IgG. In the 768 wells (8×96 wells) tested 215 wells were positive for IgG expression and were transferred to 24 wells plates. In the 24 well plates 81 clones were growing and supernatant from those cells were analysed. Positive clones were further transferred in T25 flasks and supernatants screened for IgG production, ELISA and TAUPIR (table 5).

The clones 5D10 and 7C2 were the only ones positive in the 3 screens and were selected for subcloning. The clone 5D10 binds only the peptide T8.5, while the clone 7C2 binds to the two peptides of the ACI-41 vaccine (T8.5 and T9.5) (see FIG. 10 in PCT application PCT/EP2010/054418).

The subclone 5D10A4 originating from 5D10 was specific for pTau peptide.

1.3. Conclusion

The antibodies generated have shown high specificity to pTau peptides with only marginal binding to non-phosphorylated peptides.

From the 4 fusions (ACI-33, ACI-36, ACI-35 and ACI-41), a total of 16 clones were deposited at DSMZ (table 1) and selected for further subcloning.

The positive motherclones mentioned above were further cultivated in 96 well plates, then 24 well plates and finally T25 flasks. At each stage, the supernatants of the hybridoma clones were screened by ELISA, Taupir and Western Blot.

Example 2: Cloning of Antibody Light Chain and Heavy Chain Variable Regions

Antibody heavy and light variable region genes from the hybridoma cells are cloned and the DNA sequences and location of the complementarity determining regions (CDRs) determined as well as the antibodies binding features.

Total RNA was prepared from $3\times10^6$ hybridoma cells (1 vial) using the Qiagen RNeasy mini kit (Cat No: 74104). RNA was eluted in 50 mL water and checked on a 1.2% agarose gel.

$V_H$ and $V_K$ cDNAs were prepared using reverse transcriptase with IgG and kappa constant region primers. The first strand cDNAs were amplified by PCR using a large set of signal sequence primers. The amplified DNAs were gel-purified and cloned into the vector pGem® T Easy (Promega). The $V_H$ and $V_K$ clones obtained were screened for inserts of the expected size. The DNA sequence of selected clones was determined in both directions by automated DNA sequencing. The locations of the complementarity determining regions (CDRs) in the sequences were determined with reference to other antibody sequences (Kabat E A et al., 1991).

Example 3: Binding Studies I

The objective was to measure the phospho-Tau (pTau) binding of the antibodies generated from subcloned hybridomas derived from mice immunized with the tau liposomal vaccines. To test this, an enzyme-linked immunosorbant assay (ELISA) was used to measure the binding of the purified antibodies to both phosphorylated and non-phosphorylated full-length Tau protein, as well as the phosphorylated and non-phosphorylated Tau antigenic peptides used for the liposomal vaccine preparation.

The screening was completed by two other methods. Immunohistochemistry (IHC) on brain sections from a Tau transgenic animal (TAUPIR) using an anti-tau antibody as the primary antibody was done. Additionally, a western blot (WB) on brain protein homogenates from Tau transgenic mice was performed, using an anti-tau antibody as the blotting antibody.

3.1 Methods 3.1.1 Phospho-Tau Binding Assay

The anti-phospho Tau antibodies (mouse IgG3 isotype) were generated from liposomal tau vaccinated mice. The liposomal vaccines are phosphorylated preparations of a phospho-Tau (pTau) peptide. The hybridoma sub-clones producing the anti-tau antibodies were selected by limiting dilution from the mother-clones. Isotyping was done to indicate the presence of a single isotype clone. The antibodies was produced in roller-bottles, purified by affinity chromatography, subjected to sterile 0.22 μm filtration, and quantified. To test the binding of the antibody to Tau and pTau, an ELISA assay was used. Briefly, Nunc MaxiSorp 96-well plates (Nunc, Roskilde, Denmark) were coated with 1 μg/mL of full-length (441 aa) Tau protein (SignalChem, Richmond, Canada) or phosphorylated full-length (441 aa)

Tau protein (Vandebroek et al., 2005). Additionally, plates were coated with 10 µg/mL of the Tau-derived peptide. To test for cross-reactivity to Tau and pTau sequences that were not used in the vaccine preparation, plates were coated with 10 µg/mL of the following peptides: Tau5-20 (phosphorylated or not on Y18), Tau393-408 (phosphorylated or not on S396 and S404), Tau401-418 (phosphorylated or not on S404 and S409), Tau206-221 (phosphorylated or not on T212 and S214), and Tau196-211 (phosphorylated or not on S202 and T205). Coating was done overnight in phosphate-buffered saline (PBS) at 4° C. Plates were washed thoroughly with 0.05% Tween20/PBS and then blocked with 1% bovine serum albumin (BSA) in 0.05% Tween20/PBS for 1 hr at 37° C. The antibody being tested was then added in an 8 or 16 two-fold dilution series between 20 and 0 µg/mL, and allowed to incubate for 2 hr at 37° C. Plates were then washed as described previously, and AP-conjugated anti-mouse IgG secondary antibody (Jackson ImmunoResearch Laboratories, Suffolk, England) was added at 1/6000 dilution in 0.05% Tween20/PBS for 2 hr at 37° C. After washing, plates were incubated with p-nitrophenyl phosphate disodium hexahydrate (pNPP; Sigma-Aldrich, Buchs, Switzerland) phosphatase substrate solution, and read at 405 nm following 2 or 16 hr incubation using an ELISA plate reader. Results are expressed as optical density (O.D.).

3.1.2 Binding of Anti-Tau Antibody to Tau Tangles in Brain Sections from a Tau Transgenic Animal (TAUPIR)

Brain slices used were from old (>18 months old) double transgenic biGT (GSK-3β transgenic mice crossed with TPLH mice, containing the longest isoform (441aa) of human Tau with the P301L mutation) transgenic mice. Additionally, sections from Tau knock-out mice (TKO; 6 months old) were also used. Brain sections were washed for 5 min in PBS then incubated for 15 min at RT in 1.5% $H_2O_2$ in PBS:MeOH (1:1) to block endogenous peroxidase activity. After washing the sections 3 times in PBST (PBS/0.1% TritonX100) they were incubated for 30 min at RT in PBST+10% FCS (fetal calf serum) blocking solution. The incubation with the anti-Tau antibody being tested was done overnight at 4° C. at indicated dilutions in PBST/10% FCS. Sections were next washed 3 times in PBST before incubation with an HRP-conjugated goat anti-mouse (purchased from Dako, Glostrup, Denmark) secondary antibody in PBST/10% FCS for 1 hour at RT. Prior to detection, sections were washed 3 times with PBST and incubated in 50 mM Tris/HCl pH7.6 for 5 min. Detection was done by incubating the sections for 3 min in Diaminobenzidine (DAB: 1 tablet in 10 ml of 50 mM Tris.HCl+3 ul $H_2O_2$ 30%; MP Biomedicals, Solon, Ohio, USA). The reaction was stopped by washing the sections 3 times in PBST. Sections were then transferred onto silanized glass-plates and air-dried on warm-plate at 50° C. for 2 hours. Counterstaining was done using incubation with Mayers hematoxylin (Fluka Chemie, Buchs, Switzerland) for 1 min, followed by a washing step for 4 min in running tap-water. Sections were dehydrated by passing in 50%, 70%, 90% and twice in 100% ethanol bath then in Xylol 2 times for 1 min. Finally sections were mounted with DePeX (BDH Chemicals Ltd., Poole, England) under glass cover-slips.

Additionally, hybridoma supernatants at 1/10 dilution (all ACI-35-derived antibodies shown in Table 1) were used to blot membranes containing SDS-PAGE separated brain homogenate proteins from Tau transgenic mice, wild-type mice, or Tau knock-out mice.

3.1.3. Binding of Anti-Tau Antibody to Tau Tangles in Brain Sections from AD and Tauopathy Patients (TAUPIR)

The assay for the immunoreaction of the anti-pTau antibody ACI-36-3A8-Ab1 to pTau in human brain was done by TAUPIR. Brain paraffin sections were de-paraffinized by passing in Xylol 2 times for 5 min and 2 times for 1 min in 100% EtOH, followed by 1 min wash in 90%, 70%, and 50% EtOH and distilled water, followed by 2 times 5 min washes in PBS. For antigen retrieval, sections were treated by heating for 10 min in 0.01 M citric acid solution in water (pH 6.0) and cooled down for 20 min. Sections were incubated for 15 min at RT in 1.5% $H_2O_2$ in PBS:MeOH (1:1) to block endogenous peroxidase activity. After washing the sections 3 times in PBST (PBS/0.05% Tween-20), they were incubated for 30 min at RT in PBST+10% fetal calf serum (FCS) as blocking solution. The incubation with the primary anti-pTau antibody ACI-36-3A8-Ab1 (410 ng/mL in blocking buffer) was done overnight at 4° C. Sections were then washed 3 times in PBST before incubation with HRP-conjugated goat anti-mouse secondary antibody (Dako, Glostrup, Denmark) diluted 1/500 in PBST/10% FCS, for 1 hour at RT. Prior to detection, sections were washed 3 times with PBS and incubated in 50 mM Tris/HCl pH 7.6 for 5 min. Detection was done by incubating the sections for 3 min in diaminobenzidine (DAB: 1 tablet in 10 mL of 50 mM Tris-HCl+3 µL $H_2O_2$ 30%; MP Biomedicals, Solon, Ohio, USA). The reaction was stopped by washing the sections 3 times in PBS. Counterstaining was done by incubating with Mayer's hematoxylin (Fluka Chemie, Buchs, Switzerland) for 1 min, followed by washing for 4 min in running tap-water. Sections were dehydrated by passing through 50%, 70%, 90% and twice in 100% ethanol baths, followed by Xylol for 2 times 1 min.

Finally, sections were mounted with DePeX (BDH Chemicals Ltd., Poole, England) under glass cover-slips. Stained sections were examined by white light microscopy and digital images taken with a 3CCD camera (Leica, Wetzlar, Germany). Images were captured and analyzed using dedicated software (IM500, Leica). Images are shown at 20×1.6 magnification.

3.1.4. Western Blot (WB)

Binding of the test antibody to pTau in the brain extract from transgenic animal was done by WB. Brain homogenization from wild-type FVB, TPLH, biGT and TKO mice was done in the following buffer: 25 mM Tris/HCl pH7.6, 150 mM NaCl, 1 mM EDTA, 1 mM EGTA, 30 mM NaF, 0.2 mM $Na_3VO_4$, 1 nM Okadaic acid, 1 mM phenylmethylsulfonyl fluoride (PMSF), 5 mM Na4P2O7, 1 tablet complete protease inhibitor cocktail (CPIC) per 12 ml total. To obtain total brain homogenate the brain was homogenized on ice in 1 vol/weight hemisphere (ml/g) with a motor-driven potter-like glass tube/teflon pestle at 700 rpm. Total brain homogenates were diluted by half in sample buffer (125 mM Tris/HCl pH6.8, 4% (w/v) sodium dodecyl sulfate (SDS), 20% glycerol, 0.01% bromophenol blue and 5% beta-mercapto-ethanol), then heated rapidly to 95° C. Samples were kept 5 min, diluted 1/4 in sample buffer, heated again to 95° C. and then cooled down and spun at 14.000 rpm for 5 min to clear debris that were not solubilized. Supernatants were collected and loaded onto a SDS-PAGE gel. The transfer to nitrocellulose membrane (Hybond-ECL) was done in transfer buffer (25 mM Tris pH 8.6, 190 mM Glycine, 20% methanol). Membranes were transferred to the blocking solution (0.1% Tween in TBS (50 mM Tris.HCl, pH7.6, 150 mM NaCl, and 5% dry-milk powder) prior to overnight incubation at 4° C. with the test antibody diluted in the blocking solution. Incubation with secondary antibody HRP-conjugated goat anti-mouse (Dako, Glostrup, Denmark) diluted 1/10,000 in blocking solution was performed at RT for 1 hour. Detection was done using the ECI Western Blotting Detection Reagents from GE Healthcare.

3.2 Results 3.2.1 ELISA Assays and TAUPIR Using Brain Sections from Tangle Positive Tau Transgenic Mice The binding of antibodies were measured against the phosphorylated Tau peptide used as the immunogen, and against the phosphorylated full-length human Tau protein. This is the longest isoform of human Tau protein consisting of 441 amino acids. The corresponding non-phosphorylated peptide and full-length human Tau protein were also included. As indicated in the table 6 antibodies demonstrated high binding to the phosphorylated Tau peptide, with only limited or no binding to the phosphorylated full-length human Tau protein. No binding was observed to the corresponding non-phosphorylated Tau peptide or to the non-phosphorylated full-length human Tau protein. This demonstrates high binding of anti-tau antibodies to phosphorylated human Tau peptides.

To test for non-specific binding to other phosphorylated and non-phosphorylated Tau sequences, the antibody was tested for binding to five phospho and non-phospho Tau peptides one of which was used as the antigen peptide sequence. No cross-reactivity to phospho or non-phospho Tau peptides, other than the peptide used in the vaccine was observed, even at high concentrations of peptide.

The binding of anti-tau antibodies to pTau in brains of Tau transgenic mice was evaluated by TAUPIR staining (FIG. 1) and by WB (FIG. 1). Antibodies demonstrated binding to Tau tangles and neuropil threads present in cortex and hippocampus in brains of Tau transgenic (biGT) mice. The antibody dilutions used for the TAUPIR ranged from 0.05 to 0.0033 ug/mL. Anti-tau antibodies were also used as a primary antibody in a WB using total brain homogenates from wild-type FVB, TPLH, biGT and TKO mice, and separated by SDS-PAGE. Two commercial anti-pTau antibodies were used as controls, MC1 and Tau5. All anti-tau antibodies bound to pTau present in brains of Tau transgenic mice. Blotting On membranes containing SDS-PAGE separated protein homogenates from Tau transgenic mice, wild-type mice, and Tau knock-out mice, all ACI-35 antibodies (disclosed in Table 1) bound to protein bands having identical 46 kDa migration pattern as Tau and pTau (data not shown).

3.2.2 TAUPIR Study in Brain Sections from AD and Tauopathy Patients

Figure 2:
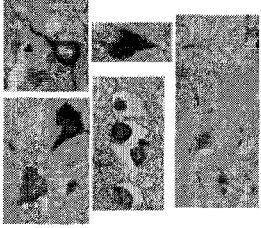
FIG. 2 shows antibody binding to phospho-Tau in brain sections from AD and tauopathy patients using TAUPIR using ACI-36-3A8-Ab1 antibody.
Figure 2:
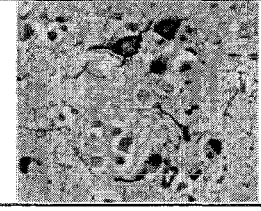
Figure 2:
Figure 2:
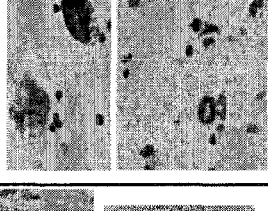
Figure 2:
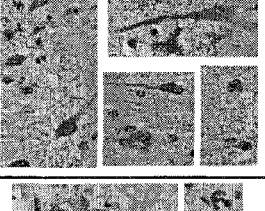
Figure 2:
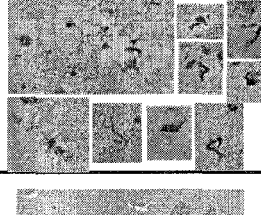
Figure 2:
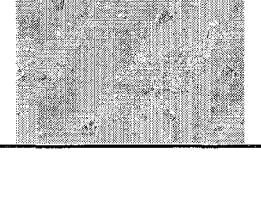

The ability of antibody ACI-36-3A8-Ab1 to bind to Tau-aggregates, lodged in human brain sections from subjects with diagnosed tauopathies, including AD, FAD, AGD, FTDP-17, CBD, and PSP, was examined by TAUPIR immunohistochemistry (FIG. 2). The anti-pTau antibody ACI-36-3A8-Ab1 bound to pTau containing neurofibrillary tangles (NFTs), neuropil threads in human brain sections, and other forms of pTau accumulations present in neurons and in glial cell-types. More specifically, ACI-36-3A8-Ab1 prominently stained NFTs, neuropil threads, and dystrophic neurites surrounding amyloid plaques in AD brains, which was readily apparent in the subjects diagnosed with AD and FAD. In brain sections from AGD, ACI-36-3A8-Ab1 stained both NFTs and neuropil threads, with multiple argyrophilic grains/granules clearly visible (FIG. 2,). Staining of brain sections from PSP with ACI-36-3A8-Ab1 showed NFTs, neuropil threads, and dystrophic neurites. Additionally, Pick body-like inclusions and tufted pTau positive astrocytes were clearly noted, being an abundant feature in PSP, where pTau staining extends throughout the cell, including in distal processes. In FTDP-17, the staining pattern also illustrated the known heterogeneity of the disease, with not only NFTs but also achromatic "ballooned" neurons detected. The ACI-36-3A8-Ab1 antibody also stained swollen achromatic neurons that were faintly Tau-positive, the main characteristic of CBD. Another prominent pathological feature of CBD, i.e. oligodendroglial inclusions, called coiled bodies, were also well detected by the ACI-36-3A8-Ab1 antibody. No staining was detected in an AT8-negative control subject whereas weak staining was identified in an AT8-positive control subject.

Using TAUPIR on human brain sections from subjects previously diagnosed with different forms of tauopathy, the anti-pTau antibody ACI-36-3A8-Ab1 demonstrated good binding to various known pTau-rich pathological features present in the brains of these subjects.

Example 4: Binding Studies II

The objective of the study was to determine the binding affinity between anti-tau antibodies and the phospho-tau peptide using Surface Plasmon Resonance (SPR). Phospho-tau peptide correspond to the peptide sequence used in the vaccine preparation to generate the anti-tau antibody. To study this interaction, phosphopeptides were immobilized to the surface of a sensor chip and the binding monitored in real-time using SPR upon passing antibody over the chip.

4.1 Methods 4.1.1 SPR Binding Assay

All SPR experiments were carried out on a Biacore X instrument (GE Healthcare). Reagents for immobilization (EDC, NHS and Ethanolamine), sensor chip CM5 (carboxymethyl dextran) as well as running buffer HBS-EP were purchased from GE Healthcare. Phospho-tau peptide were solubilized in PBS/sodium acetate buffer (10 mM, pH 5.0) in a 1:1 (v/v) ratio to give a final peptide concentration of 250 μg/ml. This peptide solution was then coupled via to flow cell (fc) 2 of a CM5 sensor chip that was preactivated using EDC/NHS. After coupling, Ethanolamine was passed over the surface and giving a final immobilization level of 218 RUs. Five concentrations of the anti-tau antibodies were assayed by serial dilutions using running buffer. Injections were performed starting from the lowest concentration and were passed over both fc 1 and 2 at a flow rate of 30 μL/min for 180 s. Flow cell 1 was underivatized and responses were subtracted from fc 2 to correct for instrument noise and bulk refractive changes. After injection was finished, the surfaces were washed immediately with running buffer for 300 s. To remove remaining bound antibody from the chip, surface regeneration was performed by injecting a pulse (typically 3 μl) of 8 mM NaOH in water containing 1M NaCl. Kinetic analysis was performed using algorithms for numerical integration and global analysis using BIAevaluation 3.0. The sensograms obtained for injections of antibody at different concentrations were overlaid and the baselines adjusted to zero. For curve fitting, all data were fit simultaneously to a 1:1 homogeneous (Langmuir) model.

Alternatively, immobilized biotinylated T3 peptide (T3.30) was immobilized to a Streptavidin Biacore SA chip (GE Healthcare) using a Biacore X instrument. Antibodies were diluted in HBS-EP running buffer (GE Healthcare) and injected at 50 ul/min for 120 s followed by 100 s dissociation. Surface regeneration was performed using a pulse (1-3 ul) of 16 mM NaOH. Fitting was performed using BIAevaluation and assuming a 1:1 Langmuir binding interaction.

Peptides Used

| | | |
|---|---|---|
| T1.5 | H-K(Ac)K(Ac)-RQEFEVMEDHAGTY[PO3H2]GL-K(Ac)K(Ac)-NH2 | lot AW11309D |
| T4.5 | H-K(Ac)K(Ac)-GDTS[PO3H2]PRHLS[PO3H2]NVSSTGSID-K(Ac)K(Ac)-NH2 | lot CF09168 |
| T3.30 | Biotin-LC linker-GVYKS[PO3H2]PVVSGDTS[PO3H2]PRHL-NH2 | lot MI89P9-P12-2 |

4.2 Results

The binding of the anti-tau antibodies to the phosphorylated Tau peptide was monitored in real-time using SPR. Analyses of the association and dissociation phases of antibody binding could be used to determine the association rate constant ($k_a$), dissociation rate constant ($k_d$) as well as dissociation constant $K_D$. Antibody ACI-33-6C10-Ab1 binds specifically to peptide T1.5 over the non-derivatized carboxymethyl dextran surface in the range 3.7→367 nM of antibody. Kinetic analyses of the sensograms revealed a fast association rate constant of $9.46 \times 10^5$ $M^{-1}s^{-1}$ and a dissociation rate constant of $3.27 \times 10^{-3}$ $s^{-1}$ (Table 7). The dissociation constant $K_D$ was determined therefore to be 3.46 nM showing that the antibody recognizes the phosphopeptide T1.5 with very high affinity. All tested antibodies displayed a high affinity to their respective phosphopeptides used for immunization and hybridoma generation, but they displayed little affinity to non-phosphopeptides.

Example 5: Epitope Mapping of Anti pTau Antibodies

5.1 Methods

Epitope mapping of anti-phospho Tau mouse monoclonal antibodies was performed by ELISA using different phospho and non-phospho peptide libraries. The amino acid sequences of peptide libraries used are shown in Table 8. Each library consisted of short biotinylated peptides spanning phospho and non-phospho sequences present in the peptide vaccine. Peptide libraries were purchased from ANAWA Trading SA. Epitope mapping was done according to the manufacturer's (Mimotopes) instructions. Briefly, streptavidin coated plates (NUNC) were blocked with 0.1% BSA in phosphate-buffered saline (PBS) overnight at 4° C. After washing with PBS-0.05% Tween 20, plates were coated for 1 hr at RT with the different peptides from each library, diluted in 0.1% BSA, 0.1% sodium azide in PBS to a final concentration of 10 µM. After washing, plates were incubated for 1 hr at RT with the antibody to be tested diluted to 40 ng/ml in 2% BSA, and 0.1% sodium azide in PBS. Plates were washed again and incubated with AP-conjugated anti-mouse IgG secondary antibody (Jackson ImmunoResearch Laboratories, Suffolk, England) at 1/6000 dilution for 1 hr at RT. After a final wash, plates were incubated with p-nitrophenyl phosphate disodium hexahydrate (pNPP; Sigma-Aldrich, Buchs, Switzerland) phosphatase substrate solution, and read at 405 nm following 2 hr incubation using an ELISA plate reader. Binding was considered positive if the optical density (O.D.) was at least 2-times over background O.D.

5.2 Results

As a result of the epitope mapping experiments, epitopes could be identified including the required phosphorylated amino acid residue (see table 9) to which the antibodies disclosed herein specifically bind.

Tau aa 15-20, with requirement for pY18 (6C10F9C12A11; 6C10E5E9C12)

Tau aa 405-412, with requirement for pS409 (6H1A11C11; 6H1G6E6)

Tau aa 405-411, with requirement for pS409 (2B6A10C11; 2B6G7A12; 3A8A12G7; 3A8E12H8)

Tau aa 208-218, with requirement for pT212 and pS214 (7C2(1)F10C10D3)

Tau aa 393-401, with requirement for pS396 (A4-2A1-18; A4-2A1-40)

Tau aa 396-401, with requirement for pS396 (A4-4A6-18)

Tau aa 394-400, with requirement for pS396 (A6-1D2-12)

Tau aa 402-406, with requirement for pS404 (A6-2G5-08)

Tau aa 393-400, with requirement for p396 (A6-2G5-30; A6-2G5-41)

Example 6: 1-Week Passive Immunization of Tau Transgenic Mice

6.1. Methods

For all in vivo studies, Tau transgenic mice were used and administered the treatment antibodies as shown in the Table below.

Transgenic Mice and Antibodies Used for In Vivo Studies

| Study no. | Tau transgenic model | Age of mice at study start (months) | Study duration (weeks) | Antibodies administered | Doses (mg/kg) | Number of i.p. administrations | Readout |
|---|---|---|---|---|---|---|---|
| 1 | TMHT (hTau$^{V337M/R406W}$) | 6.3 | 1 | ACI-36-2B6-Ab1 | 0*, 3 or 10 | 2 | MSD, IHC, WB |
| | | | | ACI-36-3A8-Ab1 | 0 or 3 | | |
| 2 | TMHT (hTau$^{V337M/R406W}$) | 4.2 | 4 | ACI-36-2B6-Ab1 or ACI-36-3A8-Ab1 | 0, 1 or 3 | 4 | MSD, IHC, WB, MWM |
| 3 | TMHT (hTau$^{V337M/R406W}$) | 3.0 | 12 | ACI-36-2B6-Ab1 or ACI-36-3A8-Ab1 | 0, 1 or 3 | 13 | MSD, IHC, WB, MWM |

-continued

| Study no. | Tau transgenic model | Age of mice at study start (months) | Study duration (weeks) | Antibodies administered | Doses (mg/kg) | Number of i.p. administrations | Readout |
|---|---|---|---|---|---|---|---|
| 4 | biGT (hTau$^{P301L}$ × hGSK3β) | 4.5 | 12 | ACI-36-2B6-Ab1 or ACI-36-3A8-Ab1 | 0, 1 or 3 | 13 | WB |

*vehicle control for all of the studies; intraperitoneally (i.p.)

6.1.1. Mice and Treatments

Female and male 6.3 months old (±3 days) Tg mice over-expressing the full-length human TAU isoform TAU441, bearing the missense mutations V337M and R406W under the control of murine Thy-1 promoter (TMHT mice), were used for Study no. 1 (see Table above). Mice were euthanized 1 day following the last administration to determine TAU pathology in the brain.

6.1.2 Animal Identification and Housing

In the course of tail tipping for genotyping, animals were numbered consecutively by classical earmarking. All animals were re-genotyped prior to the start of the study. Mice were kept according to the JSW Standard Operating Procedures based on international standards. Animals were housed in individual ventilated cages on standardized rodent bedding supplied by Rettenmaier®. The temperature was maintained at approximately 24° C. and the relative humidity was maintained between 40 to 70%. Animals were housed under a constant light-cycle (12 hours light/dark). Dried, pelleted standard rodent chow (Altromin®) and normal tap water were available to the animals ad libitum. Each individual animal was checked regularly for any clinical signs that were noted in the individual animal datasheet.

6.1.3 In Vivo Bleedings

Seven days before the first immunization, in vivo bleedings were performed by mandibular sampling from the facial vein/artery. The blood samples are a mixture of venous and arterial blood. To get plasma, blood was collected in heparin tubes and centrifuged (1000×g, 10 minutes, room temperature). Plasma was frozen in two aliquots until used.

6.1.4. Immunohistochemical (IHC) Quantitation

All cryo-frozen brain hemispheres were analyzed. 15 cryo-sections per level (altogether 5 levels), each 10 µm thick (Leica CM 3050S) were sagittally cut. Brain levels were chosen according to the morphology atlas "The Mouse Brain" from Paxinos and Franklin (2nd edition). The cut of the five levels started with a random slice then sampling continued uniformly and systematically, always retaining 15 slices per level in series and discarding 150 µm in between the levels. For determination of TAU pathology in the hippocampus and the amygdala 5 slices (1 from each level) per brain region and animal were stained using AT180 (# MN1040, Thermo Scientific) and HT7 (# MN1000, Thermo Scientific) antibodies. The primary antibodies were visualized by Cy-3-coupled secondary antibody (Jackson Laboratories) and subsequently immunoreactive area were evaluated using Image Pro Plus (v6.2) software.

Immunoreactive objects were measured above a size restriction (30 µm$^2$ in the amygdala, 7 µm$^2$ in the hippocampus) and above a dynamic intensity threshold. Total area and intensity of objects and the individual threshold were automatically filed. If used, a dynamic threshold was defined as "mean intensity within AOI plus factor times the standard deviation of pixel intensities within the AOI". In any case, values had to exceed a minimal set threshold. Exact threshold levels are given in the table below.

| Thresholds | Minimum | Dynamice factor |
|---|---|---|
| AT180 Amygdala | 25 | 2 |
| AT180 Hippocampus | 28 | — |
| HT7 Amygdala | 35 | 2 |
| HT7 Hippocampus | 25 | 0.5 |

The region size was measured by manual delineation of the hippocampus and amygdala. HT7 and AT180 IR area data were normalized to the regions size.

All IHC related data with n>4 followed a Gaussian distribution according to Kolmogorov Smirnov normality test and are represented as mean+SEM. For the vehicle group consisting of four animals only, thus too few for normality testing, Gaussian distribution was assumed. Group differences were calculated by means of a parametric one-way ANOVA followed by Newman Keuls post hoc testing, calculated with GraphPadPrism software. The alpha-error level was set to 0.05.

Brain TAU pathology was determined in hippocampus and amygdala by immunohistochemical (IHC) quantitation using AT180 (anti-pTAU) and HT7 (anti-TAU) antibodies. Furthermore, the treatment effects on soluble pTAU and TAU in cortex and hippocampus was measured in the soluble homogenate fraction using MesoScale Discovery (MSD) duplex technology, probing for pTAU and total TAU.

None of the antibodies used for either the IHC or the MSD assays have an epitope that overlaps with the two treatment antibodies used in this study.

6.1.5. Generation of Fraction for the Quantification of Soluble Tau Protein Level in the Soluble Brain Fractions of Tg Mice Mice treated according to method 6.1.1. were euthanized 1 day following the second administration to determine Tau pathology in the brain. Briefly, soluble cortex samples from one brain hemisphere were homogenized in 100 to 200 µL of cold extraction buffer (25 mM Tris-HCl pH=7.4, 150 mM NaCl, 1 mM EDTA, 1 mM EGTA, 10 mM β-glycerophosphate, 30 mM NaF, 2 mM Na$_3$VO$_4$, protease and phosphatase inhibitor cocktail). The homogenates were centrifuged (74,200×g for 15 min at 4° C.) and the supernatants were used for the analysis of soluble Tau. The concentration of total protein in the soluble fractions of cortex samples was determined by a BCA protein quantitation assay (Thermo Fisher Scientific, Rockford, Ill., USA).

6.1.6. Analysis of pTau Presence by Western Blot

To probe for immunoreactivity in the brains of mice administered ACI-36-2B6-Ab2 and ACI-36-3A8-Ab2, two antibodies reported to bind pTau PHF epitopes (Greenberg et al., 1992; Reig et al., 1995; Hoffmann et al., 1997) were used in Western-blot (WB) assays. Soluble fractions from cortex were diluted by adding an equal volume of sample buffer A (125 mM Tris-HCl pH 6.8, 4% [w/v] sodium dodecyl sulfate [SDS], 20% glycerol, 0.01% bromophenol blue, 5% β-mercaptoethanol), and the samples were heated to 95° C. for 10 min. 30 µg of sample was loaded onto a 4-12% Bis-Tris gel (Invitrogen, Basel, Switzerland) and run in MOPS SDS buffer (Invitrogen). Proteins were transferred to a 0.45 µm PVDF membrane in transfer buffer (25 mM Tris pH 8.6, 190 mM glycine, 20% methanol). To verify protein transfer, the membranes were stained with Ponceau S for 5 min, washed, and blocked for 1 hour in blocking buffer (5% BSA in TBS [50 mM Tris-HCl, pH 7.6, 150 mM NaCl]). Membranes were blotted over-night at 4° C. with the primary antibodies in blocking buffer and 0.1% Tween. The two pTau PHF-specific primary antibodies used for the WBs were: anti-pS396 (PHF-13 epitope; AbCam, Cambridge, UK; used at 3 µg/mL), specific to phosphorylated Ser396 (pS396) of human or murine pTau (Hoffmann et al., 1997), and AD2 (PHF-1 epitope; BioRad, Reinach, Switzerland; used at 0.4 µg/mL), specific for human and murine pS396 and phosphorylated Ser404 (pS404; Reig et al., 1995). For total Tau WBs, Tau5 (0.5 µg/mL), an antibody that binds both human and murine Tau (BD Biosciences, Allschwil, Switzerland), was used. Following incubation with the primary antibody, membranes were washed with 0.1% Tween in TBS, and incubated with the secondary antibodies: goat anti-mouse-IRDye800 or goat anti-rabbit-IRDye680 (both from Li-Cor Biosciences, NE, USA), both diluted 1:15000 in BB and 0.1% Tween. Membranes were then incubated 1 hour at room-temperature protected from light, washed for 15 min 3-times with 0.1% Tween in TBS, and for 5 min 2-times with TBS, and bands quantified using Li-Cor Odyssey near-infrared imaging system (Li-Cor). Bands were normalized to β-actin expression (AbCam; used at 0.4 µg/mL). To verify the identification of the human transgenic versus the mouse endogenous Tau bands, blots were probed with an antibody specific for human total Tau (Tau13, AbCam; not shown). Additionally, membranes were probed with an anti-mouse primary antibody, to verify that the treatment antibodies, ACI-36-2B6-Ab2 and ACI-36-3A8-Ab2, were not present in the denatured test samples in sufficient quantity to interfere with the binding of anti-pS396 or AD2. No intact or denatured treatment antibodies were detected (results not shown) in the samples used for this study.

6.1.7. Statistical Analysis

Data were analyzed using non-parametric Kruskal-Wallis rank sum statistics, and if significant at the $P<0.05$ level, a Dunn's post-hoc test was used comparing all groups (GraphPad Prism, GraphPad Software, CA, USA). Results are presented as individual data points showing mean±SEM. Differences with $P<0.05$ were considered as statistically significant.

6.2 Results 6.2.1. Brain TAU Pathology by Immunohistochemical (IHC) Quantitation Two i.p. injections of ACI-36-2B6-Ab2 and ACI-36-3A8-Ab2 did not show any gross adverse effects during the study period. Staining for pT231 and pS235 using AT180 by IHC, showed increased immunoreactive area (IR) in the amygdala following ACI-36-3A8-Ab2 treatment ( ). Mice treated with 3 mg/kg ACI-36-2B6-Ab2 had significantly less AT180 IR area in the hippocampus ( ).

ACI-36-3A8-AB2 treatment increased AT180 IR pTAU compared to the PBS group in the amygdala. In the hippocampus ACI-36-2B6-AB2 treatment decreased pTAU. AT180 specifically labels pTAU. The frequency of AT180 IR cells was decreased in ACI-36-2B6-AB2 treated mice. This effect was stronger in the low dose (3 mg/kg) group (ACI-36-2B6-AB2 LD). The somal staining pattern does not differ among groups.

At the higher 10 mg/kg dose, a non-significant trend for less AT180 IR was seen in the hippocampus for both ACI-36-2B6-Ab2 and ACI-36-3A8-Ab2, when compared to vehicle control treated mice. Qualitatively, ACI-36-2B6-Ab2 treated animals showed a lower number of hippocampal neurons with highly intense AT180 labeling.

Figure 3:
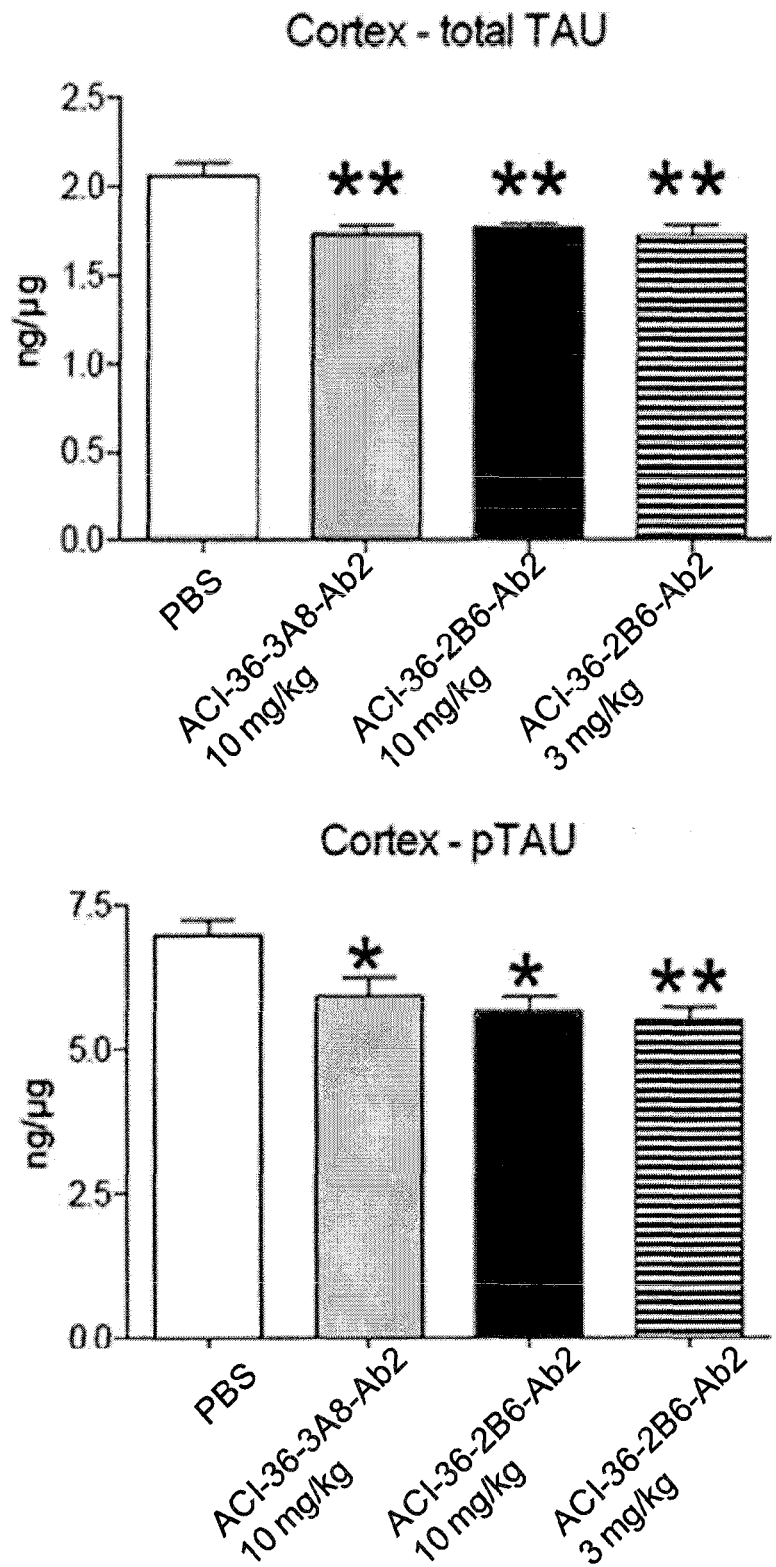
FIG. 3 shows the effect of anti-Tau antibody treatment following 1 week in vivo study on pTau epitope pT231 using MSD.

6.2.2. Reduction of Total Tau Level in Brain Fraction Following Passive Immunization The effect of the treatments on pTAU and TAU in the brain fraction containing soluble proteins was measured using an MSD duplex assay. Levels of total soluble TAU in the cortex was significantly reduced in mice treated with ACI-36-2B6-Ab2 and ACI-36-3A8-Ab2 ($p<0.01$; FIG. 3 upper panel). The levels of soluble pTAU was also significantly reduced ($p<0.05$; FIG. 3 lower panel), with the 3 mg/kg dose of ACI-36-2B6-Ab2 demonstrating the greatest decrease ($p<0.01$). The ratio of pTAU to total TAU remained unchanged. The levels of soluble TAU and pTAU did not change in samples from hippocampus (not shown here).

6.2.3. Effects of ACI-36-2B6-Ab2 and ACI-36-3A8-Ab2 Administration on the Presence of Phospho-Tau Epitopes Present in Paired Helical Filaments (PHFs)

Structurally, neurofibrillary tangles (NFTs) consist of paired helical filaments (PHFs) composed of the microtubule-associated protein Tau, found primarily in a hyperphosphorylated state (Alonso et al., 1997). The objective of this study was to use antibodies that recognize pTau PHF to probe for and quantify these pTau PHF epitopes in the brains of Tau transgenic mice, following the administration of ACI-36-2B6-Ab2 and ACI-36-3A8-Ab2.

To measure the effects of two ACI-36-2B6-Ab2 or ACI-36-3A8-Ab2 administrations on the quantity of well documented Tau PHF phospho epitopes, brain cortex soluble fractions from treated Tau Tg mice were probed with AD2 (PHF-1 epitope, pS396/pS404) and anti-pS396 antibody (PHF-13 epitope, pS396) using WBs. The immunoreactivity was quantified using an infrared imaging system. The effects of ACI-36-3A8-AB2 and ACI-36-2B6-AB2 treatment on AD2 PHF immunoreactivity in the cortex of Tau Tg mice were determined using AD2 which probes for pS396 and pS404, two previously documented PHF phospho residues of Tau (Greenberg et al., 1992; Reig et al., 1995).

Bands, indicating human and mouse pTau phosphorylated on S396 and S404 using the AD2 (PHF-1) antibody, were quantified using a Li-Cor infrared imaging system. Values for individual mice as well as the mean±SEM are determined.

A non-significant trend was observed for a reduction in AD-2-positive pTau immunoreactivity was observed for the transgenic human pTau band. However, a significant reduction in the quantity of mouse AD2-positive pTau was observed in mice treated with 3 mg/kg of ACI-36-2B6-Ab2, and a non-significant trend when treated with either 10 mg/kg of ACI-36-2B6-Ab2 or ACI-36-3A8-Ab2.

When a different antibody that specifically recognizes pTau pS396 was used for staining (Hoffmann et al., 1997), an even greater effect was observed. Mice treated with 3 mg/kg of ACI-36-2B6-Ab2 had significantly less pS396-positive human transgenic and mouse endogenous pTau, with a trend towards reduction when treated with 10 mg/kg ACI-36-2B6-Ab2 or ACI-36-3A8-Ab2. To assess the effects on total human and mouse Tau, which includes both non-phosphorylated and all pTau, blots were probed with the Tau5 antibody. Compared to vehicle control, total Tau was not modulated by ACI-36-2B6-Ab2 or ACI-36-3A8-Ab2 administered at 10 mg/kg, however a trend for reduced total Tau was observed for mice administered ACI-36-2B6-Ab2 at 3 mg/kg.

6.2.4 Summary

Two peripheral administrations of Tau Tg mice with the anti-pTAU antibody ACI-36-3A8-Ab2 significantly reduced soluble TAU and soluble pTAU in the brain cortex. Two peripheral administrations of Tau Tg mice with the anti-pTAU antibody ACI-36-2B6-Ab2 significantly reduced soluble TAU and soluble pTAU in the brain cortex. Additionally, ACI-36-2B6-Ab2 significantly reduced pTAU immunoreactivity in the hippocampus. These results demonstrate the ability of passive anti-pTAU immunization, using ACI-36-2B6-Ab2 and ACI-36-3A8-Ab2 antibodies, in reducing tauopathy.

Two peripheral administrations of ACI-36-2B6-Ab2 at 3 mg/kg to Tau Tg mice reduced the presence of pTau PHF epitopes in the cortex as measured by Western-blotting. At a higher dose of 10 mg/kg, both ACI-36-2B6-Ab2 and ACI-36-3A8-Ab2 showed a trend towards reduced pTau PHF epitope immunoreactivity. These results show that ACI-36-2B6-Ab2 and ACI-36-3A8-Ab2 antibodies may be suitably used in passive immunotherapy against tauopathies such as Alzheimer's Disease.

Example 7: 1-Month Treatment of Human Tau Over-Expressing Mice 7.1 Methods 7.1.1 Mice and Treatments Tau transgenic mice were used and administered the treatment antibodies as shown in the Table in Method 6.1. (study no. 2.)

7.1.2. Behavioral Testing—Morris Water-Maze (MWM) Task

Following the last administration, a water-maze (MWM) task was performed to test for spatial memory performance on mice treated according to 6.1.1. The MWM testing was performed with all enclosed animals in week 4 after start. The MWM consists of a white circular pool with a diameter of 100 cm, filled with tap water at a temperature of 21±2° C. The pool is virtually divided into four sectors. A transparent platform (8 cm diameter) is placed about 0.5 cm beneath the water surface. During all test sessions, the platform is located in the southwest quadrant of the pool. Each mouse had to perform three trials on each of four consecutive days. A single trial lasted for a maximum of one minute. During this time, the mouse had the chance to find the hidden, diaphanous target. After each trial mice were allowed to rest on the platform for 10-15 sec to orientate in the surrounding. At least one hour after the last trial on day 4, mice had to fulfill a so-called probe trial (PT). During the PT, the platform was removed from the pool and the number of crossings over the former target position was recorded by the experimenter together with the abidance in this quadrant. For the quantification of escape latency (the time [seconds] the mouse needed to find the hidden platform and therefore to escape from the water), of pathway (the length of the trajectory [meter] to reach the target), of target zone crossings and of the abidance in the target quadrant in the PT, a computerized tracking system (Biobserve Software) was used. All animals had to perform a visual test after the PT on the last day to exclude influence of insufficient seeing abilities on behavioral results.

7.1.3. Brain Tau Pathology Determination by Immunohistochemical (IHC) Quantitation Mice were euthanized 1 day following the MWM (1 week following last administration) to determine Tau pathology in the brain. Brain Tau pathology was determined in hippocampus and amygdala by immunohistochemical (IHC) quantitation using AT180 (anti-pTau, pT231/pS235) and HT7 (human-specific anti-Tau) antibodies. Furthermore, the treatment effects on soluble pTau and soluble Tau in cortex and hippocampus was measured in the homogenate fraction using MesoScale Discovery (MSD) duplex technology, probing for pTau (pT231) and total Tau. None of the antibodies used for either the IHC or the MSD assays have an epitope that overlaps with the treatment antibody used in this study.

Figure 4A:
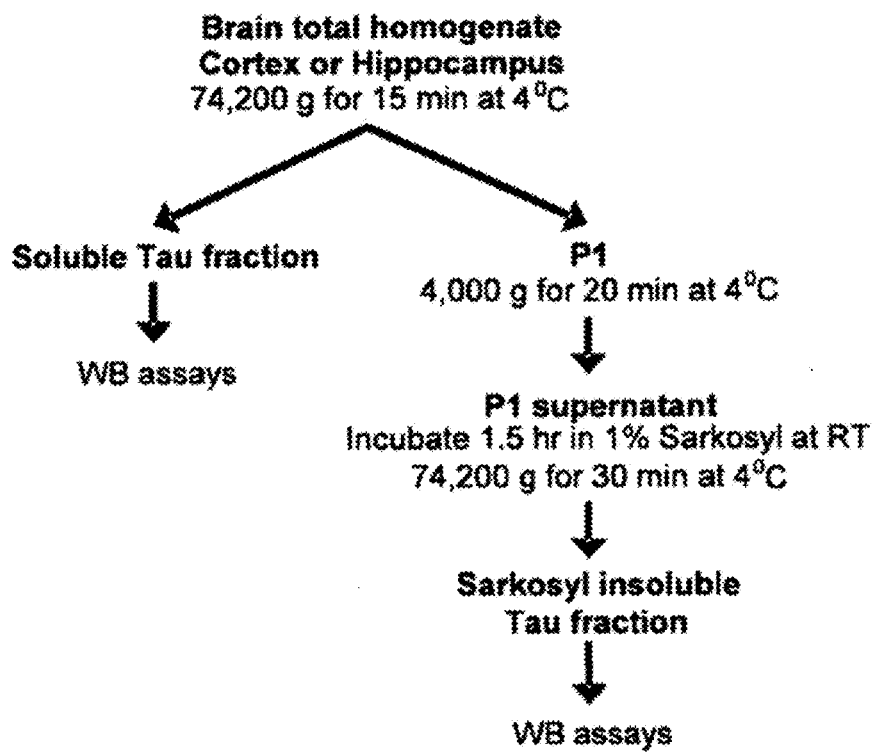
FIGS. 4A and 4B show a diagram demonstrating how brains were prepared for soluble and sarkosyl insoluble (Sin T) Tau protein fractions.
Figure 4B:
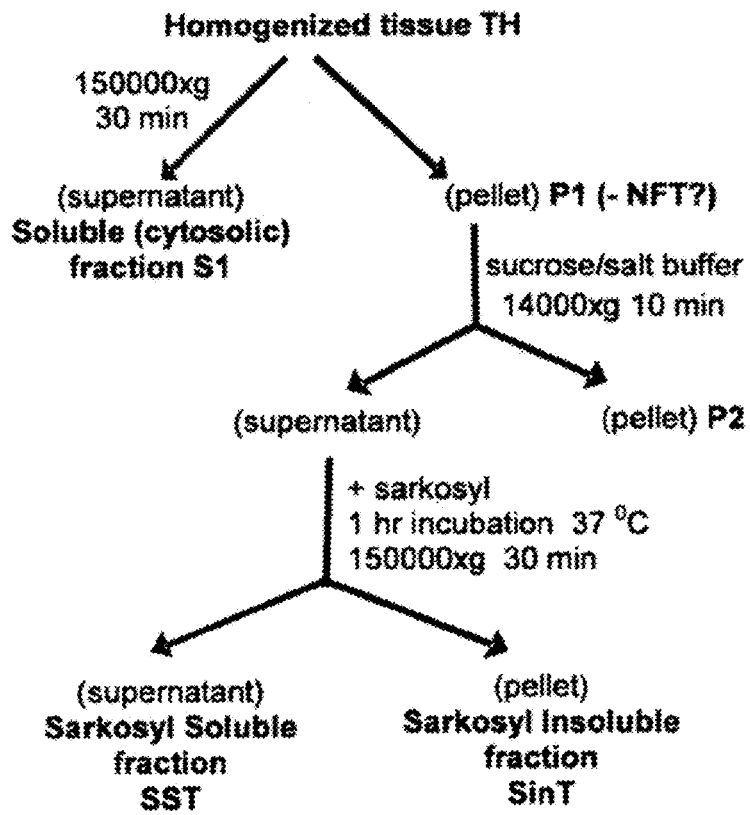

7.1.4. Sample Preparation for the Analysis of Soluble Tau in Cortex and Hippocampus Mice were euthanized for tissue collection, one week following the last treatment administration. Cortex and hippocampus were homogenized in 100 to 200 µL of cold extraction buffer 1 (25 mM Tris HCl pH=7.4, 150 mM NaCl, 1 mM EDTA, 1 mM EGTA, 10 mM β-glycerophosphate, 30 mM NaF, 2 mM $Na_3VO_4$, protease and phosphatase inhibitor cocktails). The homogenates were centrifuged (74,200 g for 15 min at 4° C.) and the supernatants were used for the analysis of soluble Tau in cortex and hippocampus (FIG. 4A). The pellets were resuspended in 100-200 µL extraction buffer 2 (10 mM Tris HCl pH=7.4, 800 mM NaCl, 300 mM sucrose, 1 mM EGTA, protease and phosphatase inhibitor cocktails) and transferred to a 1.5 mL tube. The solutions were centrifuged (4,000 g for 20 min at 4° C.) and the supernatants transferred to ultracentrifugation tubes. Sarkosyl (a 30% aqueous solution) was then added to a final concentration of 1% and incubated for 1.5 hours at room temperature. After centrifugation (74,200 g for 30 min at 4° C.) the supernatants were discarded and the pellets were re-suspended in 100 µL buffer 3 (50 mM Tris-HCl, pH=7.4). The re-suspended pellets were used as sarkosyl-insoluble (Sin T) Tau in cortex and hippocampus. The concentration of total protein in the soluble and Sin T fractions samples was determined by a BCA protein quantitation assay (Thermo Fisher Scientific, Rockford, Ill., USA).

7.1.5. Western Blots for pTau PHF and Tau

To evaluate the effect of ACI-36-2B6-Ab1 administration on the presence of pTau PHF in brain cortex and hippocampus, two antibodies reported to bind pTau PHF epitopes (Greenberg et al., 1992; Reig et al., 1995; Hoffmann et al., 1997) were used in Western-blot (WB) assays. Soluble and Sin T fractions from cortex and hippocampus were diluted by adding an equal volume of sample buffer A (125 mM Tris-HCl pH 6.8, 4% [w/v] sodium dodecyl sulfate [SDS], 20% glycerol, 0.01% bromophenol blue, 5% β-mercaptoethanol), and the samples were heated to 95° C. for 10 min. 30 µg of sample was loaded onto a 4-12% Bis-Tris gel (Invitrogen, Basel, Switzerland) and run in MOPS SDS buffer (Invitrogen). Proteins were transferred to a 0.45 µm PVDF membrane in transfer buffer (25 mM Tris pH 8.6, 190 mM glycine, 20% methanol). To verify protein transfer, membranes were stained with Ponceau S for 5 min. Membranes were then washed, and blocked for 1 hour in blocking buffer (5% BSA in TBS [50 mM Tris-HCl, pH 7.6, 150 mM NaCl]). Membranes were blotted over-night at 4° C. with the primary antibodies in blocking buffer and 0.1% Tween.

The two pTau PHF-specific primary antibodies used for the WBs were: anti-pS396 (PHF-13 epitope; AbCam, Cambridge, UK; used at 3 µg/mL), specific to phosphorylated Ser396 (pS396) of human or murine pTau (Hoffmann et al., 1997), and AD2 (PHF-1 epitope; BioRad, Reinach, Switzerland; used at 0.4 µg/mL), specific for human and murine pS396 and phosphorylated Ser404 (pS404; Reig et al., 1995). For detection of target effects, ACI-36-2B6-Ab1 was used for blotting at 1.6 µg/mL. For total Tau WBs, Tau5, an antibody that binds both human and murine Tau (BD Biosciences, Allschwil, Switzerland), was used at 0.5 µg/mL. All membranes were additionally blotted for β-actin (AbCam; used at 0.4 µg/mL) to normalize for protein loading.

Following incubation with the primary antibody, membranes were washed with 0.1% Tween in TBS, and incubated with the secondary antibodies: goat anti-mouse-IRDye800 or goat anti-rabbit-IRDye680 (both from Li-Cor Biosciences, NE, USA), both diluted 1:15,000 in BB and 0.1% Tween. Membranes were then incubated 1 hour at room-temperature protected from light, washed for 15 min 3-times with 0.1% Tween in TBS, and for 5 min 2-times with TBS, and bands quantified using Li-Cor Odyssey near-infrared imaging system (Li-Cor). Bands of interest were normalized to β-actin expression. To verify the identification of the human transgenic versus the mouse endogenous Tau bands, blots were probed with an antibody specific for human total Tau and does not cross-react with murine Tau (Tau13, AbCam; not shown). Additionally, membranes were probed with an anti-mouse primary antibody, to verify that the treatment-antibody, was not present in the denatured test samples in sufficient quantity to interfere with the binding of the primary blotting antibodies. No intact or denatured treatment antibodies were detected (results not shown) in the samples used for this study. Values are expressed as arbitrary β-actin-corrected immunoreactivity (IR).

7.1.6. Statistical Analysis

Data were analyzed using a one-way ANOVA, followed by Dunnett's multiple comparison post-hoc test (GraphPad Prism, GraphPad Software, CA, USA) comparing each treatment to Tg control-treated mice. Results are presented as individual data points showing mean±SEM. Differences with p<0.05 were considered as statistically significant. Single values that were identified as significant (p<0.05) outliers by Grubb's extreme studentized deviate test, were excluded 7.2 Results 7.2.1. Behavioral Testing—Morris Water-Maze (MWM) Task Following Passive Immunization Four i.p. injections of ACI-36-2B6-Ab1 administered weekly at 3 mg/kg or 1 mg/kg over a four week period did not show any gross adverse effects.

During the last week of treatment, spatial navigation learning and memory of animals were evaluated. Animals had to fulfill 4 days of training with 3 trials per day followed by one probe trial and visual test. Escape latency (the time [seconds] the mouse needed to find the hidden platform and therefore to escape from the water), the pathway (the length of the trajectory [meter] to reach the target), the swim speed (calculated quotient of pathway and escape latency), the number of target crossings and the abidance in the target quadrant were evaluated.

Tg (group A) as well as nTg (F) control animals treated with vehicle showed the expected learning curves when evaluating escape latency and length of the swimming path to reach the platform over the four testing days. Tg control (A) animals had a significant learning impairment as shown by flatter learning curves in escape latencies and swimming paths compared to nTg control animals (F). Escape latencies and swimming path were significantly (Two Way ANOVA) longer on training days 3 and 4 (p<0.001; Bonferroni's post test). Treatment with ACI-36-2B6-Ab1 and ACI-36-3A8-Ab1, low or high dose (groups B and C and D and E, respectively) did not lead to a significant improvement of spatial learning abilities compared to Tg control animals (group A) and showed similar learning curves. When adjusting the day 1 performance of each group to 100% and all further days as percentage of day 1, an improvement can be seen for the ACI-36-3A8-Ab1 treated mice (both dosages). The effect reached statistical significance for swimming path length on day 3 (p<0.01 group D and p<0.05 group E) and day 4 (p<0.05 group D).

For the ACI-36-2B6-Ab1 treated mice (both dosages) a slight improvement can be seen in swimming path length, although without statistical significance.

No differences between treatment groups were detected in terms of swimming speed on all four training days.

The results from the MWM test demonstrated trends toward improved spatial learning for mice treated with ACI-36-2B6-Ab1 and ACI-36-3A8-Ab1.

7.2.2. Brain TAU Pathology by Immunohistochemical (IHC) Quantification

The AT180 antibody stains the endogenous and human pTAU (doubly phosphorylated at Thr231 and Ser235).

AT180 IR in the amygdala and hippocampus after ACI-36-2B6-AB1 and ACI-36-3A8-AB1 immunization was determined. The AT180 IR area percentage in the amygdala and hippocampus was measured.

The amount of intrasomal pTAU in nTg controls was significantly lower compared to Tg groups (p<0.001). In the amygdala, a tendency to increase somal pTAU was observed for the 3 mg/kg ACI-36-2B6-Ab1 treatment. In contrast, both dosages of ACI-36-2B6-Ab1 tended to lower pTAU compared to vehicle treated animals in the hippocampus. Mean staining intensities were comparable in all transgenic groups.

ACI-36-3A8-Ab1 treatment did not alter somal pTAU in the hippocampus and amygdala and neuronal pTAU levels in the amygdala and hippocampus did not differ significantly among treated transgenic groups. Mean and sum of staining intensities were comparable in all transgenic groups.

Since the HT7 antibody is specific for human TAU, only little signal was measured in nTg controls, that derives from autofluorescence of lipofuscine dots above seven pixel in size. ACI-36-2B6-Ab1 treatment did not alter somal HT7 positive IR area in the hippocampus ( ) compared to the vehicle control (PBS). In the amygdala, mice receiving the lower dose of ACI-36-2B6-Ab1 tended to have higher levels of total human TAU (T-test: p=0.0954) in terms of IR area ( ). This increase was also qualitatively visible as increase of the area of staining and the staining intensity in individual neuronal somata. No statistically significant treatment induced differences were observed in the hippocampal neurons.

ACI-36-3A8-Ab1 treatment did not significantly alter somal HT7 positive IR area in the amygdala ( ) and the hippocampus ( ) compared to the vehicle control (PBS). Mean and sum of staining intensities were comparable in all transgenic groups (data not shown).

Brain Tau pathology did not show a change in total Tau or pTau levels in the brain soluble fraction, however immunostaining of brain sections demonstrated a reduction in hippocampus pTau in mice treated with ACI-36-2B6-Ab1.

7.2.3. Effects of Anti-Tau Antibody Administration on Phospho-Tau Epitopes Present in Paired Helical Filaments (PHFs)

Alzheimer's Disease (AD) is characterized neuropathologically by neurofibrillary tangles (NFTs; Braak, Braak, & Bohl, 1993). Structurally, NFTs consist of paired helical filaments (PHFs) composed of the microtubule-associated protein Tau, found primarily in a hyper-phosphorylated state (Alonso et al., 1997). The objective of this study was to reduce these pTau PHF epitopes in the brains of Tau transgenic mice by four administrations of the anti-pTau antibody ACI-36-2B6-Ab1 and ACI-36-3A8-Ab1.

To measure the effects of four ACI-36-2B6-Ab1 administrations on the quantity of well documented Tau PHF phospho epitopes, brain cortex and hippocampus soluble and Sin T fractions from treated Tau Tg mice were probed with AD2 (PHF-1 epitope, pS396/pS404) and anti-pS396 antibody (PHF-13 epitope, pS396) using WBs. As markers of Tau PHFs, the presence of pS396/pS404 have been previously documented (Greenberg et al., 1992; Reig et al., 1995), and more specifically the pS396 site (Hoffmann et al., 1997). In the Tau Tg mice, Tau is expressed as endogenous murine Tau and as the human Tau transgene, with a molecular-weight difference that can be clearly identified on WBs when a blotting antibody binds Tau from both species and Tau from the two different transcripts is expressed in sufficient amounts. Therefore when possible, the endogenous mouse and human transgenic Tau bands were identified for each blotting antibody and quantified separately. To verify the migration patterns for these Tau bands in our WB assays, an anti-Tau antibody that binds to total Tau, but is human specific (Tau13), and therefore only shows the human transgene in Tau Tg brains was used for Tau Tg control samples to verify migration patterns for human and mouse Tau in the Tau transgenic mice. Additionally, all quantified bands were normalized to β-actin.

Figure 5B:
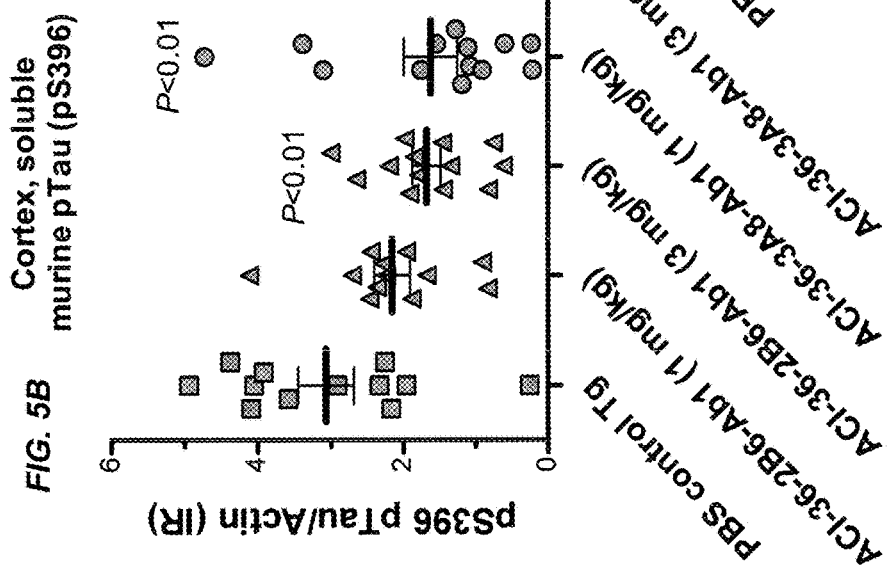
FIGS. 5A through 5I show pTau epitope Western Blot results after anti-Tau antibody treatment for the 1 month (FIG. 5A, 5B, 5C, 5G, 5H, 5I) or 3 month in vivo study (FIG. 5D, 5E, 5F)
Figure 5A:
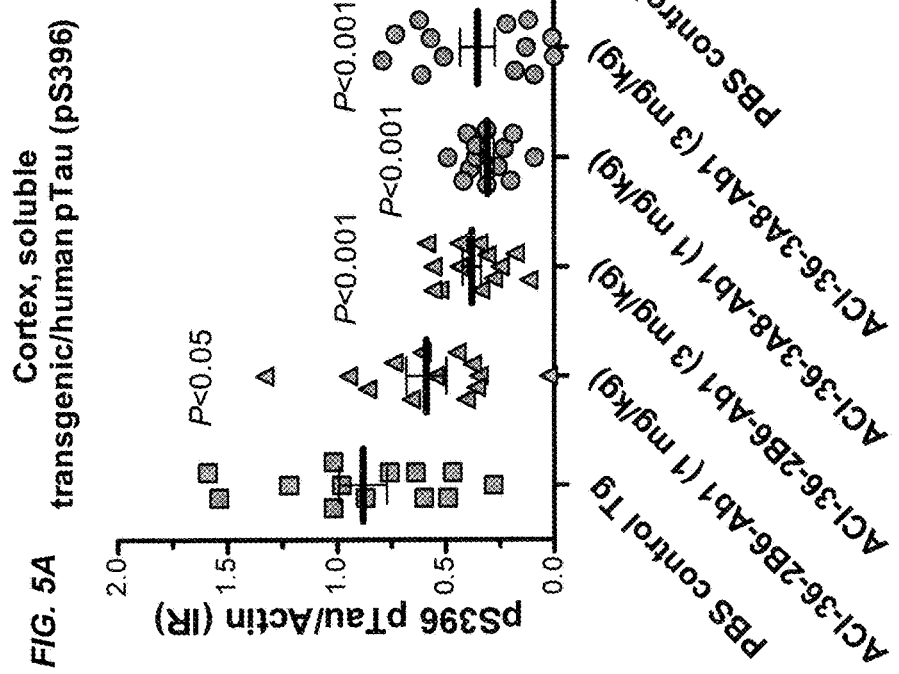

The presence of PHF epitopes, probed for in the soluble fraction from brain cortex, was reduced in ACI-36-2B6-Ab1 and in ACI-36-3A8-Ab1 treated mice. This was significant for both the mouse and human bands, using the pS396 (PHF-13) antibody for the WBs (FIGS. 5A and B).

Figure 5D:
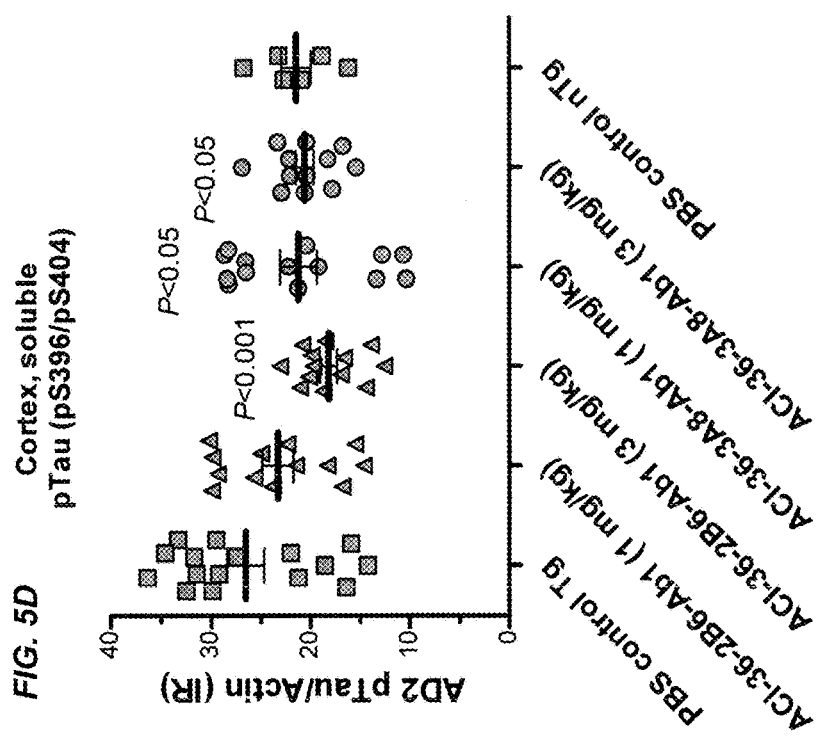
Figure 5C:
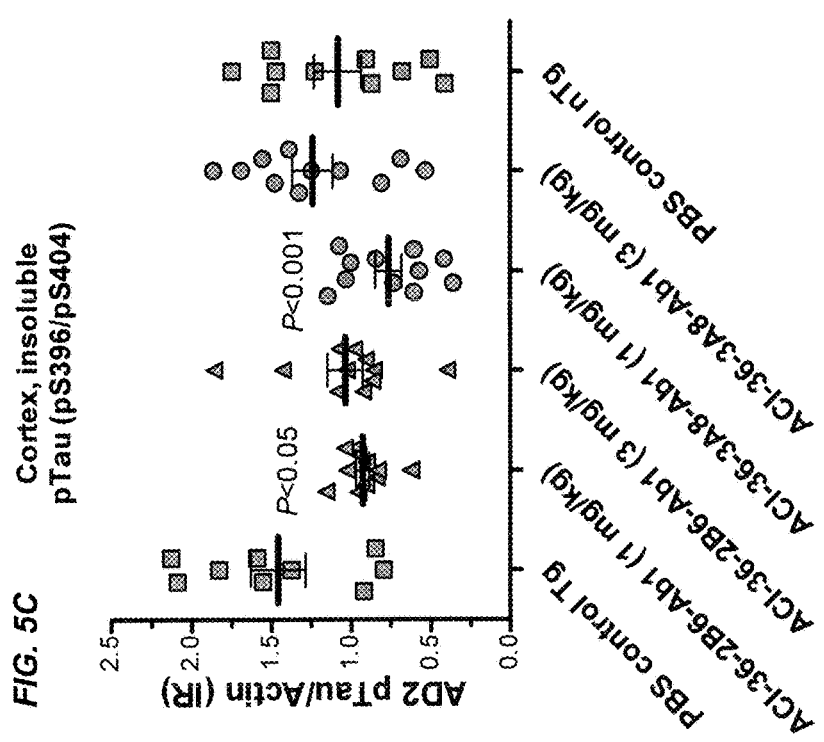

When the AD2 (PHF-1, pS396/pS404) antibody was used for WBs of extracts from ACI-36-2B6-Ab1 and ACI-36-3A8-Ab1 treated mice, a significant reduction was observed (FIG. 5C).

A note should be made that even though the two PHF-specific antibodies that were used for these WBs have similar epitopes and good specificity to their phosphorylated target(s), the pS396 (PHF-13) antibody appears to have a better signal-to-noise ratio and was the better overall antibody for these WBs.

The direct target effect of the treatment-antibody was probed for in the cortex using ACI-36-2B6-Ab1 and the ACI-36-2B6-Ab1, respectively, as the blotting antibody. This anti-pTau antibody binds to the same phospho-Tau epitope as the treatment antibody used in this study. Blots had previously been probed with a secondary anti-mouse IgG antibody only.

Bands were quantified using an infrared imaging system. Values for individual mice as well as the mean±SEM are determined.

No signal above background was detected, verifying the lack of blocking effects or interference by the treatment antibody in these samples (data not shown).

Figure 5F:
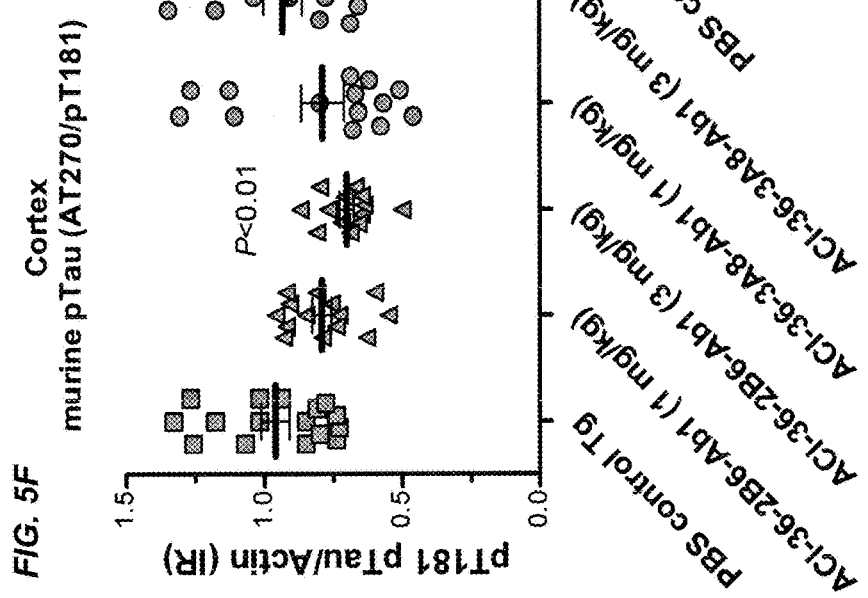
Figure 5E:
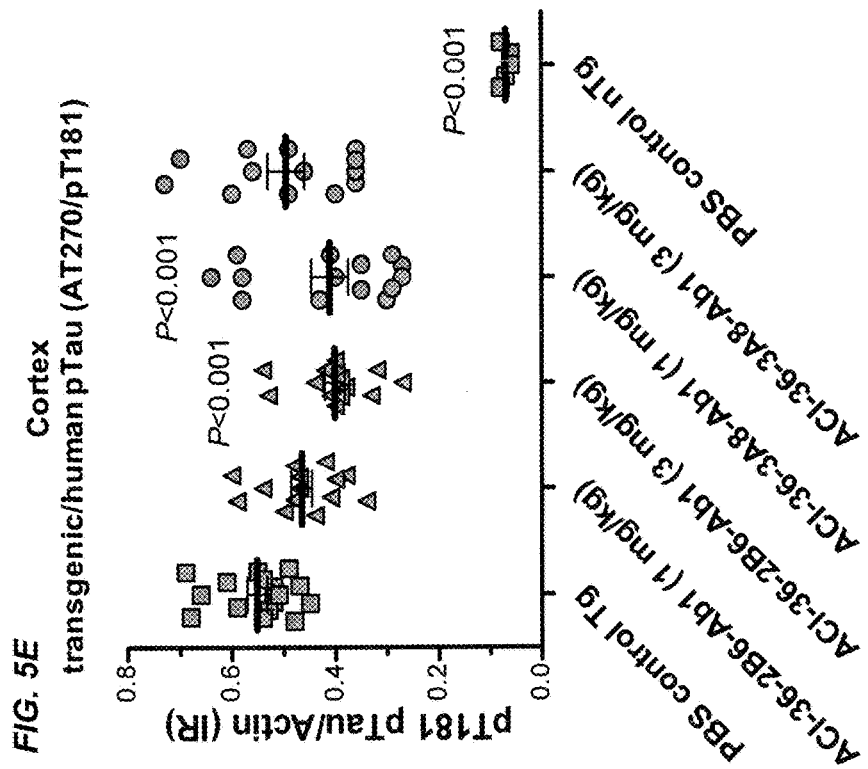
Figure 5G:
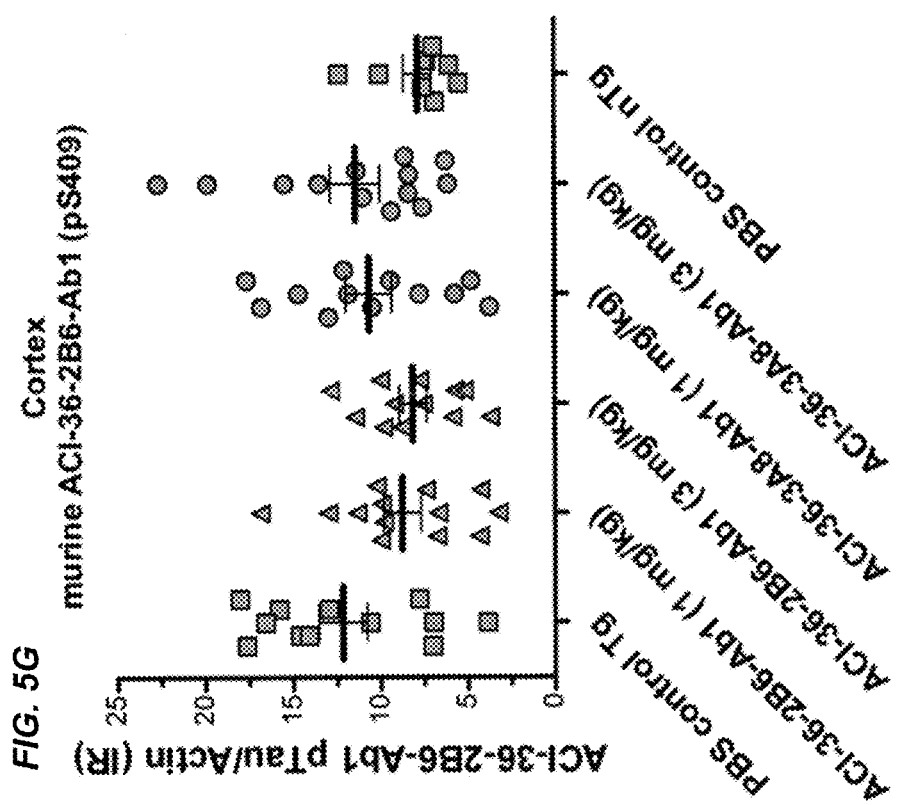

In ACI-36-2B6-Ab1 treated mice, a trend towards a reduced signal down to the level of control-treated nTg mice was observed, indicative of a direct target effect (FIG. 5G).

In ACI-36-3A8-Ab1 treated mice no significant effects of treatment were observed (FIG. 5G).

Figure 5H:
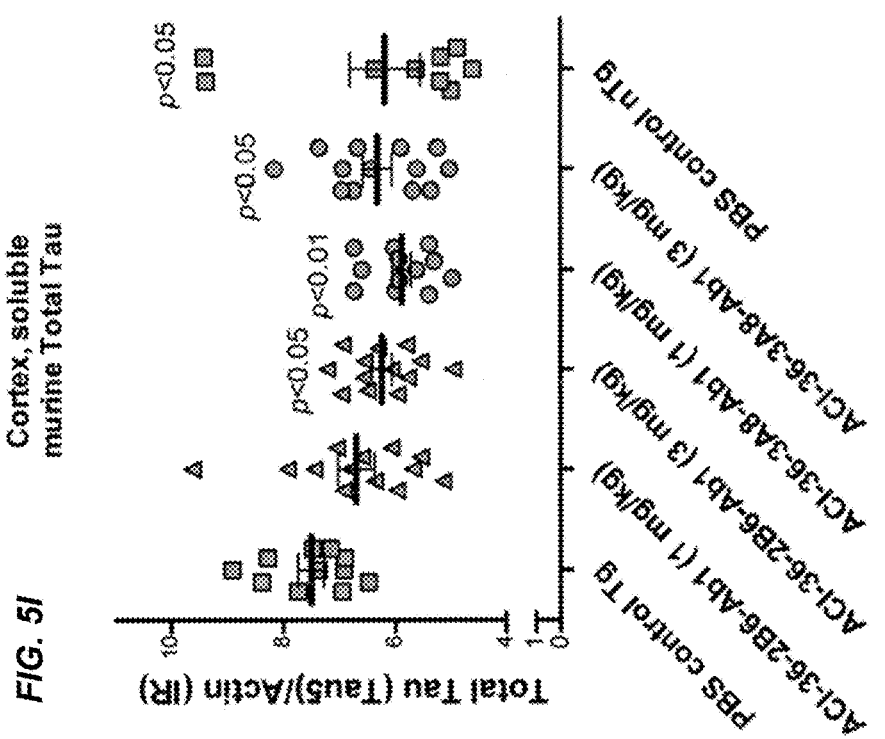
Figure 5I:
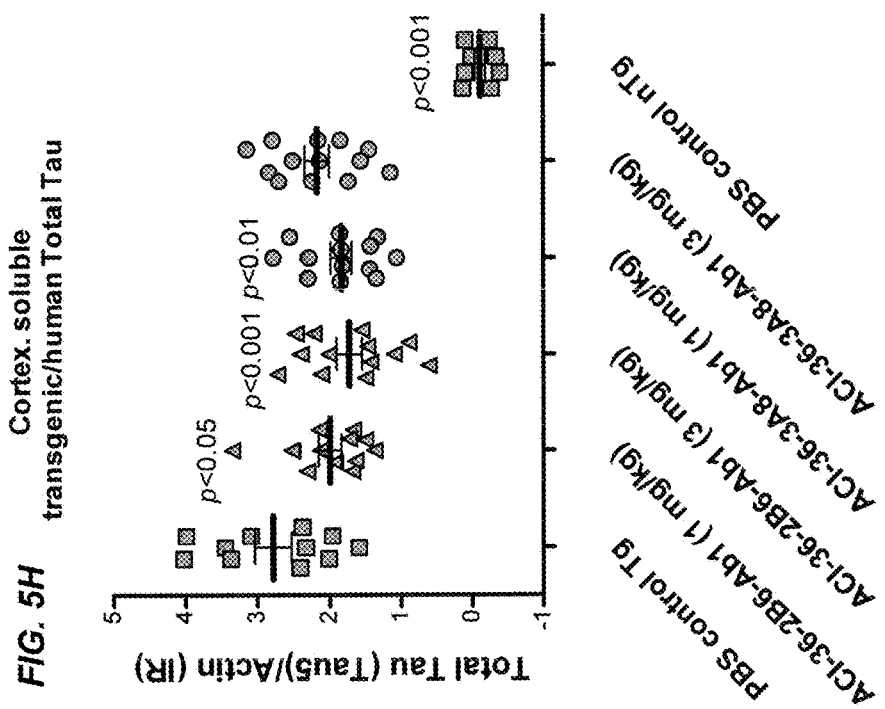

The significant effect of ACI-36-2B6-Ab1 treatment on total Tau in the soluble cortex of Tau Tg mice was observed, using a Tau5 antibody for blotting which binds both the endogenous mouse Tau and the transgenic human Tau (FIGS. 5H and 5I). A significant reduction in total Tau was observed for both endogenous mouse Tau and the transgenic human Tau in the soluble fraction of brain cortex.

Bands, indicating the mouse A) and human B) total Tau (Tau5), were quantified using an infrared imaging system. Values for individual mice as well as the mean±SEM are determined.

The presence of PHF epitopes in the detergent insoluble Tau fraction was done by preparing sarkosyl-insoluble (Sin T) brain fractions.

Bands were quantified using an infrared imaging system. Values for individual mice as well as the mean±SEM are determined.

Much less Tau was present in this fraction when compared to the soluble Tau fraction, both in the cortex and in hippocampus. This may be due to the age of the Tau Tg mice used in this study, which at 4 months may not have accumulated a significant amount of insoluble and aggregated Tau in the hippocampus and cortex. Therefore, when probing for PHF epitopes in the Sin T fraction, only the AD2 (PHF-1, pS396/pS404) antibody provided a signal that was sufficient for reliable quantization of bands.

Mice treated with 1 mg/kg of ACI-36-2B6-Ab1 and with 1 mg/kg of ACI-36-3A8-Ab1, respectively, had a significant reduction in the PHF-1 epitope in bands representing the endogenous mouse Tau (FIG. 5C). Signals observed for the transgenic human band were not intense enough to be quantitated reliably.

The hippocampus was also probed, using the same antibodies and fractions as that for the cortex. Lower signals for all blotting antibodies were detected in fractions from hippocampus compared to that of cortex.

The effects of ACI-36-2B6-AB1 and ACI-36-3A8-AB1 treatment on pS396 (PHF-13) immunoreactivity in the soluble hippocampus of Tau Tg mice was determined. Bands, indicating the mouse A) and human B) pTau pS396 (PHF-13) epitopes, were quantified using an infrared imaging system. Values for individual mice as well as the mean±SEM are determined.

ACI-36-2B6-Ab1 treatment did not significantly alter the presence of the pS396 (PHF-13) epitope in the mouse Tau soluble hippocampus fraction, with a small trend for a reduction in the human transgene band.

ACI-36-3A8-Ab1 treatment showed trends towards a reduction in the presence of the pS396 (PHF-13) epitope in the mouse Tau soluble hippocampus fraction and the human transgene band.

Similarly to what was observed for pS396 (PHF-13) WBs, a trend for a reduced signal was detected in both extracts of ACI-36-2B6-Ab1 and ACI-36-3A8-Ab1 treated mice for total Tau in the human Tau soluble hippocampus fraction.

Akin to the cortex Sin T samples, the Sin T fraction from hippocampus had very low levels of pTau. Mice treated with ACI-36-2B6-Ab1 and ACI-36-3A8-Ab1, respectively, had no change in the PHF-1 (pS396/pS404) epitope in bands representing the endogenous mouse Tau.

Signals observed for the transgenic human band were not intense enough for reliable quantization.

7.2.4 Summary

The study indicates that passive immunization using four administrations of a phosphosite-specific anti-pTau antibody ACI-36-2B6-Ab1 and ACI-36-3A8-Ab1 antibodies improves spatial learning and reduces brain pTau pathology.

Four peripheral administrations of the anti-pTau antibody ACI-36-2B6-Ab1 at 1 and 3 mg/kg to Tau Tg mice reduced the presence of pTau PHF epitopes in the cortex as measured by Western-blotting. A trend for reduction was observed in the hippocampus. Similarly, a reduction in total Tau was also observed. A significant reduction in pTau PHF-1 immunoreactivity was observed in the insoluble cortex fraction, and a trend was also observed which indicated direct target effects of the antibody treatment. These results provide further support for anti-pTau antibodies ACI-36-2B6-Ab1 and ACI-36-3A8-Ab1 in passive immunotherapy against tauopathies such as Alzheimer's Disease.

Example 8: 3-Month Treatment of Human Tau Over-Expressing Mice 8.1 Methods
8.1.1 Mice and Treatments Tau transgenic mice were used and administered the treatment antibodies as shown in the Table in Method 6.1. (study no. 3) and mice were assigned to 4 different treatment groups as described in the table below.

| Group | Mouse strain | Genotype | Age at start | Sex | n | Treatment | | |
|---|---|---|---|---|---|---|---|---|
| A | TMHT | Tg | 3 months (±2 weeks) | mixed | 15 + 1 | PBS (control) | i.p. 10 µl/g b.w. | weekly |
| B | TMHT | Tg | 3 months (±2 weeks) | mixed | 15 + 1 | ACI-36-2B6-Ab1 (1 mg/kg) | i.p. 10 µl/g b.w. | weekly |
| C | TMHT | Tg | 3 months (±2 weeks) | mixed | 15 + 1 | ACI-36-2B6-Ab1 (3 mg/kg) | i.p. 10 µl/g b.w. | weekly |
| F | TMHT | nTg | 3 months (±2 weeks) | mixed | 15 + 1 | PBS (control) | i.p. 10 µl/g b.w. | weekly |

In total 45 Tg mice plus 3 reserves allocated to treatment groups A to C and 15 nTg mice plus 1 reserve (group F) were treated on day 0, 7, 14, 21, 28, 35, 42, 49, 56, 63, 70, 77, and 84 by i.p. injection of either PBS (vehicle control) or anti-pTAU antibody, ACI-36-2B6-Ab1 or ACI-36-3A8-Ab1. Animals were randomly enclosed in 5 different starting groups (scales) comprising animals of all treatment groups. The number of animals in a scale was limited to ensure same age and uniform handling. Following the 12$^{th}$ administration, a water-maze (MWM) task was performed to test for spatial memory performance. Following the MWM, mice were administered the test article one additional time (13$^{th}$ injection) before being euthanized 24 hours later do determine Tau pathology. Brain Tau pathology was determined in hippocampus and amygdala by immunohistochemical (IHC) quantitation using the AT180 (anti-pTau, pT231/pS235) antibody. Furthermore, the treatment effects on soluble and sarkosyl-insoluble Tau and pTau in cortex and hippocampus were measured using MesoScale Discovery (MSD) technology, probing for pTau (pT231 and pS396) and total Tau.

8.1.2. Behavioral Testing—Morris Water-Maze (MWM) Task

This experiment was performed according to the protocol described in Example 7.1.2. In week 12, spatial navigation was tested in the Morris Water Maze (MWM) to evaluate learning and memory.

8.1.3. Molecular Biology

Total TAU and Tau phosphorylated at Thr231 and at pS396 was quantified in brain homogenates of Tg animals by using an immunosorbent assay from MesoScale Discovery (MSD)

8.1.4. Brain Tau Pathology Determination by Immunohistochemical (IHC) Quantitation This experiment was performed according to the protocol described in Example 7.1.3. TAU pathology was determined by AT180 immunoreactivity in the hippocampus and amygdala of 8 animals per group.

8.1.5. Effects of Three Month Anti-Tau Antibody Administration on Phospho-Tau Epitopes Present in Paired Helical Filaments (PHFs)

This experiment was performed according to the protocols described in 7.1.4., 7.1.5. and 7.1.6. To measure the effects of four ACI-36-2B6-Ab1 and ACI-36-3A8-Ab1 administrations on the quantity of well documented Tau PHF phospho epitopes, brain cortex and hippocampus soluble and Sin T fractions from treated Tau Tg mice were probed with AD2 (PHF-1 epitope, pS396/pS404), anti-pS396 antibody (PHF-13 epitope, pS396) and AT180 (pT231/pS235) using WBs.

8.1.6. Effect of 3 Month Anti-Tau Antibody Administration on Phospho-Tau Epitopes Using biGT Tau Bigenic Mice Study no. 4 was done using bigenic Tau mice as shown in Method 6.1. Brain cortex samples were prepared as shown in the figure below, using the total homogenate (TH) or the soluble fraction (51) for western blotting. Membranes were probed using the following blotting antibodies for pTau or total Tau:

HT-7 (26 ng/ml), specific to total human Tau
PHF-13 (pS396) at 1/7500 dilution
AT180 (pT231) at 2.47 ug/ml
AT8 (pS202) at 3 ug/ml
pS404 at 1:5000 dilution
pS400 at 1:5000 dilution
All quantifications were normalized to β-actin.

8.2 Results for ACI-36-2B6-Ab1 Antibody

Thirteen i.p. injections of ACI-36-2B6-Ab1 administered weekly at 1 or 3 mg/kg over a twelve week study period did not show any gross adverse effects.

8.2.1 Behavioral Results—Morris Water Maze

Figure 9:
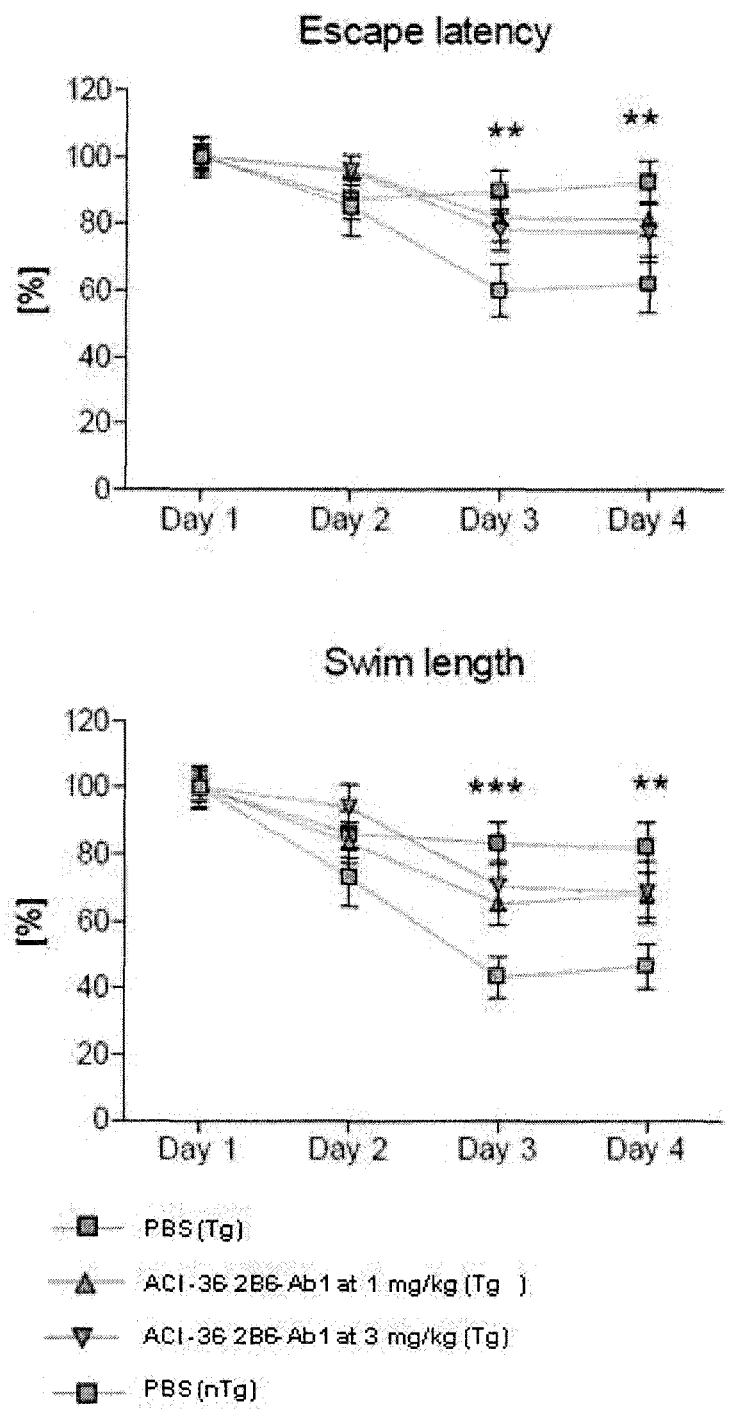
FIG. 9 shows the Morris Water-Maze results after anti-Tau antibody treatment by ACI-36-2B6-Ab1 in 3 month in vivo study.

The results from the MWM test demonstrated strong trends toward improved spatial learning for mice treated with ACI-36-2B6-Ab1 (FIG. 9).

During the last week of treatment, spatial navigation learning and memory of animals were evaluated. Animals had to fulfill 4 days of training with 3 trials per day followed by one probe trial and visual test. Escape latency (the time [seconds] the mouse needed to find the hidden platform and therefore to escape from the water), the pathway (the length of the trajectory [meter] to reach the target), the swim speed (calculated quotient of pathway and escape latency), the number of target crossings and the abidance in the target quadrant were evaluated. Vehicle treated Tg (group A) and nTg (group F) control animals showed expected learning curves in terms of escape latency and length of the swimming path to reach the platform over the four testing days. Tg control (A) animals showed a significant impairment of learning abilities reflected in flatter learning curves of escape latencies and swimming paths compared to nTg control animals (group F). Escape latencies and swimming paths were significantly (Two Way ANOVA) different on training days 3 ($p<0.01$, latency; $p<0.001$, length; Bonferroni's post test) and 4 ($p<0.01$; Bonferroni's post test). Treatment with ACI-36-2B6-Ab1, low or high dose (B and C) did not significantly improve spatial learning abilities compared to Tg control animals (A). When adjusting the performance of each group to 100% on training day 1 and all further days as percentage of day 1, a slight improvement can be seen for the ACI-36-2B6-Ab1 treated mice (low and high dosage) in swimming path length, although without statistical significance. No differences between treatment groups were detected when calculating the swimming speed on all four training days. In the probe trial (PT), the abidance in the target quadrant (south west quadrant) as well as target zone crossings were recorded. nTg controls (group F) spent more time in the target quadrant and crossed the target zone more often relative to Tg controls (group A) but without statistical significance.

Treatment with neither the low nor the high dose led to an improvement of spatial learning abilities in comparison to Tg control mice as evaluated in the PT.

8.2.2 Molecular Biology 8.2.2.1 TAU in Soluble Fraction of Cortex Homogenates

Total TAU, p231TAU, p396TAU, and the ratios of pTAU to total TAU were evaluated in the soluble fraction of cortex homogenates of n=16 animals from group A (Tg vehicle group; PBS), B (Tg, ACI-36-2B6-Ab1 1 mg/kg), and C (Tg, ACI-36-2B6-Ab1 3 mg/kg). A treatment with ACI-36-2B6-Ab1 did not significantly affect total TAU and pTAU in the in soluble cortex homogenates. However, a slight increase (without significance) of mean total TAU, p231TAU, and p396TAU was observed upon ACI-36-2B6-Ab1 treatment. TAU phosphorylation evaluated as the ratios of pTAU to total TAU was not affected.

8.2.2.2 TAU in Sarcosyl Insoluble Fraction of Cortex Homogenates

Total TAU, p231TAU, p396TAU, and the ratios of pTAU to total TAU were evaluated in the sarcosyl insoluble fractions of cortex homogenates of n=16 animals from group A (Tg vehicle group; PBS), B (Tg, ACI-36-2B6-Ab1 1 mg/kg), and C (Tg, ACI-36-2B6-Ab1 3 mg/kg). A treatment with ACI-36-2B6-Ab1 did not significantly affect total TAU and pTAU in the in sarcosyl insoluble cortex homogenates. A slight decrease (without significance) of mean total TAU and p231TAU was observed upon ACI-36-2B6-Ab1 treatment. TAU phosphorylation evaluated as the ratios of pTAU to total TAU was not affected.

8.2.2.3 TAU in Soluble Fraction of Hippocampus Homogenates

Total TAU, p231TAU, p396TAU, and the ratios of pTAU to total TAU were evaluated in the soluble fraction of hippocampus homogenates of n=16 animals from group A (Tg vehicle group; PBS), B (Tg, ACI-36-2B6-Ab1, 1 mg/kg), and C (Tg, ACI-36-2B6-Ab1, 3 mg/kg). treatment with ACI-36-2B6-Ab1 did not significantly affect total TAU and pTAU in the in soluble hippocampus homogenates. A slight decrease (without significance) of TAU phosphorylation evaluated as the ratios of pTAU to total TAU was observed upon ACI-36-2B6-Ab1 treatment.

8.2.2.4 TAU in Sarcosyl Insoluble Fraction of Hippocampus Homogenates

Total TAU, p231TAU, p396TAU, and the ratios of pTAU to total TAU were evaluated in the sarcosyl insoluble fractions of hippocampus homogenates of n=16 animals from group A (Tg vehicle group; PBS), B (Tg, ACI-36-2B6-Ab1, 1 mg/kg), and C (Tg, ACI-36-2B6-Ab1, 3 mg/kg). A treatment with ACI-36-2B6-Ab1 did not significantly affect total TAU and pTAU in the in sarcosyl insoluble hippocampus homogenates. Treatment with 3 mg/kg increased the mean total TAU, p231TAU as well as p396TAU, although without reaching significance, whereas a slight reduction of the mean total TAU, p231TAU as well as p396TAU upon 1 mg/kg treatment was observed. TAU phosphorylation evaluated as the ratios of pTAU to total TAU was slightly increased upon 3 mg/kg ACI-36-2B6-Ab1 treatment.

8.2.2.5. Western Blots for Soluble Cortex

Treatment with ACI-36-2B6-Ab1 dose-dependently reduced the presence of both the pS396/pS404 (FIG. 5D) and pT181 (FIGS. 5E and 5F) pTau epitopes in the soluble fraction of brain cortex, with a significant effect at the 3 mg/kg dose.

Figure 6A:
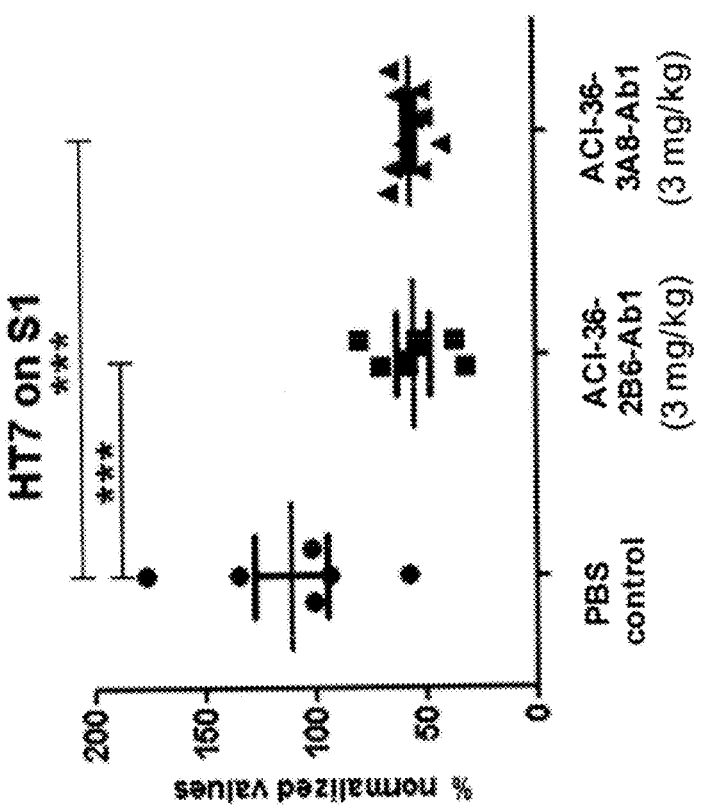
FIGS. 6A through 6O show pTau epitope Western Blot results after anti-Tau antibody treatment for the 3 month in vivo study using biGT bigenic mice.
Figure 6B:
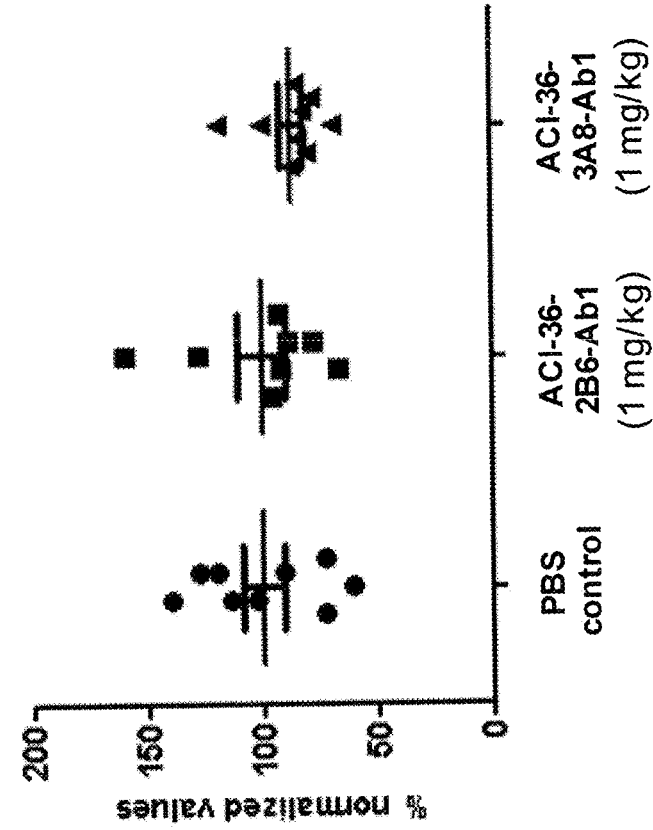
Figure 6D:
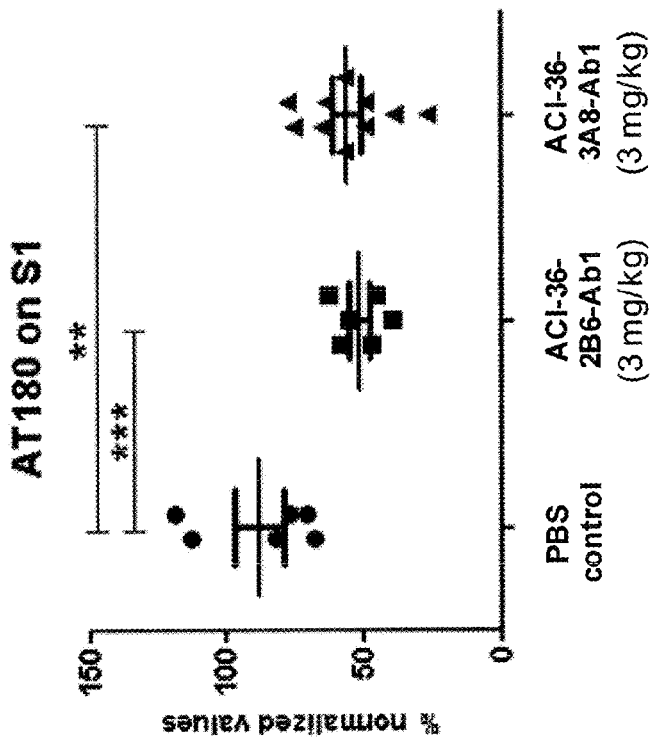
Figure 6C:
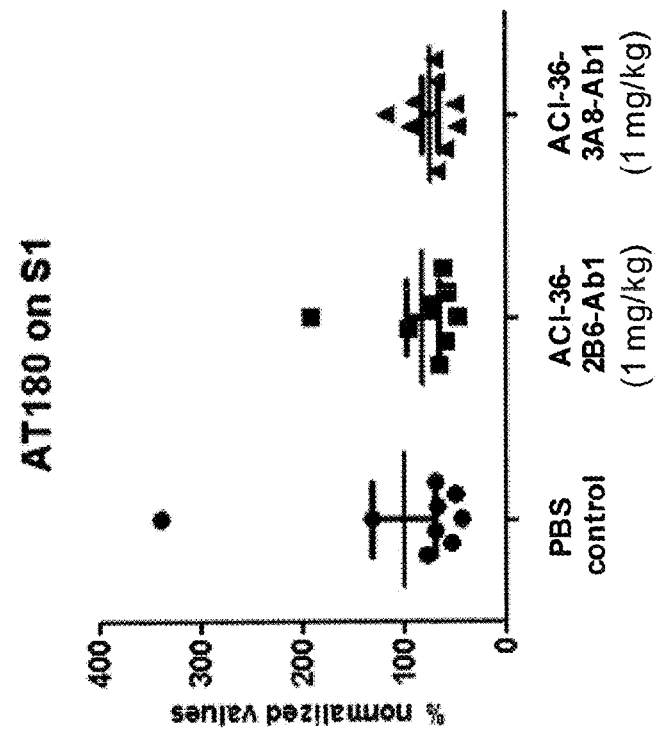
Figure 6E:
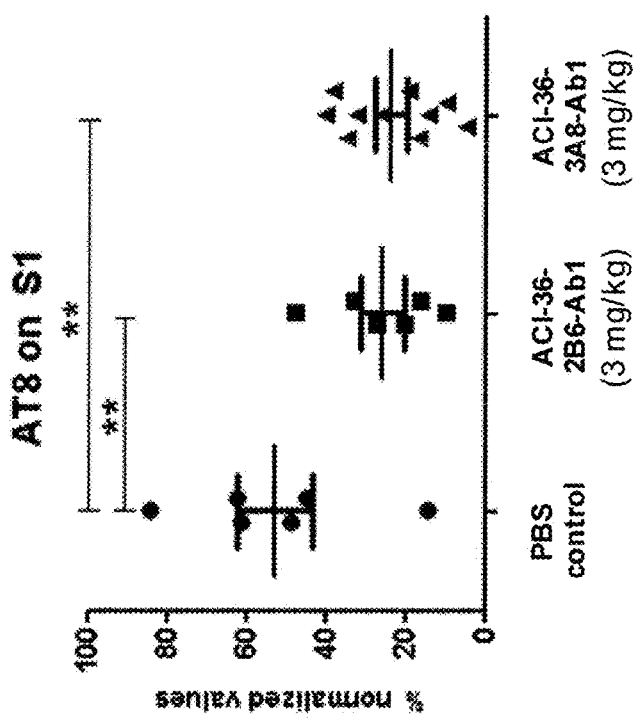
Figure 6G:
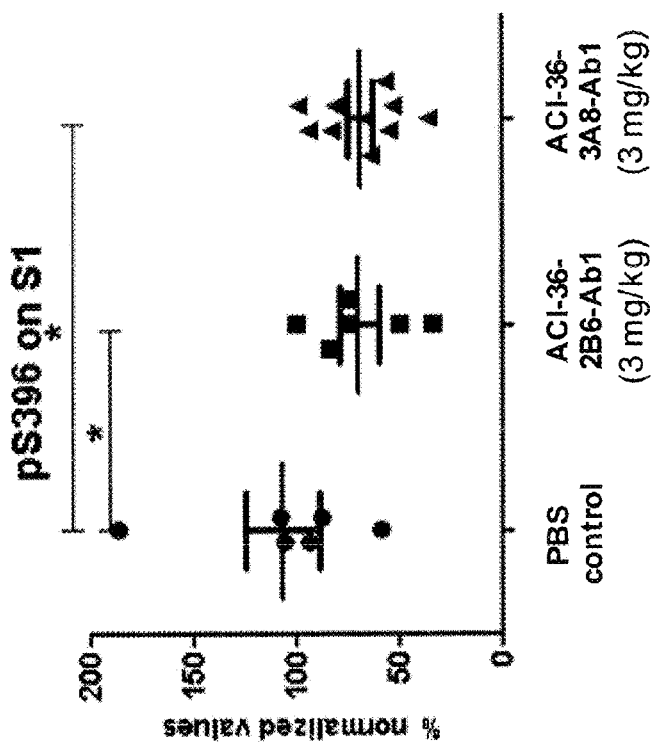
Figure 6F:
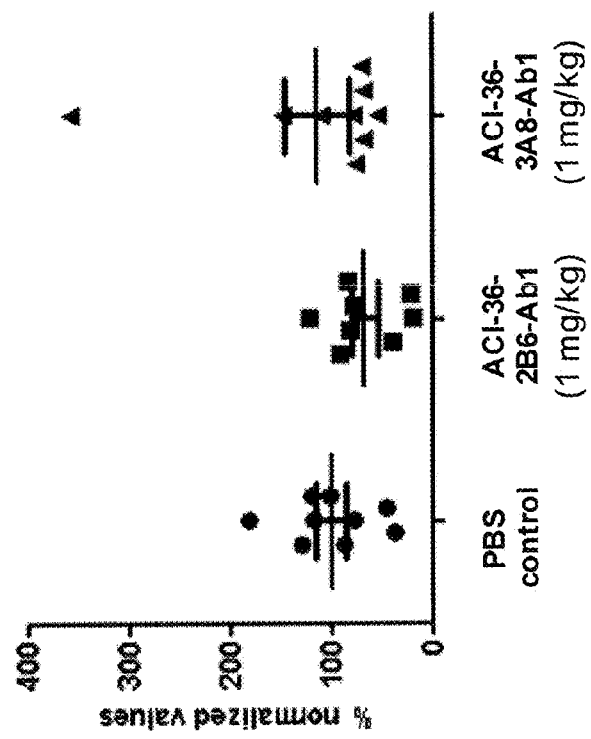
Figure 6I:
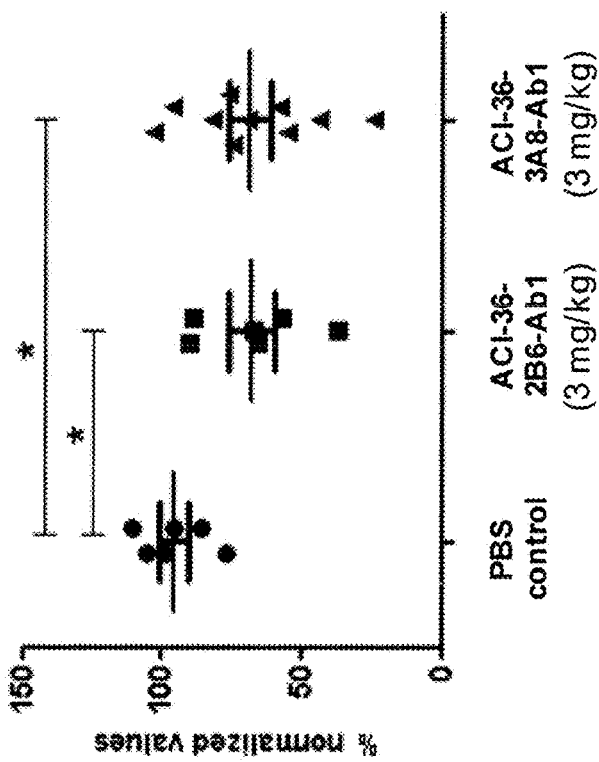
Figure 6H:
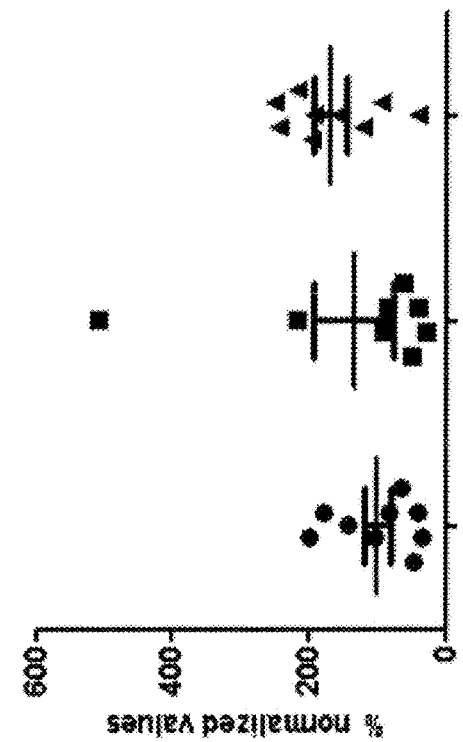
Figure 6K:
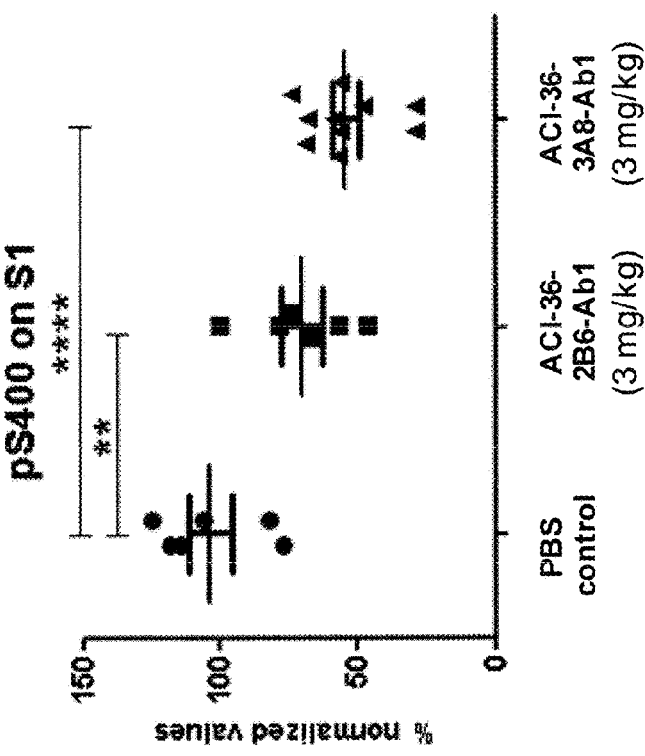
Figure 6J:
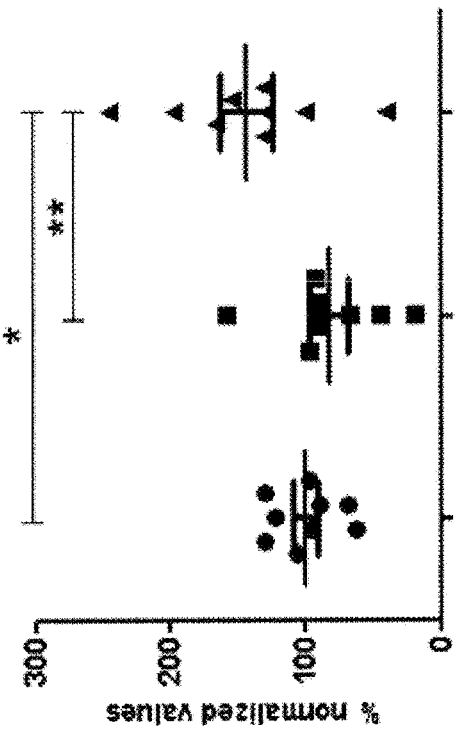
Figure 6L:
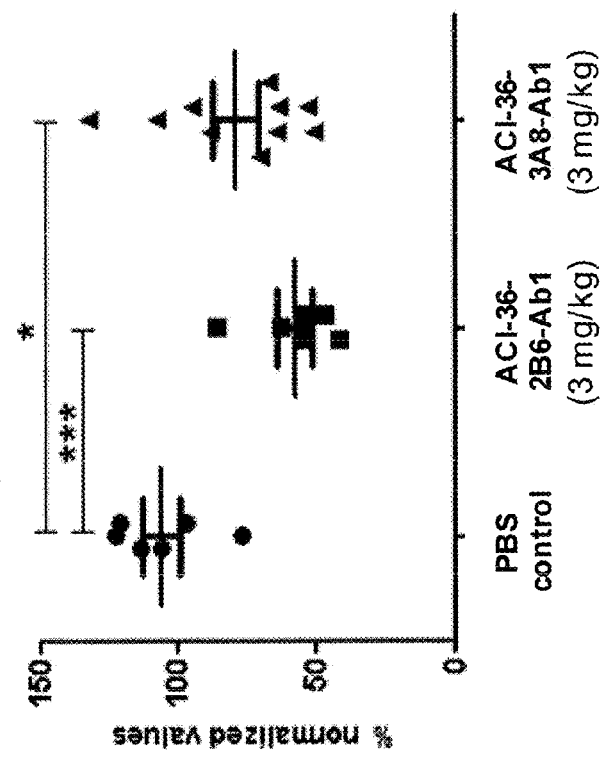
Figure 6M:
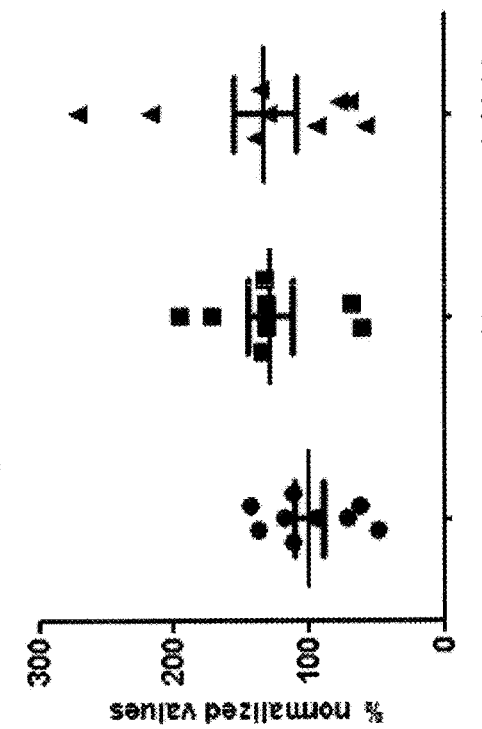
Figures 6N, 6O:
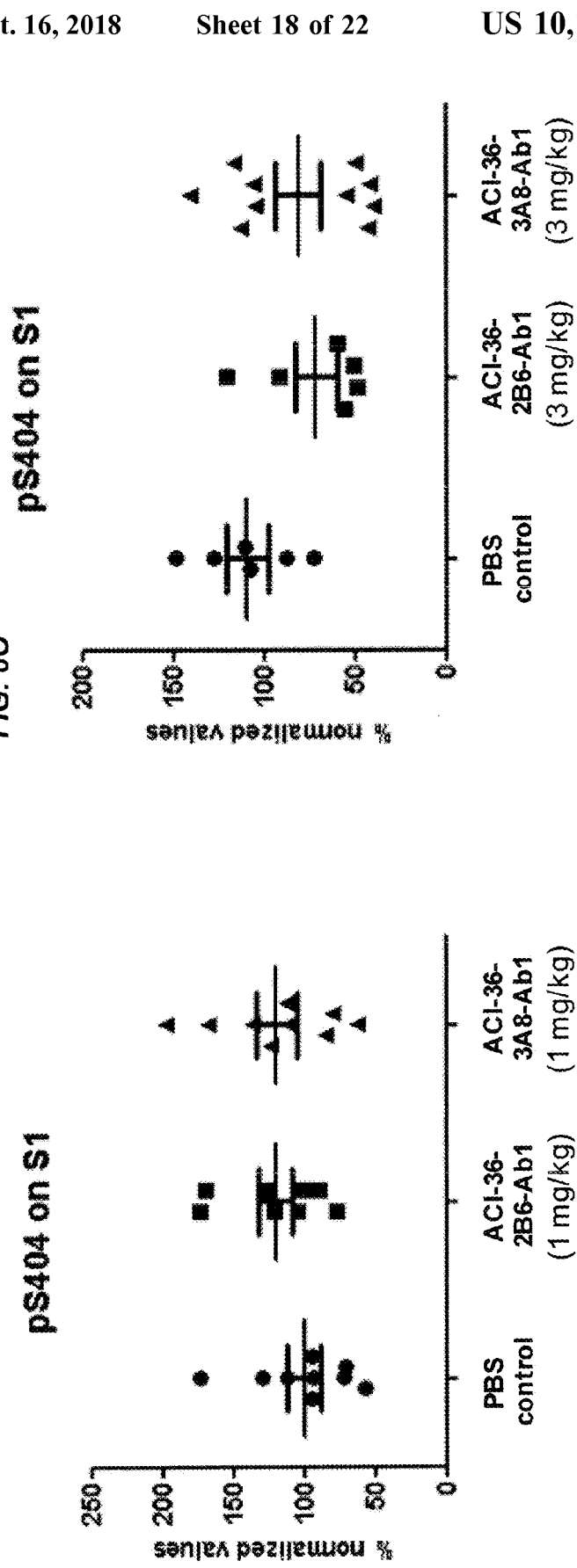

8.2.2.6 TAU in biGT Tau Bigenic Mice biGT mice treated with ACI-36-2B6-Ab1 for 3 months had significantly reduced total Tau in brain cortex soluble fraction (FIGS. 6A and 6B). A significant reduction was observed for pTau epitopes pT231/AT180 (FIGS. 6C and 6D), pS202/AT8 (FIG. 6E), and pS396 (FIGS. 6F and 6G). A significant reduction was also observed in both total homogenate (TH) for pTau epitope pS400 (FIGS. 6H and 6I) and pS404 (FIGS. 6L and 6M). Furthermore, a significant reduction was also observed in soluble fraction for pTau epitopes pS400 (FIGS. 6J and 6K) and a trend for reduction for pTau epitope pS404 (FIGS. 6N and 6O).

8.2.3 Histology 8.2.3.1 Morphometry—Determination of Region Areas

Measured region areas of the hippocampus and the amygdala not differ significantly throughout all investigated brains which excludes negative effects on tissue during dissection and IHC or staining (e.g. unequivocal shrinkage, different sectioning) and to a certain degree treatment induced atrophy. Individual sections may deviate from the individual and group mean because of e.g. folding of tissue or loss of parts of the section during execution of the labeling protocol. Therefore, the total immunoreactive area [in µm2] of any labeling was normalized to the section's individual region area [in mm2] by calculating the percentage of the labeled area within the region area [labeled area/(region area*10.000)].

8.2.3.2 Results of AT180 IH

Figure 7:
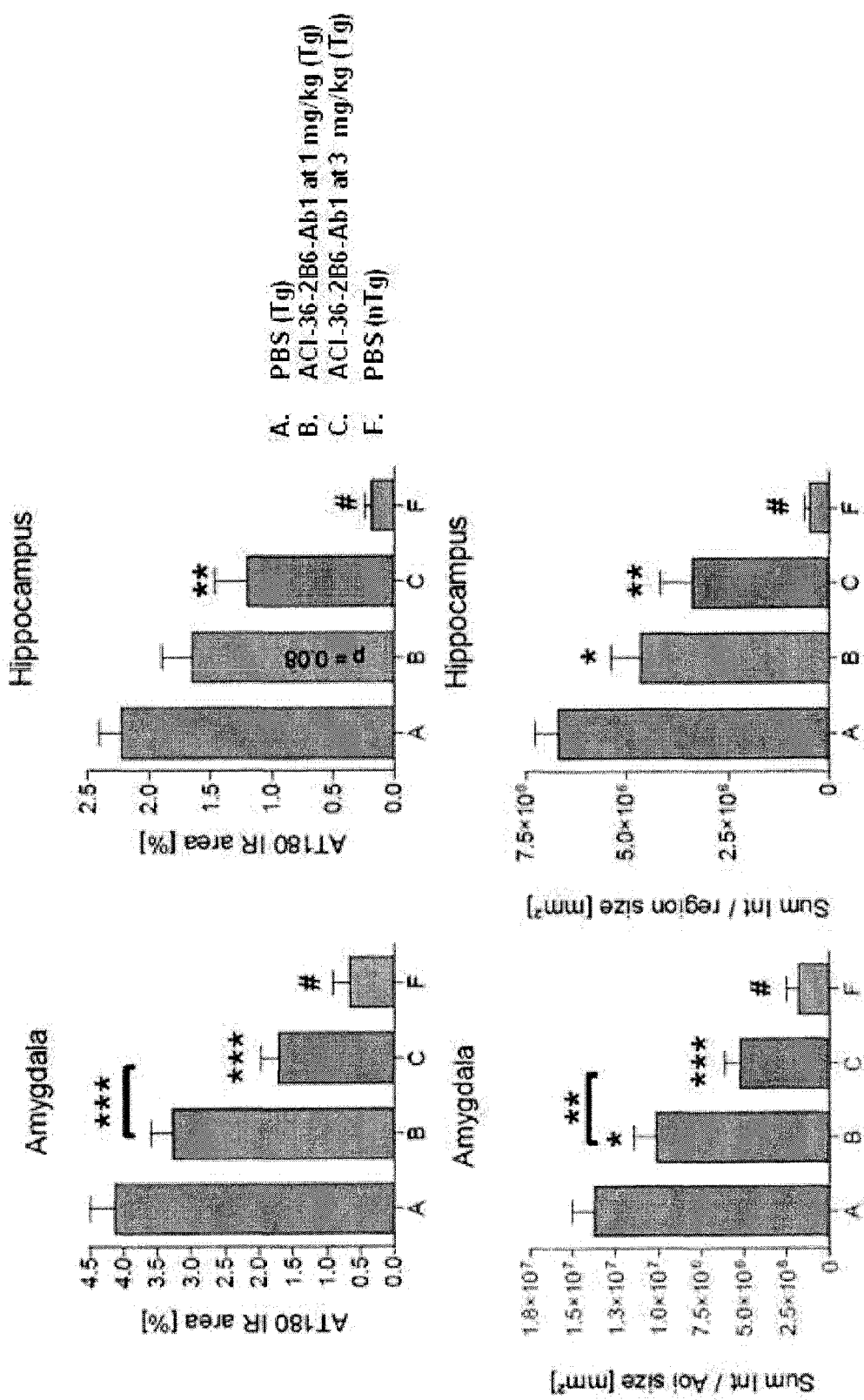
FIG. 7 shows IHC after anti-Tau antibody treatment by ACI-36-2B6-Ab1 in 3 month in vivo study.

The AT180 antibody detects the endogenous and human pTAU (doubly phosphorylated at Thr231 and Ser235). The amount of intrasomal pTAU in nTg controls was significantly lower compared to Tg groups ($p<0.01$ as well as $p<0.001$). In the amygdala, the higher dose of ACI-36-2B6-Ab1 (3 mg/kg—group C) significantly decreased the somal pTAU compared to vehicle treated animals (FIG. 7, left). The lower dose (1 mg/kg—group C) showed the same tendency but did not reach significance. The same effect was detectable in the hippocampus where ACI-36-2B6-Ab1 reduced pTAU dose-dependently, significant for the higher dose and tendentiously for the lower (FIG. 7, right). This decrease was also qualitatively visible as decrease of the area of staining and the staining intensity in individual neuronal somata. Results of the sum staining intensities normalized to A01 size of the measured AT180 IR in the neuronal somata were comparable with measured AT180 IR area percentage, including a significant dose-dependence of the greater effect of the higher dose in the amygdala. In the hippocampus the post hoc comparisons did not reach significance level.

8.2.4 Summary

Brain Tau pathology as measured by MSD did not show a significant change, however immunostaining of brain sections demonstrated a dose-dependent with up to 60% reduction in AT180 (pT231/pS235) immunostaining in neuronal somata.

The study shows that passive immunization using thirteen administrations of a phosphosite-specific anti-pTau antibody ACI-36-2B6-Ab1 can improve spatial learning and significantly reduces brain pTau pathology.

8.3 Results ACI-36-3A8-Ab1 Antibody

Thirteen i.p. injections of ACI-36-3A8-Ab1 administered weekly at 1 or 3 mg/kg over a twelve week study period did not show any gross adverse effects.

8.3.1 Behavioral Results—Morris Water Maze

Figure 10:
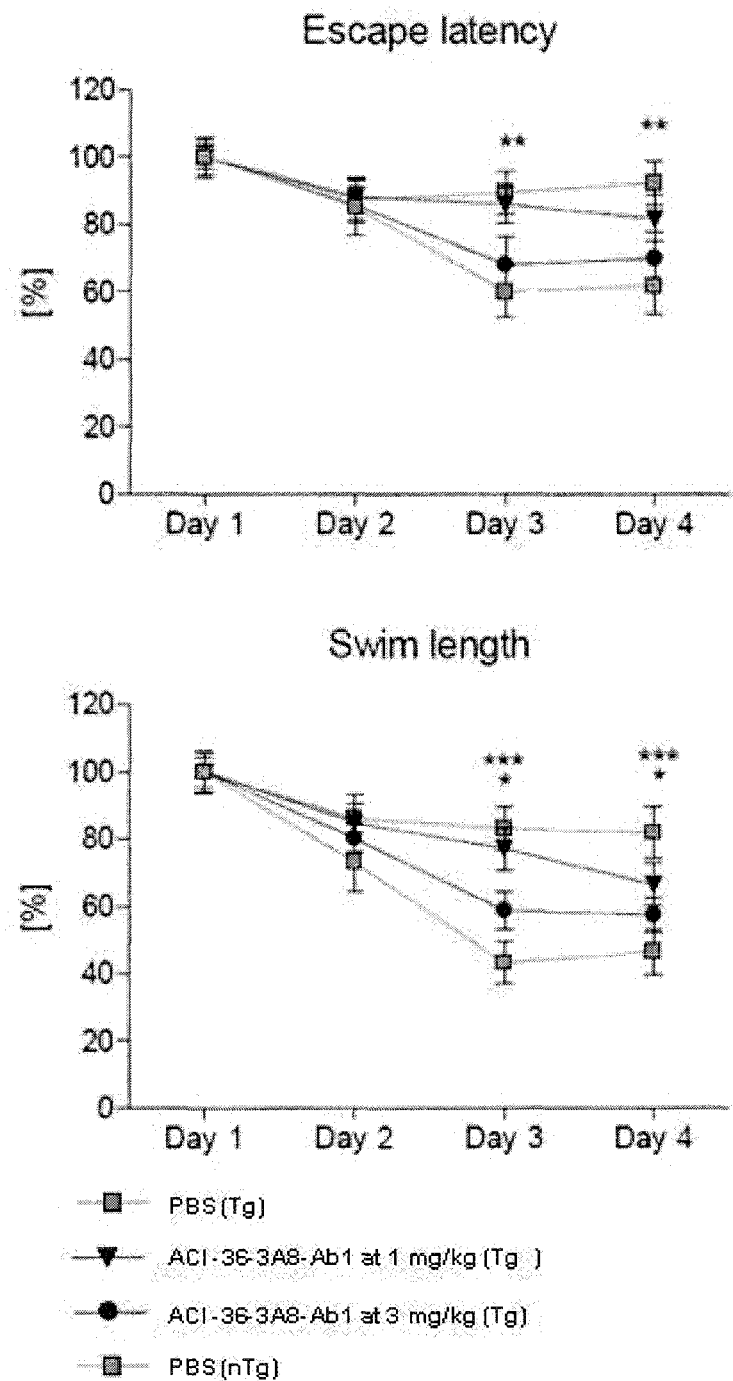
FIG. 10 shows the Morris Water-Maze results after anti-Tau antibody treatment by ACI-36-3A8-Ab1 in 3 month in vivo study.

The results from the MWM test demonstrated a significant effect of improved spatial learning for mice treated with ACI-36-3A8-Ab1 at 3 mg/kg (FIG. 10).

Vehicle treated Tg (group A) and nTg (group F) control animals showed expected learning curves in terms of escape latency and length of the swimming path to reach the platform over the four testing days. Tg control (A) animals showed a significant impairment of learning abilities reflected in flatter learning curves of escape latencies and swimming paths compared to nTg control animals (group F). Escape latencies and swimming paths were significantly (Two Way ANOVA) different on training days 3 ($p<0.01$, latency; $p<0.001$, length; Bonferroni's post test) and 4 ($p<0.01$; Bonferroni's post test). Treatment with ACI-36-3A8-Ab1, low or high dose (D and E) did not significantly improve spatial learning abilities compared to Tg control animals (A) when absolute values are analyzed. When adjusting the performance of each group to 100% on training day 1 and all further days as percentage of day 1, an improvement of learning and memory abilities can be upon ACI-36-3A8-Ab1 treatment (low and high dosage). Animals treated with the low dose of ACI-36-3A8-Ab1 (group D) performed only slightly better in the MWM compared to Tg controls (group A). The effect of a weekly treatment with 3 mg/kg ACI-36-3A8-Ab1 (group E) was much more pronounced and almost restored the performance of nTg animals. Compared to the Tg controls (A) the effect of 3 mg/kg ACI-36-3A8-Ab1 was statistically significant for swimming path length on day 3 and day 4 ($p<0.05$). No differences between treatment groups were detected when calculating the swimming speed on all four training days.

In the probe trial (PT), the abidance in the target quadrant (south west quadrant) as well as target zone crossings were recorded. nTg controls (group F) spent more time in the target quadrant and crossed the target zone more often relative to Tg controls (group A) but without statistical significance. Treatment with neither the low nor the high dose led to a statistically significant improvement in comparison to Tg control mice as evaluated in the PT. However, ACI-36-3A8-Ab1 treated animals had—although statistically insignificantly—more target zone crossings compared to Tg control, that is in accordance with the outcome of the swim length over the 4 training days.

8.3.2 Molecular Biology 8.3.2.1 TAU in Soluble Fraction of Cortex Homogenates

Total TAU, p231TAU, p396TAU, and the ratios of pTAU to total TAU were evaluated in the soluble fraction of cortex homogenates of n=16 animals from group A (Tg vehicle group; PBS) and D (Tg, ACI-36-3A8-Ab1, 1 mg/kg) and of n=15 animals from group E (Tg, ACI-36-3A8-Ab1, 3 mg/kg). A treatment with ACI-36-3A8-Ab1 did not significantly affect total TAU and pTAU in the in soluble cortex homogenates. However, a slight increase (without significance) of mean total TAU, p231TAU, and p396TAU was observed upon ACI-36-3A8-Ab1 treatment. TAU phosphorylation at 231 evaluated as the ratio of p231TAU to total TAU was slightly decreased after treatment with 3 mg/kg ACI-36-3A8-AB1.

8.3.2.2 TAU in Sarcosyl Insoluble Fraction of Cortex Homogenates

Total TAU, p231TAU, p396TAU, and the ratios of pTAU to total TAU were evaluated in the sarcosyl insoluble fractions of cortex homogenates of n=16 animals from group A (Tg vehicle group; PBS) and D (Tg, ACI-36-3A8-Ab1, 1 mg/kg) and of n=15 animals from group E (Tg, ACI-36-3A8-Ab1, 3 mg/kg). A treatment with ACI-36-3A8-AB1 did not significantly affect total TAU and pTAU in the in sarcosyl insoluble cortex homogenates. A slight decrease (without significance) of mean total TAU, p231TAU, and p396TAU was observed upon 1 mg/ACI-36-3A8-Ab1 treatment. Further the p231TAU to total TAU ratios of 1 mg/kg ACI-36-3A8-Ab1 treated animals showed slightly lower variability compared to vehicle treated animals (but with lacking significance in F-Test: $p=0.184$) without changing the mean p231TAU to total TAU ratios of the two groups. For 1 mg/kg and 3 mg/kg ACI-36-3A8-Ab1 treated groups a slight increase of p396TAU phosphorylation was observed.

8.3.2.3 TAU in Soluble Fraction of Hippocampus Homogenates

Total TAU, p231TAU, p396TAU, and the ratios of pTAU to total TAU were evaluated in the soluble fraction of hippocampus homogenates of n=16 animals from group A (Tg vehicle group; PBS) and D (Tg, ACI-36-3A8-Ab1, 1 mg/kg) and of n=15 animals from group E (Tg, ACI-36-3A8-Ab1, 3 mg/kg). TAU and pTAU levels in the soluble hippocampus fractions of IRN6301 (group D) were outliers and were excluded. A treatment with ACI-36-3A8-Ab1 did not significantly affect total TAU and pTAU in the in soluble hippocampus homogenates. A slight decrease (without significance) of TAU phosphorylation at 231 evaluated as the ratios of p231TAU to total TAU was observed upon ACI-36-3A8-Ab1 treatment.

8.3.2.4 TAU in Sarcosyl Insoluble Fraction of Hippocampus Homogenates

Total TAU, p231TAU, p396TAU, and the ratios of pTAU to total TAU were evaluated in the sarcosyl insoluble fractions of hippocampus homogenates of n=16 animals from group A (Tg vehicle group; PBS), B (Tg ACI-36-3A8-Ab1, 1 mg/kg), and C (Tg, ACI-36-3A8-Ab1, 3 mg/kg). A treatment with ACI-36-3A8-Ab1 did not significantly affect total TAU and pTAU in the in sarcosyl insoluble hippocampus homogenates. A slight increase (without significance) of mean total TAU, p231TAU as well as p396TAU was observed upon ACI-36-3A8-Ab1 treatment. TAU phosphorylation evaluated as the ratio of p231TAU to total TAU was not affected and treatment with 1 mg/kg ACI-36-3A8-Ab1 slightly reduced the ratio of p396TAU to total TAU.

8.3.2.5. Western Blots for Soluble Cortex

A significant reduction of the pS396/pS404 pTau epitope in the soluble brain cortex in mice treated with 1 or 3 mg/kg of ACI-36-3A8-Ab1 (FIG. 5D). The presence of the human/transgenic pT181 pTau epitope was reduced in the soluble cortex fraction, with a significant effect in mice treated with 1 mg/kg and trend in mice treated with 3 mg/kg (FIG. 5E). A trend for a reduction was observed in the amount of endogenous pT181 pTau (FIG. 5F).

8.3.2.6 TAU in biGT Tau Bigenic Mice biGT mice treated with ACI-36-3A8-Ab1 for 3 months had significantly reduced total Tau in brain cortex soluble fraction (FIGS. 6A and 6B). A significant reduction was observed for pTau epitopes pT231/AT180 (FIGS. 6C and 6D), pS202/AT8 (FIG. 6E), and pS396 (FIGS. 6F and 6G). A significant reduction was also observed in both total homogenate (TH) for pTau epitope pS400 (FIGS. 6H and 6I) and pS404 (FIGS. 6L and 6M). Furthermore, a significant reduction was also observed in soluble fraction for pTau epitopes pS400 (FIGS. 6J and 6K) and a trend for reduction for pTau epitope pS404 (FIGS. 6N and 6O).

8.3.3 Histology
8.3.3.1 Morphometry—Determination of Region Areas

See Example 8.2.3.1

8.3.3.2 Results of AT180 IH

Figure 8:
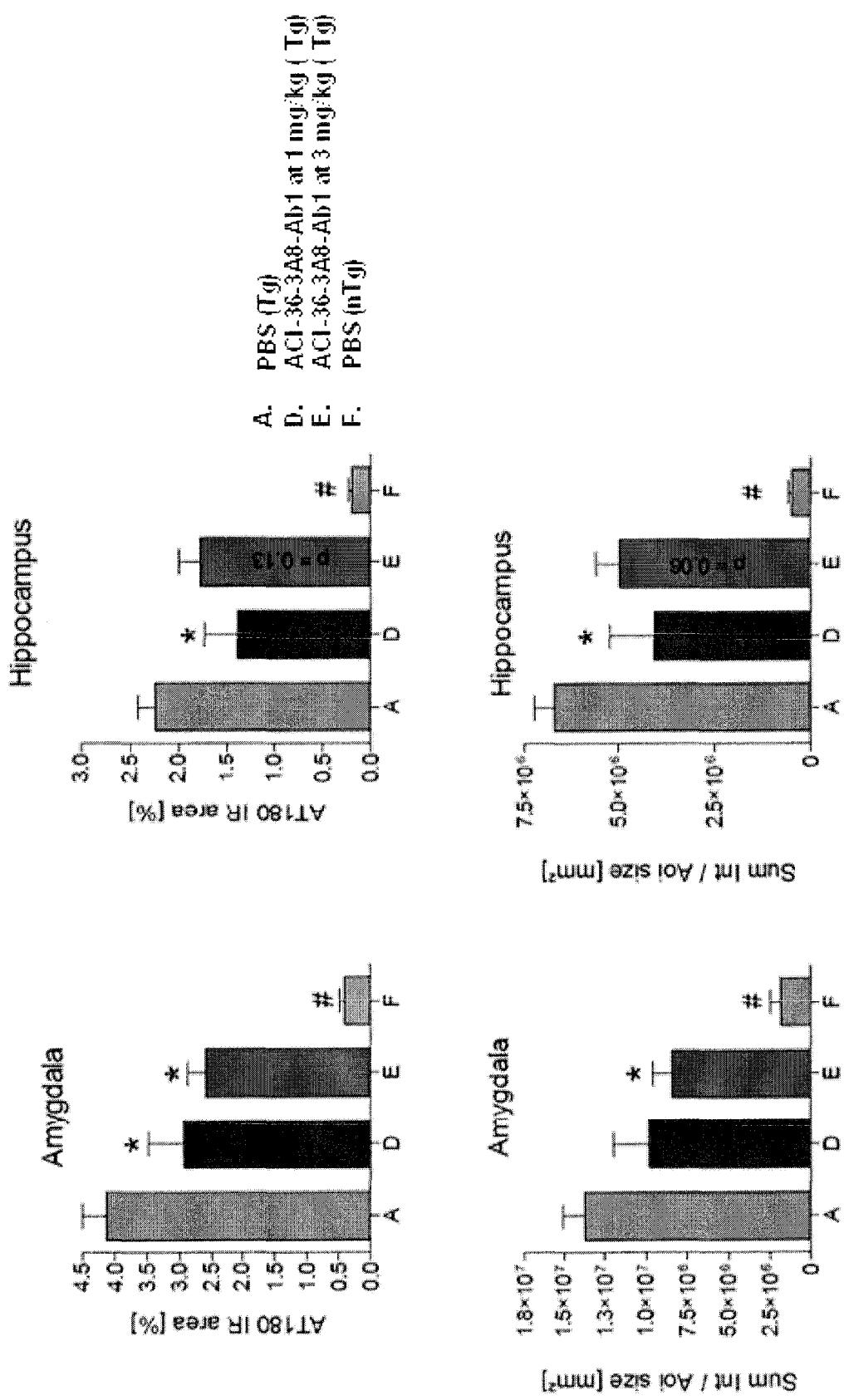
FIG. 8 shows IHC after anti-Tau antibody treatment by ACI-36-3A8-Ab1 in 3 month in vivo study.

The AT180 antibody detects the endogenous and human pTAU (doubly phosphorylated at Thr231 and Ser235). The amount of intrasomal pTAU in nTg controls was significantly lower compared to Tg groups (p<0.001). In the amygdala, both doses of ACI-36-3A8-Ab1 [1 mg/kg (group D) and 3 mg/kg (group E)] significantly decreased the somal pTAU compared to vehicle treated animals (FIG. 8, left). A similar effect was detectable in the hippocampus where the lower dosage ACI-36-3A8-Ab1 reduced pTAU, however in this case the higher dose was less effective and just led to a tendentious decrease (FIG. 8, right). This decrease was also qualitatively visible as decrease of the area of staining and the staining intensity in individual neuronal somata. Results of the normalized sum of intensities of the measured AT180 IR in the neuronal somata were comparable in the amygdala with measured AT180 IR area percentage but reached significance for the higher dose only. In the hippocampus the result was totally comparable to IR area percentage.

8.3.4 Summary

Brain Tau pathology as measured by MSD did not show a significant change, however immunostaining of brain sections demonstrated a dose-dependent with up to 40% reduction in AT180 (pT231/pS235) immunostaining in neuronal somata.

The study shows that passive immunization using thirteen administrations of a phosphosite-specific anti-pTau antibody ACI-36-3A8-Ab1 improves spatial learning and significantly reduces brain pTau pathology.

Deposits

The following hybridoma cell lines were deposited in the name of AC Immune SA, PSE-EPFL Building B, 1015 Lausanne, Switzerland and Katholieke Universiteit Leuven, Minderbroedersstraat 8a—Box 5105, B-3000 Leuven with the "Deutsche Sammlung von Mikroorganismen and Zellkulturen GmbH (DSMZ) in Braunschweig, Inhoffenstrasse 7 B, 38124 Braunschweig, under the provisions of the Budapest Treaty:

| Hybridoma name | Deposit number | Date of deposit |
| --- | --- | --- |
| 6C10F9C12A11 | DSM ACC3079 | Aug. 25, 2010 |
| 6C10E5E9C12 | DSM ACC3081 | Aug. 25, 2010 |
| 6H1A11C11 | DSM ACC3080 | Aug. 25, 2010 |
| 6H1G6E6 | DSM ACC3088 | Aug. 25, 2010 |
| 2B6A10C11 | DSM ACC3084 | Aug. 25, 2010 |
| 2B6G7A12 | DSM ACC3087 | Aug. 25, 2010 |
| 3A8A12G7 | DSM ACC3086 | Aug. 25, 2010 |
| 3A8E12H8 | DSM ACC3085 | Aug. 25, 2010 |
| 7C2(1)F10C10D3 | DSM ACC3082 | Aug. 25, 2010 |
| 7C2(2)B9F11D5 | DSM ACC3083 | Aug. 25, 2010 |
| A4-4A6-48 | DSM ACC3136 | Aug. 30, 2011 |
| A6-2G5-30 | DSM ACC3137 | Aug. 30, 2011 |
| A6-2G5-41 | DSM ACC3138 | Aug. 30, 2011 |
| A4-2A1-18 | DSM ACC3139 | Aug. 30, 2011 |
| A4-2A1-40 | DSM ACC3140 | Aug. 30, 2011 |
| A6-1D2-12 | DSM ACC3141 | Sep. 6th, 2011 |

TABLE 1

Tau sequence, vaccine and antibody description

| Description | Vaccine | Sequence*, length (n), sequence ID number | Hybridomas | Antibodies |
| --- | --- | --- | --- | --- |
| T1: Tau 5-20 [pY18] | ACI-33 | RQEFEVMEDHAGTY(p)GL (n = 16) (SEQ ID NO: 59) | 6C10F9C12A11<br>6C10E5E9C12 | ACI-33-6C10-Ab1<br>ACI-33-6C10-Ab2 |
| T8: Tau 206-221 [pT212, pS214] | ACI-41 | PGSRSRT(p)PS(p)LPTPPTR (n = 16) (SEQ ID NO: 60) | 7C2(1)F10C10D3 | ACI-41-7C2-Ab1 |
| T9: Tau 196-211 [pS202, pT205] | ACI-41 | GYSSPGS(p)PGT(p)PGSRSR (n = 16) (SEQ ID NO: 61) | 7C2(2)B9F11D5 | ACI-41-7C2-Ab1 |
| T4: Tau 401-418 [pS404, pS409] | ACI-36 | GDTS(p)PRHLS(p)NVSSIGSID (n = 18) (SEQ ID NO: 63) | 6H1A11C11<br>6H1G6E6<br>2B6A10C11<br>2B6G7A12<br>3A8A12G7<br>3A8E12H8 | ACI-36-6H1-Ab1<br>ACI-36-6H1-Ab2<br>ACI-36-2B6-Ab1<br>ACI-36-2B6-Ab2<br>ACI-36-3A8-Ab1<br>ACI-36-3A8-Ab2 |
| T3: Tau 393-408 [pS396, pS404] | ACI-35 | VYKS(p)PVVSGDTS(p)PRHL (n = 16) (SEQ ID NO: 62) | A4-4A6-48<br>A6-2G5-30<br>A6-2G5-41<br>A4-2A1-18 | ACI-35-4A6-Ab2<br>ACI-35-2G5-Ab2<br>ACI-35-2G5-Ab3<br>ACI-35-2A1-Ab1 |

TABLE 1-continued

Tau sequence, vaccine and antibody description

| Description | Vaccine | Sequence*, length (n), sequence ID number | Hybridomas | Antibodies |
|---|---|---|---|---|
| | | | A4-2A1-40 | ACI-35-2A1-Ab2 |
| | | | A6-1D2-12 | ACI-35-1D2-Ab1 |
| T5: Control sequence: Tau 379-408 [pS396, pS404] | ACI-37 | RENAKAKTDHGAEIVYKS(p)PVVSGDTS(p)PRHL (n = 30) (SEQ ID NO: 58) | | |
| T8: Tau 206-221 [pT212, pS214] | ACI-39 | PGSRSRT(p)PS(p)LPTPPTR (n = 16) (SEQ ID NO: 60) | | |
| T9: Tau 196-211 [pS202, pT205] | ACI-40 | GYSSPGS(p)PGT(p)PGSRSR (n = 16) (SEQ ID NO: 61) | | |
| T2: Tau 200-216 [pS202 + pT205 & pT212 + pS214] | ACI-34 | PGS(p)PGT(p)PGSRSRT(p)PS(p)LP (n = 17) (SEQ ID NO: 64) | | |
| T10: Tau 407-418 [pS409] | ACI-42 | HLS(p)NVSSTGSID (n = 12) (SEQ ID NO: 65) | | |
| T11: Tau 399-408 [pS404] | ACI-43 | VSGDTS(p)PRHL (n = 10) (SEQ ID NO: 66) | | |

*Based on the longest isoform of human Tau (Tau441). p indicates phosphorylated residue.

TABLE 2

Results of ACI-33 hybridoma screen

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| 1A7 | | 1A7 | | |
| | 1A11 | | | |
| | 1C11 | 1C11 | | |
| 2C9 | | 2C9 | | |
| 3C3 | | 3C3 | 3C3 | |
| 3C5 | | 3C5 | | |
| 3E8 | | 3E8 | | |
| 3G10 | 3G10 | 3G10 | 3G10 | |
| 6C10 | 6C10 | 6C10 | 6C10 | 6C10 |
| 6F3 | | 6F3 | | |
| 6F8 | | 6F8 | | |

TABLE 3

Results of ACI-36 hybridoma screen

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| 2B6 | 2B6 | 2B6 | 2B6 | 2B6 |
| 2F9 | 2F9 | 2F9 | 2F9 | 2F9 |
| 2G1 | | 2G1 | 2G1 | 2G1 |
| 3A8 | 3A8 | 3A8 | 3A8 | 3A8 |
| 3B9 | | 3B9 | 3B9 | 3B9 |
| 3F11 | 3F11 | 3F11 | | 3F11 |
| | 4A3 | | | 4A3 |

TABLE 3-continued

Results of ACI-36 hybridoma screen

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| 4C1 | 4C1 | 4C1 | 4C1 | 4C1 |
| 4C12 | | 4C12 | 4C12 | 4C12 |
| 4E12 | | 4E12 | 4E12 | 4E12 |
| 5E10 | | 5E10 | 5E10 | |
| 5F5 | | 5F5 | 5F5 | |
| 7D6 | 7D6 | 7D6 | 7D6 | 7D6 |
| 6H1 | | 6H1 | 6H1 | 6H1 |

TABLE 4

Ranking for positive clones in ELISA and TAUPIR of ACI-36

| ranking for ELISA | ranking for TAUPIR |
|---|---|
| 3A8 | 6H1 |
| 2B6 | 4C1 |
| 4C1 | 3A8 |
| 6H1 | 4C12 |
| 4C12 | 2B6 |
| 2G1 | 2F9 |
| 2F9 | 3B9 |
| 7D6 | 2G1 |
| 3B9 | 7D6 |
| 4E12 | 4E12 |

TABLE 5

Results of ACI-41 hybridoma screen

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| | 3D11 | 3D11 | | 3D11 |
| 4H6 | 4H6 | 4H6 | | 4H6 |
| 5D10 | 5D10 | 5D10 | 5D10 | 5D10 |
| 5E6 | 5E6 | | | |
| 5F10 | | 5F10 | | |

TABLE 5-continued

Results of ACI-41 hybridoma screen

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| 6B7 | | 6B7 | 6B7 | |
| 7C2 | 7C2 | 7C2 | 7C2 | 7C2 |
| | | 8G8 | | 8G8 |
| | | 8H8 | 8H8 | 8H8 |

TABLE 6

Screening of hybridomas for binding to target

| Hybridomas | Antibodies | ELISA Tau p-peptide | Tau peptide | Full-length pTau | Full-length Tau | TAUPIR | Western Blot |
|---|---|---|---|---|---|---|---|
| 6C10F9C12A11 | ACI-33-6C10-Ab1 | + | − | +/− | − | + | − |
| 6C10E5E9C12 | ACI-33-6C10-Ab2 | + | − | +/− | − | + | − |
| 6H1A11C11 | ACI-36-6H1-Ab1 | + | − | + | − | + | + |
| 6H1G6E6 | ACI-36-6H1-Ab2 | + | − | + | − | + | + |
| 2B6A10C11 | ACI-36-2B6-Ab1 | + | − | + | − | + | + |
| 2B6G7A12 | ACI-36-2B6-Ab2 | + | − | + | − | + | + |
| 3A8A12G7 | ACI-36-3A8-Ab1 | + | − | + | − | + | + |
| 3A8E12H8 | ACI-36-3A8-Ab2 | + | − | + | −/+ | + | + |
| 7C2(1)F10C10D3 | ACI-41-7C2-Ab1 | + | − | + | − | + | − |
| 7C2(2)B9F11D5 | ACI-41-7C2-Ab2 | + | − | + | − | + | − |
| A4-2A1-18 | ACI-35-2A1-Ab1 | + | − | + | − | | |
| A4-2A1-40 | ACI-35-2A1-Ab2 | + | − | + | − | | |
| A4-4A6-18 | ACI-35-4A6-Ab1 | + | − | − | | + | |
| A4-4A6-48 | ACI-35-4A6-Ab2 | | | | | | |
| A6-1D2-12 | ACI-35-1D2-Ab1 | + | − | + | − | | |
| A6-2G5-08 | ACI-35-2G5-Ab1 | + | − | − | − | | |
| A6-2G5-30 | ACI-35-2G5-Ab2 | + | − | + | − | | |
| A6-2G5-41 | ACI-35-2G5-Ab3 | + | − | + | − | | |

TABLE 7

Binding affinity of anti-tau antibodies

| Hybridomas | Antibodies | Association rate constant ($k_d$) (1/Ms) | Dissociation rate constant ($k_a$) (1/s) | Dissociation constant ($K_D$) (nM) |
|---|---|---|---|---|
| 6C10F9C12A11 | ACI-33-6C10-Ab1 | $9.46 \times 10^5$ | $3.27 \times 10^{-3}$ | 3.46 |
| 6H1A11C11 | ACI-36-6H1-Ab1 | $3.53 \times 10^4$ | $6.80 \times 10^{-5}$ | 1.93 |
| 6H1G6E6 | ACI-36-6H1-Ab2 | $9.99 \times 10^4$ | $9.58 \times 10^{-5}$ | 0.96 |
| 2B6A10C11 | ACI-36-2B6-Ab1 | $6.90 \times 10^5$ | $1.63 \times 10^{-4}$ | 0.24 |
| 2B6G7A12 | ACI-36-2B6-Ab2 | $9.11 \times 10^5$ | $1.11 \times 10^{-4}$ | 0.12 |
| 3A8A12G7 | ACI-36-3A8-Ab1 | $1.01 \times 10^6$ | $1.09 \times 10^{-4}$ | 0.11 |
| 3A8E12H8 | ACI-36-3A8-Ab2 | $8.43 \times 10^5$ | $1.43 \times 10^{-4}$ | 0.17 |
| A4-4A6-18 | ACI-35-4A6-Ab1 | $2.00 \times 10^5$ | $3.10 \times 10^{-3}$ | 16 |
| A6-1D2-12 | ACI-35-1D2-Ab1 | $1.60 \times 10^3$ | $9.30 \times 10^{-6}$ | ≤6 |
| A6-2G5-08 | ACI-35-2G5-Ab1 | $4.80 \times 10^5$ | $5.30 \times 10^{-3}$ | 10 |

TABLE 8

Peptide libraries used for epitope mapping

Peptide library for T1

Tau(441) amino acid number

| Peptide no | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| | R | Q | E | F | E | V | M | E | D | H | A | G | T | Y(P) | G | L |

Phospho peptides

| Peptide no | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| T1.18 | | | | | | | | | | | A | G | T | Y(P) | G | L |
| T1.17 | | | | | | | | | | H | A | G | T | Y(P) | G | L |
| T1.16 | | | | | | | | | D | H | A | G | T | Y(P) | G | L |
| T1.15 | | | | | | | | E | D | H | A | G | T | Y(P) | G | L |
| T1.14 | | | | | | | M | E | D | H | A | G | T | Y(P) | G | L |
| T1.13 | | | | | | V | M | E | D | H | A | G | T | Y(P) | G | L |
| T1.12 | | | | | E | V | M | E | D | H | A | G | T | Y(P) | G | L |
| T1.11 | | | | F | E | V | M | E | D | H | A | G | T | Y(P) | G | L |
| T1.10 | | | E | F | E | V | M | E | D | H | A | G | T | Y(P) | G | L |
| T1.9 | | Q | E | F | E | V | M | E | D | H | A | G | T | Y(P) | G | L |
| T1.7 | R | Q | E | F | E | V | M | E | D | H | A | G | T | Y(P) | G | L |

| Peptide no | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| | R | Q | E | F | E | V | M | E | D | H | A | G | T | Y | G | L |

Non-phospho peptides

| Peptide no | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| T1.28 | | | | | | | | | | | A | G | T | Y | G | L |
| T1.27 | | | | | | | | | | H | A | G | T | Y | G | L |
| T1.26 | | | | | | | | | D | H | A | G | T | Y | G | L |
| T1.25 | | | | | | | | E | D | H | A | G | T | Y | G | L |
| T1.24 | | | | | | | M | E | D | H | A | G | T | Y | G | L |
| T1.23 | | | | | | V | M | E | D | H | A | G | T | Y | G | L |
| T1.22 | | | | | E | V | M | E | D | H | A | G | T | Y | G | L |
| T1.21 | | | | F | E | V | M | E | D | H | A | G | T | Y | G | L |
| T1.20 | | | E | F | E | V | M | E | D | H | A | G | T | Y | G | L |
| T1.19 | | Q | E | F | E | V | M | E | D | H | A | G | T | Y | G | L |
| T1.8 | R | Q | E | F | E | V | M | E | D | H | A | G | T | Y | G | L |

Peptide library for T4

Tau(441) amino acid number

| Peptide no. | 401 | 402 | 403 | 404 | 405 | 406 | 407 | 408 | 409 | 410 | 411 | 412 | 413 | 414 | 415 | 416 | 417 | 418 |
|---|---|---|---|---|---|---|---|---|---|---|---|---|---|---|---|---|---|---|
| | G | D | T | S(p) | P | R | H | L | S(p) | N | V | S | S | T | G | S | I | D |

Phospho peptides

| Peptide no. | 401 | 402 | 403 | 404 | 405 | 406 | 407 | 408 | 409 | 410 | 411 | 412 | 413 | 414 | 415 | 416 | 417 | 418 |
|---|---|---|---|---|---|---|---|---|---|---|---|---|---|---|---|---|---|---|
| T3.17 | G | D | T | S(p) | P | R | H | L | | | | | | | | | | |
| T4.11 | | D | T | S(p) | P | R | H | L | S(p) | | | | | | | | | |
| T4.12 | | | T | S(p) | P | R | H | L | S(p) | N | | | | | | | | |
| T4.13 | | | | S(p) | P | R | H | L | S(p) | N | V | | | | | | | |
| T4.14 | | | | | P | R | H | L | S(p) | N | V | S | | | | | | |

TABLE 8-continued

Peptide libraries used for epitope mapping

| | | | | | | | | | | | | | | | | | | |
|---|---|---|---|---|---|---|---|---|---|---|---|---|---|---|---|---|---|---|
| T4.15 | | | | | | R | H | L | S(p) | N | V | S | S | | | | | |
| T4.16 | | | | | | | H | L | S(p) | N | V | S | S | T | | | | |
| T4.17 | | | | | | | | L | S(p) | N | V | S | S | T | G | | | |
| T4.18 | | | | | | | | | S(p) | N | V | S | S | T | G | S | | |
| T4.19 | | | | | | | | | | N | V | S | S | T | G | S | I | |
| T4.20 | | | | | | | | | | | V | S | S | T | G | S | I | D |

| Peptide no. | Amino acid | | | | | | | | | | | | | | | | | |
|---|---|---|---|---|---|---|---|---|---|---|---|---|---|---|---|---|---|---|
| | G | D | T | S | P | R | H | L | S | N | V | S | S | T | G | S | I | D |

Non-phospho peptides

| | | | | | | | | | | | | | | | | | | |
|---|---|---|---|---|---|---|---|---|---|---|---|---|---|---|---|---|---|---|
| T3.26 | G | D | T | S | P | R | H | L | | | | | | | | | | |
| T4.21 | | D | T | S | P | R | H | L | S | | | | | | | | | |
| T4.22 | | | T | S | P | R | H | L | S | N | | | | | | | | |
| T4.23 | | | | S | P | R | H | L | S | N | V | | | | | | | |
| T4.24 | | | | | P | R | H | L | S | N | V | S | | | | | | |
| T4.25 | | | | | | R | H | L | S | N | V | S | S | | | | | |
| T4.26 | | | | | | | H | L | S | N | V | S | S | T | | | | |
| T4.27 | | | | | | | | L | S | N | V | S | S | T | G | | | |
| T4.28 | | | | | | | | | S | N | V | S | S | T | G | S | | |
| T4.19 | | | | | | | | | | N | V | S | S | T | G | S | I | |
| T4.20 | | | | | | | | | | | V | S | S | T | G | S | I | D |

Peptide library for T8

Tau(441) amino acid number

| 206 | 207 | 208 | 209 | 210 | 211 | 212 | 213 | 214 | 215 | 216 | 217 | 218 | 219 | 220 | 221 |
|---|---|---|---|---|---|---|---|---|---|---|---|---|---|---|---|

Amino acid

| Peptide no | P | G | S | R | S | R | T(p) | P | S(p) | L | P | T | P | P | T | R |
|---|---|---|---|---|---|---|---|---|---|---|---|---|---|---|---|---|

Phospho peptides

| | | | | | | | | | | | | | | | | |
|---|---|---|---|---|---|---|---|---|---|---|---|---|---|---|---|---|
| T8.7 | P | G | S | R | S | R | T(p) | P | | | | | | | | |
| T8.8 | | G | S | R | S | R | T(p) | P | S(p) | | | | | | | |
| T8.9 | | | S | R | S | R | T(p) | P | S(p) | L | | | | | | |
| T8.10 | | | | R | S | R | T(p) | P | S(p) | L | P | | | | | |
| T8.11 | | | | | S | R | T(p) | P | S(p) | L | P | T | | | | |
| T8.12 | | | | | | R | T(p) | P | S(p) | L | P | T | P | | | |
| T8.13 | | | | | | | T(p) | P | S(p) | L | P | T | P | P | | |
| T8.14 | | | | | | | | P | S(p) | L | P | T | P | P | T | |
| T8.15 | | | | | | | | | S(p) | L | P | T | P | P | T | R |

Amino acid

| Peptide no | P | G | S | R | S | R | T | P | S | L | P | T | P | P | T | R |
|---|---|---|---|---|---|---|---|---|---|---|---|---|---|---|---|---|

Non-phospho peptides

| | | | | | | | | | | | | | | | | |
|---|---|---|---|---|---|---|---|---|---|---|---|---|---|---|---|---|
| T8.16 | P | G | S | R | S | R | T | P | | | | | | | | |
| T8.17 | | G | S | R | S | R | T | P | S | | | | | | | |
| T8.18 | | | S | R | S | R | T | P | S | L | | | | | | |
| T8.19 | | | | R | S | R | T | P | S | L | P | | | | | |
| T8.20 | | | | | S | R | T | P | S | L | P | T | | | | |
| T8.21 | | | | | | R | T | P | S | L | P | T | P | | | |
| T8.22 | | | | | | | T | P | S | L | P | T | P | P | | |
| T8.23 | | | | | | | | P | S | L | P | T | P | P | T | |
| T8.24 | | | | | | | | | S | L | P | T | P | P | T | R |

Peptide library for T9

Tau(441) amino acid number

| 196 | 197 | 198 | 199 | 200 | 201 | 202 | 203 | 204 | 205 | 206 | 207 | 208 | 209 | 210 | 211 |
|---|---|---|---|---|---|---|---|---|---|---|---|---|---|---|---|

Amino acid

| Peptide no | G | Y | S | S | P | G | S(p) | P | G | T(p) | P | G | S | R | S | R |
|---|---|---|---|---|---|---|---|---|---|---|---|---|---|---|---|---|

TABLE 8-continued

Peptide libraries used for epitope mapping

Phospho peptides

| | | | | | | | | | | | | | | | |
|---|---|---|---|---|---|---|---|---|---|---|---|---|---|---|---|
| T9.7 | G | Y | S | S | P | G | S(p) | P | | | | | | | |
| T9.8 | | Y | S | S | P | G | S(p) | P | G | | | | | | |
| T9.9 | | | S | S | P | G | S(p) | P | G | T(p) | | | | | |
| T9.10 | | | | S | P | G | S(p) | P | G | T(p) | P | | | | |
| T9.11 | | | | | P | G | S(p) | P | G | T(p) | P | G | | | |
| T9.12 | | | | | | G | S(p) | P | G | T(p) | P | G | S | | |
| T9.13 | | | | | | | S(p) | P | G | T(p) | P | G | S | R | |
| T9.14 | | | | | | | | P | G | T(p) | P | G | S | R | S |
| T9.15 | | | | | | | | | G | T(p) | P | G | S | R | S | R |

Amino acid

| Peptide no | G | Y | S | S | P | G | S | P | G | T | P | G | S | R | S | R |
|---|---|---|---|---|---|---|---|---|---|---|---|---|---|---|---|---|

Non-phospho peptides

| | | | | | | | | | | | | | | | |
|---|---|---|---|---|---|---|---|---|---|---|---|---|---|---|---|
| T9.16 | G | Y | S | S | P | G | S | P | | | | | | | |
| T9.17 | | Y | S | S | P | G | S | P | G | | | | | | |
| T9.18 | | | S | S | P | G | S | P | G | T | | | | | |
| T9.19 | | | | S | P | G | S | P | G | T | P | | | | |
| T9.20 | | | | | P | G | S | P | G | T | P | G | | | |
| T9.21 | | | | | | G | S | P | G | T | P | G | S | | |
| T9.22 | | | | | | | S | P | G | T | P | G | S | R | |
| T9.23 | | | | | | | | P | G | T | P | G | S | R | S |
| T9.24 | | | | | | | | | G | T | P | G | S | R | S | R |

Peptide library for T3

Tau(441) amino acid number

| | 393 | 394 | 395 | 396 | 397 | 398 | 399 | 400 | 401 | 402 | 403 | 404 | 405 | 406 | 407 | 408 |
|---|---|---|---|---|---|---|---|---|---|---|---|---|---|---|---|---|
| Peptide no. | V | Y | K | S(p) | P | V | V | S | G | D | T | S(p) | P | R | H | L |

Phospho peptides

| | | | | | | | | | | | | | | | |
|---|---|---|---|---|---|---|---|---|---|---|---|---|---|---|---|
| T3.9 | V | Y | K | S(p) | P | V | V | S | | | | | | | | |
| T3.10 | | Y | K | S(p) | P | V | V | S | G | | | | | | | |
| T3.11 | | | K | S(p) | P | V | V | S | G | D | | | | | | |
| T3.12 | | | | S(p) | P | V | V | S | G | D | T | | | | | |
| T3.13 | | | | | P | V | V | S | G | D | T | S(p) | | | | |
| T3.14 | | | | | | V | V | S | G | D | T | S(p) | P | | | |
| T3.15 | | | | | | | V | S | G | D | T | S(p) | P | R | | |
| T3.16 | | | | | | | | S | G | D | T | S(p) | P | R | H | |
| T3.17 | | | | | | | | | G | D | T | S(p) | P | R | H | L |

| Peptide no. | V | Y | K | S | P | V | V | S | G | D | T | S | P | R | H | L |
|---|---|---|---|---|---|---|---|---|---|---|---|---|---|---|---|---|

Non-phospho peptides

| | | | | | | | | | | | | | | | |
|---|---|---|---|---|---|---|---|---|---|---|---|---|---|---|---|
| T3.18 | V | Y | K | S | P | V | V | S | | | | | | | | |
| T3.19 | | Y | K | S | P | V | V | S | G | | | | | | | |
| T3.20 | | | K | S | P | V | V | S | G | D | | | | | | |
| T3.21 | | | | S | P | V | V | S | G | D | T | | | | | |
| T3.22 | | | | | P | V | V | S | G | D | T | S | | | | |
| T3.23 | | | | | | V | V | S | G | D | T | S | P | | | |
| T3.24 | | | | | | | V | S | G | D | T | S | P | R | | |
| T3.25 | | | | | | | | S | G | D | T | S | P | R | H | |
| T3.26 | | | | | | | | | G | D | T | S | P | R | H | L |

TABLE 9

Tau amino acids and phospho-residues required for antibody binding.

| Vaccine | Hybridoma | Epitope* |
|---|---|---|
| ACI-33 | 6C10F9C12A11 | Tau aa 15-20, with requirement for pY18 |
| ACI-33 | 6C10E5E9C12 | Tau aa 15-20, with requirement for pY18 |
| ACI-36 | 6H1A11C11 | Tau aa 405-412, with requirement for pS409 |
| ACI-36 | 6H1G6E6 | Tau aa 405-412, with requirement for pS409 |
| ACI-36 | 2B6A10C11 | Tau aa 405-411, with requirement for pS409 |
| ACI-36 | 2B6G7A12 | Tau aa 405-411, with requirement for pS409 |
| ACI-36 | 3A8A12G7 | Tau aa 405-411, with requirement for pS409 |
| ACI-36 | 3A8E12H8 | Tau aa 405-411, with requirement for pS409 |
| ACI-41 | 7C2(1) F10C10D3 | Tau aa 208-218, with requirement for pT212 and pS214 |
| ACI-35 | A4-2A1-18 | Tau aa 393-401, with requirement for pS396 |
| ACI-35 | A4-2A1-40 | Tau aa 393-401, with requirement for pS396 |
| ACI-35 | A4-4A6-18 | Tau aa 396-401, with requirement for pS396 |
| ACI-35 | A6-1D2-12 | Tau aa 394-400, with requirement for pS396 |
| ACI-35 | A6-2G5-08 | Tau aa 402-406, with requirement for pS404 |
| ACI-35 | A6-2G5-30 | Tau aa 393-400, with requirement for pS396 |
| ACI-35 | A6-2G5-41 | Tau aa 393-400, with requirement for pS396 |

*Based on the longest isoform of human Tau (Tau441)

TABLE 10

Amino Acid Sequence of the heavy chain and light chain variable regions (VH and VK) and the CDRs

| Vaccine | Hybridoma | VH Primer (mix) | VK Primer (mix) | VH | VK | VH CDR1 | VH CDR2 | VH CDR3 | VK CDR1 | VK CDR2 | VK CDR3 |
|---|---|---|---|---|---|---|---|---|---|---|---|
| ACI-36 | 3A8A12G7* | SEQ ID NO: 46 and SEQ ID NO: 47 | VK_AD (SEQ ID NO: 48/ SEQ ID NO: 49/ and SEQ ID NO: 51) | EVQLQQSGPELVKPGA SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 1) | DIVMTQSPSSLAMSVG QKVTMSCKSSQSVFNS GNQKNSLAWYQQKPG QSPKLLVYFASTRESGV PDRFIGSGSGTDFSLTI SSVQAEDLADYFCQEH YTTPPTFGTGTKLELK (SEQ ID NO: 6) | GYTFTD YYMN (SEQ ID NO: 12) | DINPNR GGTTYN QKFKG (SEQ ID NO: 13) | YYAVG Y (SEQ ID NO: 14) | KSSQSVF NSGNQK NSLA (SEQ ID NO: 21) | FASTRE S (SEQ ID NO: 22) | QEHYTT PPT (SEQ ID NO: 23) |
| ACI-36 | 3A8A12G7* | SEQ ID NO: 46 and SEQ ID NO: 47 | VK_G (SEQ ID NO: 50 and SEQ ID NO: 51) | EVQLQQSGPELVKPGA SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 1) | DVVMTQTPLSLPVSLG DQASISCRSSQRLVHS HGKTYLHWYLQKPGQS PKLLIYKVSNRFSGVPD RFSGSGSGTDFTLKISR VEAEDLGVYFCSQTAH FPYTFGGGTKLEIK (SEQ ID NO: 7) | GYTFTD YYMN (SEQ ID NO: 12) | DINPNR GGTTYN QKFKG (SEQ ID NO: 13) | YYAVG Y (SEQ ID NO: 14) | RSSQRLV HSHGKT YLH (SEQ ID NO: 24) | KVSNRF S (SEQ ID NO: 25) | SQTAHF PYT (SEQ ID NO: 26) |
| ACI-36 | 3A8E12H8* | SEQ ID NO: 46 and SEQ ID NO: 47 | VK_AD (SEQ ID NO: 48/ SEQ ID NO: 49 and SEQ ID NO: 51) | EVQLQQSGPELVKPGA SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 1) | DIVMTQSPSSLAMSVG QKVTMSCKSSQSVFNS GNQKNSLAWYQQKPG QSPKLLVYFASTRESGV PDRFIGSGSGTDFSLTI SSVQAEDLADYFCQEH YTTPPTFGTGTKLELK (SEQ ID NO: 6) | GYTFTD YYMN (SEQ ID NO: 12) | DINPNR GGTTYN QKFKG (SEQ ID NO: 13) | YYAVG Y (SEQ ID NO: 14) | KSSQSVF NSGNQK NSLA (SEQ ID NO: 21) | FASTRE S (SEQ ID NO: 22) | QEHYTT PPT (SEQ ID NO: 23) |
| ACI-36 | 3A8E12H8* | SEQ ID NO: 46 and SEQ ID NO: 47 | VK_G (SEQ ID NO: 50 and SEQ ID NO: 51) | EVQLQQSGPELVKPGA SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 1) | DVVMTQTPLSLPVSLG DQASISCRSSQRLVHS HGKTYLHWYLQKPGQS PKLLIYKVSNRFSGVPD RFSGSGSGTDFTLKISR VEAEDLGVYFCSQTAH FPYTFGGGTKLEIK (SEQ ID NO: 7) | GYTFTD YYMN (SEQ ID NO: 12) | DINPNR GGTTYN QKFKG (SEQ ID NO: 13) | YYAVG Y (SEQ ID NO: 14) | RSSQRLV HSHGKT YLH (SEQ ID NO: 24) | KVSNRF S (SEQ ID NO: 25) | SQTAHF PYT (SEQ ID NO: 26) |
| ACI-36 | 2B6A10C11 | SEQ ID NO: 46/ SEQ ID NO: 52 and SEQ ID NO: 47 | SEQ ID NO: 50 and SEQ ID NO: 51 | EVQLQQSGPELVKPGT SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 2) | DVVMTQTPLSLPVSLG DQASISCRSSQSLVHSH GKTYLHWYLQKPGQSP KLLIYKVSNRFSGVPDR FSGSGSGTDFTLKISRV EAEDLGVYFCSQTAHF PYTFGGGTKLEIK (SEQ ID NO: 8) | GYTFTD YYMN (SEQ ID NO: 12) | DINPNR GGTTYN QKFKG (SEQ ID NO: 13) | YYAVG Y (SEQ ID NO: 14) | RSSQSLV HSHGKT YLH (SEQ ID NO: 27) | KVSNRF S (SEQ ID NO: 25) | SQTAHF PYT (SEQ ID NO: 26) |

TABLE 10-continued

Amino Acid Sequence of the heavy chain and light chain variable regions (VH and VK) and the CDRs

| Vaccine | Hybridoma | VH Primer (mix) | VK Primer (mix) | VH | VK | VH CDR1 | VH CDR2 | VH CDR3 | VK CDR1 | VK CDR2 | VK CDR3 |
|---|---|---|---|---|---|---|---|---|---|---|---|
| ACI-36 | 2B6G7A12 | SEQ ID NO: 46/ SEQ ID NO: 52 and SEQ ID NO: 47 | SEQ ID NO: 50 and SEQ ID NO: 51 | EVQLQQSGPELVKPGT SVKISCKASGYTFTDYY MNWVKQSHGKSLEWIG DINPNRGGTTYNQKFK GKATLTVDKSSSTAYM ELRSLTSEDSAVYYCAS YYAVGYWGQGTTLTVS S (SEQ ID NO: 2) | DVVMTQTPLSLPVSLG DQASISCRSSQSLVHSH GKTYLHWYLQKPGQSP KLLIYKVSNRFSGVPDR FSGSGSGTDFTLKISRV EAEDLGVFCSQTAHF PYTFGGGTKLEIK (SEQ ID NO: 8) | GYTFTD YYMN (SEQ ID NO: 12) | DINPNR GGTTYN QKFKG (SEQ ID NO: 13) | YYAVG Y (SEQ ID NO: 14) | RSSQSLV HSHGKT YLH (SEQ ID NO: 27) | KVSNRF S (SEQ ID NO: 25) | SQTAHF PYT (SEQ ID NO: 26) |
| ACI-36 | 6H1A11C11 | SEQ ID NO: 46 and SEQ ID NO: 47 | SEQ ID NO: 50 and SEQ ID NO: 51 | EVQLQQSGPELVKPGA SVKISCKASGYTFTDYY MNWVKQSHGKSLEWIG DINPNRGGTTYNQKFK GKATLTVDTSSSTAYME LRSLTSEDSAVYYCASY YAVGYWGQGTTLTVSS (SEQ ID NO: 3) | DVVMTQTPLSLPVSLG DQASISCRSSQSLLHSH GNTYLHWYLQKPGQSP KLLIYKVSNRFSGVPDR FSGSGSGTDFTLKISRV EAEDLGVFCSQTAHF PYTFGGGTKLEIK (SEQ ID NO: 9) | GYTFTD YYMN (SEQ ID NO: 12) | DINPNR GGTTYN QKFKG (SEQ ID NO: 13) | YYAVG Y (SEQ ID NO: 14) | RSSQSLL HSHGNT YLH (SEQ ID NO: 28) | KVSNRF S (SEQ ID NO: 25) | SQTAHF PYT (SEQ ID NO: 26) |
| ACI-36 | 6H1G6E6 | SEQ ID NO: 46 and SEQ ID NO: 47 | SEQ ID NO: 50 and SEQ ID NO: 51 | EVQLQQSGPELVKPGA SVKISCKASGYTFTDYY MNWVKQSHGKSLEWIG DINPNRGGTTYNQKFK GKATLTVDTSSSTAYME LRSLTSEDSAVYYCASY YAVGYWGQGTTLTVSS (SEQ ID NO: 3) | DVVMTQTPLSLPVSLG DQASISCRSSQSLLHSH KLLIYKVSNRFSGVPDR FSGSGSGTDFTLKISRV EAEDLGVFCSQTAHF PYTFGGGTKLEIK (SEQ ID NO: 9) | GYTFTD YYMN (SEQ ID NO: 12) | DINPNR GGTTYN QKFKG (SEQ ID NO: 13) | YYAVG Y (SEQ ID NO: 14) | RSSQSLL HSHGNT YLH (SEQ ID NO: 28) | KVSNRF (SEQ ID NO: 25) NO: 26) | SQTAHF PYT (SEQ ID NO: 26) |
| ACI-33 | 6C10E5E9C 12 | SEQ ID NO: 53/ SEQ ID NO: 54 and SEQ ID NO: 47 | SEQ ID NO: 48/ SEQ ID NO: 49 and SEQ ID NO: 51 | EVQLVESGGGLVKPGG SLKLSCAPSGFTFSDYG MHWVRQAPEKGLEWV AYISSGSSTIYYGDTVK GRFTISRDNAKNTLFLQ MTSLRSEDTAMYYCAR RGQLRLRLFAYWGQGT LVTVSA (SEQ ID NO: 4) | DIVMTQSHKFMSTSVG DRVSITCKASQDVSTAV AWYQQKPGQSPKLLIY SASYRYTGVPDRFTGS GSTDFTFTISSVQAED LAVYYCQQHYTTPLTFG AGTKLELK (SEQ ID NO: 10) | GFTFSD YGMH (SEQ ID NO: 15) | YISSGSS TIYYGDT VKG (SEQ ID NO: 16) | RGQLR LRLFAY (SEQ ID NO: 17) | KASQDV STAVA (SEQ ID NO: 29) | SASYRY T (SEQ ID NO: 30) | QQHYTT PLT (SEQ ID NO: 31) |
| ACI-33 | 6C10F9C12 A11 | SEQ ID NO: 53/ SEQ ID NO: 54 and SEQ ID NO: 47 | SEQ ID NO: 48/ SEQ ID NO: 49 and SEQ ID NO: 51 | EVQLVESGGGLVKPGG SLKLSCAPSGFTFSDYG MHWVRQAPEKGLEWV AYISSGSSTIYYGDTVK GRFTISRDNAKNTLFLQ MTSLRSEDTAMYYCAR RGQLRLRLFAYWGQGT LVTVSA (SEQ ID NO: 4) | DIVMTQSHKFMSTSVG DRVSITCKASQDVSTAV AWYQQKPGQSPKLLIY SASYRYTGVPDRFTGS GSTDFTFTISSVQAED LAVYYCQQHYTTPLTFG AGTKLELK (SEQ ID NO: 10) | GFTFSD YGMH (SEQ ID NO: 15) | YISSGSS TIYYGDT VKG (SEQ ID NO: 16) | RGQLR LRLFAY (SEQ ID NO: 17) | KASQDV STAVA (SEQ ID NO: 29) | SASYRY T (SEQ ID NO: 30) | QQHYTT PLT (SEQ ID NO: 31) |

TABLE 10-continued

Amino Acid Sequence of the heavy chain and light chain variable regions (VH and VK) and the CDRs

| Vaccine | Hybridoma | VH Primer (mix) | VK Primer (mix) | VH | VK | VH CDR1 | VH CDR2 | VH CDR3 | VK CDR1 | VK CDR2 | VK CDR3 |
|---|---|---|---|---|---|---|---|---|---|---|---|
| ACI-41 | 7C2(1)F10C 10D3 | SEQ ID NO: 53/ SEQ ID NO: 55 and SEQ ID NO: 47 | SEQ ID NO: 49/SEQ ID NO: 56/SEQ ID NO: 57 and SEQ ID NO: 51 | EVKLMESGGGLVHPGA SLRLYCAASGFTFTDYY MSWVRQPPGKAPEWL ALIRNKANGYTTEYTAS VKGRFTISRDNSQNILY LQMNTLRAEDSATYYC VKALGRYFDVWGTGTT VTVSS (SEQ ID NO: 5) | DIVMSQSPSSLAVSVGE KVTMSCKSSQSLLYSS NQKNYLAWYQQKPGQ SPKLLIYWASTRESGVP DRFTGSGSGTDFTLTIS SVKAEDLAVYYCQQYY SYPFTFGSGTKLEIK (SEQ ID NO: 11) | GFTFTD YYMS (SEQ ID NO: 18) | LIRNKAN GYTTEY TASVKG (SEQ ID NO: 19) | ALGRY FDV (SEQ ID NO: 20) | KSSQSLL YSSNQK NYLA (SEQ ID NO: 32) | WASTRE S (SEQ ID NO: 33) | QQYYSY PFT (SEQ ID NO: 34) |
| ACI-41 | 7C2(2)B9F1 1D5 | SEQ ID NO: 53/ SEQ ID NO: 55 and SEQ ID NO: 47 | SEQ ID NO: 57 and SEQ ID NO: 51 | EVKLMESGGGLVHPGA SLRLYCAASGFTFTDYY MSWVRQPPGKAPEWL ALIRNKANGYTTEYTAS VKGRFTISRDNSQNILY LQMNTLRAEDSATYYC VKALGRYFDVWGTGTT VTVSS (SEQ ID NO: 5) | DIVMSQSPSSLAVSVGE KVTMSCKSSQSLLYSS NQKNYLAWYQQKPGQ SPKLLIYWASTRESGVP DRFTGSGSGTDFTLTIS SVKAEDLAVYYCQQYY SYPFTFGSGTKLEIK (SEQ ID NO: 11) | GFTFTD YYMS (SEQ ID NO: 18) | LIRNKAN GYTTEY TASVKG (SEQ ID NO: 19) | ALGRY FDV (SEQ ID NO: 20) | KSSQSLL YSSNQK NYLA (SEQ ID NO: 32) | WASTRE S (SEQ ID NO: 33) | QQYYSY PFT (SEQ ID NO: 34) |
| ACI-35 | A4-4A6-18 | | | QVQLQQPGAELLKPGA SVKLSCKASGYTFTSY WMHWVKQRPGRGLE WIGRIDPNSDRTKYNEK FKRKATLTVDKSSSTAY MQLSSLTSEDSAVYYC ARDDYAWFAYWGQGT LVTVSA (SEQ ID NO: 68) | DVLMTQTPLSLPVSLGD QASISCRSSQSIVHSNG NTYLEWYLQKPGQSPK LLIYKLSNRFSGVPDRF SGSGSGTDFTLKISRVE AEDLGVYYCFQGSHVP PTFGGGTKLEIK (SEQ ID NO: 69) | GYTFTS YWMH (SEQ ID NO: 70) | RIDPNS DRTKYN EKFKR (SEQ ID NO: 71) | DDYAW FAY (SEQ ID NO: 72) | RSSQSIV HSNGNT YLE (SEQ ID NO: 73) | KLSNRF S (SEQ ID NO: 74) | FQGSHV PPT (SEQ ID NO: 75) |
| ACI-35 | A6-1D2-12 | | | QVTLKESGPGILQSQT LSLTCSFSGFSLSTSGM GVSWIRQPSGKGLEWL AHIYWDDDKRYNASLK SRLTISKDTSRNQVFLKI TCVDTADTATYYCARLL RPYALDYWGQGTSVTV SS (SEQ ID NO: 76) | NILMTQSPSSLAVSAGE KVTMSCKSSQSVLYSS NQKNYLAWYQQKPGQ SPKLLIYWASTRESGVP DRFTGSGSGTDFTLTIS SVQAEDLAVYYCLQYLS SLTFGAGTKLELK (SEQ ID NO: 77) | GFSLST SGMGVS (SEQ ID NO: 78) | HIYWDD DKRYNA SLKS (SEQ ID NO: 79) | LLRPYA LDY (SEQ ID NO: 80) | KSSQSVL YSSNQK NYLA (SEQ ID NO: 81) | WASTRE S (SEQ ID NO: 82) | LQYLSSL T (SEQ ID NO: 83) |
| ACI-35 | A4-2A1-18 | | | EVQLQQSGPBLVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIVMTQAAPSVPVTPGE SVSISCRSSKSLLHSNG NTYLYWFLQRPGQSPQ LLIHRMSNLASGVPDRF SGSGSGTAFTLRISRVE AEDVGVYYCMQHLKSP YTFGGGTKLEIK (SEQ ID NO: 116) | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |

TABLE 10-continued

Amino Acid Sequence of the heavy chain and light chain variable regions (VH and VK) and the CDRs

| Vaccine | Hybridoma | VH Primer (mix) | VK Primer (mix) | VH | VK | VH CDR1 | VH CDR2 | VH CDR3 | VK CDR1 | VK CDR2 | VK CDR3 |
|---|---|---|---|---|---|---|---|---|---|---|---|
| ACI-35 | A4-2A1-40 | | | EVQLQQSGPELVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIX*MTQAAPSVPTPG ESVSISCRSSKSLLHSN GNTYLYWFLQRPGQSP QLLIYRMSNLASGVPDR FSGSGSGTAFTLRISRV EAEDVGVYYCMQHLKS PYTFGGGTKLEIK (SEQ ID NO: 92) *X = M or V | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |
| ACI-35 | A4-4A6-48 | | | EVQLQQSGPELVKPGA SVKISCKASGYTFTDYY MNWVKQSHGKSLEWIG DINPNNGGTSYNQKFK GKATLTVDKSSSTAYM ELRSLTSEDSAVYYCVR EGRFAYWGHGTLVTVS A (SEQ ID NO: 88) | DIVMTQAAPSVPTPGE SVSISCRSSKSLLHSNG NTYLYWFLQRPGQSPQ LLIYRMSNLASGVPDRF SGSGSGTAFTLRISRVE AEDVGVYYCMQHLKSP YTFGGGTKLEIK (SEQ ID NO: 118) | GYTFTD YYMN (SEQ ID NO: 89) | DINPNN GGTSYN QKFKG (SEQ ID NO: 90) | EGRFA Y (SEQ ID NO: 91) | RSSKSLL HSNGNT YLY (SEQ ID NO: 93) | RMSNLA S (SEQ ID NO: 94) | MQHLKS PYT (SEQ ID NO: 95) |
| ACI-35 | A6-2G5-08 | | | QVQLKQSGAELVRPGA SVKLSCKASGYTFTDYY INWVKQRPGQGLEWIA RIYPGRGNIYYNEKPKG KATLTAEKSSSTAYMQL SSLTSEDSAVYFCARF WDVTYWGQGTLVTVSA (SEQ ID NO: 96) | DVLMTQTPLSLPVSLGD QASISCRSSQSIVHSNG NTYLEWFLQKPGQSPK LLIYKVSNRFSGVPDRF SGSGSGTDFTLKISRVE AEDLGVYCFQGSHVP YTFGGGTKLEIK (SEQ ID NO: 97) | GYTFTD YYIN (SEQ ID NO: 98) | RIYPGR GNIYYN EKFKG (SEQ ID NO: 99) | FWDVT Y (SEQ ID NO: 100) | RSSQSIV HSNGNT YLE (SEQ ID NO: 101) | KVSNRF S (SEQ ID NO: 102) | FQGSHV PYT (SEQ ID NO: 103) |
| ACI-35 | A6-2G5-30 | | | EVQLQQSGPELVKPGA SVKISCKASGFTFTDYY MNWVKQSHGKSLEWIG DINPNNGGTSYHQKFK GKATLTVDKSSSTAYM ELRSLTSEDSAVYYCVR EGRFAYWGQGTLVTVS A (SEQ ID NO: 104) | DIVMTQSQKFMSTSVG DRVSVTCKASQNVGTN VAWYQQKPGQSPKALI YSASYRYSGVPDRFTG SGSGTDFTLTISNVQSE DLAEYFCQQYNSYPYT FGGGTKLEIK (SEQ ID NO: 105) | GFTFTD YYMN (SEQ ID NO: 89) | DINPNN GGTSYH QKFKG (SEQ ID NO: 115) | EGRFA Y (SEQ ID NO: 91) | KASQNV GTNVA (SEQ ID NO: 106) | SASYRY S (SEQ ID NO: 107) | QQYNSY PYT (SEQ ID NO: 108) |
| ACI-35 | A6-2G5-41 | | | EVQLQQSGPELVKPGA SVKISCKASGFTFTDYY MNWVKQSHGKSLEWIG DINPNNGGTSYHQKFK GKATLTVDKSSSTAYM ELRSLTSEDSAVYYCVR EGRFAYWGQGTLVTVS A (SEQ ID NO: 104) | DIVMTQSQKFMSTSVG DRVSVTCKASGNVGTN VAWYQQKPGQSPKALI YSASYRYSGVPDRFTG SGSGTDFTLTISNVQSE DLAEYFCQQYNSYPYT FGGGTKLEIK (SEQ ID NO: 105) | GFTFTD YYMN (SEQ ID NO: 89) | DINPNN GGTSYH QKFKG (SEQ ID NO: 115) | EGRFA Y (SEQ ID NO: 91) | KASQNV GTNVA (SEQ ID NO: 106) | SASYRY S (SEQ ID NO: 107) | QQYNSY PYT (SEQ ID NO: 108) |

*Two productive VK sequences sequences 6 and 7 in Table 10; sequences 40 and 41 in Table 11) were isolated from cell lines 3A8A12G7 and 3A8E12H8; the "V$_K$G" sequences were prepared from clones made using "G" primer mix and "V$_K$AD" sequences from clones made using "A" and "D" primer mixes. Accordingly, two antibodies with different kappa sequences are produced by these hybridomas.

TABLE 11

Nucleotide Sequence of the heavy chain and light chain variable regions (VH and VK)

| Vaccine | Hybridoma | VH Primer (mix) | VK Primer (mix) | VH |
|---|---|---|---|---|
| ACI-36 | 3A8A12G7* | SEQ ID NO: 46 and SEQ ID NO: 47 | VK_AD (SEQ ID NO: 48/ SEQ ID NO: 49/ and SEQ ID NO: 51) | GAGGTCCAGCTGCAACAATCTGGACCTGAACTGGTG AAGCCTGGGGCTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 35) |
| ACI-36 | 3A8A12G7* | SEQ ID NO: 46 and SEQ ID NO: 47 | VK_G (SEQ ID NO: 50 and SEQ ID NO: 51) | GAGGTCCAGCTGCAACAATCTGGACCTGAACTGGTG AAGCCTGGGGCTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 35) |
| ACI-36 | 3A8E12H8* | SEQ ID NO: 46 and SEQ ID NO: 47 | VK_AD (SEQ ID NO: 48/ SEQ ID NO: 49 and SEQ ID NO: 51) | GAGGTCCAGCTGCAACAATCTGGACCTGAACTGGTG AAGCCTGGGGCTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 35) |
| ACI-36 | 3A8E12H8* | SEQ ID NO: 46 and SEQ ID NO: 47 | VK_G (SEQ ID NO: 50 and SEQ ID NO: 51) | GAGGTCCAGCTGCAACAATCTGGACCTGAACTGGTG AAGCCTGGGGCTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 35) |
| ACI-36 | 2B6A10C11 | SEQ ID NO: 46/ SEQ ID NO: 52 and SEQ ID NO: 47 | SEQ ID NO: 50 and SEQ ID NO: 51 | GAGGTCCAGCTGCAACAATCTGGACCTGAACTGGTG AAGCCTGGGACTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTTAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 36) |
| ACI-36 | 2B6G7A12 | SEQ ID NO: 46/SEQ ID NO: 52 and SEQ ID NO: 47 | SEQ ID NO: 50 and SEQ ID NO: 51 | GAGGTCCAGCTGCAACAATCTGGACCTGAACTGGTG AAGCCTGGGACTTCAGTGAAGATATCCTGTAAGGCT TCTGGATATACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTTAAGGGCAAGGCCACGTTGACTGTAGA CAAGTCCTCCAGCACAGCCTACATGGAACTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 36) |
| ACI-36 | 6H1A11O11 | SEQ ID NO: 46 and SEQ ID NO: 47 | SEQ ID NO: 50 and SEQ ID NO: 51 | GAGGTCCAGCTGCAACAATCTGGACCTGAACTGGTG AAGCCTGGGGCTTCAGTGAAGATATCCTGTAAGGCT TCTGGATACACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CACGTCCTCCAGCACAGCCTACATGGAGCTCCGCAG |

TABLE 11-continued

Nucleotide Sequence of the heavy chain and light chain variable regions (VH and VK)

| Vaccine | Hybridoma | VH Primer (mix) | VK Primer (mix) | VH |
|---|---|---|---|---|
| | | | | CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 37) |
| ACI-36 | 6H1G6E6 | SEQ ID NO: 46 and SEQ ID NO: 47 | SEQ ID NO: 50 and SEQ ID NO: 51 | GAGGTCCAGCTGCAACAATCTGGACCTGAACTGGTG AAGCCTGGGGCTTCAGTGAAGATATCCTGTAAGGCT TCTGGATACACGTTCACTGACTACTACATGAACTGGG TGAAGCAGAGCCATGGAAAGAGCCTTGAGTGGATTG GAGATATTAATCCTAACCGTGGTGGAACTACTTACAA CCAGAAGTTCAAGGGCAAGGCCACGTTGACTGTAGA CACGTCCTCCAGCACAGCCTACATGGAGCTCCGCAG CCTGACATCTGAGGACTCTGCAGTCTATTACTGTGCA AGTTACTACGCCGTGGGCTACTGGGGCCAAGGCAC CACTCTCACAGTCTCCTCA (SEQ ID NO: 37) |
| ACI-33 | 6C10E5E9C12 | SEQ ID NO: 53/SEQ ID NO: 54 and SEQ ID NO: 47 | SEQ ID NO: 48/ SEQ ID NO: 49 and SEQ ID NO: 51 | GAGGTGCAGCTGGTGGAGTCTGGGGGAGGCTTAGT GAAGCCTGGAGGGTCCCTGAAACTCTCCTGTGCACC CTCTGGATTCACTTTCAGTGACTATGGAATGCACTGG GTTCGTCAGGCTCCAGAGAAGGGACTGGAGTGGGT TGCATACATTAGTAGTGGCAGTAGTACCATCTACTAT GGAGACACAGTGAAGGGCCGATTCACCATCTCCAGA GACAATGCCAAGAACACCCTGTTCCTGCAAATGACC AGTCTGAGGTCTGAGGACACGGCCATGTATTACTGT GCAAGAAGGGGACAGCTCAGGCTACGCCTGTTTGCT TACTGGGGCCAAGGGACTCTGGTCACTGTCTCTGCA (SEQ ID NO: 38) |
| ACI-33 | 6C10F9C12 A11 | SEQ ID NO: 53/SEQ ID NO:54 and SEQ ID NO: 47 | SEQ ID NO: 54 and SEQ ID NO: 51 | GAGGTGCAGCTGGTGGAGTCTGGGGGAGGCTTAGT GAAGCCTGGAGGGTCCCTGAAACTCTCCTGTGCACC CTCTGGATTCACTTTCAGTGACTATGGAATGCACTGG GTTCGTCAGGCTCCAGAGAAGGGACTGGAGTGGGT TGCATACATTAGTAGTGGCAGTAGTACCATCTACTAT GGAGACACAGTGAAGGGCCGATTCACCATCTCCAGA GACAATGCCAAGAACACCCTGTTCCTGCAAATGACC AGTCTGAGGTCTGAGGACACGGCCATGTATTACTGT GCAAGAAGGGGACAGCTCAGGCTACGCCTGTTTGCT TACTGGGGCCAAGGGACTCTGGTCACTGTCTCTGCA (SEQ ID NO: 38) |
| ACI-41 | 7C2(1)F10C 10D3 | SEQ ID NO: 53/ SEQ ID NO: 55 and SEQ ID NO: 47 | SEQ ID NO: 49/ SEQ ID NO: 56/ SEQ ID NO: 57 and SEQ ID NO: 51 | GAGGTGAAGCTGATGGAATCTGGAGGAGGCTTGGTA CACCCTGGGGCTTCTCTGAGACTCTACTGTGCAGCT TCTGGATTCACCTTTACTGATTACTACATGAGCTGGG TCCGCCAGCCTCCAGGGAAGGCACCTGAGTGGTTG GCTTTGATTAGAAACAAAGCTAATGGTTACACAACAG AGTATACTGCATCTGTTAAGGGTCGGTTCACCATCTC CAGAGATAATTCCCAAAACATCCTCTATCTTCAAATG AACACCCTGAGGGCTGAGGACAGTGCCACTTATTAC TGTGTAAAAGCTCTGGGACGTTACTTCGATGTCTGG GGCACAGGGACCACGGTCACCGTCTCCTCA (SEQ ID NO: 39) |
| ACI-41 | 7C2(2)B9F1 1D5 | SEQ ID NO: 53/ SEQ ID NO:55 and SEQ ID NO: 47 | SEQ ID NO: 57 and SEQ ID NO: 51 | GAGGTGAAGCTGATGGAATCTGGAGGAGGCTTGGTA CACCCTGGGGCTTCTCTGAGACTCTACTGTGCAGCT TCTGGATTCACCTTTACTGATTACTACATGAGCTGGG TCCGCCAGCCTCCAGGGAAGGCACCTGAGTGGTTG GCTTTGATTAGAAACAAAGCTAATGGTTACACAACAG AGTATACTGCATCTGTTAAGGGTCGGTTCACCATCTC CAGAGATAATTCCCAAAACATCCTCTATCTTCAAATG AACACCCTGAGGGCTGAGGACAGTGCCACTTATTAC TGTGTAAAAGCTCTGGGACGTTACTTCGATGTCTGG GGCACAGGGACCACGGTCACCGTCTCCTCA (SEQ ID NO: 39) |
| ACI-35 | A4-4A6-18 | | | CAGGTCCAACTGCAGCAGCCTGGGGCTGAGCTTCT GAAGCCTGGGGCTTCAGTGAAACTGTCCTGCAAGGC TTCTGGCTACACCTTCACCAGCTACTGGATGCACTG GGTGAAGCAGAGGCCTGGACGAGGCCTTGAGTGGA TTGGAAGGATTGATCCTAATAGTGATCGTACTAAGTA CAATGAGAAGTTCAAGCGCAAGGCCACACTGACTGT AGACAAATCCTCCAGCACAGCCTACATGCAGCTCAG |

TABLE 11-continued

Nucleotide Sequence of the heavy chain and light chain variable regions (VH and VK)

| Vaccine | Hybridoma | VH Primer (mix) | VK Primer (mix) | VH |
|---|---|---|---|---|
| | | | | CAGCCTGACATCTGAGGACTCTGCGGTCTATTATTGT<br>GCAAGGGATGATTACGCCTGGTTTGCTTACTGGGGC<br>CAAGGGACTCTGGTCACTGTCTCTGCA<br>(SEQ ID NO: 84) |
| ACI-35 | A6-1D2-12 | | | CAGGTTACTCTGAAAGAGTCTGGCCCTGGGATATTG<br>CAGTCCTCCCAGACCCTCAGTCTGACTTGTTCTTTCT<br>CTGGGTTTTCACTGAGCACTTCTGGTATGGGTGTGA<br>GCTGGATTCGTCAGCCTTCAGGAAAGGGTCTGGAGT<br>GGCTGGCACACATTTACTGGGATGATGACAAGCGCT<br>ATAACGCATCCCTGAAGAGCCGGCTCACAATCTCCA<br>AGGATACCTCCAGAAACCAGGTATTCCTCAAGATCA<br>CCTGTGTGGACACTGCAGATACTGCCACATACTACT<br>GTGCTCGGTTACTGCGTCCTTATGCTTTGGACTACTG<br>GGGTCAAGGAACCTCAGTCACCGTCTCCTCA (SEQ ID NO: 86) |
| ACI-35 | A4-2A1-18 | | | GAGGTCCAGCTGCAACAATCTGGACCTGAGCTGGTG<br>AAGCCTGGGGCTTCAGTGAAGATATCCTGTAAGGCT<br>TCTGGATACACGTTCACTGACTACTACATGAACTGGG<br>TGAAGCAGAGCCATGGAAAGAGCCTTGAGTGGATTG<br>GAGATATTAATCCTAACAATGGTGGTACTAGCTACAA<br>CCAGAAGTTCAAGGGCAAGGCCACATTGACTGTAGA<br>CAAGTCCTCCAGCACAGCCTACATGGAGCTCCGCAG<br>TCTGACATCTGAGGACTCTGCAGTCTATTATTGTGTA<br>AGAGAGGGGCGGTTTGCTTACTGGGGTCATGGGAC<br>TCTGGTCACTGTCTCTGCA (SEQ ID NO: 109) |
| ACI-35 | A4-2A1-40 | | | GAGGTCCAGCTGCAACAATCTGGACCTGAGCTGGTG<br>AAGCCTGGGGCTTCAGTGAAGATATCCTGTAAGGCT<br>TCTGGATACACGTTCACTGACTACTACATGAACTGGG<br>TGAAGCAGAGCCATGGAAAGAGCCTTGAGTGGATTG<br>GAGATATTAATCCTAACAATGGTGGTACTAGCTACAA<br>CCAGAAGTTCAAGGGCAAGGCCACATTGACTGTAGA<br>CAAGTCCTCCAGCACAGCCTACATGGAGCTCCGCAG<br>TCTGACATCTGAGGACTCTGCAGTCTATTATTGTGTA<br>AGAGAGGGGCGGTTTGCTTACTGGGGTCATGGGAC<br>TCTGGTCACTGTCTCTGCA (SEQ ID NO: 109) |
| ACI-35 | A4-4A6-48 | | | GAGGTCCAGCTGCAACAATCTGGACCTGAGCTGGTG<br>AAGCCTGGGGCTTCAGTGAAGATATCCTGTAAGGCT<br>TCTGGATACACGTTCACTGACTACTACATGAACTGGG<br>TGAAGCAGAGCCATGGAAAGAGCCTTGAGTGGATTG<br>GAGATATTAATCCTAACAATGGTGGTACTAGCTACAA<br>CCAGAAGTTCAAGGGCAAGGCCACATTGACTGTAGA<br>CAAGTCCTCCAGCACAGCCTACATGGAGCTCCGCAG<br>TCTGACATCTGAGGACTCTGCAGTCTATTATTGTGTA<br>AGAGAGGGGCGGTTTGCTTACTGGGGTCATGGGAC<br>TCTGGTCACTGTCTCTGCA (SEQ ID NO: 109) |
| ACI-35 | A6-2G5-08 | | | CAGGTCCAGCTGAAGCAGTCTGGGGCTGAGCTGGT<br>GAGGCCTGGGGCTTCAGTGAAACTGTCCTGCAAGG<br>CTTCTGGCTACACTTTCACTGACTACTATATAAACTG<br>GGTGAAGCAGAGGCCTGGACAGGGACTTGAGTGGA<br>TTGCAAGGATTTATCCTGGAAGAGGTAATATTTACTA<br>CAATGAGAAGTTCAAGGGCAAGGCCACACTGACTGC<br>AGAAAAATCCTCCAGCACTGCCTACATGCAGCTCAG<br>CAGCCTGACATCTGAGGACTCTGCTGTCTATTTCTGT<br>GCAAGATTCTGGACGTGACTTACTGGGGCCAAGG<br>GACTCTGGTCACTGTCTCTGCA<br>(SEQ ID NO: 111) |
| ACI-35 | A6-2G5-30 | | | GAGGTCCAGCTGCAACAATCTGGACCTGAGCTGGTG<br>AAGCCTGGGGCTTCAGTGAAGATATCCTGTAAGGCT<br>TCTGGATTCACGTTCACTGACTACTACATGAACTGGG<br>TGAAGCAGAGCCATGGAAAGAGCCTTGAGTGGATTG<br>GAGATATTAATCCTAACAATGGTGGTACTAGCTACCA<br>CCAGAAGTTCAAGGGCAAGGCCACATTGACTGTAGA<br>CAAGTCCTCCAGCACAGCCTACATGGAGCTCCGCAG<br>CCTGACATCTGAGGACTCTGCAGTCTATTACTGTGTA<br>AGAGAGGGAAGATTTGCTTACTGGGGCCAAGGGACT<br>CTGGTCACTGTCTCTGCA (SEQ ID NO: 113) |

TABLE 11-continued

Nucleotide Sequence of the heavy chain and light chain variable regions (VH and VK)

| Vaccine | Hybridoma | VH Primer (mix) | VK Primer (mix) | VH |
|---|---|---|---|---|
| ACI-35 | A6-2G5-41 | | | GAGGTCCAGCTGCAACAATCTGGACCTGAGCTGGTG<br>AAGCCTGGGGCTTCAGTGAAGATATCCTGTAAGGCT<br>TCTGGATTCACGTTCACTGACTACTACATGAACTGGG<br>TGAAGCAGAGCCATGGAAAGAGCCTTGAGTGGATTG<br>GAGATATTAATCCTAACAATGGTGGTACTAGCTACCA<br>CCAGAAGTTCAAGGGCAAGGCCACATTGACTGTAGA<br>CAAGTCCTCCAGCACAGCCTACATGGAGCTCCGCAG<br>CCTGACATCTGAGGACTCTGCAGTCTATTACTGTGTA<br>AGAGAGGGAAGATTTGCTTACTGGGGCCAAGGGACT<br>CTGGTCACTGTCTCTGCA (SEQ ID NO: 113) |

| Vaccine | VK |
|---|---|
| ACI-36 | GACATTGTGATGACACAGTCTCCATCCTCCCTGGCTATGT<br>CAGTAGGACAGAAGGTCACTATGAGCTGCAAGTCCAGTC<br>AGAGTGTTTTTAATAGTGGCAATCAAAAGAACTCTTTGGC<br>CTGGTACCAGCAGAAACCAGGACAGTCTCCTAAACTTCT<br>GGTATACTTTGCATCCACTAGGGAATCTGGGGTCCCTGA<br>TCGCTTCATAGGCAGTGGATCTGGGACAGATTTCAGTCTT<br>ACCATCAGCAGTGTGCAGGCTGAGGACCTGGCAGATTAC<br>TTCTGTCAGGAACATTATACCACTCCTCCCACGTTCGGTA<br>CTGGGACCAAGCTGGAGCTGAAA (SEQ ID NO: 40) |
| ACI-36 | GATGTTGTGATGACCCAAACTCCACTCTCCCTGCCTGTCA<br>GTCTTGGAGATCAAGCCTCCATCTCTTGCAGATCTAGTCA<br>GAGGCTTGTACACAGTCATGGAAAAACCTATTTACATTGG<br>TACCTGCAGAAGCCAGGCCAGTCTCCAAAGCTCCTGATC<br>TACAAAGTTTCCAACCGGTTTTCTGGGGTCCCAGACAGG<br>TTCAGTGGCAGTGGATCAGGGACAGATTTCACACTCAAG<br>ATCAGCAGAGTGGAGGCTGAGGATCTGGGAGTTTATTTC<br>TGTTCTCAAACTGCACATTTTCCGTACACGTTCGGAGGG<br>GGGACCAAGCTGGAAATAAAA (SEQ ID NO: 41) |
| ACI-36 | GACATTGTGATGACACAGTCTCCATCCTCCCTGGCTATGT<br>CAGTAGGACAGAAGGTCACTATGAGCTGCAAGTCCAGTC<br>AGAGTGTTTTTAATAGTGGCAATCAAAAGAACTCTTTGGC<br>CTGGTACCAGCAGAAACCAGGACAGTCTCCTAAACTTCT<br>GGTATACTTTGCATCCACTAGGGAATCTGGGGTCCCTGA<br>TCGCTTCATAGGCAGTGGATCTGGGACAGATTTCAGTCTT<br>ACCATCAGCAGTGTGCAGGCTGAGGACCTGGCAGATTAC<br>TTCTGTCAGGAACATTATACCACTCCTCCCACGTTCGGTA<br>CTGGGACCAAGCTGGAGCTGAAA (SEQ ID NO: 40) |
| ACI-36 | GATGTTGTGATGACCCAAACTCCACTCTCCCTGCCTGTCA<br>GTCTTGGAGATCAAGCCTCCATCTCTTGCAGATCTAGTCA<br>GAGGCTTGTACACAGTCATGGAAAAACCTATTTACATTGG<br>TACCTGCAGAAGCCAGGCCAGTCTCCAAAGCTCCTGATC<br>TACAAAGTTTCCAACCGGTTTTCTGGGGTCCCAGACAGG<br>TTCAGTGGCAGTGGATCAGGGACAGATTTCACACTCAAG<br>ATCAGCAGAGTGGAGGCTGAGGATCTGGGAGTTTATTTC<br>TGTTCTCAAACTGCACATTTTCCGTACACGTTCGGAGGG<br>GGGACCAAGCTGGAAATAAAA (SEQ ID NO: 41) |
| ACI-36 | GATGTTGTGATGACCCAAACTCCACTCTCCCTGCCTGTCA<br>GTCTTGGAGATCAAGCCTCCATCTCTTGCAGATCTAGTCA<br>GAGCCTTGTACACAGTCATGGAAAAACCTATTTACATTGG<br>TACCTGCAGAAGCCAGGCCAGTCTCCAAAGCTCCTGATC<br>TACAAAGTTTCCAACCGGTTTTCTGGGGTCCCAGACAGG<br>TTCAGTGGCAGTGGATCAGGGACAGATTTCACACTCAAG<br>ATCAGCAGAGTGGAGGCTGAGGATCTGGGAGTTTATTTC<br>TGTTCTCAAACTGCACATTTTCCGTACACGTTCGGAGGG<br>GGGACCAAGCTGGAAATAAAA (SEQ ID NO: 42) |
| ACI-36 | GATGTTGTGATGACCCAAACTCCACTCTCCCTGCCTGTCA<br>GTCTTGGAGATCAAGCCTCCATCTCTTGCAGATCTAGTCA<br>GAGCCTTGTACACAGTCATGGAAAAACCTATTTACATTGG<br>TACCTGCAGAAGCCAGGCCAGTCTCCAAAGCTCCTGATC<br>TACAAAGTTTCCAACCGGTTTTCTGGGGTCCCAGACAGG<br>TTCAGTGGCAGTGGATCAGGGACAGATTTCACACTCAAG<br>ATCAGCAGAGTGGAGGCTGAGGATCTGGGAGTTTATTTC<br>TGTTCTCAAACTGCACATTTTCCGTACACGTTCGGAGGG<br>GGGACCAAGCTGGAAATAAAA (SEQ ID NO: 42) |

TABLE 11-continued

Nucleotide Sequence of the heavy chain and light chain variable regions (VH and VK)

| Vaccine | Hybridoma | VH Primer (mix) | VK Primer (mix) | VH |
|---------|-----------|-----------------|-----------------|-----|
| ACI-36 | | | | GATGTTGTGATGACCCAAACTCCACTCTCCCTGCCTGTCA GTCTTGGAGATCAAGCCTCCATCTCTTGCAGATCTAGTCA GAGCCTTCTACACAGTCATGGAAACACCTATTTACATTGG TACCTGCAGAAGCCAGGCCAGTCTCCAAAGCTCCTGATC TACAAAGTTTCCAACCGGTTTTCTGGGGTCCCAGACAGG TTCAGTGGCAGTGGATCAGGGACAGATTTCACACTCAAG ATCAGCAGAGTGGAGGCTGAGGATCTGGGAGTTTATTTC TGCTCTCAAACTGCACATTTTCCGTACACGTTCGGAGGG GGGACCAAGCTGGAAATAAAA (SEQ ID NO: 43) |
| ACI-36 | | | | GATGTTGTGATGACCCAAACTCCACTCTCCCTGCCTGTCA GTCTTGGAGATCAAGCCTCCATCTCTTGCAGATCTAGTCA GAGCCTTCTACACAGTCATGGAAACACCTATTTACATTGG TACCTGCAGAAGCCAGGCCAGTCTCCAAAGCTCCTGATC TACAAAGTTTCCAACCGGTTTTCTGGGGTCCCAGACAGG TTCAGTGGCAGTGGATCAGGGACAGATTTCACACTCAAG ATCAGCAGAGTGGAGGCTGAGGATCTGGGAGTTTATTTC TGCTCTCAAACTGCACATTTTCCGTACACGTTCGGAGGG GGGACCAAGCTGGAAATAAAA (SEQ ID NO: 43) |
| ACI-33 | | | | GACATTGTGATGACCCAGTCTCACAAATTCATGTCCACAT CAGTAGGAGACAGGGTCAGCATCACCTGCAAGGCCAGT CAGGATGTGAGTACTGCTGTAGCCTGGTATCAACAGAAA CCAGGACAATCTCCTAAACTACTGATTTACTCGGCATCCT ACCGGTACACTGGAGTCCCTGATCGCTTCACTGGCAGTG GATCTGGGACGGATTTCACTTTCACCATCAGCAGTGTGC AGGCTGAAGACCTGGCAGTTTATTACTGTCAGCAACATTA TACTACTCCGCTCACGTTCGGTGCTGGGACCAAGCTGGA GCTGAAA (SEQ ID NO: 44) |
| ACI-33 | | | | GACATTGTGATGACCCAGTCTCACAAATTCATGTCCACAT CAGTAGGAGACAGGGTCAGCATCACCTGCAAGGCCAGT CAGGATGTGAGTACTGCTGTAGCCTGGTATCAACAGAAA CCAGGACAATCTCCTAAACTACTGATTTACTCGGCATCCT ACCGGTACACTGGAGTCCCTGATCGCTTCACTGGCAGTG GATCTGGGACGGATTTCACTTTCACCATCAGCAGTGTGC AGGCTGAAGACCTGGCAGTTTATTACTGTCAGCAACATTA TACTACTCCGCTCACGTTCGGTGCTGGGACCAAGCTGGA GCTGAAA (SEQ ID NO: 44) |
| ACI-41 | | | | GACATTGTGATGTCACAGTCTCCATCCTCCCTAGCTGTGT CAGTTGGAGAGAAGGTTACTATGAGCTGCAAGTCCAGTC AGAGCCTTTTATATAGTAGCAATCAAAAGAACTACTTGGC CTGGTACCAGCAGAAACCAGGGCAGTCTCCTAAACTGCT GATTTACTGGGCATCCACTAGGGAATCTGGGGTCCCTGA TCGCTTCACAGGCAGTGGATCTGGGACAGATTTCACTCT CACCATCAGCAGTGTGAAGGCTGAAGACCTGGCAGTTTA TTACTGTCAGCAATATTATAGCTATCCATTCACGTTCGGC TCGGGGACAAAGTTGGAAATAAAA (SEQ ID NO: 45) |
| ACI-41 | | | | GACATTGTGATGTCACAGTCTCCATCCTCCCTAGCTGTGT CAGTTGGAGAGAAGGTTACTATGAGCTGCAAGTCCAGTC AGAGCCTTTTATATAGTAGCAATCAAAAGAACTACTTGGC CTGGTACCAGCAGAAACCAGGGCAGTCTCCTAAACTGCT GATTTACTGGGCATCCACTAGGGAATCTGGGGTCCCTGA TCGCTTCACAGGCAGTGGATCTGGGACAGATTTCACTCT CACCATCAGCAGTGTGAAGGCTGAAGACCTGGCAGTTTA TTACTGTCAGCAATATTATAGCTATCCATTCACGTTCGGC TCGGGGACAAAGTTGGAAATAAAA (SEQ ID NO: 45) |
| ACI-35 | | | | GATGTTTTGATGACCCAAACTCCACTCTCCCTGCCTGTCA GTCTTGGAGATCAAGCCTCCATCTCTTGCAGATCTAGTCA GAGCATTGTACATAGTAATGGAAACACCTATTTAGAATGG TACCTGCAGAAACCAGGCCAGTCTCCAAAGCTCCTGATC TACAAACTTTCCAACCGATTTCTGGGGTCCCAGACAGGT TCAGTGGCAGTGGATCAGGGACAGATTTCACACTCAAGA TCAGCAGAGTGGAGGCTGAGGATCTGGAGTTTATTACT GCTTTCAAGGTTCACATGTTCCTCCGACGTTCGGTGGAG GCACCAAGCTGGAAATCAAA (SEQ ID NO: 85) |
| ACI-35 | | | | AACATTTTGATGACACAGTCGCCATCATCTCTGGCTGTGT CTGCAGGAGAAAAGGTCACTATGAGCTGTAAGTCCAGTC AAAGTGTTTTATACAGTTCAAATCAGAAGAACTACTTGGC |

TABLE 11-continued

Nucleotide Sequence of the heavy chain and light chain variable regions (VH and VK)

| Vaccine | Hybridoma | VH Primer (mix) | VK Primer (mix) | VH |
|---------|-----------|-----------------|-----------------|----|
| | | | | CTGGTACCAGCAGAAACCAGGGCAGTCTCCTAAACTGCT GATCTACTGGGCATCCACTAGGGAATCTGGTGTCCCTGA TCGCTTCACAGGCAGTGGATCTGGGACAGATTTTACTCTT ACCATCAGCAGTGTACAAGCTGAAGACCTGGCAGTTTATT ACTGTCTTCAATACCTCTCCTCGCTCACGTTCGGTGCTGG GACCAAGCTGGAGCTGAAA (SEQ ID NO: 87) |
| ACI-35 | | | | GATATTGTGATGACTCAGGCTGCACCCTCTGTACCTGTCA CTCCTGGAGAGTCAGTATCCATCTCCTGCAGGTCTAGTA AGAGTCTCCTGCATAGTAATGGCAACACTTACTTGTATTG GTTCCTGCAGAGGCCAGGCCAGTCTCCTCAGCTCCTGAT ACATCGGATGTCCAACCTTGCCTCAGGAGTCCCAGACAG GTTCAGTGGCAGTGGGTCAGGAACTGCTTTCACACTGAG AATCAGTAGAGTGGAGGCTGAGGATGTGGGTGTTTATTA CTGTATGCAACATCTAAAATCTCCGTACACGTTCGGAGG GGGGACCAAGCTGGAAATAAAA (SEQ ID NO: 117) |
| ACI-35 | | | | GATATTR*TGATGACTCAGGCTGCACCCICTGTACCTGIC ACTCCTGGAGAGTCAGTATCCATCTCCTGCAGGTCTAGT AAGAGTCTCCTGCATAGTAATGGCAACACTTACTTGTATT GGTTCCTGCAGAGGCCAGGCCAGTCTCCTCAGCTCCTGA TATATCGGATGTCCAACCTTGCCTCAGGAGTCCCAGACA GGTTCAGTGGCAGTGGGTCAGGAACTGCTTTCACACTGA GAATCAGTAGAGTGGAGGCTGAGGATGTGGGTGTTTATT ACTGTATGCAACATCTAAAATCTCCGTACACGTTCGGAGG GGGGACCAAGCTGGAAATAAAA (SEQ ID NO: 110) R* = A or G |
| ACI-35 | | | | GATATTGTGATGACTCAGGCTGCACCCTCTGTACCTGTCA CTCCTGGAGAGTCAGTATCCATCTCCTGCAGGTCTAGTA AGAGTCTCCTGCATAGTAATGGCAACACTTACTTGTATTG GTTCCTGCAGAGGCCAGGCCAGTCTCCTCAGCTCCTGAT ATATCGGATGICCAACCTTGCCTCAGGAGTCCCAGACAG GTTCAGTGGCAGTGGGTCAGGAACTGCTTTCACACTGAG AATCAGTAGAGTGGAGGCTGAGGATGTGGGTGTTTATTA CTGTATGCAACATCTAAAATCTCCGTACACGTTCGGAGG GGGGACCAAGCTGGAAATAAAA (SEQ ID NO: 119) |
| ACI-35 | | | | GATGTTTTGATGACCCAAACTCCACTCTCCCTGCCTGTCA GTCTTGGAGATCAAGCCTCCATCTCTTGCAGATCTAGTCA GAGCATTGTACATAGTAATGGAAACACCTATTTAGAATGG TTCCTGCAGAAACCAGGCCAGTCTCCAAAGCTCCTGATC TACAAAGTTTCCAACCGATTTTCTGGGGTCCCAGACAGGT TCAGTGGCAGTGGATCAGGGACAGATTTCACACTCAAGA TCAGCAGAGTGGAGGCTGAGGATCTGGGAGTTTATTACT GCTTTCAAGGTTCACATGTTCCGTACACGTTCGGAGGGG GGACCAAGCTGGAAATAAAA (SEQ ID NO: 112) |
| ACI-35 | | | | GACATTGTGATGACCCAGTCTCAAAAATTCATGTCCACAT CAGTAGGAGACAGGGTCAGCGTCACCTGCAAGGCCAGT CAGAATGTGGGTACTAATGTAGCCTGGTATCAACAGAAA CCAGGGCAATCTCCTAAAGCACTGATTTACTCGGCATCCT ACCGGTACAGTGGAGTCCCTGATCGCTTCACAGGCAGTG GATCTGGGACAGATTTCACTCTCACCATCAGCAATGTGCA GTCTGAAGACTTGGCAGAGTATTTCTGTCAGCAATATAAC AGCTATCCGTACACGTTCGGAGGGGGGACCAAGCTGGA AATAAAA (SEQ ID NO: 114) |
| ACI-35 | | | | GACATTGTGATGACCCAGTCTCAAAAATTCATGTCCACAT CAGTAGGAGACAGGGTCAGCGTCACCTGCAAGGCCAGT CAGAATGTGGGTACTAATGTAGCCTGGTATCAACAGAAA CCAGGGCAATCTCCTAAAGCACTGATTTACTCGGCATCCT ACCGGTACAGTGGAGTCCCTGATCGCTTCACAGGCAGTG GATCTGGGACAGATTTCACTCTCACCATCAGCAATGTGCA GTCTGAAGACTTGGCAGAGTATTTCTGTCAGCAATATAAC AGCTATCCGTACACGTTCGGAGGGGGGACCAAGCTGGA AATAAAA (SEQ ID NO: 114) |

*Two productive $V_K$ sequences (sequences 6 and 7 in Table 10; sequences 40 and 41 in Table 11) were isolated from cell lines 3A8A12G7 and 3A8E12H8; the "VK_G" sequences were prepared from clones made using "G" primer mix and "$V_K$_AD" sequences from clones made using "A" and "D" primer mixes. Accordingly, two antibodies with different kappa sequences are produced by these hybridomas.

TABLE 12

Primers used for CDR sequencing of antibody variable regions

| Subclone | Ab isotype | | | Primer sequences | SEQ ID NO |
|---|---|---|---|---|---|
| 3A8A 12G7 | IgG2b | VH primers | 5' | GGGAATTCATGRAATGSASCTGGGTYWTYCTCTT | 46 |
| | | | 3' | CCCAAGCTTCCAGGGRCCARKGGATARACIGRTGG | 47 |
| | | VK primers | 5' | GGGAATTCATGRAGWCACAKWCYCAGGTCTTT | 48 |
| | | | AD | ACTAGTCGACATGGGCWTCAAGATGRAGTCACAKWYYCWGG | 49 |
| | | | 5' | GACTAGTCGACATGAAGTTGCCTGTTAGGCTGTTGGTGCT | 50 |
| | | | 3' | CCCAAGCTTACTGGATGGTGGGAAGATGGA | 51 |
| 3A8E 12H8 | IgG2b | VH primers | 5' | GGGAATTCATGRAATGSASCTGGGTYWTYCTCTT | 46 |
| | | | 3' | CCCAAGCTTCCAGGGRCCARKGGATARACIGRTGG | 47 |
| | | VK primers | 5' | GGGAATTCATGRAGWCACAKWCYCAGGTCTTT | 48 |
| | | | AD | ACTAGTCGACATGGGCWTCAAGATGRAGTCACAKWYYCWGG | 49 |
| | | | 5' | GACTAGTCGACATGAAGTTGCCTGTTAGGCTGTTGGTGCT | 50 |
| | | | 3' | CCCAAGCTTACTGGATGGTGGGAAGATGGA | 51 |
| 2B6A 10C11 | IgG2b | VH primers | 5' | GGGAATTCATGRAATGSASCTGGGTYWTYCTCTT | 46 |
| | | | | ACTAGTCGACATGGGATGGAGCTRTATCATSYTCTT | 52 |
| | | | 3' | CCCAAGCTTCCAGGGRCCARKGGATARACIGRTGG | 47 |
| | | VK primers | 5' | ACTAGTCGACATGAAGTTGCCTGTTAGGCTGTTGGTGCT | 50 |
| | | | 3' | CCCAAGCTTACTGGATGGTGGGAAGATGGA | 51 |
| 2B6G 7A12 | IgG2b | VH primers | 5' | GGGAATTCATGRAATGSASCTGGGTYWTYCTCTT | 46 |
| | | | | ACTAGTCGACATGGGATGGAGCTRTATCATSYTCTT | 52 |
| | | | 3' | CCCAAGCTTCCAGGGRCCARKGGATARACIGRTGG | 47 |
| | | VK primers | 5' | ACTAGTCGACATGAAGTTGCCTGTTAGGCTGTTGGTGCT | 50 |
| | | | 3' | CCCAAGCTTACTGGATGGTGGGAAGATGGA | 51 |
| 6H1A11C11 | IgG2b | VH primers | 5' | GGGAATTCATGRAATGSASCTGGGTYWTYCTCTT | 46 |
| | | | 3' | CCCAAGCTTCCAGGGRCCARKGGATARACIGRTGG | 47 |
| | | VK primers | 5' | ACTAGTCGACATGAAGTTGCCTGTTAGGCTGTTGGTGCT | 50 |
| | | | 3' | CCCAAGCTTACTGGATGGTGGGAAGATGGA | 51 |
| 6H1G 6E6 | IgG2b | VH primers | 5' | GGGAATTCATGRAATGSASCTGGGTYWTYCTCTT | 46 |
| | | | 3' | CCCAAGCTTCCAGGGRCCARKGGATARACIGRTGG | 47 |
| | | VK primers | 5' | ACTAGTCGACATGAAGTTGCCTGTTAGGCTGTTGGTGCT | 50 |
| | | | 3' | CCCAAGCTTACTGGATGGTGGGAAGATGGA | 51 |
| 6C10F9 C12A11 | IgG3 | VH primers | 5' | GGGAATTCATGRASTTSKGGYTMARCTKGRTTT | 53 |
| | | | | ACTAGTCGACATGGACTCCAGGCTCAATTTAGTTTTCCT | 54 |
| | | | 3' | CCCAAGCTTCCAGGGRCCARKGGATARACIGRTGG | 47 |
| | | VK primers | 5' | ACTAGTCGACATGGACTCCAGGCTCAATTTAGTTTTCCT | 54 |
| | | | 3' | CCCAAGCTTACTGGATGGTGGGAAGATGGA | 51 |
| 6C10E5E 9C12 | IgG3 | VH primers | 5' | GGGAATTCATGRASTTSKGGYTMARCTKGRTTT | 53 |
| | | | | ACTAGTCGACATGGACTCCAGGCTCAATTTAGTTTTCCT | 54 |
| | | | 3' | CCCAAGCTTCCAGGGRCCARKGGATARACIGRTGG | 47 |
| | | VK primers | 5' | GGGAATTCATGRAGWCACAKWCYCAGGTCTTT | 48 |
| | | | | ACTAGTCGACATGGGCVVTCAAGATGRAGTCACAKVVYYCWGG | 49 |
| | | | 3' | CCCAAGCTTACTGGATGGTGGGAAGATGGA | 51 |
| 7C2(1)F10C 10D3 | IgG2b | VH primers | 5' | GGGAATTCATGRASTTSKGGYTMARCTKGRTTT | 53 |
| | | | | ACTAGTCGACATGAAGVVTGTGGBTRAACTGGRT | 55 |
| | | | 3' | CCCAAGCTTCCAGGGRCCARKGGATARACIGRTGG | 47 |
| | | VK primers | 5' | ACTAGTCGACATGGAGWCAGACACACISCTGYTATGGGT | 56 |
| | | | | ACTAGTCGACATGGGCVVTCAAGATGRAGTCACAKVVYYCWGG | 49 |
| | | | | ACTAGTCGACATGGTYCTYATVTTRCTGCTGCTATGG | 57 |
| | | | 3' | CCCAAGCTTACTGGATGGTGGGAAGATGGA | 51 |
| 7C2(2)B9F 11D5 | IgG2b | VH primers | 5' | GGGAATTCATGRASTTSKGGYTMARCTKGRTTT | 53 |
| | | | | ACTAGTCGACATGAAGWTGTGGBTRAACTGGRT | 55 |
| | | | 3' | CCCAAGCTTCCAGGGRCCARKGGATARACIGRTGG | 47 |
| | | VK primers | 5' | ACTAGTCGACATGGTYCTYATVTTRCTGCTGCTATGG | 57 |
| | | | 3' | CCCAAGCTTACTGGATGGTGGGAAGATGGA | 51 |
| A6-2G5-08 | IgG2a | VH primers | 5' | GGGAATTCATGGAATGCAGCTGGGTTTTTCTCTT | 120 |
| | | | | GGGAATTCATGGAATGGAGCTGGGTCTTTCTCTT | 121 |
| | | | | GGGAATTCATGGAATGCAGCTGGGTCATTCTCTT | 122 |
| | | | | GGGAATTCATGGAATGGAGCTGGGTTTTTCTCTT | 123 |
| | | | | GGGAATTCATGGAATGGAGCTGGGTTATTCTCTT | 124 |
| | | | | GGGAATTCATGAAATGGAGCTGGGTCTTTTCTT | 125 |
| | | | | GGGAATTCATGGAATGGAGCTGGGTCTTCCTCTT | 126 |
| | | | | GGGAATTCATGGAATGGAGCTGGGTTTTCCTCTTC | 127 |
| | | | 3' | CCCAAGCTTCCAGGGACCAATGGATAACGGGTGG | 128 |
| | | | | CCCAAGCTTCCAGGGACCAATGGATAAACGATGG | 129 |
| | | | | CCCAAGCTTCCAGGGACCAATGGATAAACGGTGG | 130 |
| | | | | CCCAAGCTTCCAGGGACCAATGGATAAACGGATGG | 131 |

TABLE 12-continued

Primers used for CDR sequencing of antibody variable regions

| Subclone | Ab isotype | Primer sequences | | | SEQ ID NO |
|---|---|---|---|---|---|
| | | | | CCCAAGCTTCCAGGGACCAGTGGATAGACGGGTGG | 132 |
| | | | | CCCAAGCTTCCAGGGACCAAGGGATAGATGATGG | 133 |
| | | | | CCCAAGCTTCCAGGGGCCAATGGATAAACGGTGG | 134 |
| | | | | CCCAAGCTTCCAGGGGCCAATGGATAAACGATGG | 135 |
| | | VK primers | 5' | ACTAGTCGACATGAAGTTGCCTGTTAGGCTGTTGGTGCT | 50 |
| | | | 3' | CCCAAGCTTACTGGATGGTGGGAAGATGGA | 51 |
| A4-2A1-18 | IgG2b | VH primers | 5' | GGGAATTCATGGAATGGAGCTGGGTCATTCTCTT | 136 |
| | | | | GGGAATTCATGGAATGCAGCTGGGTTTTTCTCTT | 120 |
| | | | | GGGAATTCATGGAATGGAGCTGGGTTTTTCTCTT | 123 |
| | | | | GGGAATTCATGGAATGCACCTGGGTTTTCCTCTT | 137 |
| | | | | GGGAATTCATGGAATGGAGCTGGGTCTTCCTCTT | 138 |
| | | | | GGGAATTCATGGAATGGAGCTGGGTCATCCTCTT | 139 |
| | | | | GGGAATTCATGGAATGGAGCTGGGTTATTCTCTT | 124 |
| | | | | ACTAGTCGACATGGGATGAGCTTATCATCCTCTT | 140 |
| | | | 3' | CCCAAGCTTCCAGGGGCCAATGGATAACGGTGG | 141 |
| | | | | CCCAAGCTTCCAGGGACCAGTGGGATAAACGGGTGG | 142 |
| | | | | CCCAAGCTTCCAGGGGCCAATGGATAAACGGGTGG | 134 |
| | | | | CCCAAGCTTCCAGGGACCAAGGGATAGACGGGTGG | 143 |
| | | | | CCCAAGCTTCCAGGGACCAAGGGATAAACGGATGG | 144 |
| | | | | CCCAAGCTTCCAGGGACCAGGGGATAAACGGATGG | 145 |
| | | | | CCCAAGCTTCCAGGGACCAATGGATAAACGGATGG | 131 |
| | | | | CCCAAGCTTCCAGGGGCCAGGGATAAACGGGTGG | 146 |
| | | | | CCCAAGCTTCCAGGGGCCAATGGATAAACGGTGG | 147 |
| | | | | CCCAAGCTTCCAGGGACCAGTGGATAAACGGTGG | 148 |
| | | VK primers | 5' | ACTAGTCGACATGGTGTCCACAGCTCAGTTCCTTG | 149 |
| | | | 3' | CCCAAGCTTACTGGATGGTGGGAAGATGGA | 51 |
| A6-2G5-30 | IgG2b | VH primers | 5' | GGGAATTCATGAAATGGAGCTGGGTCTTCCTCTT | 150 |
| | | | | GGGAATTCATGGAATGCAGCTGGGTTATTCTCTT | 151 |
| | | | | GGGAATTTATGGAATGGAGCTGGGTCTTCCTCTT | 152 |
| | | | | GGGAATTCATGGAATGGAGCTGGGTTTTCCTCTT | 127 |
| | | | | GGGAATTCATGGAATGCAGCTGGGTCATCCTCTT | 153 |
| | | | | GGGAATTCATGGAATGGAGCTGGGTTATTCTCTT | 124 |
| | | | | GGGAATTCATGGAATGCAGCTGGGTTTTCCTCTT | 154 |
| | | | | GGGAATTCATGGAATGCAGCTGGGTCTTTCTCTT | 155 |
| | | | | ACTAGTCGACATGGGATGGAGCTATATCATCCTCTT | 156 |
| | | | | ACTAGTCGACATGGGATGGAGCTTATCATCTTCTT | 157 |
| | | | | ACTAGTCGACATGTAGATGTGGTTAAACTGGGT | 158 |
| | | | 3' | CCCAAGCTTCCAGGGGCCAGGGGATAAACGGATGG | 159 |
| | | | | CCCAAGCTTCCAGGGGCCAAGGGATAGACGGATGG | 160 |
| | | | | CCCAAGCTTCCAGGGACCAGGGGATAGACGGGTGG | 161 |
| | | | | CCCAAGCTTCCAGGGACCAGGGGATAGACGGATGG | 162 |
| | | | | CCCAAGCTTCCAGGGGCCAGTGGATAAACGGATGG | 163 |
| | | | | CCCAAGCTTCCAGGGGCCAATGGATAACGATGG | 164 |
| | | | | CCCAAGCTTCCAGGGGCCAGTGGATAAACGATGG | 165 |
| | | | | CCCAAGCTTCCAGGGACCAATGGATAAACGGTGG | 130 |
| | | | | CCCAAGCTTCCAGGGACCAGTGGATAAACGATGG | 166 |
| | | | | CCCAAGCTTCCAGGGACCAATGGATAACGATGG | 167 |
| | | | | CCCAAGCTTCCAGGGACCATGGATAAACGGGTGG | 168 |
| | | VK primers | 5' | ACTAGTCGACATGGGCATCAAGATGAAGTCACATACTCTGG | 169 |
| | | | | ACTAGTCGACATGGGCATCAAGATGAGTCACATACTCTGG | 170 |
| | | | | ACTAGTCGACTGGGCATCAGATGAGTCACATACTCTGG | 171 |
| | | | | ACTAGTCGACATGGGCATCAAGATGAAGTCACAGACCCAGG | 172 |
| | | | | ACTAGTCGACATGGGCTTCAAGATGAAGTCACATTCTCTGG | 173 |
| | | | | ACTAGTCGACATGGGCTTCAAGATGAAGTCACATATTCAGG | 174 |
| | | | | CCCAAGCTTACTGGATGGTGGGAAGATGGA | 51 |
| | | | 3' | CCCAAGCTTACTGGATGGTGGGAAGATGGA | 51 |
| A4-2A1-40 | IgG2b | VH primers | 5' | GGGAATTCATGGAATGGAGCTGGGTCATCCTCTT | 139 |
| | | | | GGGAATTCATGGAATGCAGCTGGGTTTTCCTCTT | 154 |
| | | | | GGGAATTCATGGAATGCAGCTGGGTCTTTCTCTT | 155 |
| | | | | GGGAATTCATGGAATGGAGCTGGGTTTTCCTCTT | 127 |
| | | | | GGGAATTCATGGAATGGAGCTGGGTCTTTCTCTT | 121 |
| | | | | ACTAGTCGACATGGATGGAGCTTATCATCCTCTT | 175 |
| | | | 3' | CCCAAGCTTCCAGGGACCAAGGGATAAACGGTGG | 176 |
| | | | | CCCAAGCTTCCAGGGGCCAATGGATAAACCGGTGG | 147 |
| | | | | CCCAAGCTTCCAGGGACCAATGGATAAACGATGG | 129 |
| | | | | CCCAAGCTTCCAGGGGCCAGTGGATAAACGGGTGG | 177 |
| | | | | CCCAAGCTTCCAGGGACCAATGGATAACGGGTGG | 128 |
| | | VK primers | 5' | ACTAGTCGACATGAGGTACTCGGCTCAGTTCCTGGG | 178 |
| | | | | ACTAGTCGACATGAGGTCCCCGGCTCAGTTCCTGGG | 179 |
| | | | | ACTAGTCGACATGAGGACGTCGATTCAGTTCTTGGG | 180 |
| | | | 3' | CCCAAGCTTACTGGATGGTGGGAAGATGGA | 51 |

TABLE 12-continued

Primers used for CDR sequencing of antibody variable regions

| Subclone | Ab isotype | Primer sequences | | | SEQ ID NO |
|---|---|---|---|---|---|
| A6-2G5-41 | IgG2b | VH primers | 5' | GGGAATTCATGGAATGGACCTGGGTCATCCTCTT | 181 |
| | | | | GGGAATTCATGGAATGCAGCTGGGTTTTTCTCTT | 120 |
| | | | | GGGAATTCATGGAATGCAGCTGGGTTATCCTCTT | 182 |
| | | | | GGGAATTCATGGAATGGAGCTGGGTTATTCTCTT | 124 |
| | | | | GGGAATTCATGGAATGCAGCTGGGTCTTCCTCTT | 126 |
| | | | | GGGAATTCATGAATGGATCTGGGTTATTCTCTT | 183 |
| | | | 3' | CCCAAGCTTCCAGGGACCAGGGGATAAACGGGTGG | 184 |
| | | | | CCCAAGCTTCCAGGGACCAAGGGACGGGTGG | 185 |
| | | | | CCCAAGCTTCCAGGGACCAATGGATAAACAGATGG | 186 |
| | | | | CCCAAGCTTCCAGGGACCAAGGGATAAACGGATGG | 144 |
| | | | | CCCAAGCTTCCAGGGACCAGGGGATAAACGGATGG | 145 |
| | | | | CCCAAGCTTCCAGGGACCAAGGGATAAACGGGTGG | 187 |
| | | VK primers | 5' | GGGAATTCATGGAGACACATTCCCAGGTCTTT | 188 |
| | | | | GGGAATTCATGGAGTCACAGTCTCAGGTCTTT | 189 |
| | | | | ACTAGTCGACATGGGCTTCAAGATGGAGTCACATTTTCAGG | 190 |
| | | | | ACTAGTCGACATGGGCATCAAGATGAAGTCACATATTCAGG | 191 |
| | | | | ACTAGTCGACATGGGCTTCAAGATGAAGTCACATTCTCAGG | 192 |
| | | | | CCCAAGCTTACTGGATGGTGGGAAGATGGA | 51 |
| | | | 3' | CCCAAGCTTACTGGATGGTGGGAAGATGGA | 51 |
| A4-4A6-48 | IgG2b | VH primers | 5' | ACTAGTCGACATGGGATGGAGCTTATCATGTTCTT | 193 |
| | | | | ACTAGTCGACATGGGATGGAGCTTATCATGCTCTT | 194 |
| | | | | GGGAATTCATGGAATGCACCTGGGTTTTCCTCTT | 137 |
| | | | | GGGAATTCATGGAATGGACCTGGGTTTTCCTCTT | 195 |
| | | | | GGGAATTCATGGAATGGACCTGGGTCTTTCTCTT | 196 |
| | | | | GGGAATTCATGAAATGGAGCTGGGTTATTCTCTT | 197 |
| | | | | GGGAATTCATGGAATGCAGCTGGGTTATTCTCTT | 151 |
| | | | | GGGAATTCATGGAATGGAGCTGGGTCTTTCTCTT | 121 |
| | | | 3' | CCCAAGCTTCCAGGGGCCAATGGATAGACGATGG | 198 |
| | | | | CCCAAGCTTCCAGGGACCAAGGGATAGACGGATGG | 199 |
| | | | | CCCAAGCTTCCAGGGACCAAGGGATAGACGATGG | 200 |
| | | | | CCCAAGCTTCCAGGGGCCAATGGATAACGGTGG | 141 |
| | | | | CCCAAGCTTCCAGGGACCAGTGGATAAACGATGG | 166 |
| | | | | CCCAAGCTTCCAGGGACCAATGGATAAACGGATGG | 131 |
| | | | | CCCAAGCTTCCAGGGACCAAGGGATAAACGGATGG | 144 |
| | | VK primers | 5' | ACTAGTCGACATGATGTACCCGGCTCAGTTTCTGGG | 201 |
| | | | | ACTAGTCGACATGAGGACTTCGATTCAGTTCTTGGG | 202 |
| | | | | ACTAGTCTACATGAAGTTGCCTGTTAGGCTGTTGGTGCT | 203 |
| | | | | ACTAGTCGACATGAAGTTGTCTGTTAGGCTGTTGGTGCT | 204 |
| | | | | ACTAGTCGACATGAAGTTGCCTGTTAGGCTGTTGGTGCT | 50 |
| | | | 3' | CCCAAGCTTACTGGATGGTGGGAAGATGGA | 51 |
| A4-4A6-18 | IgG2b | VH primers | 5' | ATGGGATGGAGCTRTATCATSYTCTT | 205 |
| | | | | ATGAAGWTGTGGBTRAACTGGRT | 206 |
| | | | | ATGGRATGGASCKKIRTCTTTMTCT | 207 |
| | | | 3' | CCAGGGRCCARKGGATARACIGRTGG | 208 |
| | | VK primers | 5' | ATGGAGACAGACACACTCCTGCTAT | 209 |
| | | | | ATGGAGWCAGACACACTSCTGYTATGGGT | 210 |
| | | | | ATGAAGTTGCCTGTTAGGCTGTTGGTGCT | 211 |
| | | | | ATGGATTTWCARGTGCAGATTWTCAGCTT | 212 |
| | | | | ATGGTYCTYATVTCCTTGCTGTTCTGG | 213 |
| | | | | ATGGTYCTYATVTTRCTGCTGCTATGG | 214 |
| | | | 3' | ACTGGATGGTGGGAAGATGGA | 215 |
| A6-1D2-12 | IgG2a | VH primers | 5' | ATGAAATGCAGCTGGRTYATSTTCTT | 216 |
| | | | | ATGGRCAGRCTTACWTYYTCATTCCT | 217 |
| | | | | ATGATGGTGTTAAGTCTTCTGTACCT | 218 |
| | | | 3' | CCAGGGRCCARKGGATARACIGRTGG | 208 |
| | | VK primers | 5' | ATGRAGWCACAKWCYCAGGTCTTT | 219 |
| | | | | ATGGAGACAGACACACTCCTGCTAT | 209 |
| | | | | ATGGAGWCAGACACACTSCTGYTATGGGT | 210 |
| | | | | ATGAGGRCCCCTGCTCAGWTTYTTGGIWTCTT | 220 |
| | | | | ATGGGCWTCAAGATGRAGTCACAKWYYCWGG | 221 |
| | | | | ATGAAGTTGCCTGTTAGGCTGTTGGTGCT | 211 |
| | | | | ATGGATTTWCARGTGCAGATTWTCAGCTT | 212 |
| | | | | ATGGTYCTYATVTCCTTGCTGTTCTGG | 213 |
| | | | | ATGGTYCTYATVTTRCTGCTGCTATGG | 214 |
| | | | 3' | ACTGGATGGTGGGAAGATGGA | 215 |

DegenerateCodons:
R = A or G  S = C or G  D = A or G or T  B = C or G or T
Y = C or T  M = A or C  H = A or C or T
K = G or T  W = A or T  V = A or G or C

TABLE 13

Longest isoform of human Tau (441aa), also called Tau40

| | |
|---|---|
| Longest isoform of human Tau (441aa), also called Tau40 (SEQ ID NO: 67) Microtubule-associated protein tau isoform 2 [Homo sapiens] NCBI Reference Sequence: NP_005901.2 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQARMVSK SKDGTGSDDK KAKGADGKTK IATPRGAAPP GQKGQANATR IPAKTPPAPK TPPSSGEPPK SGDRSGYSSP GSPGTPGSRS RTPSLPTPPT REPKKVAVVR TPPKSPSSAK SRLQTAPVPM PDLKNVKSKI GSTENLKHQP GGGKVQIINK KLDLSNVQSK CGSKDNIKHV PGGGSVQIVY KPVDLSKVTS KCGSLGNIHH KPGGGQVEVK SEKLDFKDRV QSKIGSLDNI THVPGGGNKK IETHKLTFRE NAKAKTDHGA EIVYKSPVVS GDTSPRHLSN VSSTGSIDMV DSPQLATLAD EVSASLAKQG L (SEQ ID NO: 67) |

REFERENCE LIST

Alonso A. D., et al. (1997), *Proc. Natl. Acad. Sci. U.S.A.*, 94, 298-303
Alving et al., (1992) Infect. Immun. 60:2438-2444
Asuni et al., (2007) J Neurosc. 27 (34), 9115-29
Braak H., et al. (1993), *Eur. Neurol.*, 33, 403-408
Gill et al., Nature Med. 9: 589-595 (2003)
Greenberg S. G., et al. (1992), *J. Biol. Chem.*, 267, 564-569.
Harlow and Lane, Antibodies: A Laboratory Manual (Cold Spring Harbor Laboratory, New York 1988 555-612
Hodgson et al., (1991) Bio/Technoloy, 9:421
Hoffmann R., et al (1997), *Biochemistry*, 36, 8114-8124.
Kabat E A, Wu T T, Perry H M, Gottesman K S, Foeller C. *Sequences of proteins of Immunological Interest*, US Department of Health and Human Services, 1991
Kennedy, J. H., et al., 1976 (Clin. Chim. Acta 70:1-31)
Khaw, B. A. et al. (1982) J. Nucl. Med. 23:1011-1019
Lewis et al., (2000) Nature Genetics, 25:402-405
Masliah et al., (2005) Neuron, 46(6), 857-68
Masliah et al., (2011) PLoS ONE, Volume 6(4), e19338, pp—1-17
Muhs et al., (2007) Proc Natl Acad Sci USA, 104(23), 9810-5
Muyllaert et al, (2006) Rev Neurol, 162(10), 903-907
Muyllaert et al, (2008) Genes Brain Behav., Suppl. 1, 57-66
Neuwelt, E. A., Implication of the Blood-Brain Barrier and its Manipulation, Vols 1 & 2, Plenum Press, N. Y. (1989))
Nicolau et. al. (2002) Proc Natl. Acad. Sci USA 99, 2332-2337
Nicoll et al., (2003) Nature Med, 9, 448-452
Oddo et al., (2004) Neuron, 43, 321-332
Queen et al., (1989) Proc. Natl Acad Sci USA, 86:10029-10032
Papanastassiou et al., Gene Therapy 9: 398-406 (2002)
Reig S., et al. (1995), Acta Neuropathol., 90, 441-447
Ribe et al., (2005) Neurobiol Dis, 20(3), 814-22
Roberson et al, (2007) Science, 316 (5825), 750-4
Rosenmann et al., (2006) Arch Neurol, 63(10), 1459-67
Rousseaux et al. Methods Enzymology, (1986), Academic Press 121:663-69
Schurs, A. H. W. M., et al. 1977 {Clin. Chim Acta 57:1-40
Terwel et al., (2006) J Biol Chem, 280, 3963-3973
Terwel et al, (2008) Am J pathol., 172(3), 786-98
Urushitiani et al., (2007) Proc. Natl Acad Sci USA, 104(79, 2495-500
Vandebroek et al., "Phosphorylation and Aggregation of Protein Tau in Humanized Yeast Cells and in Transgenic Mouse Brain"; 7th International Conference on Alzheimer's and Parkinson's Disease, Sorrento, Italy, Mar. 9-13, 2005, pp 15-19
Wagner et al (2002) Journal of Liposome Research Vol 12(3), pp 259-270
WO 2004/058258
WO 96/13590
WO 96/29605
U.S. Patent Publication No. 2002/0038086
U.S. Patent Publication No. 2003/0083299
U.S. Patent Publication No. 2002/0025313
U.S. Patent Publication No 2004/0204354
U.S. Patent Publication No 2004/0131692
U.S. Patent Publication No 2002/0065259
U.S. Patent Publication No 2003/0162695
U.S. Patent Publication No 2005/0124533
U.S. Patent Publication No 2005/0089473
U.S. Patent Publication No 2003/0073713
U.S. Patent Publication No 2003/0129186
U.S. Pat. No. 5,112,596,
U.S. Pat. No. 5,268,164,
U.S. Pat. No. 5,506,206,
U.S. Pat. No. 5,686,416
U.S. Pat. No. 5,004,697

The invention claimed is:

1. A method of diagnosing a tau-protein-associated disease, disorder or condition in a patient comprising detecting the immunospecific binding of an antibody or an active fragment thereof to tau protein in a sample or in situ which includes the steps of:
   a. bringing the sample or a specific body part or body area suspected to contain the tau protein into contact with an antibody or active fragment thereof, wherein the antibody or active fragment thereof comprises a heavy chain complementarity determining region 1 (HC-CDR1) comprising the amino acid sequence of SEQ ID NO: 12, an HC-CDR2 comprising the amino acid sequence of SEQ ID NO: 13, an HC-CDR3 comprising the amino acid sequence of SEQ ID NO: 14, a light chain CDR1 (LC-CDR1) comprising the amino acid sequence of SEQ ID NO: 27, an LC-CDR2 comprising the amino acid sequence of SEQ ID NO: 25, and an LC-CDR3 comprising the amino acid sequence of SEQ ID NO: 26;
   b. allowing the antibody or active fragment thereof to bind to the tau protein to form an immunological complex;
   c. detecting the formation of the immunological complex; and
   d. wherein the presence of the immunological complex is indicative of the presence of tau protein in the sample or specific body part or area, and wherein the presence of tau protein in the sample or specific body part or area is indicative of a tau-protein-associated disease, disorder or condition.

2. A method for diagnosing a predisposition to tau-protein-associated disease, disorder or condition in a patient comprising detecting the immunospecific binding of an antibody or an active fragment thereof to tau protein in a sample or in situ which includes the steps of:
   a. bringing the sample or a specific body part or body area suspected to contain the tau protein into contact with an antibody or active fragment thereof, wherein the antibody or active fragment thereof comprises a heavy chain complementarity determining region 1 (HC-CDR1) comprising the amino acid sequence of SEQ ID NO: 12, an HC-CDR2 comprising the amino acid sequence of SEQ ID NO: 13, an HC-CDR3 comprising the amino acid sequence of SEQ ID NO: 14, a light chain CDR1 (LC-CDR1) comprising the amino acid sequence of SEQ ID NO: 27, an LC-CDR2 comprising the amino acid sequence of SEQ ID NO: 25, and an LC-CDR3 comprising the amino acid sequence of SEQ ID NO: 26;
   b. allowing the antibody or active fragment thereof to bind to the tau protein to form an immunological complex;
   c. detecting the formation of the immunological complex; and d. comparing the amount of said immunological complex to a normal control value, wherein the amount of said immunological complex is indicative of the amount of said tau protein in the sample or specific body part area, and wherein an increase in the amount of said tau protein compared to a normal control value indicates that said patient is suffering from or is at risk of developing a tau protein-associated disease or condition.

3. A method for monitoring minimal residual disease in a patient following treatment with an anti-tau antibody, wherein said method comprises:
   a. bringing a sample or a specific body part or body area suspected to contain tau protein into contact with an antibody or active fragment thereof, wherein the antibody or active fragment thereof comprises a heavy chain complementarity determining region 1 (HC-CDR1) comprising the amino acid sequence of SEQ ID NO: 12, an HC-CDR2 comprising the amino acid sequence of SEQ ID NO: 13, an HC-CDR3 comprising the amino acid sequence of SEQ ID NO: 14, a light chain CDR1 (LC-CDR1) comprising the amino acid sequence of SEQ ID NO: 27, an LC-CDR2 comprising the amino acid sequence of SEQ ID NO: 25, and an LC-CDR3 comprising the amino acid sequence of SEQ ID NO: 26;
   b. allowing the antibody or active fragment thereof to bind to the tau protein to form an immunological complex;
   c. detecting the formation of the immunological complex; and
   d. comparing the amount of said immunological complex to a normal control value, wherein the amount of said immunological complex is indicative of the amount of said tau protein in the sample or specific body part area, and wherein an increase in the amount of said tau protein compared to a normal control value indicates that said patient still suffers from a minimal residual disease.

4. A method for predicting responsiveness of a patient being treated with an anti-tau antibody comprising:
   a. bringing a sample or a specific body part or body area suspected to contain tau protein into contact with an antibody or active fragment thereof, wherein the antibody or active fragment thereof comprises a heavy chain complementarity determining region 1 (HC-CDR1) comprising the amino acid sequence of SEQ ID NO: 12, an HC-CDR2 comprising the amino acid sequence of SEQ ID NO: 13, an HC-CDR3 comprising the amino acid sequence of SEQ ID NO: 14, a light chain CDR1 (LC-CDR1) comprising the amino acid sequence of SEQ ID NO: 27, an LC-CDR2 comprising the amino acid sequence of SEQ ID NO: 25, and an LC-CDR3 comprising the amino acid sequence of SEQ ID NO: 26;
   b. allowing the antibody or active fragment thereof to bind to the tau protein to form an immunological complex;
   c. detecting the formation of the immunological complex; and
   d. comparing the amount of said immunological complex before and after onset of the treatment, wherein the amount of said immunological complex is indicative of the amount of said tau protein in the sample or specific body part area, and wherein a decrease in the amount of said tau protein indicates that said patient has a high potential of being responsive to the treatment.

5. The method of claim 1, wherein the antibody or active fragment thereof comprises a heavy chain variable region comprising the amino acid sequence of SEQ ID NO: 2 and a light chain variable region comprising the amino acid sequence of SEQ ID NO: 8.

6. The method of claim 2, wherein the antibody or active fragment thereof comprises a heavy chain variable region comprising the amino acid sequence of SEQ ID NO: 2 and a light chain variable region comprising the amino acid sequence of SEQ ID NO: 8.

7. The method of claim 3, wherein the antibody or active fragment thereof comprises a heavy chain variable region comprising the amino acid sequence of SEQ ID NO: 2 and a light chain variable region comprising the amino acid sequence of SEQ ID NO: 8.

8. The method of claim 4, wherein the antibody or active fragment thereof comprises a heavy chain variable region comprising the amino acid sequence of SEQ ID NO: 2 and a light chain variable region comprising the amino acid sequence of SEQ ID NO: 8.

9. The method of claim 1, wherein the tau-protein-associated disease, disorder or condition is a neurodegenerative disease or disorder.

10. The method of claim 9, wherein the neurodegenerative disease or disorder is selected from Alzheimer's Disease, Creutzfeldt-Jacob disease, Dementia pugilistica, Down's Syndrome, Gerstmann-Strässler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, and Myotonic dystrophy.

11. The method of claim 10, wherein the neurodegenerative disease or disorder is Alzheimer's Disease.

12. The method of claim 2, wherein the tau-protein-associated disease, disorder or condition is a neurodegenerative disease or disorder.

13. The method of claim 12, wherein the neurodegenerative disease or disorder is selected from Alzheimer's Disease, Creutzfeldt-Jacob disease, Dementia pugilistica, Down's Syndrome, Gerstmann-Strässler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, and Myotonic dystrophy.

14. The method of claim 13, wherein the neurodegenerative disease or disorder is Alzheimer's Disease.

15. The method of claim 3, wherein the patient suffers from a tau-protein-associated disease, disorder or condition.

16. The method of claim 15, wherein the tau-protein-associated disease, disorder or condition is a neurodegenerative disease or disorder.

17. The method of claim 16, wherein the neurodegenerative disease or disorder is selected from Alzheimer's Disease, Creutzfeldt-Jacob disease, Dementia pugilistica, Down's Syndrome, Gerstmann-Strässler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, and Myotonic dystrophy.

18. The method of claim 17, wherein the neurodegenerative disease or disorder is Alzheimer's Disease.

19. The method of claim 4, wherein the patient suffers from a tau-protein-associated disease, disorder or condition.

20. The method of claim 19, wherein the tau-protein-associated disease, disorder or condition is a neurodegenerative disease or disorder.

21. The method of claim 20, wherein the neurodegenerative disease or disorder is selected from Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, and Myotonic dystrophy.

22. The method of claim 21, wherein the neurodegenerative disease or disorder is Alzheimer's Disease.

23. The method of claim 1, wherein the sample comprises cerebrospinal fluid.

24. The method of claim 2, wherein the sample comprises cerebrospinal fluid.

25. The method of claim 3, wherein the sample comprises cerebrospinal fluid.

26. The method of claim 4, wherein the sample comprises cerebrospinal fluid.

* * * * *